United States Patent
Dower et al.

(10) Patent No.: US 11,248,025 B2
(45) Date of Patent: Feb. 15, 2022

(54) IL-2ALPHA RECEPTOR SUBUNIT BINDING COMPOUNDS

(71) Applicant: MEDIKINE, INC., Menlo Park, CA (US)

(72) Inventors: William J. Dower, Menlo Park, CA (US); Michael C. Needels, Menlo Park, CA (US); Ronald W. Barrett, Menlo Park, CA (US); Alice V. Bakker, Menlo Park, CA (US); Steven E. Cwirla, Menlo Park, CA (US)

(73) Assignee: MEDIKINE, INC., Menlo Park, CA (US)

( * ) Notice: Subject to any disclaimer, the term of this patent is extended or adjusted under 35 U.S.C. 154(b) by 9 days.

(21) Appl. No.: 16/890,749

(22) Filed: Jun. 2, 2020

(65) Prior Publication Data

US 2020/0399314 A1    Dec. 24, 2020

Related U.S. Application Data

(60) Provisional application No. 62/856,305, filed on Jun. 3, 2019.

(51) Int. Cl.
*C07K 7/08* (2006.01)
*A61K 38/00* (2006.01)

(52) U.S. Cl.
CPC ............... *C07K 7/08* (2013.01); *A61K 38/00* (2013.01)

(58) Field of Classification Search
None
See application file for complete search history.

(56) References Cited

U.S. PATENT DOCUMENTS 5,635,597 A    6/1997   Barrett et al.

OTHER PUBLICATIONS

Morrison, Combinatorial alanine-scanning, Current Opinion in Chemical Biology 2001, 5:302-307 (Year: 2001).*
Partial Search for Application No. PCT/US2020/035747, dated Oct. 5, 2020, 18 pages.
International Search Report and Written Opinion for Application No. PCT/US2020/035747, dated Dec. 1, 2020, 22 pages.
Gronwall et al., "Generation of Affibody ligands binding interleukin-2 receptor α/CD25", Biotechnology and Applied Biochemistry, 2008, vol. 50, p. 97-112.
Malek, T., "The Biology of Interleukin-2", Annual Review of Immunology, Annual Reviews Inc., 2008, vol. 26, p. 453-479.
Uniprot Database, Accession No. A0A3P7JJB2, Feb. 13, 2019, 1 page.

* cited by examiner

*Primary Examiner* — Thomas S Heard

(57) ABSTRACT

Peptidyl IL-2Rα ligands and compounds comprising the IL-2Rα ligands are disclosed. The IL-2Rα ligands and compounds such as synthetic monomers, homodimers, or heteromers and recombinant fusion proteins comprising the IL-2Rα ligands can be used as targeting or imaging agents, as diagnostics or to treat cancers and autoimmune diseases.

26 Claims, No Drawings

Specification includes a Sequence Listing.

IL-2 ALPHA RECEPTOR SUBUNIT BINDING COMPOUNDS

This application claims the benefit under 35 U.S.C. § 119(e) of U.S. Provisional Application No. 62/856,305 filed on Jun. 3, 2019, which is incorporated by reference in its entirety.

FIELD

The present disclosure relates to peptidyl IL-2Rα ligands and to compounds having a peptidyl IL-2Rα ligand. Compounds such as synthetic monomers, homodimers, heteromers, and recombinant fusion proteins comprising the IL-2Rα ligands can be used as targeting agents, imaging agents, diagnostic agents, and as therapeutics to treat cancer and autoimmune diseases.

SEQUENCE LISTING

The Sequence Listing associated with this application is filed in electronic format via EFS-Web and is incorporated by reference in its entirety. Said ASCII copy, created on Jul. 28, 2020, is named 62AJ-000210US-309981_SL.txt and is 200,417 bytes in size.

BACKGROUND

Interleukin-2 (IL-2) plays a crucial role in regulating immune responses and maintaining peripheral self-tolerance by having both immuno-stimulatory and immuno-regulatory functions. IL-2 acts primarily as a T cell growth factor and is essential for the proliferation and survival of T cells as well as the generation of effector and memory T cells. IL-2 is a four α-helical bundle cytokine that belongs to a family of structurally related cytokines that includes IL-4, IL-7, IL-9, IL-15, and IL-21. IL-2 is produced by activated CD4$^+$ T cells in response to antigen stimulation and can also be produced by CD8$^+$ T cells and innate immune cells such as activated dendritic cells (DCs) and natural killer (NK) cells.

IL-2 binds to various forms of the IL-2 receptor (IL-2R), notably the monomeric, dimeric, and trimeric forms. Monomeric IL-2R consists of the membrane-associated IL-2Rα (CD25) chain, which also exists in a soluble form; however, it is not capable of inducing signaling events. The trimeric IL-2R consists of IL-2Rα, IL2-Rβ (CD122), and IL-2Rγ, also known as the common γ-chain (γc) or CD132 and is shared by all members of the IL-2 cytokine family. Dimeric IL-2R comprises the IL-2Rγc and IL-2Rβ subunits. In contrast to monomeric IL-2R, both the dimeric and trimeric IL-2 receptors lead to a downstream signaling cascade upon IL-2 binding. IL-2 binds with high affinity to the trimeric IL-2R but with low-moderate affinity to the dimeric IL-2R, varying the sensitivity of the cell to IL-2. Additionally, IL-2 can bind to IL-2Rα expressed on the surface of activated dendritic cells for trans presentation to neighboring cells including antigen-specific naïve T cells and NK cells that express both IL-2Rβ and IL-2Rγc subunits. This trans presentation of IL-2 has been shown to facilitate initial high affinity IL-2 signaling, required early in the immune response to prime naïve T-cells to produce IL-2.

TL-2 is first captured by IL-2Rα, bringing about a conformational change to IL-2, increasing its affinity for IL-2Rβ. Association of IL-2 with the IL-2Rαγc subunits induces the dimerization of the signaling motifs in the cytoplasmic tails of IL-2Rβ and IL-2Rγc leading to the phosphorylation/activation of the Janus kinases, JAK1 and JAK3, which in turn exert kinase activity on key tyrosine residues in the tail of the IL-2Rβ subunit.

Downstream signaling occurs via three major pathways, the JAK-STAT pathway, the phosphoinositide 3-kinase (PI3K)-AKT pathway, and the mitogen-activated protein kinase (MAPK) pathway. These pathways ultimately result in the transcription of target genes that contribute to IL-2-dependent biological actions, through the recruitment of the adaptor protein She and the transcription factor STAT5. Target genes of TL-2 signaling include cyclin D2, bcl-2, fasL, cd25 (encoding IL-2Rα), socs1-2, and the IL-2 silencing gene prdm1, which encodes for the transcription factor, BLIMP. The production of the negative regulator of IL-2 BLIMP1 is essential for maintaining the balance between effector T cells and Treg cells, which is crucial for immune homeostasis.

IL-2 plays a dual role in T cell activation by stimulating the proliferation and differentiation or T cells as well as by maintaining and expanding the population of immuno-suppressive Treg cells. The conventional naïve CD4+ and CD8+ T cells express the dimeric TL-2R, and therefore require a high concentration of IL-2 to induce their initial proliferation. Once activated, these T cells express the high-affinity trimeric IL-2R, driving the differentiation of the cells into either effector (Teff) or memory cells. This differentiation depends on the strength and duration of the IL-2 signal.

During the primary expansion of CD8$^+$ T cells due to low-moderate levels of IL-2, a subset of CD8$^+$ T cells will differentiate into memory T cells. They do this by down-regulating CD25 and upregulating CD127 (IL-7R) and CD62 (L-selectin), which are crucial receptors for secondary responses upon re-infection. During an acute infection, sustained high levels of IL-2 leads to a rapid up-regulation of CD25, and the differentiation of CD8+ cells into cytotoxic effector cells. The upregulation induces an IL-2 driven expression of the death receptor fas and fasL, causing activation-induced cell death (AICD) upon pathogen clearance. For CD4$^+$ T cells, the activation of STAT5 signaling by IL-2 influences their differentiation into multiple helper T cell populations, including Th1, Th2, and Th17 by regulating the expression of the appropriate receptors for each response.

Homeostatic or background levels of IL-2 are essential for the survival and function of Treg cells by maintaining the expression of FOXP3 and CD25. Treg cells naturally occur in the thymus and upon contact with self-peptides become activated. Additionally, Treg cells can be generated by stimulation of conventional CD4$^+$ T cells upon interaction with antigens in peripheral lymphoid organs. Because Treg cells do not produce IL-2, Treg cells are dependent on IL-2 producing cells such as conventional T cells. Additionally, due to the high expression of IL-2Rα (CD25) Treg cells are able to consume and limit the systemic concentration of IL-2, ensuring the regulation of the immune balance. In the absence of IL-2, the number of Treg cells decreases and the number of effector T cells increases, leading to an enhanced susceptibility to autoimmune and inflammatory disorders. Therefore, the unique activation of Treg cells at low levels of IL-2, which does not activate CD4$^+$ or CD8$^+$ T cells, has allowed for the development of IL-2 as a therapeutic in autoimmune and inflammatory diseases.

The production of IL-2 from both arms of the immune system highlights the importance of IL-2 in the early stages of infection, as well as the secondary adaptive response. Furthermore, the dual functions of IL-2 in both protective immunity and in immune tolerance allows IL-2 to be a potential therapeutic as both an immune stimulant for cancer treatment and as an immune suppressor for the treatment of autoimmune disease.

SUMMARY

According to the present invention, IL-2Rα ligands bind to the human IL-2Rα subunit with an $IC_{50}$ of less than 100 µM.

According to the present invention, compounds comprise an IL-2Rα ligand according to the present invention.

According to the present invention, pharmaceutical compositions comprise an IL-2Rα ligand according to the present invention; a compound according to the present invention; or a combination of any of the foregoing.

According to the present invention, methods of treating cancer in a patient, comprise administering to a patient in need of such treatment a therapeutically effective amount of a pharmaceutical composition according to the present invention.

According to the present invention, methods of treating an autoimmune disease in a patient, comprise administering to a patient in need of such treatment, a therapeutically effective amount of a pharmaceutical composition according to the present invention.

According to the present invention, methods of screening compounds for IL-2α activity, comprise contacting a cell with an IL-2Rα ligand according to the present invention; the compound according to the present invention; or a combination of any of any of the foregoing wherein the cell expresses an IL-2α subunit; and contacting the cell with a test compound; and determining the activity of the test compound.

According to the present invention, methods of treating a disease in a patient, wherein the IL-2 receptor signaling pathway is associated with the etiology of the disease, comprise administering to a patient in need of such treatment a therapeutically effective amount of a compound comprising an IL-2Rα ligand according to the present invention, or a pharmaceutical composition thereof.

According to the present invention, methods of treating a disease in a patient, wherein activating the IL-2 receptor is effective in treating the disease, comprise administering to a patient in need of such treatment a therapeutically effective amount of a compound comprising an IL-2Rα ligand according to the present invention or a pharmaceutical composition thereof.

According to the present invention, methods of treating a disease in a patient, wherein inhibiting the IL-2 receptor is effective in treating the disease, comprise administering to a patient in need of such treatment a therapeutically effective amount of a compound comprising an IL-2Rα ligand according to the present invention or a pharmaceutical composition thereof.

According to the present invention, methods of treating a disease in a patient, wherein modulating the activity of the IL-2Rα subunit is effective in treating the disease, comprise administering to a patient in need of such treatment a therapeutically effective amount of a compound comprising an IL-2Rα ligand according to the present invention or a pharmaceutical composition thereof.

According to the present invention, methods of treating a disease in a patient, wherein inhibiting binding to the IL-2Rα subunit is effective in treating the disease, comprise administering to a patient in need of such treatment a therapeutically effective amount of a compound comprising an IL-2Rα ligand according to the present invention or a pharmaceutical composition thereof.

According to the present invention, methods of treating a disease in a patient, wherein the etiology of the disease is associated with activation of Treg cells, comprise administering to a patient in need of such treatment a therapeutically effective amount of a compound comprising an IL-2Rα ligand according to the present invention or a pharmaceutical composition thereof.

According to the present invention, methods of treating a disease in a patient, wherein the etiology of the disease is associated with cells exhibiting a high IL-2Rα expression, comprise administering to a patient in need of such treatment a therapeutically effective amount of a compound comprising an IL-2Rα ligand according to the present invention or a pharmaceutical composition thereof.

According to the present invention, methods of imaging cells expressing the IL-2Rα subunit comprise administering to a patient an effective amount of a compound comprising an IL-2Rα ligand according to the present invention.

According to the present invention, methods of diagnosing a disease in a patient wherein the disease is associated with cells expressing the IL-2Rα subunit comprise administering to a patient an effective amount of a compound comprising an IL-2Rα ligand according to the present invention.

According to the present invention, methods of targeting a compound to cells expressing the IL-2Rα subunit comprise administering to a patient an effective amount of a compound comprising an IL-2Rα ligand according to the present invention.

According to the present invention, methods of delivering a cytotoxic compound to cells expressing the IL-2Rα subunit comprise administering to a patient an effective amount of a compound comprising a cytotoxic moiety and an IL-2Rα ligand according to the present invention.

DETAILED DESCRIPTION

A dash ("-") that is not between two letters or symbols is used to indicate a point of attachment for a moiety or substituent. For example, $-X^1-X^2-$ denotes amino acids $X^1$ and $X^2$ covalently bonded through a single bond.

"Affinity" refers to strength of the binding interaction between a single biomolecule to its ligand/binding partner. Affinity is expressed as the $IC_{50}$.

"Agonist" refers to a biologically active ligand or compound that binds to its complementary biologically active receptor or subunit and activates the receptor to cause a biological response mediated by the receptor, or to enhance a preexisting biological activity mediated by the receptor.

"Partial agonist" refers to a compound that provides a level of activation, that is, for example, less than 75% of maximum activation, less than 50%, less than 25%, less than 10%, or less than 1% of the maximum activation. A partial IL-2R agonist exhibits a level of activation that is less than the level of activation provided by IL-2.

"Antagonist" refers to a biologically active ligand or compound that binds to its complementary receptor or subunit and blocks or reduces a biological response of the receptor.

Amino acid residues are abbreviated as follows: alanine is Ala or A; arginine is Arg is R; asparagine is Asn or N; aspartic acid is Asp or D; cysteine is Cys or C; glutamic acid is Glu or E; glutamine is Gln or Q; glycine is Gly or G; histidine is His or H; isoleucine is Ile or I; leucine is Leu or L; lysine is Lys or K; methionine is Met or M; phenylalanine is Phe or F; proline is Pro or P; serine is Ser or S; threonine is Thr or T; tryptophan is Trp or W; tyrosine is Tyr or Y; and valine is Val or V.

"Non-natural amino acids" include, for example, β-amino acids, homo-amino acids, proline and pyruvic acid derivatives, histidine derivatives with alkyl or heteroatom moieties attached to the imidazole ring, amino acids with pyridine-containing side chains, 3-substituted alanine derivatives, glycine derivatives, ring-substituted phenylalanine and tyrosine derivatives, and N-methyl amino acids.

Amino acids having a large hydrophobic side chain include isoleucine (I), leucine (L), methionine (M), valine (V), phenylalanine (F), tyrosine (Y), and tryptophan (W).

Amino acids having a small hydrophobic side chain include alanine (A), glycine (G), proline (P), serine (S), and threonine (T).

Amino acids having a basic side chain include arginine (R), lysine (K), and histidine (H).

Amino acids having an acidic side chain include aspartate (D) and glutamate (E).

Amino acids having a polar/neutral side chain include histidine (H), asparagine (N), glutamine (Q), serine (S), threonine (T), and tyrosine (Y).

Amino acids having an aromatic side chain include phenylalanine (F), histidine (H), tryptophan (W), and tyrosine (Y).

Amino acids having a hydroxyl side chain include serine (S), threonine (T), or tyrosine (Y).

"Conservative amino acid substitution" means that amino acids within each of the following groups can be substituted with another amino acid within the group: amino acids having a small hydrophobic side chain comprising alanine (A), glycine (G), proline (P), serine (S), and threonine (T); amino acids having a hydroxyl-containing side chain comprising serine (S), threonine (T), and tyrosine (Y); amino acids having an acidic side chain comprising aspartate (D) and glutamate (E); amino acids comprising a polar-neutral side chain comprising histidine (H), asparagine (N), glutamine (Q), serine (S), threonine (T), and tyrosine (Y); amino acids having a basic side chain comprising arginine (R), lysine (K), and histidine (H); amino acids having a large hydrophobic side chain comprising isoleucine (I), leucine (L), methionine (M), valine (V), phenylalanine (F), tyrosine (Y), and tryptophan (W); and amino acids having an aromatic side chain comprising phenylalanine (F), histidine (H), tryptophan (W), and tyrosine (Y).

"Expression" as used herein generally refers to expression of construct such as an IL-2 receptor or the outer surface of a cell.

Molecular weight refers to the number average molecular weight as determined by gel permeation chromatography using a polystyrene standard.

A linker refers to a moiety that binds at least one IL-2R ligand such as an IL-2Rα ligand, an IL-2Rβ ligand, and/or an IL-2Rγc ligand. A linker can bind to another IL-2R ligand which can be the same IL-2R ligand or a different IL-2R ligand. A linker can also bind to one or more additional moieties and/or compounds that can provide a desired physiological function. A linker can be divalent or multivalent. A linker can be hydrolytically stable or may be cleavable such as a physiologically hydrolyzable or enzymatically degradable linkage. A linker can bind IL-2R ligands to form dimers, trimers, or higher order multi-ligand peptides (heteromers) and compounds.

A "physiologically cleavable" or "hydrolyzable" or "degradable" bond refers to a bond that reacts with water (i.e., is hydrolyzed) under physiological conditions. The tendency of a bond to hydrolyze in water will depend not only on the general type of linkage connecting two central atoms but also on the substituents attached to these central atoms. Suitable hydrolytically unstable or weak linkages include but are not limited to carboxylate ester, phosphate ester, anhydrides, acetals, ketals, acyloxyalkyl ether, imines, orthoesters, peptides and oligonucleotides.

An "enzymatically degradable linkage" refers to a linkage that can be degraded or cleaved by one or more enzymes.

A "hydrolytically stable" linkage or bond refers to a chemical bond, such as a covalent bond, that is substantially stable in water such that the chemical bond does not undergo hydrolysis under physiological conditions to any appreciable extent over an extended period of time. Examples of hydrolytically stable linkages include, for example, carbon-carbon bonds (e.g., in aliphatic chains), ethers, amides, urethanes, and the like. Generally, a hydrolytically stable linkage is one that exhibits a rate of hydrolysis of less than about 1% to 2% per day under physiological conditions.

An "IL-2Rβ ligand" refers to a peptide capable of binding to the IL-2Rβ subunit of a mammalian IL-2 receptor, such as a human IL-2 receptor, with an affinity ($IC_{50}$) less than 100 μM. Suitable IL-2Rβ ligands are disclosed, for example, in U.S. Application Publication No. 2020/0040034 A1 and in U.S. Provisional Application No. 62/930,758 filed on Nov. 5, 2019, each of which is incorporated by reference in its entirety.

An "IL-2Rγc ligand" refers to a peptide capable of binding to the IL-2Rγc subunit of a mammalian IL-2 receptor, such as a human IL-2 receptor, with an affinity ($IC_{50}$) less than 100 μM. IL-2Rγc ligands are disclosed in U.S. Application Publication No. 2020/0040036 A1 and in U.S. Provisional Application No. 62/930,758 filed on Nov. 5, 2019, each of which is incorporated by reference in its entirety.

An "IL-2Rα ligand" refers to a peptide capable of binding to the IL-2Rα subunit of a mammalian IL-2 receptor, such as a human IL-2 receptor, with an affinity ($IC_{50}$) less than 100 μM.

The "human IL-2Rβ ligand" refers to a peptide capable of binding to the IL-2Rβ subunit of the human IL-2 receptor with an affinity less than 100 μM.

The "human IL-2Rγc ligand" refers to a peptide capable of binding to the IL-2Rγc subunit of a mammalian IL-2 receptor with an affinity ($IC_{50}$) less than 100 μM.

The "human IL-2Rα ligand" comprises refers to a peptide capable of binding to the IL-2Rα subunit of the human IL-2 receptor with an affinity ($IC_{50}$) less than 100 μM.

The "human IL-2Rβ subunit" refers to NP_000869.1.

The "human IL-2Rγc subunit" refers to NP_000197.1.

The "human IL-2Rα subunit" refers to NP_001295172.1 and/or NP_001295171.1,

An "IL-2R binding fusion protein" refers to a protein made by recombinant DNA technology in which the translational reading frame of an IL-2R ligand is fused to that of another protein ("IL-2R binding fusion partner") to produce a single recombinant polypeptide. An IL-2R fusion protein can comprise an IL-2Rα ligand, an IL-2Rβ ligand, and/or an IL-2Rγc ligand. An IL-2R binding fusion protein can be produced as a disulfide-linked dimer, joined together by disulfide bonds located in the hinge region. An IL-2R ligand binding fusion protein can include a peptide linker such as an amino acid sequence located between two proteins comprising a fusion protein, such that the linker peptide sequence is not derived from either partner protein. Peptide linkers can be incorporated into fusion proteins as spacers to promote proper protein folding and stability of the component protein moieties, to improve protein expression, or to enable better bioactivity of the two fusion partners.

Bioisosteres are atoms or molecules that fit the broadest definition for isosteres and is used interchangeably with the term isostere. The concept of bioisosterism is based on the concept that single atom, groups, moieties, or whole molecules, which have chemical and physical similarities produce similar biological effects. A bioisostere of a parent compound can still be recognized and accepted by its appropriate target, but its functions will be altered as compared to the parent molecule. Parameters affected with bioisosteric replacements include, for example, size, conformation, inductive and mesomeric effects, polarizability, capacity for electrostatic interactions, charge distribution, H-bond formation capacity, pKa (acidity), solubility, hydrophobicity, lipophilicity, hydrophilicity, polarity, potency, selectivity, reactivity, or chemical and metabolic stability, ADME (absorption, distribution, metabolism, and excretion). Although common in pharmaceuticals, carboxyl groups or carboxylic acid functional groups ($-CO_2H$) in a parent molecule may be replaced with a suitable surrogate or (bio)isostere to overcome chemical or biological shortcomings while retaining the desired attributes of the parent molecule bearing one or more carboxyl groups or carboxylic acid functional groups ($-CO_2H$).

"Isostere" or "isostere replacement" refers to any amino acid or other analog moiety having physiochemical and/or structural properties similar to a specified amino acid. An "isostere" or "suitable isostere" of an amino acid is another amino acid of the same class, wherein amino acids belong to the following classes based on the propensity of the side chain to be in contact with polar solvent like water: hydrophobic (low propensity to be in contact with water), polar or charged (energetically favorable contact with water). Examples of charged amino acid residues include lysine (+), arginine (+), aspartate (−) and glutamate (−). Examples of polar amino acids include serine, threonine, asparagine, glutamine, histidine and tyrosine. Illustrative hydrophobic amino acids include alanine, valine, leucine, isoleucine, proline, phenylalanine, tryptophan, cysteine and methionine. The amino acid glycine does not have a side chain and is hard to assign to one of the above classes. However, glycine is often found at the surface of proteins, often within loops, providing high flexibility to these regions, and an isostere may have a similar feature. Proline has the opposite effect, providing rigidity to the protein structure by imposing certain torsion angles on the segment of the polypeptide chain. An isostere can be a derivative of an amino acid, e.g., a derivative having one or more modified side chains as compared to the reference amino acid.

"Cyclized" refers to a reaction in which one part of a peptide or polypeptide molecule becomes linked to another part of the peptide or polypeptide molecule to form a closed ring, such as by forming a disulfide bridge or other similar bond, e.g., a lactam bond. A peptide monomer compound or monomer subunit of peptide dimer compounds can be cyclized via an intramolecular bond between two amino acid residues present in the peptide monomer or monomer subunit.

"Patient" refers to a mammal, for example, a human.

"Peptide" refers to a polymer in which the monomers are α-amino acids joined together through amide bonds. A peptide can comprise less than 100 amino acids, less than 50 amino acids, less than 40 amino acids, less than 30 amino acids, or less than 20 amino acids. A peptide can comprise naturally-occurring α-amino acids, non-naturally occurring amino acids, or a combination thereof.

"Polypeptide" refers to a polymer in which the monomers are α-amino acids joined together through amide bonds and comprise greater than 50 amino acids.

"N-terminus" refers to the end of a peptide or polypeptide, such as an N-terminus of a peptide or polypeptide comprising an IL-2Rα ligand, an IL-2Rβ ligand, and/or an IL-2Rγc ligand, that bears an amino group in contrast to the carboxyl end bearing a carboxyl acid group.

"C-terminus" refers to the end of a peptide or polypeptide, such as a C-terminus of a peptide or polypeptide comprising an IL-2Rα ligand, an IL-2Rβ ligand, and/or an IL-2Rγc ligand, that bears a carboxylic acid group in contrast to the amino terminus bearing an amino group.

"Pharmaceutically acceptable" refers to approved or approvable by a regulatory agency of the Federal or a state government or listed in the U.S. Pharmacopoeia or other generally recognized pharmacopoeia for use in animals, and more particularly in humans.

"Pharmaceutically acceptable salt" refers to a salt of a compound, which possesses the desired pharmacological activity of the parent compound. Such salts include acid addition salts, formed with inorganic acids and one or more protonable functional groups such as primary, secondary, or tertiary amines within the parent compound. Examples of inorganic acids include hydrochloric acid, hydrobromic acid, sulfuric acid, nitric acid, phosphoric acid, and the like. Salts can be formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like. A salt can be formed when one or more acidic protons present in the parent compound are replaced by a metal ion, e.g., an alkali metal ion, an alkaline earth ion, or an aluminum ion, or combinations thereof; or coordinates with an organic base such as ethanolamine, diethanolamine, triethanolamine, and N-methylglucamine. A pharmaceutically acceptable salt can be the hydrochloride salt. A pharmaceutically acceptable salt can be the sodium salt. A compound can have two or more ionizable groups, a pharmaceutically acceptable salt comprises one or more counterions, such as a bi-salt, for example, a dihydrochloride salt.

"Pharmaceutically acceptable salt" includes hydrates and other solvates, as well as salts in crystalline or non-crystalline form. Where a particular pharmaceutically acceptable salt is disclosed, it is understood that the particular salt (e.g., a hydrochloride salt) is an example of a salt, and that other salts may be formed using techniques known to one of skill in the art. Additionally, one of skill in the art would be able to convert the pharmaceutically acceptable salt to the corresponding compound, free base and/or free acid, using techniques generally known in the art.

"Pharmaceutically acceptable vehicle" refers to a pharmaceutically acceptable diluent, a pharmaceutically acceptable adjuvant, a pharmaceutically acceptable excipient, a pharmaceutically acceptable carrier, or a combination of any of the foregoing with which a compound provided by the present disclosure may be administered to a patient and which does not destroy the pharmacological activity thereof and which is non-toxic when administered in doses sufficient to provide a therapeutically effective amount of the compound.

"Solvate" refers to a molecular complex of a compound with one or more solvent molecules in a stoichiometric or non-stoichiometric amount. Such solvent molecules are those commonly used in the pharmaceutical arts, which are known to be innocuous to a patient, e.g., water, ethanol, and the like. A molecular complex of a compound or moiety of a compound and a solvent can be stabilized by non-covalent intra-molecular forces such as, for example, electrostatic forces, van der Waals forces, or hydrogen bonds. The term "hydrate" refers to a solvate in which the one or more solvent molecules is water.

"Pharmaceutical composition" refers to a compound comprising an IL-2Rα ligand provided by the present disclosure or a pharmaceutically acceptable salt thereof and at least one pharmaceutically acceptable vehicle, with which the compound or pharmaceutically acceptable salt thereof is administered to a patient. Pharmaceutically acceptable vehicles are known in the art.

"Disease" refers to a disease, disorder, condition, or symptom of any of the foregoing.

"Preventing" or "prevention" refers to a reduction in risk of acquiring a disease or disorder (i.e., causing at least one of the clinical symptoms of the disease not to develop in a patient that may be exposed to or predisposed to the disease but does not yet experience or display symptoms of the disease). In some embodiments, "preventing" or "prevention" refers to reducing symptoms of the disease by taking the compound in a preventative fashion. The application of a therapeutic for preventing or prevention of a disease of disorder is known as prophylaxis.

"Prodrug" refers to a derivative of a therapeutic compound that requires a transformation within the body to release the active therapeutic compound. Prodrugs are frequently, although not necessarily, pharmacologically inactive until converted to the parent drug.

"Promoiety" refers to a group bonded to a therapeutic compound, typically to a functional group of the therapeutic compound, via bond(s) that are cleavable under specified conditions of use. The bond(s) between the drug and promoiety may be cleaved by enzymatic or non-enzymatic means. Under the conditions of use, for example following administration to a patient, the bond(s) between the therapeutic compound and the promoiety may be cleaved to release the parent therapeutic compound. The cleavage of the promoiety may proceed spontaneously, such as via a hydrolysis reaction, or it may be catalyzed or induced by another agent, such as by an enzyme, by light, by acid, or by a change of or exposure to a physical or environmental parameter, such as a change of temperature or pH. The agent may be endogenous to the conditions of use, such as an enzyme present in the systemic circulation of a patient to which the prodrug is administered or the acidic conditions of the stomach or the agent may be supplied exogenously.

"Substantially" means, for example, greater than 90%, greater than 95%, greater than 98%, or greater than 99%.

"Therapeutically effective amount" refers to the amount of a compound that, when administered to a patient for treating a disease, or at least one of the clinical symptoms of a disease, is sufficient to affect such treatment of the disease or symptom thereof. A "therapeutically effective amount" may vary depending, for example, on the compound, the disease and/or symptoms of the disease, the severity of the disease and/or symptoms of the disease or disorder, the age, weight, and/or health of the patient to be treated, and the judgment of the prescribing physician. A therapeutically effective amount in any given instance may be ascertained by those skilled in the art or capable of determination by routine experimentation.

"Therapeutically effective dose" refers to a dose that provides effective treatment of a disease or disorder in a patient. A therapeutically effective dose may vary from compound to compound, and from patient to patient, and may depend upon factors such as the condition of the patient and the route of delivery. A therapeutically effective dose may be determined in accordance with routine pharmacological procedures known to those skilled in the art.

"Treating" or "treatment" of a disease refers to arresting or ameliorating a disease or at least one of the clinical symptoms of a disease or disorder, reducing the risk of acquiring a disease or at least one of the clinical symptoms of a disease, reducing the development of a disease or at least one of the clinical symptoms of the disease or reducing the risk of developing a disease or at least one of the clinical symptoms of a disease. "Treating" or "treatment" also refers to inhibiting the disease, either physically, (e.g., stabilization of a discernible symptom), physiologically, (e.g., stabilization of a physical parameter), or both, and to inhibiting at least one physical parameter or manifestation that may or may not be discernible to the patient. In certain embodiments, "treating" or "treatment" refers to delaying the onset of the disease or at least one or more symptoms thereof in a patient who may be exposed to or predisposed to a disease or disorder even though that patient does not yet experience or display symptoms of the disease.

"Tregs" or "Treg cells" refer to regulatory T-cells. Regulatory T-cells are a class of T-cells that suppress the activity of other immune cells and are defined using flow cytometry by the cell marker phenotypes CD4+/CD25+/FOXP3+, CD4+CD25+CD127lo, or CD4+/CD25+/FOXP3+/CD127lo. Because FOXP3 is an intracellular protein and requires cell fixation and permeabilization for staining, the cell surface phenotype CD4+CD25+CD127lo− can be used for defining live Tregs. Tregs also include various Treg subclasses, such as tTregs (thymus-derived) and pTregs (peripherally-derived, differentiated from naive T-cells in the periphery). All Tregs express the IL-2Rαβγc receptor, do not produce IL-2 and are dependent on IL-2 for growth. Tregs are more potently activated by an IL-2Rαβγc-biased agonist. Treg cells are characterized by expression of the α-subunit of the IL-2 receptor (CD25) and the transcription factor forkhead box P3 (FOXP3) and play a critical role in the induction and maintenance of peripheral self-tolerance to antigens, including those expressed by tumors. Treg cells require IL-2 for their function and development and induction of their suppressive characteristics.

"CD4+ T cells" are a type of lymphocyte that functions to coordinate the immune response by stimulating other immune cells such as macrophages, B lymphocytes (B cells), CD8 lymphocytes (CD8 cells) to fight infection. CD4+ T cells recognize peptides presented on MHC Class II molecules, which are found on antigen-presenting cells.

"CD8+(cytotoxic) T-cells" are generated in the thymus and express the T-cell receptor. Cytotoxic T-cells express a dimeric co-receptor, CD8, which typically comprises one CD8α and one CD8β chain. CD8+ T-cells recognize peptides presented by MHC Class 1 molecules found on all nucleated cells. The CD8 heterodimer binds to a conservative portion of MHC Class 1 during T-cell/antigen presenting cell interactions. CD8+ T-cells (cytotoxic T lymphocytes, or CTLs) are important for immune defense against intracellular pathogens including viruses and bacteria, and for tumor surveillance.

"Functional activation of Treg cells" is defined as an IL-2-mediated response in Tregs. Assays for functional activation of Treg cells include stimulation of pSTAT5, Treg cell proliferation, and stimulation of the levels of Treg effector proteins.

"Polypeptide" refers to a molecule composed of monomers (amino acids) linearly linked by amide bonds (also known as peptide bonds). The term "polypeptide" refers to any chain of two or more amino acids and does not refer to a specific length of the product. Thus, peptides, dipeptides, tripeptides, oligopeptides, "protein," "amino acid chain," or any other term used to refer to a chain of two or more amino acids, are included within the definition of "polypeptide," and the term "polypeptide" may be used instead of, or interchangeably with any of these terms. The term "polypeptide" is also intended to refer to the products of post-expression modifications of the polypeptide including, for example, glycosylation, acetylation, phosphorylation, amidation, derivatization by known protecting/blocking groups, proteolytic cleavage, and/or modification by non-naturally occurring amino acids. A polypeptide may be derived from a natural biological source or produced by recombinant technology but is not necessarily translated from a designated nucleic acid sequence. A polypeptide may be generated in any manner, including by recombinant methods or by chemical synthesis. A polypeptide may have, for example, more than 100 amino acids, more than 200 amino acids, more than 500 amino acids, more than 1,000 amino acids, or more than 2,000 amino acids. Polypeptides may have a defined three-dimensional structure, although they do not necessarily have such structure. Polypeptides with a defined three-dimensional structure are referred to as folded, and polypeptides which do not possess a defined three-dimensional structure, but rather can adopt a large number of different conformations and are referred to as unfolded.

"Polynucleotide" refers to an isolated nucleic acid molecule or construct, e.g., messenger RNA (mRNA), virally-derived RNA, or plasmid DNA (pDNA). A polynucleotide may comprise a conventional phosphodiester bond or a non-conventional bond, such as an amide bond, such as found in peptide nucleic acids (PNA).

"Nucleic acid molecule" refers to any one or more nucleic acid segments, such as DNA or RNA fragments, present in a polynucleotide.

"Vector" or "expression vector" is synonymous with "expression construct" and refers to a DNA molecule that is used to introduce and direct the expression of a specific gene to which it is operably associated in a target cell. A vector can be a self-replicating nucleic acid structure as well as a vector incorporated into the genome of a host cell into which it has been introduced. An expression vector can comprise an expression cassette. Expression vectors allow transcription of large amounts of stable mRNA. Once an expression vector is inside the target cell, the ribonucleic acid molecule or protein that is encoded by the gene is produced by the cellular transcription and/or translation machinery. An expression vector can comprise an expression cassette that comprises polynucleotide sequences that encode an IL-2Rβγc ligand or IL-2Rβγc ligand construct provided by the present disclosure.

"Host cell," "host cell line," and "host cell culture" refer to cells into which are exogenous nucleic acid has been introduced, including the progeny of such cells. Host cells include, for example, "transformants" and "transformed cells," which include the primary transformed cell and progeny derived from the primary transformed cell without regard to the number of passages.

"Antibody" in the broadest sense encompasses various antibody structures including, for example, monoclonal antibodies, polyclonal antibodies, multi-specific antibodies such as bispecific antibodies, and antibody fragments that exhibit a desired antigen binding activity.

"Full-length antibody," "intact antibody," and "whole antibody" refer to an antibody having a structure substantially similar to a native antibody structure or having heavy chains that contain both Fab and an Fc region.

"Antibody fragment" refers to a molecule other than an intact antibody that comprises a portion of an intact antibody that binds the antigen to which the intact antibody binds. Examples of antibody fragments include Fv, Fab, Fab', Fab'-SH, F(ab')2, diabodies, linear antibodies, single-chain antibody molecules such as scFv, and multi-specific antibodies formed from antibody fragments. Diabodies are antibody fragments with two antigen binding sites that may be bivalent or bispecific. Antibody fragments can be made by various techniques, including but not limited to proteolytic digestion of an intact antibody as well as production by recombinant host cells such as E. coli or phage.

"Fab" or "Fab region" refers to a polypeptide that comprises the VH, CHI, VL, and CL immunoglobulin domains, generally on two different polypeptide chains such as VH—CH on one chain and VL-CL on the other. Fab may refer to this region in isolation, or this region in the context of a bispecific antibody. In the context of a Fab, the Fab comprises an Fv region in addition to the CHI and CL domains.

"Fv" or "Fv fragment" or "Fv region" refers to a polypeptide that comprises the VL and VH domains of an antibody (Fab). Fv regions can be formatted as both Fabs (generally two different polypeptides that also include the constant regions) and scFvs, where the vi and vh domains are combined (generally with a linker as discussed) to form an scFv.

"Single chain Fv" or "scFv" refers to a variable heavy domain covalently attached to a variable light domain, generally using a scFv linker as discussed herein, to form a scFv or scFv domain. A scFv domain can be in either orientation from N- to C-terminus.

"Effector function" refers to a biochemical event that results from the interaction of an antibody Fc region with an Fc receptor or ligand. Effector functions include, for example, antibody-dependent cellular toxicity (ADCC), antibody-dependent cellular phagocytosis (ADCP), and complement-dependent cytotoxicity (CDC).

"Fc" or "Fc region" or "Fc chain" refers to polypeptide comprising the constant region of an antibody, in some instances, excluding all or a portion of the first constant region immunoglobulin domain (e.g., CHI) or a portion thereof, and in some cases, further excluding all or a portion of the hinge. Thus, an Fc can refer to the last two constant region immunoglobulin domains (e.g., CH2 and CH3) of IgA, IgD, and IgG, the last three constant region immunoglobulin domains of IgE and IgM, and optionally, all or a portion of the flexible hinge N-terminal to these domains. For IgA and IgM, Fc may include the J chain. For IgG, the Fc chain comprises immunoglobulin domains CH2 and CH3 (Cγ2 and Cγ3), and optionally all or a portion of the hinge region between CHI (Cγ1) and CH2 (Cγ2). Although the boundaries of the Fc region may vary, the human IgG heavy chain Fc region is usually defined to include residues E216, C226, or A231 to its carboxyl-terminus, wherein the numbering is according to the EU index as in Kabat. An amino acid modification can be made to the Fc region, for example to alter binding to one or more FcyR or to the FcRn. In EU numbering for human IgG1, the CH2-CH3 domain comprises amino acids 231 to 447, and the hinge is 216 to 230. Thus, the definition of Fc chain includes both amino acids 231-447 (CH2-CH3) or 216-447 (hinge-CH2-CH3), or fragments thereof. An Fc fragment can contain fewer amino acids from either or both of the N- and C-termini that retains the ability to form a dimer with another Fc chain or Fc fragment as can be detected using standard methods, generally based on size (e.g., non-denaturing chromatography, size exclusion chromatography, etc.). Human IgG Fc chains are of particular use, and can be the Fc chain from human IgG1, IgG2 or IgG4.

"Heavy constant region" refers to the CH1-hinge-CH2-CH3 portion of an antibody or fragments thereof, excluding the variable heavy domain; in EU numbering of human IgG1, such as amino acids 118-447. "Heavy chain constant region fragment" refers to a heavy chain constant region that contains fewer amino acids from either or both of the N- and C-termini that retains the ability to form a dimer with another heavy chain constant region.

"Immunoglobulin molecule" refers to a protein having the structure of a naturally occurring antibody. For example, immunoglobulins of the IgG class are heterotetrameric glycoproteins of about 150,000 Da, composed of two light chains and two heavy chains that are bonded together through disulfide bonds. From N- to C-terminus, each heavy chain has a variable region (VH), also called a variable heavy domain or a heavy chain variable domain, followed by three constant domains (CHI, CH2, and CH3), also called a heavy chain constant region. Similarly, from N- to C-terminus, each light chain has a variable region (VL), also called a variable light domain or a light chain variable domain, followed by a constant light (CL) domain, also called a light chain constant region. The heavy chain of an immunoglobulin may be assigned to one of five classes, called α (IgA), Ii (IgD), E (IgE), y (IgG), or μ (IgM), some of which may be further divided into subclasses, e.g., γ1 (IgG1), γ2 (IgG2), γ3 (IgG3), γ4 (gG4), α1 (IgA1) and α2 (IgA2). The light chain of an immunoglobulin may be assigned to one of two types, kappa (κ) or lambda (L), based on the amino acid sequence of its constant domain. An immunoglobulin essentially consists of two Fab molecules and an Fc chain, linked via the immunoglobulin hinge region.

"Immunoconjugate" refers to a polypeptide molecule that includes at least one IL-2Rβγc ligand and at least one antigen binding moiety. An immunoconjugate can comprise at least one IL-2Rβγc ligand, and at least two antigen binding moieties. An immunoconjugate can comprise at least one IL-2Rβγc ligand and two antigen binding moieties joined by one or more linker sequences. An antigen binding moiety can be joined to the IL-2Rβγc ligand by a variety of interactions and in a variety of configurations.

"Amino acid sequence similarity" refers to an amino acid sequence in which one or more amino acids of the amino has been replaced with a chemically similar amino acid. Examples of chemically similar amino acids include (a) amino acids having a small hydrophobic side chain such as alanine (A), glycine (G), proline (P), serine (S), or threonine (T); (b) amino acids having a hydroxyl-containing side chain such as serine (S), threonine (T), or tyrosine (Y); (c) amino acids having an acidic side chain such as aspartate (D) or glutamate (E); (d) amino acids having a polar-neutral side chain such as histidine (H), asparagine (N), glutamine (Q), serine (S), threonine (T), or tyrosine (Y); (e) amino acids having a basic side chain such as arginine (R), lysine (K), or histidine (H); (f) amino acids having a large hydrophobic side chain such as isoleucine (I), leucine (L), methionine (M), valine (V), phenylalanine (F), tyrosine (Y), or tryptophan (W); and (g) amino acids having an aromatic side chain comprising phenylalanine (F), histidine (H), tryptophan (W), or tyrosine (Y). A chemically similar amino acid can comprise a naturally occurring amino acid or a non-natural amino acid.

"Percent (%) sequence similarity" refers to amino acid sequences in which one or more amino acids of a reference amino acid sequence is replaced with an amino acid such as a chemically similar amino acid. For example, given a reference amino acid sequence -RDQYYPCW-MAQLGELCDLDEVF-(SEQ ID NO: 1037), the amino acid sequence -RDQYYPCYMAQLGELCDLEEVF-(SEQ ID NO: 1038) represents a similar amino acid sequence, in which an amino acid W having aromatic side chain is replaced with chemically similar amino acid Y having an aromatic side chain; and an amino acid D having an acidic side chain is replaced with chemically similar amino acid E having an acidic side chain. Referring to this example, the similar amino acid sequence, which consists of 22 amino acids, has a 90.9% (2/22) sequence similarity to the reference amino acid sequence.

"Percent (%) sequence similarity" is determined by comparing the number of amino acids that are the same in a subject peptide ligand and a reference peptide ligand. A peptide ligand provided by the present disclosure can comprise, for example, greater than 70%, greater than 80%, or greater than 90% sequence similarity to a reference peptide ligand. For example, based on a reference peptide ligand having SEQ ID NO: 1030, peptide ligands having SEQ-ID NOS: 1031-1036, have either 1, 2, 3, 4, or 5 amino acid in which an amino acid of the reference peptide has been substituted or replaced with the amino acid, alanine. Peptide ligands having SEQ ID NOS: 1031-1036 are characterized by a 95%, 90%, 85%, 80%, 75%, or 70% sequence similarity, respectively, to the amino acid sequence of the reference peptide.

```
                                         SEQ ID NO: 1030
    Y P C W L A R V G E L C D L D S G D V H

SEQ ID NO: 1031
    A P C W L A R V G E L C D L D S G D V H

SEQ ID NO: 1032
    A P C A L A R V G E L C D L D S G D V H

SEQ ID NO: 1033
    A P C A L A A V G E L C D L D S G D V H

SEQ ID NO: 1034
    A P C A L A A V G A L C D L D S G D V H

SEQ ID NO: 1035
    A P C A L A A V G A L C D L A S G D V H

SEQ ID NO: 1036
    A P C A L A A V G A L C D L A A G D V H
```

A peptide ligand provided by the present disclosure can have an amino acid sequence in which from 1 to 5 amino acids of a reference amino acid sequence is substituted with another amino acid.

For example, a peptide ligand derived from a reference peptide ligand can have from 1 to 5 amino acid substitutions, from 1 to 4, from 1 to 3, or from 1 to 2 amino acid substitutions. For example, a peptide ligand derived from a reference peptide ligand can have 1 amino acid substitution, 2 amino acid substitutions, 3 amino acid substitutions, 4 amino acid substitutions, or 5 amino acid substitutions.

An amino acid substitution can be independent of the other amino acid substitutions.

Each amino acid substitution can independently be a conservative amino acid substitution or a non-conservative amino acid substitution.

A conservative amino acid substitution refers to one of the following amino acid substitutions: amino acids having a small hydrophobic side chain comprising alanine (A), glycine (G), proline (P), serine (S), or threonine (T); amino acids having a hydroxyl-containing side chain comprising serine (S), threonine (T), or tyrosine (Y); amino acids having an acidic side chain comprising aspartate (D) or glutamate (E); amino acids having a polar-neutral side chain comprising histidine (H), asparagine (N), glutamine (Q), serine (S), threonine (T), or tyrosine (Y); amino acids having a basic side chain comprising arginine (R), lysine (K), or histidine (H); amino acids having a large hydrophobic side chain comprising isoleucine (I), leucine (L), methionine (M), valine (V), phenylalanine (F), tyrosine (Y), or tryptophan (W); and amino acids having an aromatic side chain comprising phenylalanine (F), histidine (H), tryptophan (W), or tyrosine (Y).

For example, a reference peptide ligand can have the amino acid sequence of SEQ ID NO: 1020.

```
                                      SEQ ID NO: 1020
        Y W C W M A Q V G E L C D L

SEQ ID NO: 1021
        Y H C W M A Q V G E L C D L

SEQ ID NO: 1022
        Y H C W M G Q V G E L C D L

SEQ ID NO: 1023
        Y H C W M G Q M G E L C D L

SEQ ID NO: 1024
        Y H C W M G Q M G E L C E L

SEQ ID NO: 1025
        Y H C W M G Q M G E L C E M
```

Peptide ligands having SEQ ID NOS: 1021-1025 represent peptide ligands in which the reference peptide ligand having SEQ ID NO: 1020 has been substituted with from 1 to 5 conservative amino acid substitutions, respectively.

A peptide ligand provided by the present disclosure can comprise a truncated peptide ligand. A truncated peptide ligand refers to a peptide ligand in which from 1 to 5 amino acids have independently been removed from the N-terminus, the C-terminus, or from both the N-terminus and the C-terminus of the corresponding reference peptide ligand. A truncated peptide ligand derived from the corresponding reference peptide ligand can independently have from 1 to 5 amino acids, such as from 1 to 4 amino acids, from 1 to 3 amino acids, or from 1 to 2 amino acids independently removed from the N-terminus, the C-terminus, or from both the N-terminus and the C-terminus of the reference peptide ligand. A truncated peptide ligand derived from the corresponding reference peptide ligand can independently have 1 amino acid, 2 amino acids, 3 amino acids, 4 amino acids, or 5 amino acids removed from the N-terminus, the C-terminus, or from both the N-terminus and the C-terminus of the reference peptide ligand.

For example, a reference peptide ligand can have the amino acid sequence of SEQ ID. NO: 1000. Examples of truncated peptide ligands derived from the reference peptide ligand of SEQ ID. NO: 1000 include truncated peptide ligands of amino acid sequence of SEQ ID NOS: 1001-1008.

```
                                      SEQ ID NO: 1000
        M G F Y P C W T A Q L G E L C D L S V D

SEQ ID NO: 1001
          G F Y P C W T A Q L G E L C D L S V D

SEQ ID NO: 1002
            F Y P C W T A Q L G E L C D L S V D

SEQ ID NO: 1003
              Y P C W T A Q L G E L C D L S V D

SEQ ID NO: 1004
        M G F Y P C W T A Q L G E L C D L S V

SEQ ID NO: 1005
        M G F Y P C W T A Q L G E L C D L S

SEQ ID NO: 1006
        M G F Y P C W T A Q L G E L C D L

SEQ ID NO: 1007
          G F Y P C W T A Q L G E L C D L S V

SEQ ID NO: 1008
            F Y P C W T A Q L G E L C D L
```

The truncated peptide ligands of SEQ ID NOS: 1001-1003 have amino acids removed from the N-terminus of the reference peptide ligand; truncated peptide ligands of SEQ ID NOS: 1004-1006 have amino acids removed from the C-terminus of the reference peptide ligand; and truncated peptide ligands of SEQ ID NOS: 1007-1008 have amino acids removed from both the N-terminus and from the C-terminus of the reference peptide ligand.

As another example, a reference peptide ligand can comprise an amino acid sequence of Formula (A):

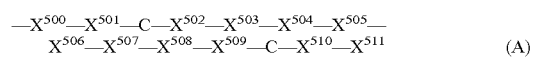

(A)

where each —X— independently represents an amino acid. Amino acid sequences of Formula (A1)-(A2) represent truncated peptide ligands derived from the reference peptide ligand comprising the amino acid sequence of Formula (A):

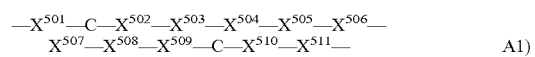

A1)

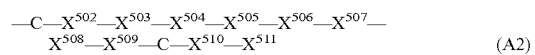

(A2)

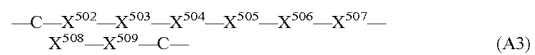

(A3)

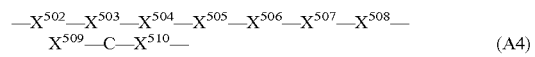

(A4)

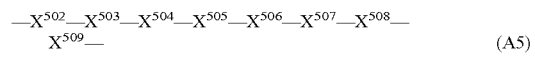

(A5)

A peptide ligand provided by the present disclosure can comprise an amino acid sequence in which from 1 to 3 glycines are independently bonded to the N-terminus, to the C-terminus, or to both the N-terminus and to the C-terminus of a reference peptide ligand.

KYCGFAQLGELCVL  SEQ ID NO: 1010

GKYCGFAQLGELCVL  SEQ ID NO: 1011

GGKYCGFAQLGELCVL  SEQ ID NO: 1012

GGGKYCGFAQLGELCVL  SEQ ID NO: 1013

KYCGFAQLGELCVLG  SEQ ID NO: 1014

KYCGFAQLGELCVLGG  SEQ ID NO: 1015

KYCGFAQLGELCVLGGG  SEQ ID NO: 1016

GKYCGFAQLGELCVLG  SEQ ID NO: 1017

GGKYCGFAQLGELCVLG  SEQ ID NO: 1018

For example, reference peptide ligand can have SEQ ID NO: 1010. Peptide ligands having SEQ ID NOS: 1011-1013 have from 1 to 3 glycines bonded to the N-terminus of the reference peptide ligand, respectively; peptide ligands having SEQ ID NOS: 1014-1016 have from 1 to 3 glycines bonded to the C-terminus of the reference peptide ligand, respectively; and peptide ligands having SEQ ID NOS: 1017-1018 independently have 1 or 2 glycines bonded to both the N-terminus and to the C-terminus of the reference peptide ligand.

A peptide ligand can comprise a truncated peptide ligand in which from 1 to 3 glycines are independently bonded to the N-terminus, to the C-terminus, or to both the N-terminus and to the C-terminus of a reference truncated peptide ligand.

"IL-2Rα binding compound" refers to an IL-2Rα ligand provided by the present disclosure, a tandem IL-2Rα ligand provided by the present disclosure, an IL-2Rα ligand construct provided by the present disclosure, and a construct comprising at least one IL-2Rα ligand and at least one IL-2Rβ ligand and/or at least one IL-2Rγc ligand.

The expression "at least one" refers to "one or more." For example, the expression at least can refer to from 1 to 10, from 1 to 8, from 1 to 6, from 1 to 5, from 1 to 4, from 1 to 3, or from 1 to 2. For example, the expression at least one can refer to 1, 2, 3, 4, 5, 6, 7, 8, 9, or 10.

Reference is now made in detail to certain embodiments of compounds, compositions, and methods. The disclosed embodiments are not intended to be limiting of the claims. To the contrary, the claims are intended to cover all alternatives, modifications, and equivalents.

IL-2Rα ligands provided by the present disclosure comprise peptide domains amenable to strategies to simultaneously mask peripheral bioactivity, target delivery to a tumor, selectively activate cytotoxic anti-tumor cells, and direct IL-2 receptor activation at tumor sites. IL-2R agonists provided by the present disclosure can also be used to treat autoimmune diseases.

IL-2R agonists can be designed to selectively activate a specific form of the IL-2 receptor. The small peptide IL-2R ligands, having an amino acid sequence that is unrelated to that of the natural cytokine, can selectively bind to and activate the IL-2Rα subunit to produce therapeutic IL-2 activity. Because the IL-2R peptidyl ligands are small, i.e. from 5 to 20 amino acids, with very low immunogenic potential, the small peptidyl IL-2R ligands can be incorporated into compounds to enhance therapeutic efficacy. For example, this allows the affinity of the IL-2R peptidyl ligands for each of the three IL-2R subunits to be tuned to direct the responsiveness of a particular immune cell population and affords flexibility to chemically target to tumor sites and mediate the immune response.

IL-2Rβ and IL-2Rγc ligands and compounds comprising IL-2Rβ and IL-2Rγc ligands are disclosed in U.S. Provisional Application No. 62/715,097 filed on Aug. 6, 2018, which is incorporated by reference in its entirety.

The present disclosure is directed to IL-2Rα ligands and compounds comprising IL-2Rα ligands. The compounds comprising IL-2Rα ligands can comprise an IL-2Rβ ligand and/or an IL-2Rγc ligand.

Peptides having a binding affinity to IL-2Rα can be identified by random peptide diversity generating systems in conjunction with an affinity enrichment process, for example, using peptides on plasmids or peptides on phage systems.

Peptidyl ligands for the IL-2Rα subunit can be identified from highly complex peptide diversity libraries such as phage display libraries, optimized by peptide synthesis, and can be assembled into monomers, homo-oligomers, heteromers or incorporated into other compounds.

Random peptides can be presented either on the surface of a phage particle, as part of a fusion protein comprising either the pIII or the pVIII coat protein of a phage fd derivative (peptides on phage) or as a fusion protein with the LacI peptide fusion protein bound to a plasmid (peptides on plasmids). The phage or plasmids, including the DNA encoding the peptides, can be identified and isolated by an affinity enrichment process using an immobilized IL-2Rα subunit. The affinity enrichment process, sometimes referred to as "panning," involves multiple rounds of incubating the phage or plasmids with the immobilized receptor, collecting the phage or plasmids that bind to the receptor (along with the accompanying DNA), and producing more of the phage or plasmids (along with the accompanying LacI-peptide fusion protein) collected. The extracellular domain (ECD) of the IL-2Rα subunit can be used during panning.

After several rounds of affinity enrichment, the phage or plasmids and accompanying peptides were examined by ELISA to determine if the peptides bind specifically to the IL-2Rα subunit. The assay can be performed using methods similar to those described for the affinity enrichment process, except that after removing unbound phage, the wells can be treated with an antibody such as a rabbit anti-phage antibody and then with alkaline phosphatase (AP)-conjugated goat anti-rabbit antibody. The amount of alkaline phosphatase in each well can be determined by standard methods.

By comparing test wells with control wells without the IL-2 receptor, one can determine whether the fusion proteins bind to the receptor specifically. The phage pools found to bind to the IL-2Rα subunit can be screened in a colony lift probing format using monovalent or divalent receptor.

IL-2Rα ligands can also be identified by panning subunits fused to Fc.

Peptides found to bind specifically to the IL-2Rα subunit can then be synthesized as the free peptide (e.g., no phage) and tested in a blocking assay. The blocking assay can be carried out in a similar manner to the ELISA, except that IL-2Rα binding peptides or a reference peptide at different concentrations can be added to the wells before the tracer peptide or fusion protein (the control wells can be of two types: (1) no receptor; and (2) IL-2Rα subunit binding peptide or reference peptide). Tracer peptides or fusion protein in the instance comprise IL-2Rα ligands wherein binding to immobilized IL-2Rα can be detected by a variety of means.

The IL-2 receptor, as well as its extracellular domain, can be produced in recombinant host cells.

Screening methods used to identify peptides that bind to IL-2Rα can involve first identifying lead peptides which bind to the extracellular domain of the receptor and then synthesizing other peptides which resemble the lead peptides. Specifically, using a pIII or pVIII-based peptides on a phage system, a random library can be screened to discover a phage that presents a peptide that binds to the IL-2Rα subunit. The phage DNAs are sequenced to determine the sequences of the peptides displayed on the surface of the phages.

For example, clones capable of specific binding to IL-2Rα can be identified from a random linear or disulfide-bridged cyclic 10-mer pVIII library and a random linear or disulfide-bridged cyclic 12-mer pVIII library. The sequences of these peptides can serve as the basis for the construction of other peptide libraries designed to contain a high frequency of derivatives of the initially identified peptides. These libraries can be synthesized so as to favor the production of peptides that differ from the binding peptide in only a few residues. This approach involves the synthesis of an oligonucleotide with the binding peptide coding sequence, except that rather than using pure preparations of each of the four nucleoside triphosphates in the synthesis, mixtures of the four nucleoside triphosphates (i.e., 55% of the “correct” nucleotide, and 15% each of the other three nucleotides is one preferred mixture for this purpose and 70% of the “correct” nucleotide and 10% of each of the other three nucleotides is another preferred mixture for this purpose) can be used so as to generate derivatives of the binding peptide coding sequence.

A variety of strategies can be used to derivatize the lead peptides by making “mutagenesis on a theme” libraries, including a pVIII phagemid mutagenesis library based on the consensus sequence and mutagenized at 70:10:10:10 frequency with 5 NNK codons on each terminus (probing with radiolabeled monovalent receptor and with or without peptide elution).

The “peptides on plasmids” method can also be used for peptide screening and mutagenesis studies. According to this approach, random peptides can be fused at the C-terminus of LacI through expression from a plasmid vector carrying the fusion gene. Linkage of the LacI-peptide fusion to its encoding DNA occurs via the lacO sequences on the plasmid, forming a stable peptide-LacI-plasmid complex that can be screened by affinity purification (panning) on an immobilized receptor. The plasmids thus isolated can then be reintroduced into *E. coli* by electroporation to amplify the selected population for additional rounds of screening, or for the examination of individual clones.

In addition, random peptide screening and mutagenesis studies can be performed using a modified C-terminal Lac-I display system in which display valency was reduced (“headpiece dimer” display system). The libraries can be screened, and the resulting DNA inserts were cloned as a pool into a maltose binding protein (MBP) vector allowing their expression as a C-terminal fusion protein. Crude cell lysates from randomly picked individual MBP fusion clones were then assayed for IL-2Rα binding in an ELISA format, as discussed above.

A variety of methods can be used to evaluate $IC_{50}$ values. For example, an equilibrium binding ELISA assay, an IL-2 or IL-2Rα peptide tracer, was used to determine whether the peptides inhibit the binding of the tracer to the extracellular domain of IL-2α. The $IC_{50}$ value can be determined using the free peptide, which optionally can be C-terminally amidated, or can be prepared as an ester or other carboxy amide. To recreate the exact sequence displayed by the phage, the N-terminal and C-terminal amino acids of the synthetic peptides are often preceded by one or two glycine residues. These glycines are not believed to be necessary for binding or activity.

Synthetic peptide library technologies such as DNA-encoded peptide libraries can also be used.

In general, peptides and peptidomimetics having an $IC_{50}$ of greater than 100 μM lack sufficient binding affinity to be useful in imaging, targeting, diagnostic, and therapeutic applications. For imaging, targeting or diagnostic purposes, peptides and peptidomimetics can have an $IC_{50}$, for example, of 1 μM or less and, for pharmaceutical purposes, peptides and peptidomimetics can have an $IC_{50}$, for example, less than 100 μm, or less than 100 nm.

An IL-2Rα ligand provided by the present disclosure can bind to the human IL-2Rα subunit with an $IC_{50}$, for example, of less than 100 μM, less than 10 μM, less than 1 μM, less than 0.1 μM, or less than 0.01 μM.

An IL-2Rα ligand provided by the present disclosure can bind to the human IL-2Rα subunit with an $IC_{50}$, for example, from 1 μM to 100 μM, from 10 μM to 10 μM, from 100 μM to 1 μM, from, 0.001 μM to 1 μM, or from 0.01 μM to 1 μM.

An IL-2Rα ligand provided by the present disclosure can bind to a mammalian IL-2Rα subunit with an $IC_{50}$, for example, of less than 100 μM, less than 10 μM, less than 1 μM, less than 0.1 μM, or less than 0.01 μM.

An IL-2Rα ligand provided by the present disclosure can bind to a mammalian IL-2Rα subunit with an $IC_{50}$, for example, from 1 μM to 100 μM, from 10 μM to 10 μM, from 100 μM to 1 μM, from, 0.001 μM to 1 μM, or from 0.01 μM to 1 μM.

An IL-2Rα ligand provided by the present disclosure can have an amino acid sequence of any one of SEQ ID NOS: 1-307 and 400-423.

An IL-2Rα ligand provided by the present disclosure can have greater than 70% sequence similarity, greater than 75% sequence similarity, greater than 80%, greater than 85% sequence similarity, greater than 90% sequence similarity, or greater than 95% sequence similarity to any one of SEQ ID NOS: 1-307 and 400-423.

IL-2Rα ligands provided by the present disclosure can comprise the amino acid sequence of Formula (1) (SEQ ID NO: 1):

$$—X^1—X^2—X^3—X^4—X^5—X^6—X^7—X^8—X^9—X^{10}—X^{11}—X^{12}— \quad (1)$$

wherein, $X^1$ can be selected from an amino acid comprising a large hydrophobic side chain or an aromatic side chain;

$X^2$ can be selected from an amino acid comprising a large hydrophobic side chain;

$X^3$ can be selected from an amino acid;

$X^4$ can be selected from an amino acid comprising a large hydrophobic side chain;

$X^5$ can be selected from an amino acid comprising a small hydrophobic side chain or a polar/neutral side chain;

$X^6$ can be selected from an amino acid comprising a large hydrophobic side chain;

$X^7$ can be selected from an amino acid comprising a large hydrophobic side chain;

$X^8$ can be selected from an amino acid comprising a large hydrophobic side chain;

$X^9$ can be selected from an amino acid comprising a small hydrophobic side chain;

$X^{10}$ can be selected from an amino acid comprising a polar/neutral side chain;

$X^{11}$ can be selected from an amino acid comprising a large hydrophobic side chain; and $X^{12}$ can be selected from an amino acid comprising a large hydrophobic side chain.

In IL-2Rα ligands of Formula (1), $X^1$ can be selected from F, H, I, L, M, V, W, and Y.

In IL-2Rα ligands of Formula (1), $X^2$ can be selected from F, I, L, M, V, W, and Y.

In IL-2Rα ligands of Formula (1), $X^3$ can be selected from A, D, E, F, G, H, I, K, L, M, N, P, Q, R, S, T, V, W, and Y.

In IL-2Rα ligands of Formula (1), $X^4$ can be selected from F, I, L, M, V, W, and Y.

In IL-2Rα ligands of Formula (1), $X^5$ can be selected from H, N, Q, Y, A, G, P, S, and T.

In IL-2Rα ligands of Formula (1), $X^6$ can be selected from F, I, L, M, V, W, and Y.

In IL-2Rα ligands of Formula (1), $X^7$ can be selected from F, I, L, M, V, W, and Y.

In IL-2Rα ligands of Formula (1), $X^9$ can be selected from A, G, P, S, and T.

In IL-2Rα ligands of Formula (1), $X^{10}$ can be selected from H, N, Q, S, T, and Y.

In IL-2Rα ligands of Formula (1), $X^{11}$ can be selected from F, I, L, M, V, W, and Y.

In IL-2Rα ligands of Formula (1), $X^{12}$ can be selected from F, I, L, M, V, W, and Y.

In IL-2Rα ligands of Formula (1), $X^1$ can be selected from L, W, and F.

In IL-2Rα ligands of Formula (1), $X^2$ can be selected from D, A, L, and V.

In IL-2Rα ligands of Formula (1), $X^3$ can be selected from L, V, H, P, and E.

In IL-2Rα ligands of Formula (1), $X^4$ can be selected from T, D, and W.

In IL-2Rα ligands of Formula (1), $X^5$ can be selected from Y, W, P, and Q.

In IL-2Rα ligands of Formula (1), $X^6$ can be selected from D, S, V, and A.

In IL-2Rα ligands of Formula (1), $X^7$ can be selected from E and Y.

In IL-2Rα ligands of Formula (1), $X^8$ can be selected from L and F.

In IL-2Rα ligands of Formula (1), $X^9$ can be selected from L, R, and S.

In IL-2Rα ligands of Formula (1), $X^{10}$ can be selected from A, R, and Q.

In IL-2Rα ligands of Formula (1), $X^{11}$ can be selected from C, R, V, and M.

In IL-2Rα ligands of Formula (1), $X^{12}$ can be selected from T, L, and M.

In IL-2Rα ligands of Formula (1), $X^1$ can be F.

In IL-2Rα ligands of Formula (1), $X^2$ can be selected from L and V.

In IL-2Rα ligands of Formula (1), $X^3$ can be selected from A, D, E, F, G, H, I, K, L, M, N, P, Q, R, S, T, V, W, and Y.

In IL-2Rα ligands of Formula (1), $X^4$ can be W.

In IL-2Rα ligands of Formula (1), $X^5$ can be P.

In IL-2Rα ligands of Formula (1), $X^6$ can be V.

In IL-2Rα ligands of Formula (1), $X^7$ can be Y.

In IL-2Rα ligands of Formula (1), $X^8$ can be F.

In IL-2Rα ligands of Formula (1), $X^9$ can be S.

In IL-2Rα ligands of Formula (1), $X^{10}$ can be Q.

In IL-2Rα ligands of Formula (1), $X^{11}$ can be selected from N and V.

In IL-2Rα ligands of Formula (1), $X^{12}$ can be selected from L and M.

In IL-2Rα ligands of Formula (1), $X^1$ can be F, $X^4$ can be W, $X^5$ can be P, $X^6$, can be V, $X^7$ can be Y, $X^8$ can be F, $X^9$ can be S, and $X^{10}$ can be Q.

In IL-2Rα ligands of Formula (1), $X^1$ can be F;

$X^2$ can be selected from F, H, I, L, M, V, W, and Y;

$X^3$ can be selected from A, D, E, F, G, H, I, K, L, M, N, P, Q, R, S, T, V, W, and Y;

$X^4$ can be W;

$X^5$ can be selected from H, N, Q, Y, A, G, P, S, and T;

$X^6$ can be V;

$X^7$ can be Y;

$X^8$ can be F;

$X^9$ can be S;

$X^{10}$ can be Q;

$X^{11}$ can be selected from F, I, L, M, V, W, and Y; and $X^{12}$ can be selected from F, I, L, M, V, W, and Y.

IL-2Rα ligands provided by the present disclosure can comprise an amino acid sequence selected from any one of SEQ ID NO: 2 to SEQ ID NO: 6:

```
                                        SEQ ID NO: 2
L D L T Y D E L L A C T

SEQ ID NO: 3
W A Y D W S C F R R R L

SEQ ID NO: 4
F L H W P V Y F C Q V M

SEQ ID NO: 5
F L P W P V Y F S Q V L

SEQ ID NO: 6
F V E W Q A Y F S Q M M
```

An IL-2Rα ligand provided by the present disclosure can comprise a truncated amino acid sequence of any one of SEQ ID NO: 1 to SEQ ID NO: 6.

An IL-2Rα ligands provided by the present disclosure can comprise an amino acid sequence selected from any one of SEQ ID NO: 1 to SEQ ID NO: 6, or a truncated amino acid sequence of any one of SEQ ID NO: 1 to SEQ ID NO: 6, wherein the amino acid sequence can independently comprise from 1 to 4 glycines (G) (SEQ ID NO: 1041) on the N-terminus, on the C-terminus, or on both the N- and C-termini.

An IL-2Rα ligands provided by the present disclosure can comprise an amino acid sequence selected from any one of SEQ ID NO: 1 to SEQ ID NO: 6, or a truncated amino acid sequence of any one of SEQ ID NO: 1 to SEQ ID NO: 6, wherein the amino acid sequence comprises one or more amino acid substitutions such as from 1 to 5 amino acid substitutions.

IL-2Rα ligands provided by the present disclosure can comprise the amino acid sequence of Formula (2) (SEQ ID NO: 7):

$$—X^1—X^2—X^3—X^4—X^5—X^6—X^7—X^8—X^9—X^{10}—X^{11}—X^{12}— \quad (2)$$

wherein,
$X^1$ can be selected from an amino acid comprising a large hydrophobic side chain;
$X^2$ can be selected from an amino acid comprising a large hydrophobic side chain;
$X^3$ can be selected from an amino acid comprising a small hydrophobic side chain;
$X^4$ can be selected from an amino acid comprising a large hydrophobic side chain;
$X^5$ can be selected from an amino acid comprising an acidic side chain;
$X^6$ can be selected from an amino acid comprising an acidic side chain;
$X^7$ can be selected from an amino acid comprising a large hydrophobic side chain;
$X^8$ can be selected from an amino acid comprising a large hydrophobic side chain;
$X^9$ can be selected from an amino acid;
$X^{10}$ can be selected from an amino acid comprising a polar/neutral side chain;
$X^{11}$ can be selected from an amino acid comprising a large hydrophobic side chain; and
$X^{12}$ can be selected from an amino acid comprising a large hydrophobic side chain.
In IL-2Rα ligands of Formula (2), $X^1$ can be selected from F, I, L, M, V, W, and Y.
In IL-2Rα ligands of Formula (2), $X^2$ can be selected from F, I, L, M, V, W, and Y.
In IL-2Rα ligands of Formula (2), $X^3$ can be selected from A, G, P, S, and T.
In IL-2Rα ligands of Formula (2), $X^4$ can be selected from F, I, L, M, V, W, and Y.
In IL-2Rα ligands of Formula (2), $X^6$ can be selected from D and E.
In IL-2Rα ligands of Formula (2), $X^7$ can be selected from F, I, L, M, V, W, and Y.
In IL-2Rα ligands of Formula (2), $X^8$ can be selected from F, I, L, M, V, W, and Y.
In IL-2Rα ligands of Formula (2), $X^9$ can be selected from A, D, E, F, G, H, I, K, L, M, N, P, Q, R, S, T, V, W, and Y.
In IL-2Rα ligands of Formula (2), $X^{10}$ can be selected from H, N, Q, S, T, and Y.
In IL-2Rα ligands of Formula (2), $X^{11}$ can be selected from F, I, L, M, V, W, and Y.
In IL-2Rα ligands of Formula (2), $X^{12}$ can be selected from F, I, L, M, V, W, and Y.
In IL-2Rα ligands of Formula (2), $X^1$ can be F.
In IL-2Rα ligands of Formula (2), $X^2$ can be selected from I, L, and V.
In IL-2Rα ligands of Formula (2), $X^3$ can be P.
In IL-2Rα ligands of Formula (2), $X^4$ can be W.
In IL-2Rα ligands of Formula (2), $X^5$ can be selected from P, D, and E.
In IL-2Rα ligands of Formula (2), $X^6$ can be selected from V and E.
In IL-2Rα ligands of Formula (2), $X^7$ can be Y.
In IL-2Rα ligands of Formula (2), $X^8$ can be F.
In IL-2Rα ligands of Formula (2), $X^9$ can be S, A, K, and L.
In IL-2Rα ligands of Formula (2), $X^{10}$ can be Q.
In IL-2Rα ligands of Formula (2), $X^{11}$ can be selected from V, I, and L.
In IL-2Rα ligands of Formula (2), $X^{12}$ can be selected from L and M.
In IL-2Rα ligands of Formula (2), $X^1$ can be F.
In IL-2Rα ligands of Formula (2), $X^2$ can be selected from L and V.

In IL-2Rα ligands of Formula (2), $X^3$ can be P.
In IL-2Rα ligands of Formula (2), $X^4$ can be W.
In IL-2Rα ligands of Formula (2), $X^5$ can be D.
In IL-2Rα ligands of Formula (2), $X^6$ can be E.
In IL-2Rα ligands of Formula (2), $X^7$ can be Y.
In IL-2Rα ligands of Formula (2), $X^8$ can be F.
In IL-2Rα ligands of Formula (2), $X^9$ can be selected from A, D, E, F, G, H, I, K, L, M, N, P, Q, R, S, T, V, W, and Y.
In IL-2Rα ligands of Formula (2), $X^9$ can be S.
In IL-2Rα ligands of Formula (2), $X^{10}$ can be Q.
In IL-2Rα ligands of Formula (2), $X^{11}$ can be selected from I, L, and V.
In IL-2Rα ligands of Formula (2), $X^{12}$ can be L.
In IL-2Rα ligands of Formula (2), $X^1$ can be F, $X^3$ can be P, $X^4$ can be W, $X^5$ can be D, $X^6$, can be E, $X^7$ can be Y, $X^8$ can be F, $X^{10}$ can be Q, and $X^{12}$ can be L.
In IL-2Rα ligands of Formula (2),
$X^1$ can be F;
$X^2$ can be selected from F, I, L, M, V, W, and Y;
$X^3$ can be P;
$X^4$ can be W;
$X^5$ can be selected from D and P;
$X^6$ can be E;
$X^7$ can be Y;
$X^8$ can be F;
$X^9$ can be selected from A, D, E, F, G, H, I, K, L, M, N, P, Q, R, S, T, V, W, and Y;
$X^{10}$ can be Q;
$X^{11}$ can be selected from F, I, L, M, V, W, and Y; and
$X^{12}$ can be L.
IL-2Rα ligands provided by the present disclosure can comprise an amino acid sequence selected from any one of SEQ ID NO: 8 to SEQ ID NO: 15:

```
F I F A Q A Q L L                 SEQ ID NO: 8

F I P W D E Y F K Q V L           SEQ ID NO: 9

F V P W D V Y F S Q I L           SEQ ID NO: 10

F I P W D E Y F K Q V L           SEQ ID NO: 11

F V P W P E Y F L Q I M           SEQ ID NO: 12

F I P W E E Y F S Q L L           SEQ ID NO: 13

F I P W P E Y F S Q L L           SEQ ID NO: 14

F V P W D E Y F L Q I L           SEQ ID NO: 15
```

An IL-2Rα ligand provided by the present disclosure can comprise a truncated amino acid sequence of any one of SEQ ID NO: 7 to SEQ ID NO: 15.

An IL-2Rα ligand provided by the present disclosure can comprise an amino acid sequence selected from any one of SEQ ID NO: 7 to SEQ ID NO: 15, or a truncated amino acid sequence of any one of SEQ ID NO: 7 to SEQ ID NO: 15, wherein the amino acid sequence can independently comprise from 1 to 4 glycines (G) (SEQ ID NO: 1041) on the N-terminus, on the C-terminus, or on both the N- and C-termini.

An IL-2Rα ligand provided by the present disclosure can comprise an amino acid sequence selected from any one of SEQ ID NO: 7 to SEQ ID NO: 15, or a truncated amino acid sequence of any one of SEQ ID NO: 7 to SEQ ID NO: 15, wherein the amino acid sequence comprises one or more amino acid substitutions such as from 1 to 5 amino acid substitutions.

IL-2Rα ligands provided by the present disclosure can comprise the amino acid sequence of Formula (3a) (SEQ ID NO: 16), the amino acid sequence of Formula (3b) (SEQ ID NO: 17), or the amino acid sequence of Formula (3c) (SEQ ID NO: 18):

  (3a)

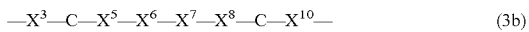  (3b)

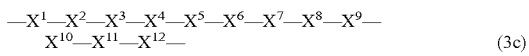  (3c)

wherein,
$X^1$ can be selected from an amino acid comprising a large hydrophobic side chain;
$X^2$ can be selected from an amino acid comprising a large hydrophobic side chain;
$X^3$ can be selected from an amino acid;
$X^4$ can be C;
$X^5$ can be selected from an amino acid comprising a small hydrophobic side chain;
$X^6$ can be selected from an amino acid;
$X^7$ can be selected from an amino acid;
$X^8$ can be selected from amino acid comprising a small hydrophobic side chain;
$X^9$ can be C;
$X^{10}$ can be selected from an amino acid comprising a basic side chain or a polar/neutral side chain;
$X^{11}$ can be selected from an amino acid comprising a small hydrophobic side chain; and
$X^{12}$ can be selected from an amino acid.

In IL-2Rα ligands of Formula (3a)-(3c), $X^1$ can be selected from F, I, L, M, V, W, and

```
                                            SEQ ID NO: 23
Y V M C S A F G C K S I

SEQ ID NO: 24
F V H C T L L G C W S G
```

An IL-2Rα ligand provided by the present disclosure can comprise a truncated amino acid sequence of any one of SEQ ID NO: 16 to SEQ ID NO: 24.

An IL-2Rα ligand provided by the present disclosure can comprise an amino acid sequence selected from any one of SEQ ID NO: 16 to SEQ ID NO: 24, or a truncated amino acid sequence of any one of SEQ ID NO: 16 to SEQ ID NO: 24, wherein the amino acid sequence can independently comprise from 1 to 4 glycines (G) (SEQ ID NO: 1041) on the N-terminus, on the C-terminus, or on both the N- and C-termini.

An IL-2Rα ligand provided by the present disclosure can comprise an amino acid sequence selected from any one of SEQ ID NO: 16 to SEQ ID NO: 24, or a truncated amino acid sequence of any one of SEQ ID NO: 16 to SEQ ID NO: 24, wherein the amino acid sequence comprises one or more amino acid substitutions such as from 1 to 5 amino acid substitutions.

IL-2Rα ligands provided by the present disclosure can comprise the amino acid sequence of Formula (4a) (SEQ ID NO: 25), the amino acid sequence of Formula (4b) (SEQ ID NO: 26), the amino acid sequence of Formula (4c) (SEQ ID NO: 27), or the amino acid sequence of Formula (4d) (SEQ ID NO: 28):

  (4a)

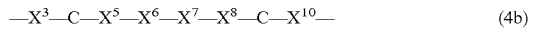  (4b)

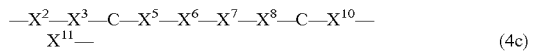  (4c)

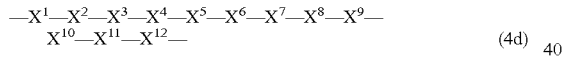  (4d)

wherein,
$X^1$ can be selected from an amino acid comprising a large hydrophobic side chain;
$X^2$ can be selected from an amino acid comprising a large hydrophobic side chain;
$X^3$ can be selected from an amino acid comprising a large hydrophobic side chain;
$X^4$ can be C;
$X^5$ can be selected from an amino acid comprising a small hydrophobic side chain;
$X^6$ can be selected from an amino acid comprising a small hydrophobic side chain;
$X^7$ can be selected from an amino acid comprising a large hydrophobic side chain;
$X^8$ can be selected from an amino acid comprising a small hydrophobic side chain;
$X^9$ can be C;
$X^{10}$ can be selected from an amino acid comprising a basic side chain;
$X^{11}$ can be selected from an amino acid comprising a small hydrophobic side chain; and
$X^{12}$ can be selected from an amino acid comprising a large hydrophobic side chain.

In IL-2Rα ligands of Formula (4a)-(4d), $X^1$ can be selected from F, I, L, M, V, W, and Y.
In IL-2Rα ligands of Formula (4a)-(4d), $X^2$ can be selected from F, I, L, M, V, W, and Y.
In IL-2Rα ligands of Formula (4a)-(4d), $X^3$ can be selected from F, I, L, M, V, W, and Y.
In IL-2Rα ligands of Formula (4a)-(4d), $X^4$ can be C.
In IL-2Rα ligands of Formula (4a)-(4d), $X^5$ can be selected from A, G, P, S, and T.
In IL-2Rα ligands of Formula (4a)-(4d), $X^6$ can be selected from A, G, P, S, and T.
In IL-2Rα ligands of Formula (4a)-(4d), $X^7$ can be selected from F, I, L, M, V, W, and Y.
In IL-2Rα ligands of Formula (4a)-(4d), $X^8$ can be selected from A, G, P, S, and T.
In IL-2Rα ligands of Formula (4a)-(4d), $X^9$ can be C.
In IL-2Rα ligands of Formula (4a)-(4d), $X^{10}$ can be selected from H, K, and R.
In IL-2Rα ligands of Formula (4a)-(4d), $X^{11}$ can be selected from A, G, P, S, and T.
In IL-2Rα ligands of Formula (4a)-(4d), $X^{12}$ can be selected from F, I, L, M, V, W, and Y.
In IL-2Rα ligands of Formula (4a)-(4d), $X^1$ can be selected from Y and W.
In IL-2Rα ligands of Formula (4a)-(4d), $X^2$ can be V.
In IL-2Rα ligands of Formula (4a)-(4d), $X^3$ can be selected from M and I.
In IL-2Rα ligands of Formula (4a)-(4d), $X^4$ can be C.
In IL-2Rα ligands of Formula (4a)-(4d), $X^5$ can be S.
In IL-2Rα ligands of Formula (4a)-(4d), $X^6$ can be A.
In IL-2Rα ligands of Formula (4a)-(4d), $X^7$ can be selected from F, L, V, and M.
In IL-2Rα ligands of Formula (4a)-(4d), $X^8$ can be G.
In IL-2Rα ligands of Formula (4a)-(4d), $X^9$ can be C.
In IL-2Rα ligands of Formula (4a)-(4d), $X^{10}$ can be selected from R and K.
In IL-2Rα ligands of Formula (4a)-(4d), $X^{11}$ can be selected from S, P, and A.
In IL-2Rα ligands of Formula (4a)-(4d), $X^{12}$ can be selected from I, M, F, and W.
In IL-2Rα ligands of Formula (4a)-(4d), $X^1$ can be W.
In IL-2Rα ligands of Formula (4a)-(4d), $X^2$ can be V.
In IL-2Rα ligands of Formula (4a)-(4d), $X^3$ can be I.
In IL-2Rα ligands of Formula (4a)-(4d), $X^4$ can be C.
In IL-2Rα ligands of Formula (4a)-(4d), $X^5$ can be S.
In IL-2Rα ligands of Formula (4a)-(4d), $X^6$ can be A.
In IL-2Rα ligands of Formula (4a)-(4d), $X^7$ can be selected from F, I, L, M, V, W, and Y.
In IL-2Rα ligands of Formula (4a)-(4d), $X^8$ can be G.
In IL-2Rα ligands of Formula (4a)-(4d), $X^9$ can be C.
In IL-2Rα ligands of Formula (4a)-(4d), $X^{10}$ can be R.
In IL-2Rα ligands of Formula (4a)-(4d), $X^{11}$ can be S.
In IL-2Rα ligands of Formula (4a)-(4d), $X^{12}$ can be selected from F, I, L, M, V, W, and Y.
In IL-2Rα ligands of Formula (4a)-(4d), $X^1$ can be W, $X^2$ can be V, $X^3$ can be I, $X^4$ can be C, $X^5$ can be S, $X^6$ can be A, $X^8$ can be G, $X^9$ can be C, $X^{10}$ can be R, and $X^{11}$ can be S.

In IL-2Rα ligands of Formula (4a)-(4d),
$X^1$ can be W;
$X^2$ can be V;
$X^3$ can be I;
$X^4$ can be C;
$X^5$ can be S;
$X^6$ can be A;
$X^7$ can be selected from F, I, L, M, V, W, and Y;
$X^8$ can be G;
$X^9$ can be C;
$X^{10}$ can be selected from R and K;
$X^{11}$ can be S; and
$X^{12}$ can be selected from F, I, L, M, V, W, and Y.

IL-2Rα ligands provided by the present disclosure can comprise an amino acid sequence selected from any one of SEQ ID NO: 29 to SEQ ID NO: 36:

```
W V I C S A L G C R S L          SEQ ID NO: 29

W V I C S A L G C R S M          SEQ ID NO: 30

W V I C S A V G C R P F          SEQ ID NO: 31

W V I C S A M G C R S I          SEQ ID NO: 32

W V I C S A L G C R S I          SEQ ID NO: 33

W V I C S A F G C R S M          SEQ ID NO: 34

W V I C S A L G C R P F          SEQ ID NO: 35

W V I C S A L G C K A W          SEQ ID NO: 36
```

An IL-2Rα ligand provided by the present disclosure can comprise a truncated amino acid sequence of any one of SEQ ID NO: 25 to SEQ ID NO: 36.

An IL-2Rα ligand†s provided by the present disclosure can comprise an amino acid sequence selected from any one of SEQ ID NO: 25 to SEQ ID NO: 36, or a truncated amino acid sequence of any one of SEQ ID NO: 25 to SEQ ID NO: 36, wherein the amino acid sequence can independently comprise from 1 to 4 glycines (G) (SEQ ID NO: 1041) on the N-terminus, on the C-terminus, or on both the N- and C-termini.

An IL-2Rα ligand†s provided by the present disclosure can comprise an amino acid sequence selected from any one of SEQ ID NO: 25 to SEQ ID NO: 36, or a truncated amino acid sequence of any one of SEQ ID NO: 25 to SEQ ID NO: 36, wherein the amino acid sequence comprises one or more amino acid substitutions such as from 1 to 5 amino acid substitutions.

IL-2Rα ligands provided by the present disclosure can comprise the amino acid sequence of Formula (5a) (SEQ ID NO: 37), the amino acid sequence of Formula (5b) (SEQ ID NO: 38), the amino acid sequence of Formula (5c) (SEQ ID NO: 39), or the amino acid sequence of Formula (5d) (SEQ ID NO: 40):

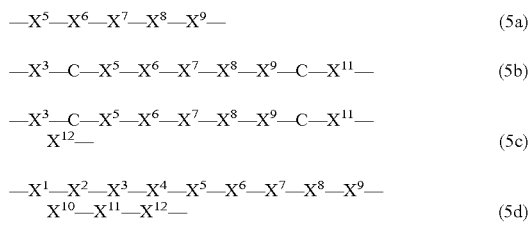

wherein, $X^1$ can be selected from an amino acid comprising an aromatic side chain or a large hydrophobic side chain;
$X^2$ can be selected from an amino acid comprising a large hydrophobic side chain;
$X^3$ can be selected from an amino acid comprising a large hydrophobic side chain;
$X^4$ can be C;
$X^5$ can be selected from an amino acid comprising a small hydrophobic side chain or an acidic side chain;
$X^6$ can be selected from an amino acid;
$X^7$ can be selected from an amino acid;
$X^8$ can be selected from an amino acid;
$X^9$ can be selected from an amino acid comprising a small hydrophobic side chain;
$X^{10}$ can be C;
$X^{11}$ can be selected from an amino acid comprising a basic side chain; and
$X^{12}$ can be selected from an amino acid.

In IL-2Rα ligands of Formula (5a)-(5d), $X^1$ can be selected from F, H, I, L, M, V, W, and Y.

In IL-2Rα ligands of Formula (5a)-(5d), $X^2$ can be selected from F, I, L, M, V, W, and Y.

In IL-2Rα ligands of Formula (5a)-(5d), $X^3$ can be selected from F, I, L, M, V, W, and Y.

In IL-2Rα ligands of Formula (5a)-(5d), $X^4$ can be C.

In IL-2Rα ligands of Formula (5a)-(5d), $X^5$ can be selected from A, G, H, K, P, R, S, and T.

In IL-2Rα ligands of Formula (5a)-(5d), $X^6$ can be selected from A, D, E, F, G, H, I, K, L, M, N, P, Q, R, S, T, V, W, and Y.

In IL-2Rα ligands of Formula (5a)-(5d), $X^7$ can be selected from A, D, E, F, G, H, I, K, L, M, N, P, Q, R, S, T, V, W, and Y.

In IL-2Rα ligands of Formula (5a)-(5d), $X^8$ can be selected from A, D, E, F, G, H, I, K, L, M, N, P, Q, R, S, T, V, W, and Y.

In IL-2Rα ligands of Formula (5a)-(5d), $X^9$ can be selected from A, G, P, S, and T.

In IL-2Rα ligands of Formula (5a)-(5d), $X^{10}$ can be C.

In IL-2Rα ligands of Formula (5a)-(5d), $X^{11}$ can be selected from H, K, and R.

In IL-2Rα ligands of Formula (5a)-(5d), $X^{12}$ can be selected from A, D, E, F, G, H, I, K, L, M, N, P, Q, R, S, T, V, W, and Y.

In IL-2Rα ligands of Formula (5a)-(5d), $X^1$ can be selected from F, H, W, and Y.

In IL-2Rα ligands of Formula (5a)-(5d), $X^2$ can be V.

In IL-2Rα ligands of Formula (5a)-(5d), $X^3$ can be selected from F, I, L, M, V, W, and Y.

In IL-2Rα ligands of Formula (5a)-(5d), $X^4$ can be selected from F, K, L, V, W, and H.

In IL-2Rα ligands of Formula (5a)-(5d), $X^5$ can be V.

In IL-2Rα ligands of Formula (5a)-(5d), $X^5$ can be selected from L, F, M, H, T, A, and I.

In IL-2Rα ligands of Formula (5a)-(5d), $X^5$ can be C.

In IL-2Rα ligands of Formula (5a)-(5d), $X^6$ can be selected from G, T, S, R, and K.

In IL-2Rα ligands of Formula (5a)-(5d), $X^6$ can be selected from L, W, K, P, A, N, W, and V, In IL-2Rα ligands of Formula (5a)-(5d), $X^7$ can be selected from Q, D, N, K, F, L, R, G, and D.

In IL-2Rα ligands of Formula (5a)-(5d), $X^8$ can be selected from G, N, Y, H, and G.

In IL-2Rα ligands of Formula (5a)-(5d), $X^9$ can be G.

In IL-2Rα ligands of Formula (5a)-(5d), $X^{10}$ can be C.

In IL-2Rα ligands of Formula (5a)-(5d), $X^{11}$ can be selected from G, S, R, T, and Y.

In IL-2Rα ligands of Formula (5a)-(5d), $X^{12}$ can be selected from S, G, A, I, G, P, R, and S.

In IL-2Rα ligands of Formula (5a)-(5d), $X^1$ can be selected from F, W, and Y.

In IL-2Rα ligands of Formula (5a)-(5d), $X^2$ can be V.

In IL-2Rα ligands of Formula (5a)-(5d), $X^3$ can be selected from F, I, L, M, V, W, and Y.

In IL-2Rα ligands of Formula (5a)-(5d), $X^4$ can be C.

In IL-2Rα ligands of Formula (5a)-(5d), $X^5$ can be selected from A, G, P, S, and T.

In IL-2Rα ligands of Formula (5a)-(5d), $X^5$ can be selected from H, K, and R.

In IL-2Rα ligands of Formula (5a)-(5d), $X^5$ can be S.

In IL-2Rα ligands of Formula (5a)-(5d), $X^6$ can be selected from F, I, L, M, V, W, and Y.

In IL-2Rα ligands of Formula (5a)-(5d), $X^6$ can be W.

In IL-2Rα ligands of Formula (5a)-(5d), $X^7$ can be selected from A, D, E, F, G, H, I, K, L, M, N, P, Q, R, S, T, V, W, and Y.

In IL-2Rα ligands of Formula (5a)-(5d), $X^8$ can be selected from A, D, E, F, G, H, I, K, L, M, N, P, Q, R, S, T, V, W, and Y.

In IL-2Rα ligands of Formula (5a)-(5d), $X^9$ can be G.

In IL-2Rα ligands of Formula (5a)-(5d), $X^{10}$ can be C.

In IL-2Rα ligands of Formula (5a)-(5d), $X^{11}$ can be R.

In IL-2Rα ligands of Formula (5a)-(5d), $X^{12}$ can be selected from A, D, E, F, G, H, I, K, L, M, N, P, Q, R, S, T, V, W, and Y.

In IL-2Rα ligands of Formula (5a)-(5d), $X^2$ can be V, $X^4$ can be C, $X^5$ can be S, $X^9$ can be G, $X^{10}$ can be C, and $X^{11}$ can be R.

In IL-2Rα ligands of Formula (5a)-(5d),
$X^1$ can be selected from F, H, I, L, M, V, W, and Y;
$X^2$ can be V;
$X^3$ can be selected from F, I, L, M, V, W, and Y;
$X^4$ can be C;
$X^5$ can be S;
$X^6$ can be selected from F, I, L, M, V, W, and Y;
$X^7$ can be selected from A, D, E, F, G, H, I, K, L, M, N, P, Q, R, S, T, V, W, and Y;
$X^8$ can be selected from A, D, E, F, G, H, I, K, L, M, N, P, Q, R, S, T, V, W, and Y;
$X^9$ can be G;
$X^{10}$ can be C;
$X^{11}$ can be R; and
$X^{12}$ can be selected from A, D, E, F, G, H, I, K, L, M, N, P, Q, R, S, T, V, W, and Y.

IL-2Rα ligands provided by the present disclosure can comprise an amino acid sequence selected from any one of SEQ ID NO: 41 to SEQ ID NO: 45:

```
                    SEQ ID NO: 41
Y V L C S N R N G C R P

SEQ ID NO: 42
Y V T C R W G Y G C T R

SEQ ID NO: 43
W V A C S W D H G C R S

SEQ ID NO: 44
H V I C S V N G G C R G

SEQ ID NO: 45
W V X C K P L H G C Y G
```

An IL-2Rα ligand provided by the present disclosure can comprise a truncated amino acid sequence of any one of SEQ ID NO: 37 to SEQ ID NO: 45.

An IL-2Rα ligand provided by the present disclosure can comprise an amino acid sequence selected from any one of SEQ ID NO: 37 to SEQ ID NO: 45, or a truncated amino acid sequence of any one of SEQ ID NO: 37 to SEQ ID NO: 45, wherein the amino acid sequence can independently comprise from 1 to 4 glycines (G) (SEQ ID NO: 1041) on the N-terminus, on the C-terminus, or on both the N- and C-termini.

An IL-2Rα ligand provided by the present disclosure can comprise an amino acid sequence selected from any one of SEQ ID NO: 37 to SEQ ID NO: 45, or a truncated amino acid sequence of any one of SEQ ID NO: 37 to SEQ ID NO: 45, wherein the amino acid sequence comprises one or more amino acid substitutions such as from 1 to 5 amino acid substitutions.

IL-2Rα ligands provided by the present disclosure can comprise the amino acid sequence of Formula (6a) (SEQ ID NO: 46), the amino acid sequence of Formula (6b) (SEQ ID NO: 47), the amino acid sequence of Formula (6c) (SEQ ID NO: 48), or the amino acid sequence of Formula (6d) (SEQ ID NO: 49):

$$-X^5-X^6-X^7-X^8-X^9-X^{10}-X^{11}- \tag{6a}$$

$$-X^3-C-X^5-X^6-X^7-X^8-X^9-X^{100}-X^{11}-C-X^{13}- \tag{6b}$$

$$-X^2-X^3-C-X^5-X^6-X^7-X^8-X^9-X^{10}-X^{11}-C-X^{13}-X^{14}- \tag{6c}$$

$$-X^1-X^2-X^3-X^4-X^5-X^6-X^7-X^8-X^9-X^{10}-X^{11}-X^{12}-X^{13}-X^{14}-X^{15}- \tag{6d}$$

wherein,
$X^1$ can be selected from an amino acid;
$X^2$ can be selected from an amino acid;
$X^3$ can be selected from an amino acid comprising a large hydrophobic side chain or an aromatic side chain;
$X^4$ can be C;
$X^5$ can be selected from an amino acid comprising a large hydrophobic side chain;
$X^6$ can be selected from an amino acid comprising a basic side chain;
$X^7$ can be selected from an amino acid comprising a small hydrophobic side chain or a polar neutral side chain;
$X^8$ can be selected from an amino acid comprising an acidic side chain;
$X^9$ can be selected from an amino acid comprising a small hydrophobic side chain;
$X^{10}$ can be selected from an amino acid;
$X^{11}$ can be selected from an amino acid comprising a small hydrophobic side chain;
$X^{12}$ can be C;
$X^{13}$ can be selected from an amino acid comprising an aromatic side chain or a large hydrophobic side chain;
$X^{14}$ can be selected from an amino acid comprising a small hydrophobic side chain or a polar neutral side chain; and
$X^{15}$ can be selected from an amino acid.

In IL-2Rα ligands of Formula (6a)-(6d),
$X^1$ can be selected from A, D, E, F, G, H, I, K, L, M, N, P, Q, R, S, T, V, W, and Y;
$X^2$ can be selected from A, D, E, F, G, H, I, K, L, M, N, P, Q, R, S, T, V, W, and Y;
$X^3$ can be selected from F, H, I, L, M, V, W, and Y;
$X^4$ can be C;
$X^5$ can be selected from F, I, L, M, V, W, and Y;
$X^6$ can be selected from H, K, and R;
$X^7$ can be selected from A, G, H, N, P, Q, S, T, and Y;
$X^8$ can be selected from D and E;
$X^9$ can be selected from A, G, P, S, and T;
$X^{10}$ can be selected from A, D, E, F, G, H, I, K, L, M, N, P, Q, R, S, T, V, W, and Y;
$X^{11}$ can be selected from A, G, P, S, and T;
$X^{12}$ can be C;
$X^{13}$ can be selected from F, H, I, L, M, V, W, and Y;
$X^{14}$ can be selected from A, G, H, N, P, Q, S, T, and Y; and X$^1$ can be selected from any A, D, E, F, G, H, I, K, L, M, N, P, Q, R, S, T, V, W, and Y.

In IL-2Rα ligands of Formula (6a)-(6d), X$^1$ can be selected from E, K, R, T, and L.

In IL-2Rα ligands of Formula (6a)-(6d), X$^2$ can be selected from Q, Y, V, K, and R.

In IL-2Rα ligands of Formula (6a)-(6d), X$^3$ can be selected from F, W, V, and L.

In IL-2Rα ligands of Formula (6a)-(6d), X$^4$ can be C.

In IL-2Rα ligands of Formula (6a)-(6d), X$^5$ can be L.

In IL-2Rα ligands of Formula (6a)-(6d), X$^6$ can be selected from V, R, A, and K.

In IL-2Rα ligands of Formula (6a)-(6d), X$^7$ can be S.

In IL-2Rα ligands of Formula (6a)-(6d), X$^8$ can be selected from D and E.

In IL-2Rα ligands of Formula (6a)-(6d), X$^9$ can be P.

In IL-2Rα ligands of Formula (6a)-(6d), X$^{10}$ can be selected from M, D, N, M Q, and T.

In IL-2Rα ligands of Formula (6a)-(6d), X$^{11}$ can be selected from A and S.

In IL-2Rα ligands of Formula (6a)-(6d), X$^{12}$ can be selected from C.

In IL-2Rα ligands of Formula (6a)-(6d), X$^{13}$ can be selected from F and W.

In IL-2Rα ligands of Formula (6a)-(6d), X$^{14}$ can be selected from S, A, and I.

In IL-2Rα ligands of Formula (6a)-(6d), X$^{15}$ can be selected from L, T, M, and V.

In IL-2Rα ligands of Formula (6a)-(6d), X$^1$ can be selected from A, D, E, F, G, H, I, K, L, M, N, P, Q, R, S, T, V, W, and Y.

In IL-2Rα ligands of Formula (6a)-(6d), X$^2$ can be selected from A, D, E, F, G, H, I, K, L, M, N, P, Q, R, S, T, V, W, and Y.

In IL-2Rα ligands of Formula (6a)-(6d), X$^3$ can be selected from F, W, and Y.

In IL-2Rα ligands of Formula (6a)-(6d), X$^4$ can be C.

In IL-2Rα ligands of Formula (6a)-(6d), X$^5$ can be L.

In IL-2Rα ligands of Formula (6a)-(6d), X$^6$ can be selected from H, K, and R.

In IL-2Rα ligands of Formula (6a)-(6d), X$^7$ can be S.

In IL-2Rα ligands of Formula (6a)-(6d), X$^8$ can be selected from D and E.

In IL-2Rα ligands of Formula (6a)-(6d), X$^9$ can be P.

In IL-2Rα ligands of Formula (6a)-(6d), X$^{10}$ can be selected from A, D, E, F, G, H, I, K, L, M, N, P, Q, R, S, T, V, W, and Y.

In IL-2Rα ligands of Formula (6a)-(6d), X$^{11}$ can be A.

In IL-2Rα ligands of Formula (6a)-(6d), X$^{12}$ can be C.

In IL-2Rα ligands of Formula (6a)-(6d), X$^{13}$ can be selected from F, W, and Y.

In IL-2Rα ligands of Formula (6a)-(6d), X$^{13}$ can be W.

In IL-2Rα ligands of Formula (6a)-(6d), X$^{14}$ can be S.

In IL-2Rα ligands of Formula (6a)-(6d), X$^{15}$ can be selected from A, D, E, F, G, H, I, K, L, M, N, P, Q, R, S, T, V, W, and Y.

In IL-2Rα ligands of Formula (6a)-(6d), X$^4$ can be C, X$^5$ can be L, X$^7$ can be S, X$^8$ can be E, X$^9$ can be P, X$^{11}$ can be A, X$^{12}$ can be C, X$^{12}$ can be W, and X$^{14}$ can be S.

In IL-2Rα ligands of Formula (6a)-(6d),

X$^1$ can be selected from A, D, E, F, G, H, I, K, L, M, N, P, Q, R, S, T, V, W, and Y;

X$^2$ can be selected from A, D, E, F, G, H, I, K, L, M, N, P, Q, R, S, T, V, W, and Y;

X$^3$ can be selected from F, H, I, L, M, V, W, and Y;

X$^4$ can be C;

X$^5$ can be L;

X$^6$ can be selected from H, K, and R;

X$^7$ can be S;

X$^8$ can be E;

X$^9$ can be P;

X$^{10}$ can be selected from A, D, E, F, G, H, I, K, L, M, N, P, Q, R, S, T, V, W, and Y;

X$^{11}$ can be A;

X$^{12}$ can be C;

X$^{13}$ can be W;

X$^{14}$ can be S; and

X$^{15}$ can be selected from A, D, E, F, G, H, I, K, L, M, N, P, Q, R, S, T, V, W, and Y.

IL-2Rα ligands provided by the present disclosure can comprise an amino acid sequence selected from any one of SEQ ID NO: 50 to SEQ ID NO: 54:

```
                                    SEQ ID NO: 50
        E Q F C LV S D P M A C WS L

SEQ ID NO: 51
        K Y W C L R S E P D A C F A T

SEQ ID NO: 52
        R V Y C L A S E P N S C W S T

SEQ ID NO: 53
        T K L C L K S E P Q A C W S M

SEQ ID NO: 54
        I R F C L R S E P T A C W I V
```

An IL-2Rα ligand provided by the present disclosure can comprise a truncated amino acid sequence of any one of SEQ ID NO: 46 to SEQ ID NO: 54.

An IL-2Rα ligand provided by the present disclosure can comprise an amino acid sequence selected from any one of SEQ ID NO: 46 to SEQ ID NO: 54, or a truncated amino acid sequence of any one of SEQ ID NO: 46 to SEQ ID NO: 54, wherein the amino acid sequence can independently comprise from 1 to 4 glycines (G) (SEQ ID NO: 1041) on the N-terminus, on the C-terminus, or on both the N- and C-termini.

An IL-2Rα ligand provided by the present disclosure can comprise an amino acid sequence selected from any one of SEQ ID NO: 46 to SEQ ID NO: 54, or a truncated amino acid sequence of any one of SEQ ID NO: 46 to SEQ ID NO: 54, wherein the amino acid sequence comprises one or more amino acid substitutions such as from 1 to 5 amino acid substitutions.

IL-2Rα ligands provided by the present disclosure can comprise the amino acid sequence of Formula (7a) (SEQ ID NO: 55), the amino acid sequence of Formula (7b) (SEQ ID NO: 56), the amino acid sequence of Formula (7c) (SEQ ID NO: 57), or the amino acid sequence of Formula (7d) (SEQ ID NO: 58):

$$-X^5-X^6-X^7-X^8-X^9-X^{10}-X^{11}- \quad (7a)$$

$$-X^3-C-X^5-X^6-X^7-X^8-X^9-X^{10}-X^{11}-C-X^{13}- \quad (7b)$$

$$-X^2-X^3-C-X^5-X^6-X^7-X^8-X^9-X^{10}-X^{11}-C-X^{13}-X^{14}- \quad (7c)$$

$$-X^1-X^2-X^3-X^4-X^5-X^6-X^7-X^8-X^9-X^{10}-X^{11}-X^{12}-X^{13}-X^{14}-X^{15}- \quad (7d)$$

wherein,

X$^1$ can be selected from a basic amino acid;

X$^2$ can be selected from a basic amino acid;

$X^3$ can be selected from an amino acid comprising a large hydrophobic side chain;
$X^4$ can be C;
$X^5$ can be selected from an amino acid comprising a large hydrophobic side chain;
$X^6$ can be selected from an amino acid comprising a basic side chain;
$X^7$ can be selected from an amino acid comprising a small hydrophobic side chain or a polar neutral side chain;
$X^8$ can be selected from an amino acid comprising a large hydrophobic side chain;
$X^9$ can be selected from an amino acid comprising a small hydrophobic side chain;
$X^{10}$ can be selected from an amino acid comprising a small hydrophobic side chain or a polar neutral side chain;
$X^{11}$ can be selected from an amino acid comprising a small hydrophobic side chain;
$X^{12}$ can be C;
$X^{13}$ can be selected from an amino acid comprising an aromatic side chain or a large hydrophobic side chain;
$X^{14}$ can be selected from an amino acid comprising a small hydrophobic side chain or a polar neutral side chain; and
$X^{15}$ can be selected from an amino acid comprising a large hydrophobic side chain.

In IL-2Rα ligands of Formula (7a)-(7d),
$X^1$ can be selected from K, and R;
$X^2$ can be selected from H, K, and R;
$X^3$ can be selected from F, I, L, M, V, W, and Y;
$X^4$ can be C;
$X^5$ can be selected from F, I, L, M, V, W, and Y;
$X^6$ can be selected from H, K, and R;
$X^7$ can be selected from A, G, H, N, P, Q, S, T, and Y;
$X^8$ can be selected from F, I, L, M, V, W, and Y;
$X^9$ can be selected from A, G, P, S, and T;
$X^{10}$ can be selected from A, G, H, N, P, Q, S, T, and Y;
$X^{11}$ can be selected from A, G, P, S, and T;
$X^{12}$ can be C;
$X^{13}$ can be selected from F, H, I, L, M, V, W, and Y;
$X^{14}$ can be selected from A, G, H, N, P, Q, S, T, and Y; and
$X^{15}$ can be selected from F, I, L, M, V, W, and Y.

In IL-2Rα ligands of Formula (7a)-(7d), $X^1$ can be selected from A, D, E, F, G, H, I, K, L, M, N, P, Q, R, S, T, V, W, and Y.
In IL-2Rα ligands of Formula (7a)-(7d), $X^2$ can be selected from A, D, E, F, G, H, I, K, L, M, N, P, Q, R, S, T, V, W, and Y.
In IL-2Rα ligands of Formula (7a)-(7d), $X^3$ can be selected from F, I, L, M, V, W, and Y.
In IL-2Rα ligands of Formula (7a)-(7d), $X^4$ can be C.
In IL-2Rα ligands of Formula (7a)-(7d), $X^5$ can be selected from F, I, L, M, V, W, and Y.
In IL-2Rα ligands of Formula (7a)-(7d), $X^5$ can be L.
In IL-2Rα ligands of Formula (7a)-(7d), $X^6$ can be selected from H, K, and R.
In IL-2Rα ligands of Formula (7a)-(7d), $X^7$ can be selected from A, G, P, S, and T.
In IL-2Rα ligands of Formula (7a)-(7d), $X^7$ can be selected from H, N, Q, S, T, and Y.
In IL-2Rα ligands of Formula (7a)-(7d), $X^7$ can be S.
In IL-2Rα ligands of Formula (7a)-(7d), $X^8$ can be selected from D and E.
In IL-2Rα ligands of Formula (7a)-(7d), $X^9$ can be P.
In IL-2Rα ligands of Formula (7a)-(7d), $X^{10}$ can be selected from A, D, E, F, G, H, I, K, L, M, N, P, Q, R, S, T, V, W, and Y.

In IL-2Rα ligands of Formula (7a)-(7d), $X^{11}$ can be A.
In IL-2Rα ligands of Formula (7a)-(7d), $X^{12}$ can be C.
In IL-2Rα ligands of Formula (7a)-(7d), $X^{13}$ can be W.
In IL-2Rα ligands of Formula (7a)-(7d), $X^{14}$ can be S.
In IL-2Rα ligands of Formula (7a)-(7d), $X^{15}$ can be selected from A, D, E, F, G, H, I, K, L, M, N, P, Q, R, S, T, V, W, and Y.
In IL-2Rα ligands of Formula (7a)-(7d), $X^1$ can be R.
In IL-2Rα ligands of Formula (7a)-(7d), $X^2$ can be R.
In IL-2Rα ligands of Formula (7a)-(7d), $X^3$ can be F.
In IL-2Rα ligands of Formula (7a)-(7d), $X^4$ can be C.
In IL-2Rα ligands of Formula (7a)-(7d), $X^5$ can be L.
In IL-2Rα ligands of Formula (7a)-(7d), $X^6$ can be R.
In IL-2Rα ligands of Formula (7a)-(7d), $X^7$ can be S.
In IL-2Rα ligands of Formula (7a)-(7d), $X^8$ can be E.
In IL-2Rα ligands of Formula (7a)-(7d), $X^9$ can be P.
In IL-2Rα ligands of Formula (7a)-(7d), $X^{10}$ can be T.
In IL-2Rα ligands of Formula (7a)-(7d), $X^{11}$ can be A.
In IL-2Rα ligands of Formula (7a)-(7d), $X^{12}$ can be C.
In IL-2Rα ligands of Formula (7a)-(7d), $X^{13}$ can be W.
In IL-2Rα ligands of Formula (7a)-(7d), $X^{14}$ can be T.
In IL-2Rα ligands of Formula (7a)-(7d), $X^{15}$ can be V.
In IL-2Rα ligands of Formula (7a)-(7d), $X^1$ can be R, $X^2$ can be R, $X^3$ can be F, $X^4$ can be C, $X^5$ can be L, $X^6$, can be R, $X^7$ can be S, $X^8$ can be E, $X^9$ can be P, $X^{10}$ can be T, $X^{11}$ can be A, $X^{12}$ can be C, $X^{13}$ can be W, and $X^{15}$ can be V.

In IL-2Rα ligands of Formula (7a)-(7d),
$X^1$ can be selected from K and R;
$X^2$ can be R;
$X^3$ can be F;
$X^4$ can be C;
$X^5$ can be L;
$X^6$ can be R;
$X^7$ can be S;
$X^8$ can be E;
$X^9$ can be P;
$X^{10}$ can be T;
$X^{11}$ can be A;
$X^{12}$ can be C;
$X^{13}$ can be W;
$X^{14}$ can be T; and
$X^{15}$ can be V.

IL-2Rα ligands provided by the present disclosure can comprise an amino acid sequence selected from any one of SEQ ID NO: 59 to SEQ ID NO: 68:

```
                                      SEQ ID NO: 59
    R R F C L R S E P T A C W I V

SEQ ID NO: 60
    K L F C L R S G D R A C W V V

SEQ ID NO: 61
    M R F C L R S E P T A C W T V

SEQ ID NO: 62
    R R F C L R S E P T A C W D V

SEQ ID NO: 63
    R R F C L R S D P T A C W I V

SEQ ID NO: 64
    K R F C L R S E P T A C W T V

SEQ ID NO: 65
    R R F C L R S E P M A C W T V

SEQ ID NO: 66
    R R F C L R S E P T A C W T V
```

```
                                          SEQ ID NO: 67
R R F C L R S E P AA C W F V

SEQ ID NO: 68
R R F C L R S E P T A C W Y V
```

An IL-2Rα ligand provided by the present disclosure can comprise a truncated amino acid sequence of any one of SEQ ID NO: 55 to SEQ ID NO: 68.

An IL-2Rα ligand provided by the present disclosure can comprise an amino acid sequence selected from any one of SEQ ID NO: 55 to SEQ ID NO: 68, or a truncated amino acid sequence of any one of SEQ ID NO: 55 to SEQ ID NO: 68, wherein the amino acid sequence can independently comprise from 1 to 4 glycines (G) (SEQ ID NO: 1041) on the N-terminus, on the C-terminus, or on both the N- and C-termini.

An IL-2Rα ligand provided by the present disclosure can comprise an amino acid sequence selected from any one of SEQ ID NO: 55 to SEQ ID NO: 68, or a truncated amino acid sequence of any one of SEQ ID NO: 55 to SEQ ID NO: 68, wherein the amino acid sequence comprises one or more amino acid substitutions such as from 1 to 5 amino acid substitutions.

IL-2Rα ligands provided by the present disclosure can comprise the amino acid sequence of Formula (8a) (SEQ ID NO: 69) the amino acid sequence of Formula (8b) (SEQ ID NO: 70), or the amino acid sequence of Formula (8c) (SEQ ID NO: 71):

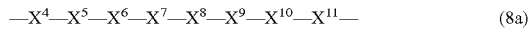  (8a)

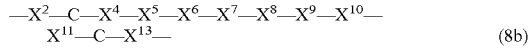  (8b)

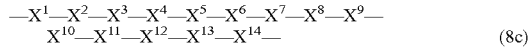  (8c)

wherein,
$X^1$ can be selected from an amino acid;
$X^2$ can be selected from an amino acid comprising a basic side chain;
$X^3$ can be C;
$X^4$ can be selected from an amino acid comprising a large hydrophobic side chain or a basic side chain;
$X^5$ can be selected from an amino acid;
$X^6$ can be selected from an amino acid comprising an acidic side chain;
$X^7$ can be selected from an amino acid;
$X^8$ can be selected from an amino acid;
$X^9$ can be selected from an amino acid;
$X^{10}$ can be selected from an amino acid comprising a small hydrophobic side chain;
$X^{11}$ can be selected from an amino acid;
$X^{12}$ can be C;
$X^{13}$ can be selected from an amino acid comprising a large hydrophobic side chain; and
$X^{14}$ can be selected from an amino acid comprising a large hydrophobic side chain.

In IL-2Rα ligands of Formula (8a)-(8c),
$X^1$ can be selected from A, D, E, F, G, H, I, K, L, M, N, P, Q, R, S, T, V, W, and Y;
$X^2$ can be selected from H, K, and R;
$X^3$ can be C;
$X^4$ can be selected from F, H, I, K, L, M, R, V, W, and Y;
$X^5$ can be selected from A, D, E, F, G, H, I, K, L, M, N, P, Q, R, S, T, V, W, and Y;
$X^6$ can be selected from D and E;
$X^7$ can be selected from A, D, E, F, G, H, I, K, L, M, N, P, Q, R, S, T, V, W, and Y;
$X^8$ can be selected from A, D, E, F, G, H, I, K, L, M, N, P, Q, R, S, T, V, W, and Y;
$X^9$ can be selected from A, D, E, F, G, H, I, K, L, M, N, P, Q, R, S, T, V, W, and Y;
$X^{10}$ can be selected from A, G, P, S, and T;
$X^{11}$ can be selected from A, D, E, F, G, H, I, K, L, M, N, P, Q, R, S, T, V, W, and Y;
$X^{12}$ can be C;
$X^{13}$ can be selected from F, I, L, M, V, W, and Y; and
$X^{14}$ can be selected from F, I, L, M, V, W, and Y.

In IL-2Rα ligands of Formula (8a)-(8c), $X^1$ can be selected from R, I, L, M, N, S, T, V, and D.

In IL-2Rα ligands of Formula (8a)-(8c), $X^2$ can be selected from S, K, R, H, G, and F.

In IL-2Rα ligands of Formula (8a)-(8c), $X^3$ can be C.

In IL-2Rα ligands of Formula (8a)-(8c), $X^4$ can be selected from N, R, I, T, V, L, and D.

In IL-2Rα ligands of Formula (8a)-(8c), $X^5$ can be selected from R, V, L, M, V, G, Y, I, F, and T.

In IL-2Rα ligands of Formula (8a)-(8c), $X^5$ can be selected from Y, L, E, D, S, I, Y, D, and R.

In IL-2Rα ligands of Formula (8a)-(8c), $X^6$ can be selected from Y, L, E, D, S, and R.

In IL-2Rα ligands of Formula (8a)-(8c), $X^7$ can be selected from G, E, K, T, P, W, L, Y, G, S, and R.

In IL-2Rα ligands of Formula (8a)-(8c), $X^8$ can be selected from I, A, Q, R, S R, L, N, P, A, I, R, D, and W.

In IL-2Rα ligands of Formula (8a)-(8c), $X^9$ can be selected from W, G, S, D, R, L, F, P, A, and T.

In IL-2Rα ligands of Formula (8a)-(8c), $X^{10}$ can be selected from G, T, E, W, Q, R, and Y.

In IL-2Rα ligands of Formula (8a)-(8c), $X^{11}$ can be selected from H, P, I, T, H, A, S, F, and Y.

In IL-2Rα ligands of Formula (8a)-(8c), $X^{12}$ can be C.

In IL-2Rα ligands of Formula (8a)-(8c), $X^{13}$ can be selected from D, V, L, I, Y, I, R, H, T, I, and W.

In IL-2Rα ligands of Formula (8a)-(8c), $X^{14}$ can be selected from T, S, F, and I.

In IL-2Rα ligands of Formula (8a)-(8c), $X^1$ can be selected from R, I, L, M, N, S, T, V, and D.

In IL-2Rα ligands of Formula (8a)-(8c), $X^2$ can be selected from S, K, R, H, G, and F.

In IL-2Rα ligands of Formula (8a)-(8c), $X^3$ can be C.

In IL-2Rα ligands of Formula (8a)-(8c), $X^4$ can be selected from F, I, L, M, V, W, and Y.

In IL-2Rα ligands of Formula (8a)-(8c), $X^4$ can be selected from H, K, and R.

In IL-2Rα ligands of Formula (8a)-(8c), $X^5$ can be selected from Y, L, E, D, S, I, Y, D, and R.

In IL-2Rα ligands of Formula (8a)-(8c), $X^6$ can be selected from Y, L, E, D, S, and R.

In IL-2Rα ligands of Formula (8a)-(8c), $X^6$ can be selected from D and E.

In IL-2Rα ligands of Formula (8a)-(8c), $X^7$ can be selected from G, E, K, T, P, W, L, Y, G, S, and R.

In IL-2Rα ligands of Formula (8a)-(8c), $X^8$ can be selected from I, A, Q, R, S R, L, N, P, A, I, R, D, and W.

In IL-2Rα ligands of Formula (8a)-(8c), $X^9$ can be selected from W, G, S, D, R, L, F, P, A, and T.

In IL-2Rα ligands of Formula (8a)-(8c), $X^{10}$ can be selected from G, T, E, W, Q, R, and Y.

In IL-2Rα ligands of Formula (8a)-(8c), $X^{10}$ can be G.

In IL-2Rα ligands of Formula (8a)-(8c), $X^{11}$ can be selected from H, P, I, T, H, A, S, F, and Y.

In IL-2Rα ligands of Formula (8a)-(8c), $X^{12}$ can be C.

In IL-2Rα ligands of Formula (8a)-(8c), $X^{13}$ can be selected from F, I, L, M, V, W, and Y.

In IL-2Rα ligands of Formula (8a)-(8c), $X^{14}$ can be F.

In IL-2Rα ligands of Formula (8a)-(8c), $X^2$ can be R, $X^3$ can be C, $X^6$, can be D, $X^{10}$ can be G, $X^{12}$ can be C, and $X^{14}$ can be F.

In IL-2Rα ligands of Formula (8a)-(8c),
$X^1$ can be selected from A, D, E, F, G, H, I, K, L, M, N, P, Q, R, S, T, V, W, and Y;
$X^2$ can be R;
$X^3$ can be C;
$X^4$ can be selected from F, H, I, K, L, M, R, V, W, and Y;
$X^5$ can be selected from A, D, E, F, G, H, I, K, L, M, N, P, Q, R, S, T, V, W, and Y;
$X^6$ can be D;
$X^7$ can be selected from A, D, E, F, G, H, I, K, L, M, N, P, Q, R, S, T, V, W, and Y;
$X^8$ can be selected from A, D, E, F, G, H, I, K, L, M, N, P, Q, R, S, T, V, W, and Y;
$X^9$ can be selected from A, D, E, F, G, H, I, K, L, M, N, P, Q, R, S, T, V, W, and Y;
$X^{10}$ can be G;
$X^{11}$ can be selected from A, D, E, F, G, H, I, K, L, M, N, P, Q, R, S, T, V, W, and Y;
$X^{12}$ can be C;
$X^{13}$ can be selected from F, I, L, M, V, W, and Y; and
$X^{14}$ can be F.

IL-2Rα ligands provided by the present disclosure can comprise an amino acid sequence selected from any one of SEQ ID NO: 72 to SEQ ID NO: 86:

```
                                        SEQ ID NO: 72
R S C N R Y G I W G H C D T

SEQ ID NO: 73
I K C R V L E A G T P C V F

SEQ ID NO: 74
I R C R Y E K Q S G I C L F

SEQ ID NO: 75
L R C R L D T R D G T C R F

SEQ ID NO: 76
M R C I L S P S R E H C L F

SEQ ID NO: 77
N H C T M D W R L G A C I F

SEQ ID NO: 78
S G C R L S L L D G H C Y F

SEQ ID NO: 79
S K C V Y D Y N F G T C I F

SEQ ID NO: 80
S R C V M S L Q L G A C I F

SEQ ID NO: 81
T R C T V I G P P W S C R F

SEQ ID NO: 82
V F C I G Y G A A Q S C H S

SEQ ID NO: 83
V R C L Y D S I T R T C T F

SEQ ID NO: 84
V S C K I D R R S G S C L F

SEQ ID NO: 85
V S C R F R P D L G F C I F

SEQ ID NO: 86
D R C D T R T W G Y Y C W I
```

An IL-2Rα ligand provided by the present disclosure can comprise a truncated amino acid sequence of any one of SEQ ID NO: 69 to SEQ ID NO: 86.

An IL-2Rα ligand provided by the present disclosure can comprise an amino acid sequence selected from any one of SEQ ID NO: 69 to SEQ ID NO: 86, or a truncated amino acid sequence of any one of SEQ ID NO: 69 to SEQ ID NO: 86, wherein the amino acid sequence can independently comprise from 1 to 4 glycines (G) (SEQ ID NO: 1041) on the N-terminus, on the C-terminus, or on both the N- and C-termini.

An IL-2Rα ligand provided by the present disclosure can comprise an amino acid sequence selected from any one of SEQ ID NO: 69 to SEQ ID NO: 86, or a truncated amino acid sequence of any one of SEQ ID NO: 69 to SEQ ID NO: 86, wherein the amino acid sequence comprises one or more amino acid substitutions such as from 1 to 5 amino acid substitutions.

IL-2Rα ligands provided by the present disclosure can comprise the amino acid sequence of Formula (9a) (SEQ ID NO: 87), the amino acid sequence of Formula (9b) (SEQ ID NO: 88), the amino acid sequence of Formula (9c) (SEQ ID NO: 89), or the amino acid sequence of Formula (9d) (SEQ ID NO: 90):

$$-X^5-X^6-X^7-X^8-X^9-X^{10}-X^{11}-X^{12}- \quad (9a)$$

$$-X^3-C-X^5-X^6-X^7-X^8-X^9-X^{10}-X^{11}-X^{12}-C-X^{14}- \quad (9b)$$

$$-X^2-X^3-C-X^5-X^6-X^7-X^8-X^9-X^{10}-X^{11}-X^{12}-C-X^{14}-X^{15}- \quad (9c)$$

$$-X^1-X^2-X^3-X^4-X^5-X^6-X^7-X^8-X^9-X^{10}-X^{11}-X^{12}-X^{13}-X^{14}-X^{15}-X^{16}- \quad (9d)$$

wherein,
$X^1$ can be selected from an amino acid;
$X^2$ can be selected from an amino acid comprising a large hydrophobic side chain;
$X^3$ can be selected from an amino acid comprising a large hydrophobic side chain or an acidic side chain;
$X^4$ can be C;
$X^5$ can be selected from an amino acid comprising a large hydrophobic side chain or a basic side chain;
$X^6$ can be selected from an amino acid comprising a large hydrophobic side chain;
$X^7$ can be selected from an amino acid;
$X^8$ can be selected from an amino acid comprising a small hydrophobic side chain;
$X^9$ can be selected from an amino acid comprising a small hydrophobic side chain;
$X^{10}$ can be selected from an amino acid comprising a large hydrophobic side chain or a basic side chain;
$X^{11}$ can be selected from an amino acid comprising a basic side chain or an acidic side chain;
$X^{12}$ can be selected from an amino acid comprising a small hydrophobic side chain or a polar neutral side chain;
$X^{13}$ can be C;
$X^{14}$ can be selected from an amino acid;
$X^{15}$ can be selected from an amino acid; and
$X^{16}$ can be selected from an amino acid.

In IL-2Rα ligands of Formula (9a)-(9d),
$X^1$ can be selected from A, D, E, F, G, H, I, K, L, M, N, P, Q, R, S, T, V, W, and Y;

$X^2$ can be selected from F, I, L, M, V, W, and Y;
$X^3$ can be selected from D, E, F, I, L, M, V, W, and Y;
$X^4$ can be C;
$X^5$ can be selected from F, H, I, K, L, M, R, V, W, and Y;
$X^6$ can be selected from F, I, L, M, V, W, and Y;
$X^7$ can be selected from A, D, E, F, G, H, I, K, L, M, N, P, Q, R, S, T, V, W, and Y;
$X^8$ can be selected from A, G, P, S, and T;
$X^9$ can be selected from A, G, P, S, and T;
$X^{10}$ can be selected from F, H, I, K, L, M, R, V, W, and Y;
$X^{11}$ can be selected from D, E, H, K, and R;
$X^{12}$ can be selected from A, G, H, N, P, Q, S, T, and Y;
$X^{13}$ can be C;
$X^{14}$ can be selected from A, D, E, F, G, H, I, K, L, M, N, P, Q, R, S, T, V, W, and Y;
$X^{15}$ can be selected from A, D, E, F, G, H, I, K, L, M, N, P, Q, R, S, T, V, W, and Y; and
$X^{16}$ can be selected from A, D, E, F, G, H, I, K, L, M, N, P, Q, R, S, T, V, W, and Y.

In IL-2Rα ligands of Formula (9a)-(9d), $X^1$ can be selected from G, E, F, K, P, Q, R, S, and V.

In IL-2Rα ligands of Formula (9a)-(9d), $X^2$ can be selected from S, W, I, F, L, and R.

In IL-2Rα ligands of Formula (9a)-(9d), $X^3$ can be selected from R, E, I, V, S, N, F, L, and M.

In IL-2Rα ligands of Formula (9a)-(9d), $X^4$ can be C.

In IL-2Rα ligands of Formula (9a)-(9d), $X^5$ can be selected from Y, R, V, T, E, I, and K.

In IL-2Rα ligands of Formula (9a)-(9d), $X^6$ can be selected from W, F, Y, L, H, I, T, S, and V.

In IL-2Rα ligands of Formula (9a)-(9d), $X^7$ can be selected from D, L, S, D, V, Y, S, Q, I, R, M, G, and A.

In IL-2Rα ligands of Formula (9a)-(9d), $X^8$ can be P.

In IL-2Rα ligands of Formula (9a)-(9d), $X^9$ can be G.

In IL-2Rα ligands of Formula (9a)-(9d), $X^{10}$ can be selected from R, S, T, N, R, V, L, H, W, and Y.

In IL-2Rα ligands of Formula (9a)-(9d), $X^{11}$ can be selected from E, R, H, G, E, K, Q, and V.

In IL-2Rα ligands of Formula (9a)-(9d), $X^{12}$ can be selected from V, G, S, A, and W.

In IL-2Rα ligands of Formula (9a)-(9d), $X^{13}$ can be C.

In IL-2Rα ligands of Formula (9a)-(9d), $X^{14}$ can be selected from I, S, R, W, H, V, K, T, R, G, and P.

In IL-2Rα ligands of Formula (9a)-(9d), $X^{13}$ can be selected from F, L, M, S, W, T, A, and R.

In IL-2Rα ligands of Formula (9a)-(9d), $X^{14}$ can be selected from K, F, V, I, F, M, L, Q, T, and N.

In IL-2Rα ligands of Formula (9a)-(9d), $X^1$ can be selected from A, D, E, F, G, H, I, K, L, M, N, P, Q, R, S, T, V, W, and Y.

In IL-2Rα ligands of Formula (9a)-(9d), $X^2$ can be selected from F, W, and Y.

In IL-2Rα ligands of Formula (9a)-(9d), $X^3$ can be W.

In IL-2Rα ligands of Formula (9a)-(9d), $X^4$ can be C.

In IL-2Rα ligands of Formula (9a)-(9d), $X^5$ can be selected from F, I, L, M, V, W, and Y.

In IL-2Rα ligands of Formula (9a)-(9d), $X^5$ can be selected from D and E.

In IL-2Rα ligands of Formula (9a)-(9d), $X^6$ can be selected from F, I, L, M, V, W, and Y.

In IL-2Rα ligands of Formula (9a)-(9d), $X^6$ can be selected from F, W, and Y.

In IL-2Rα ligands of Formula (9a)-(9d), $X^7$ can be selected from A, D, E, F, G, H, I, K, L, M, N, P, Q, R, S, T, V, W, and Y.

In IL-2Rα ligands of Formula (9a)-(9d), $X^8$ can be P.

In IL-2Rα ligands of Formula (9a)-(9d), $X^9$ can be G.

In IL-2Rα ligands of Formula (9a)-(9d), $X^{10}$ can be selected from F, I, L, M, V, W, and Y.

In IL-2Rα ligands of Formula (9a)-(9d), $X^{10}$ can be selected from F, W, and Y.

In IL-2Rα ligands of Formula (9a)-(9d), $X^{10}$ can be selected from H, K, and R.

In IL-2Rα ligands of Formula (9a)-(9d), $X^{11}$ can be selected from H, K, and R.

In IL-2Rα ligands of Formula (9a)-(9d), $X^{11}$ can be selected from D and E.

In IL-2Rα ligands of Formula (9a)-(9d), $X^{12}$ can be selected from A, G, P, S, and T.

In IL-2Rα ligands of Formula (9a)-(9d), $X^{12}$ can be selected from N, Q, S, T, and Y.

In IL-2Rα ligands of Formula (9a)-(9d), $X^{11}$ can be C.

In IL-2Rα ligands of Formula (9a)-(9d), $X^{14}$ can be selected from A, D, E, F, G, H, I, K, L, M, N, P, Q, R, S, T, V, W, and Y.

In IL-2Rα ligands of Formula (9a)-(9d), $X^{15}$ can be selected from A, D, E, F, G, H, I, K, L, M, N, P, Q, R, S, T, V, W, and Y.

In IL-2Rα ligands of Formula (9a)-(9d), $X^{16}$ can be selected from A, D, E, F, G, H, I, K, L, M, N, P, Q, R, S, T, V, W, and Y.

In IL-2Rα ligands of Formula (9a)-(9d), $X^{16}$ can be selected from F, I, L, M, V, W, and Y.

In IL-2Rα ligands of Formula (9a)-(9d), $X^{16}$ can be selected from F, W, and Y.

In IL-2Rα ligands of Formula (9a)-(9d), $X^2$ can be W, $X^3$ can be E, $X^4$ can be C, $X^5$, can be R, $X^8$ can be P, $X^9$ can be G, $X^{10}$ can be R, $X^{11}$ can be R, $X^{12}$ can be G, and $X^{11}$ can be C.

In IL-2Rα ligands of Formula (9a)-(9d), $X^1$ can be selected from A, D, E, F, G, H, I, K, L, M, N, P, Q, R, S, T, V, W, and Y;

$X^2$ can be W;

$X^3$ can be E;

$X^4$ can be C;

$X^5$ can be R;

$X^6$ can be selected from F, H, I, L, M, V, W, and Y;

$X^7$ can be selected from A, D, E, F, G, H, I, K, L, M, N, P, Q, R, S, T, V, W, and Y;

$X^8$ can be P;

$X^9$ can be G $X^{10}$ can be R;

$X^{11}$ can be R;

$X^{12}$ can be G;

$X^{13}$ can be C;

$X^{14}$ can be selected from A, D, E, F, G, H, I, K, L, M, N, P, Q, R, S, T, V, W, and Y;

$X^{15}$ can be selected from A, D, E, F, G, H, I, K, L, M, N, P, Q, R, S, T, V, W, and Y; and $X^{16}$ can be selected from A, D, E, F, G, H, I, K, L, M, N, P, Q, R, S, T, V, W, and Y.

IL-2Rα ligands provided by the present disclosure can comprise an amino acid sequence selected from any one of SEQ ID NO: 91 to SEQ ID NO: 104:

SEQ ID NO: 91
G S R C Y W D P G R E V C I F K

SEQ ID NO: 92
E W E C R F L P G R R G C S L F

-continued

```
                              SEQ ID NO: 93
F W E C V Y S P G S R G C R M V

SEQ ID NO: 94
G F R C T Y D P G T H S C W S I

SEQ ID NO: 95
K W I C R L V P G N G A C H S F

SEQ ID NO: 96
P W V C E H Y P G R R G C V L M

SEQ ID NO: 97
Q W S C V F S P G V R G C K L V

SEQ ID NO: 98
R F I C R I Q P G R E G C W S L

SEQ ID NO: 99
R W E C I Y I P G R K G C T L Q

SEQ ID NO: 100
S L N C K T R P G L R W C T W T

SEQ ID NO: 101
S W E C V Y M P G H Q G C L R F

SEQ ID NO: 102
V R F C R S G P G W V S C G T Q

SEQ ID NO: 103
V R L C R V G P G Y E S C P A N

SEQ ID NO: 104
V R M C Y V A P G Y V S C P R M
```

An IL-2Rα ligand provided by the present disclosure can comprise a truncated amino acid sequence of any one of SEQ ID NO: 87 to SEQ ID NO: 104.

An IL-2Rα ligand provided by the present disclosure can comprise an amino acid sequence selected from any one of SEQ ID NO: 87 to SEQ ID NO: 104, or a truncated amino acid sequence of any one of SEQ ID NO: 87 to SEQ ID NO: 104, wherein the amino acid sequence can independently comprise from 1 to 4 glycines (G) (SEQ ID NO: 1041) on the N-terminus, on the C-terminus, or on both the N- and C-termini.

An IL-2Rα ligand provided by the present disclosure can comprise an amino acid sequence selected from any one of SEQ ID NO: 87 to SEQ ID NO: 104, or a truncated amino acid sequence of any one of SEQ ID NO: 87 to SEQ ID NO: 104, wherein the amino acid sequence comprises one or more amino acid substitutions such as from 1 to 5 amino acid substitutions.

IL-2Rα ligands provided by the present disclosure can comprise the amino acid sequence of Formula (10a) (SEQ ID NO: 105), the amino acid sequence of Formula (10b) (SEQ ID NO: 106), the amino acid sequence of Formula (10c) (SEQ ID NO: 107), or the amino acid sequence of Formula (10d) (SEQ ID NO: 108):

$$-X^5-X^6-X^7-X^8-X^9-X^{10}-X^{11}-X^{12}- \quad (10a)$$

$$-X^3-C-X^5-X^6-X^7-X^8-X^9-X^{10}-X^{11}-X^{12}-C-X^{14}- \quad (10b)$$

$$-X^2-X^3-C-X^5-X^6-X^7-X^8-X^9-X^{10}-X^{11}-X^{12}-C-X^{14}-X^{15}- \quad (10c)$$

$$-X^1-X^2-X^3-X^4-X^5-X^6-X^7-X^8-X^9-X^{10}-X^{11}-X^{12}-X^{13}-X^{14}-X^{15}-X^{16}- \quad (10d)$$

wherein, $X^1$ can be selected from an amino acid comprising an acidic side chain;

$X^2$ can be selected from an amino acid comprising a large hydrophobic side chain;

$X^3$ can be selected from an amino acid comprising an acidic side chain;

$X^4$ can be C;

$X^5$ can be selected from an amino acid comprising a large hydrophobic side chain;

$X^6$ can be selected from an amino acid comprising a large hydrophobic side chain;

$X^7$ can be selected from an amino acid comprising a large hydrophobic side chain;

$X^8$ can be selected from an amino acid comprising a small hydrophobic side chain;

$X^9$ can be selected from an amino acid comprising a small hydrophobic side chain;

$X^{10}$ can be selected from an amino acid comprising a basic side chain;

$X^{11}$ can be selected from an amino acid comprising a basic side chain;

$X^{12}$ can be selected from an amino acid comprising a small hydrophobic side chain;

$X^{13}$ can be C;

$X^{14}$ can be selected from an amino acid comprising a small hydrophobic side chain or a polar neutral side chain;

$X^{15}$ can be selected from an amino acid comprising a large hydrophobic side chain; and $X^{16}$ can be selected from an amino acid comprising a large hydrophobic side chain.

In IL-2Rα ligands of Formula (10a)-(10d), $X^1$ can be selected from A, D, E, F, G, H, I, K, L, M, N, P, Q, R, S, T, V, W, and Y;

$X^2$ can be selected from F, I, L, M, V, W, and Y;

$X^3$ can be selected from D and E;

$X^4$ can be C;

$X^5$ can be selected from F, I, L, M, V, W, and Y;

$X^6$ can be selected from F, I, L, M, V, W, and Y;

$X^7$ can be selected from F, I, L, M, V, W, and Y;

$X^8$ can be selected from A, G, P, S, and T;

$X^9$ can be selected from A, G, P, S, and T;

$X^{10}$ can be selected from H, K, and R;

$X^{11}$ can be selected from H, K, and R;

$X^{12}$ can be selected from A, G, P, S, and T;

$X^{13}$ can be C;

$X^{14}$ can be selected from A, G, H, N, P, Q, S, T, and Y;

$X^{15}$ can be selected from F, I, L, M, V, W, and Y; and $X^{16}$ can be selected from F, I, L, M, V, W, and Y.

In IL-2Rα ligands of Formula (10a)-(10d), $X^1$ can be selected from N, D, E, A, V, and T.

In IL-2Rα ligands of Formula (10a)-(10d), $X^2$ can be selected from W and Y.

In IL-2Rα ligands of Formula (10a)-(10d), $X^3$ can be selected from E, H, and D.

In IL-2Rα ligands of Formula (10a)-(10d), $X^4$ can be C.

In IL-2Rα ligands of Formula (10a)-(10d), $X^5$ can be selected from I, 1, W, and V.

In IL-2Rα ligands of Formula (10a)-(10d), $X^6$ can be selected from F and I.

In IL-2Rα ligands of Formula (10a)-(10d), $X^7$ can be selected from S, L, and M.

In IL-2Rα ligands of Formula (10a)-(10d), $X^8$ can be P.

In IL-2Rα ligands of Formula (10a)-(10d), $X^9$ can be G.

In IL-2Rα ligands of Formula (10a)-(10d), $X^{10}$ can be selected from R and H.

In IL-2Rα ligands of Formula (10a)-(10d), $X^{11}$ can be selected from R and K.

In IL-2Rα ligands of Formula (10a)-(10d), $X^{12}$ can be G.
In IL-2Rα ligands of Formula (10a)-(10d), $X^{13}$ can be C.
In IL-2Rα ligands of Formula (10a)-(10d), $X^{14}$ can be selected from S, L, T, and F.
In IL-2Rα ligands of Formula (10a)-(10d), $X^{13}$ can be selected from L and G.
In IL-2Rα ligands of Formula (10a)-(10d), $X^{14}$ can be selected from F, M, T, and I.
In IL-2Rα ligands of Formula (10a)-(10d), $X^{1}$ can be selected from D and E.
In IL-2Rα ligands of Formula (10a)-(10d), $X^{2}$ can be W.
In IL-2Rα ligands of Formula (10a)-(10d), $X^{3}$ can be selected from D and E.
In IL-2Rα ligands of Formula (10a)-(10d), $X^{4}$ can be C.
In IL-2Rα ligands of Formula (10a)-(10d), $X^{5}$ can be selected from F, I, L, M, V, W, and Y.
In IL-2Rα ligands of Formula (10a)-(10d), $X^{5}$ can be selected from I and L.
In IL-2Rα ligands of Formula (10a)-(10d), $X^{6}$ can be F.
In IL-2Rα ligands of Formula (10a)-(10d), $X^{7}$ can be selected from L and M.
In IL-2Rα ligands of Formula (10a)-(10d), $X^{8}$ can be P.
In IL-2Rα ligands of Formula (10a)-(10d), $X^{9}$ can be G.
In IL-2Rα ligands of Formula (10a)-(10d), $X^{10}$ can be selected from H and R.
In IL-2Rα ligands of Formula (10a)-(10d), $X^{11}$ can be selected from K and R.
In IL-2Rα ligands of Formula (10a)-(10d), $X^{12}$ can be G.
In IL-2Rα ligands of Formula (10a)-(10d), $X^{13}$ can be C.
In IL-2Rα ligands of Formula (10a)-(10d), $X^{14}$ can be selected from S and T.
In IL-2Rα ligands of Formula (10a)-(10d), $X^{15}$ can be L.
In IL-2Rα ligands of Formula (10a)-(10d), $X^{16}$ can be selected from F and M.

In IL-2Rα ligands of Formula (10a)-(10d),
$X^{1}$ can be D;
$X^{2}$ can be W;
$X^{3}$ can be E;
$X^{4}$ can be C;
$X^{5}$ can be L;
$X^{6}$ can be F;
$X^{7}$ can be L;
$X^{8}$ can be P;
$X^{9}$ can be G;
$X^{10}$ can be selected from H and R;
$X^{11}$ can be selected from K and R;
$X^{12}$ can be G;
$X^{13}$ can be C;
$X^{14}$ can be T;
$X^{15}$ can be L; and
$X^{16}$ can be F.

IL-2Rα ligands provided by the present disclosure can comprise an amino acid sequence selected from any one of SEQ ID NO: 109 to SEQ ID NO: 121:

```
                                      SEQ ID NO: 109
N W E C I F S P G R R G C S L T

SEQ ID NO: 110
D W E C L F L P G R R G C L L F

SEQ ID NO: 111
E W E C L F M P G R R G C L L M

SEQ ID NO: 112
A W E C L F L P G H R G C S L F

SEQ ID NO: 113
E W E C L F L P G R K G C T L F

SEQ ID NO: 114
D W E C I F L P G R R G C T L F

SEQ ID NO: 115
V Y E C L F M P G R K G CF G M

SEQ ID NO: 116
E W E C W F L P G R R G C T L I

SEQ ID NO: 117
D W H C L F L P G H R G C T L F

SEQ ID NO: 118
D W E C L F L P G R R G C T L F

SEQ ID NO: 119
Y W E C V F M P G H R G C S L I

SEQ ID NO: 120
T W D C L F L P G R R G C T L M

SEQ ID NO: 121
N W E C I F S P G R R G C S L T
```

An IL-2Rα ligand provided by the present disclosure can comprise a truncated amino acid sequence of any one of SEQ ID NO: 105 to SEQ ID NO: 121.

An IL-2Rα ligand provided by the present disclosure can comprise an amino acid sequence selected from any one of SEQ ID NO: 105 to SEQ ID NO: 121, or a truncated amino acid sequence of any one of SEQ ID NO: 105 to SEQ ID NO: 121, wherein the amino acid sequence can independently comprise from 1 to 4 glycines (G) (SEQ ID NO: 1041) on the N-terminus, on the C-terminus, or on both the N- and C-termini.

An IL-2Rα ligand provided by the present disclosure can comprise an amino acid sequence selected from any one of SEQ ID NO: 105 to SEQ ID NO: 121, or a truncated amino acid sequence of any one of SEQ ID NO: 105 to SEQ ID NO: 121, wherein the amino acid sequence comprises one or more amino acid substitutions such as from 1 to 5 amino acid substitutions.

IL-2Rα ligands provided by the present disclosure can comprise the amino acid sequence of Formula (11a) (SEQ ID NO: 122), the amino acid sequence of Formula (11b) (SEQ ID NO: 123), the amino acid sequence of Formula (11c) (SEQ ID NO: 124), or the amino acid sequence of Formula (11d) (SEQ ID NO: 125):

$$-X^5-X^6-X^7-X^8-X^9-X^{10}-X^{11}-X^{12}- \quad (11a)$$

$$-X^3-C-X^5-X^6-X^7-X^8-X^9-X^{10}-X^{11}-X^{12}-C-X^{14}- \quad (11b)$$

$$-X^2-X^3-C-X^5-X^6-X^7-X^8-X^9-X^{10}-X^{11}-X^{12}-C-X^{14}-X^{15}- \quad (11c)$$

$$-X^1-X^2-X^3-X^4-X^5-X^6-X^7-X^8-X^9-X^{10}-X^{11}-X^{12}-X^{13}-X^{14}-X^{15}-X^{16}- \quad (11d)$$

wherein,
$X^{1}$ can be selected from an amino acid;
$X^{2}$ can be selected from an amino acid;
$X^{3}$ can be selected from an amino acid;
$X^{4}$ can be C;
$X^{5}$ can be selected from an amino acid comprising an acidic side chain;

$X^6$ can be selected from an amino acid
$X^7$ can be selected from an amino acid comprising an acidic side chain or an aromatic side chain;
$X^8$ can be selected from an amino acid comprising a small hydrophobic side chain;
$X^9$ can be selected from an amino acid comprising a small hydrophobic side chain;
$X^{10}$ can be selected from an amino acid comprising an aromatic chain;
$X^{11}$ can be selected from an amino acid;
$X^{12}$ can be selected from an amino acid;
$X^{13}$ can be C;
$X^{14}$ can be selected from an amino acid;
$X^{15}$ can be selected from an amino acid comprising a large hydrophobic side chain; and
$X^{16}$ can be selected from an amino acid comprising a large hydrophobic side chain.

In IL-2Rα ligands of Formula (11a)-(11d),
$X^1$ can be selected from A, D, E, F, G, H, I, K, L, M, N, P, Q, R, S, T, V, W, and Y;
$X^2$ can be selected from A, D, E, F, G, H, I, K, L, M, N, P, Q, R, S, T, V, W, and Y;
$X^3$ can be selected from A, D, E, F, G, H, I, K, L, M, N, P, Q, R, S, T, V, W, and Y;
$X^4$ can be C;
$X^5$ can be selected from D and E;
$X^6$ can be selected from A, D, E, F, G, H, I, K, L, M, N, P, Q, R, S, T, V, W, and Y;
$X^7$ can be selected from D, E, F, H, W, and Y;
$X^8$ can be selected from A, G, P, S, and T;
$X^9$ can be selected from A, G, P, S, and T;
$X^{10}$ can be selected from F, H, W, and Y;
$X^{11}$ can be selected from A, D, E, F, G, H, I, K, L, M, N, P, Q, R, S, T, V, W, and Y;
$X^{12}$ can be selected from A, D, E, F, G, H, I, K, L, M, N, P, Q, R, S, T, V, W, and Y;
$X^{13}$ can be C;
$X^{14}$ can be selected from A, D, E, F, G, H, I, K, L, M, N, P, Q, R, S, T, V, W, and Y;
$X^{15}$ can be selected from F, I, L, M, V, W, and Y; and
$X^{16}$ can be selected from F, I, L, M, V, W, and Y.

In IL-2Rα ligands of Formula (11a)-(11d), $X^1$ can be selected from A, E, F, G, K, R, T, Y, and W.
In IL-2Rα ligands of Formula (11a)-(11d), $X^2$ can be selected from G, T, K, Q, S, L, Q, R, and A.
In IL-2Rα ligands of Formula (11a)-(11d), $X^3$ can be selected from F, Y, W, and H.
In IL-2Rα ligands of Formula (11a)-(11d), $X^3$ can be selected from G, W, P, L, R, F, M, V, S, and P.
In IL-2Rα ligands of Formula (11a)-(11d), $X^4$ can be C.
In IL-2Rα ligands of Formula (11a)-(11d), $X^5$ can be selected from K, D, Y, T, Y, Q, F, L, and S.
In IL-2Rα ligands of Formula (11a)-(11d), $X^6$ can be selected from L, D, F, Y, W, N, D, M, V, D, L, and Y.
In IL-2Rα ligands of Formula (11a)-(11d), $X^7$ can be selected from N, H, F, D, N, S, L, and Y.
In IL-2Rα ligands of Formula (11a)-(11d), $X^8$ can be P.
In IL-2Rα ligands of Formula (11a)-(11d), $X^9$ can be G.
In IL-2Rα ligands of Formula (11a)-(11d), $X^{10}$ can be selected from T, H, L, S, Q, R, N, Y, W, V, S, and H.
In IL-2Rα ligands of Formula (11a)-(11d), $X^{11}$ can be selected from Q, W, P, D, E, S, P, E, H, G, R, and G.
In IL-2Rα ligands of Formula (11a)-(11d), $X^{12}$ can be selected from V, S, R, I, A, D, S, E, Y, and G.
In IL-2Rα ligands of Formula (11a)-(11d), $X^{13}$ can be C.
In IL-2Rα ligands of Formula (11a)-(11d), $X^{14}$ can be selected from S, E, T, V, I, D, Q, W, P, I, and Y.
In IL-2Rα ligands of Formula (11a)-(11d), $X^{15}$ can be selected from F, M, W, I, V, T, N, L, and S.
In IL-2Rα ligands of Formula (11a)-(11d), $X^{16}$ can be selected from Y, V, I, L, S, K, E, and R.
In IL-2Rα ligands of Formula (11a)-(11d), $X^4$ can be C.
In IL-2Rα ligands of Formula (11a)-(11d), $X^5$ can be D.
In IL-2Rα ligands of Formula (11a)-(11d), $X^7$ can be selected from D and H.
In IL-2Rα ligands of Formula (11a)-(11d), $X^8$ can be P.
In IL-2Rα ligands of Formula (11a)-(11d), $X^9$ can be G.
In IL-2Rα ligands of Formula (11a)-(11d), $X^{10}$ can be selected from F, H, W, and Y.
In IL-2Rα ligands of Formula (11a)-(11d), $X^{13}$ can be C.
In IL-2Rα ligands of Formula (11a)-(11d), $X^{15}$ can be selected from F, M, I, W, V, and L.
In IL-2Rα ligands of Formula (11a)-(11d), $X^{16}$ can be selected from Y, V, I, and L.

In IL-2Rα ligands of Formula (11a)-(11d),
$X^1$ can be selected from A, D, E, F, G, H, I, K, L, M, N, P, Q, R, S, T, V, W, and Y;
$X^2$ can be selected from A, D, E, F, G, H, I, K, L, M, N, P, Q, R, S, T, V, W, and Y;
$X^3$ can be selected from A, D, E, F, G, H, I, K, L, M, N, P, Q, R, S, T, V, W, and Y;
$X^4$ can be C;
$X^5$ can be selected from D and E;
$X^6$ can be selected from A, D, E, F, G, H, I, K, L, M, N, P, Q, R, S, T, V, W, and Y;
$X^7$ can be selected from D, E, H, F, W, and Y;
$X^8$ can be P;
$X^9$ can be G;
$X^{10}$ can be selected from H, F, W, and Y;
$X^{11}$ can be selected from A, D, E, F, G, H, I, K, L, M, N, P, Q, R, S, T, V, W, and Y;
$X^{12}$ can be selected from A, D, E, F, G, H, I, K, L, M, N, P, Q, R, S, T, V, W, and Y;
$X^{13}$ can be C;
$X^{14}$ can be selected from A, D, E, F, G, H, I, K, L, M, N, P, Q, R, S, T, V, W, and Y;
$X^{15}$ can be selected from F, I, L, M, V, W, and Y; and
$X^{16}$ can be selected from F, I, L, M, V, W, and Y.

IL-2Rα ligands provided by the present disclosure can comprise an amino acid sequence selected from any one of SEQ ID NO: 126 to SEQ ID NO: 140:

```
                                            SEQ ID NO: 126
    A G W C K L N P G T Q V C S F Y

SEQ ID NO: 127
    E T P C D L H P G H W S C S M V

SEQ ID NO: 128
    F F L C D D F P G L P R C E W I

SEQ ID NO: 129
    G L R C Y F D P G S Q I C T F L

SEQ ID NO: 130
    G Q R C T Y D P G Q D A C V F S

SEQ ID NO: 131
    G S R C Y W D P G R E V C I I F

SEQ ID NO: 132
    K L W C Q N N P G N S I C D M Y

SEQ ID NO: 133
    K S W C F D H P G Y P I C Q F Y
```

```
                                SEQ ID NO: 134
R L F C L M N P G P P D C W I Y

SEQ ID NO: 135
R Q F C L V S P G Y E D C W F V

SEQ ID NO: 136
T R M C F D D P G W H S C P V V

SEQ ID NO: 137
T R W C S L H P G V G E C V T L

SEQ ID NO: 138
T T V C D Y H P G S R Y C I N E

SEQ ID NO: 139
Y A S C T Y L P G H R G C T L V

SEQ ID NO: 140
W L P C D D Y P G H G Y C Y S R
```

An IL-2Rα ligand provided by the present disclosure can comprise a truncated amino acid sequence of any one of SEQ ID NO: 122 to SEQ ID NO: 140.

An IL-2Rα ligand provided by the present disclosure can comprise an amino acid sequence selected from any one of SEQ ID NO: 122 to SEQ ID NO: 140, or a truncated amino acid sequence of any one of SEQ ID NO: 122 to SEQ ID NO: 140, wherein the amino acid sequence can independently comprise from 1 to 4 glycines (G) (SEQ ID NO: 1041) on the N-terminus, on the C-terminus, or on both the N- and C-termini.

An IL-2Rα ligand provided by the present disclosure can comprise an amino acid sequence selected from any one of SEQ ID NO: 122 to SEQ ID NO: 140, or a truncated amino acid sequence of any one of SEQ ID NO: 122 to SEQ ID NO: 140, wherein the amino acid sequence comprises one or more amino acid substitutions such as from 1 to 5 amino acid substitutions.

IL-2Rα ligands provided by the present disclosure can comprise the amino acid sequence of Formula (12a) (SEQ ID NO: 141), the amino acid sequence of Formula (12b) (SEQ ID NO: 142), or the amino acid sequence of Formula (12c) (SEQ ID NO: 143):

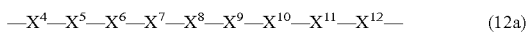  (12a)

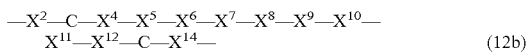  (12b)

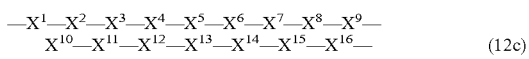  (12c)

wherein,
$X^1$ can be selected from an amino acid;
$X^2$ can be selected from an amino acid;
$X^3$ can be C;
$X^4$ can be selected from an amino acid;
$X^5$ can be selected from an amino acid comprising a large hydrophobic side chain;
$X^6$ can be selected from an amino acid;
$X^7$ can be selected from an amino acid;
$X^8$ can be selected from an amino acid;
$X^9$ can be selected from an amino acid comprising an acidic side chain, a small hydrophobic side chain, or a polar neutral side chain;
$X^{10}$ can be selected from an amino acid;
$X^{11}$ can be selected from an amino acid comprising a large hydrophobic side chain;
$X^{12}$ can be selected from an amino acid comprising a large hydrophobic side chain;
$X^{13}$ can be C;
$X^{14}$ can be selected from an amino acid comprising a large hydrophobic side chain;
$X^{15}$ can be selected from an amino acid comprising a large hydrophobic side chain; and
$X^{16}$ can be selected from an amino acid.

In IL-2Rα ligands of Formula (12a)-(12c),
$X^1$ can be selected from A, D, E, F, G, H, I, K, L, M, N, P, Q, R, S, T, V, W, and Y;
$X^2$ can be selected from A, D, E, F, G, H, I, K, L, M, N, P, Q, R, S, T, V, W, and Y;
$X^3$ can be C;
$X^4$ can be selected from A, D, E, F, G, H, I, K, L, M, N, P, Q, R, S, T, V, W, and Y;
$X^5$ can be selected from F, I, L, M, V, W, and Y;
$X^6$ can be selected from A, D, E, F, G, H, I, K, L, M, N, P, Q, R, S, T, V, W, and Y;
$X^7$ can be selected from A, D, E, F, G, H, I, K, L, M, N, P, Q, R, S, T, V, W, and Y;
$X^8$ can be selected from A, D, E, F, G, H, I, K, L, M, N, P, Q, R, S, T, V, W, and Y;
$X^9$ can be selected from A, D, E, G, H, N, P, Q, S, T, and Y;
$X^{10}$ can be selected from A, D, E, F, G, H, I, K, L, M, N, P, Q, R, S, T, V, W, and Y;
$X^{11}$ can be selected from F, I, L, M, V, W, and Y;
$X^{12}$ can be selected from F, I, L, M, V, W, and Y;
$X^{13}$ can be C;
$X^{14}$ can be selected from F, I, L, M, V, W, and Y; and
$X^{15}$ can be selected from F, I, L, M, V, W, and Y.

In IL-2Rα ligands of Formula (12a)-(12c), $X^1$ can be selected from S, N, Q, R, and G.

In IL-2Rα ligands of Formula (12a)-(12c), $X^2$ can be selected from A, H, R, and G.

In IL-2Rα ligands of Formula (12a)-(12c), $X^3$ can be C.

In IL-2Rα ligands of Formula (12a)-(12c), $X^4$ can be selected from Q, T, N, M, and S.

In IL-2Rα ligands of Formula (12a)-(12c), $X^5$ can be selected from L and R.

In IL-2Rα ligands of Formula (12a)-(12c), $X^6$ can be selected from K, S, R, and V.

In IL-2Rα ligands of Formula (12a)-(12c), $X^7$ can be selected from W, K, and L.

In IL-2Rα ligands of Formula (12a)-(12c), $X^8$ can be selected from D, T, L, Q, and A.

In IL-2Rα ligands of Formula (12a)-(12c), $X^9$ can be selected from E, Y, D, and P.

In IL-2Rα ligands of Formula (12a)-(12c), $X^{10}$ can be selected from G, P, A, E, and S.

In IL-2Rα ligands of Formula (12a)-(12c), $X^{11}$ can be selected from W and L.

In IL-2Rα ligands of Formula (12a)-(12c), $X^{12}$ can be selected from T, V, I, and A.

In IL-2Rα ligands of Formula (12a)-(12c), $X^{13}$ can be C.

In IL-2Rα ligands of Formula (12a)-(12c), $X^{14}$ can be selected from L, V, Q, and I.

In IL-2Rα ligands of Formula (12a)-(12c), $X^{13}$ can be selected from F and A.

In IL-2Rα ligands of Formula (12a)-(12c), $X^1$ can be selected from A, D, E, F, G, H, I, K, L, M, N, P, Q, R, S, T, V, W, and Y.

In IL-2Rα ligands of Formula (12a)-(12c), $X^2$ can be selected from A, D, E, F, G, H, I, K, L, M, N, P, Q, R, S, T, V, W, and Y.

In IL-2Rα ligands of Formula (12a)-(12c), $X^3$ can be C.

In IL-2Rα ligands of Formula (12a)-(12c), $X^4$ can be selected from A, D, E, F, G, H, I, K, L, M, N, P, Q, R, S, T, V, W, and Y.

In IL-2Rα ligands of Formula (12a)-(12c), $X^5$ can be L.

In IL-2Rα ligands of Formula (12a)-(12c), $X^6$ can be selected from A, D, E, F, G, H, I, K, L, M, N, P, Q, R, S, T, V, W, and Y.

In IL-2Rα ligands of Formula (12a)-(12c), $X^7$ can be selected from A, D, E, F, G, H, I, K, L, M, N, P, Q, R, S, T, V, W, and Y.

In IL-2Rα ligands of Formula (12a)-(12c), $X^8$ can be selected from A, D, E, F, G, H, I, K, L, M, N, P, Q, R, S, T, V, W, and Y.

In IL-2Rα ligands of Formula (12a)-(12c), $X^9$ can be selected from D and E.

In IL-2Rα ligands of Formula (12a)-(12c), $X^{10}$ can be selected from A, D, E, F, G, H, I, K, L, M, N, P, Q, R, S, T, V, W, and Y.

In IL-2Rα ligands of Formula (12a)-(12c), $X^{11}$ can be selected from F, I, L, M, V, W, and Y.

In IL-2Rα ligands of Formula (12a)-(12c), $X^{11}$ can be W.

In IL-2Rα ligands of Formula (12a)-(12c), $X^{12}$ can be selected from F, I, L, M, V, W, and Y.

In IL-2Rα ligands of Formula (12a)-(12c), $X^{13}$ can be C.

In IL-2Rα ligands of Formula (12a)-(12c), $X^{14}$ can be selected from F, I, L, M, V, W, and Y.

In IL-2Rα ligands of Formula (12a)-(12c), $X^{15}$ can be F.

In IL-2Rα ligands of Formula (12a)-(12c), $X^3$ can be C, $X^5$ can be L, $X^9$ can be D or E, $X^{11}$ can be W, $X^{13}$ can be C, and $X^{15}$ can be F.

In IL-2Rα ligands of Formula (12a)-(12c),
$X^1$ can be selected from A, D, E, F, G, H, I, K, L, M, N, P, Q, R, S, T, V, W, and Y;
$X^2$ can be selected from A, D, E, F, G, H, I, K, L, M, N, P, Q, R, S, T, V, W, and Y;
$X^3$ can be C;
$X^4$ can be selected from A, D, E, F, G, H, I, K, L, M, N, P, Q, R, S, T, V, W, and Y;
$X^5$ can be L;
$X^6$ can be selected from A, D, E, F, G, H, I, K, L, M, N, P, Q, R, S, T, V, W, and Y;
$X^7$ can be selected from A, D, E, F, G, H, I, K, L, M, N, P, Q, R, S, T, V, W, and Y;
$X^8$ can be selected from A, D, E, F, G, H, I, K, L, M, N, P, Q, R, S, T, V, W, and Y;
$X^9$ can be selected from D and E;
$X^{10}$ can be selected from A, D, E, F, G, H, I, K, L, M, N, P, Q, R, S, T, V, W, and Y:
$X^{11}$ can be selected from F, I, L, M, V, W, and Y;
$X^{12}$ can be selected from F, I, L, M, V, W, and Y;
$X^{13}$ can be C;
$X^{14}$ can be selected from F, I, L, M, V, W, and Y; and
$X^{15}$ can be F.

In IL-2Rα ligands of Formula (12a)-(12c), $X^3$ can be C, $X^5$ can be L, $X^{11}$ can be W, $X^{13}$ can be C, and $X^{15}$ can be F.

IL-2Rα ligands provided by the present disclosure can comprise an amino acid sequence selected from any one of SEQ ID NO: 144 to SEQ ID NO: 148:

```
                               SEQ ID NO: 144
        S A C Q L K W D E G W T C L F

SEQ ID NO: 145
        N H C T L S K T Y P W V C V F

SEQ ID NO: 146
        Q R C N R S L L D A L I C Q A

SEQ ID NO: 147
        R G C M L R L Q P E L A C V F

SEQ ID NO: 148
        G G C S L V W A D S W V C I F
```

An IL-2Rα ligand provided by the present disclosure can comprise a truncated amino acid sequence of any one of SEQ ID NO: 141 to SEQ ID NO: 148.

An IL-2Rα ligand provided by the present disclosure can comprise an amino acid sequence selected from any one of SEQ ID NO: 141 to SEQ ID NO: 148, or a truncated amino acid sequence of any one of SEQ ID NO: 141 to SEQ ID NO: 148, wherein the amino acid sequence can independently comprise from 1 to 4 glycines (G) (SEQ ID NO: 1041) on the N-terminus, on the C-terminus, or on both the N- and C-termini.

An IL-2Rα ligand provided by the present disclosure can comprise an amino acid sequence selected from any one of SEQ ID NO: 141 to SEQ ID NO: 148, or a truncated amino acid sequence of any one of SEQ ID NO: 141 to SEQ ID NO: 148, wherein the amino acid sequence comprises one or more amino acid substitutions such as from 1 to 5 amino acid substitutions.

IL-2Rα ligands provided by the present disclosure can comprise the amino acid sequence of Formula (13a) (SEQ ID NO: 149), the amino acid sequence of Formula (13b) (SEQ ID NO: 150), or the amino acid sequence of Formula (13c) (SEQ ID NO: 151):

$$-X^4-X^5-X^6-X^7-X^8-X^9-X^{10}-X^{11}-X^{12}- \quad (13a)$$

$$-X^2-C-X^4-X^5-X^6-X^7-X^8-X^9-X^{10}-X^{11}-X^{12}-C-X^{14}- \quad (13b)$$

$$-X^1-X^2-X^3-X^4-X^5-X^6-X^7-X^8-X^9-X^{10}-X^{11}-X^{12}-X^{13}-X^{14}-X^{15}- \quad (13c)$$

wherein,
$X^1$ can be selected from an amino acid comprising a small hydrophobic side chain or a basic side chain;
$X^2$ can be selected from an amino acid comprising a small hydrophobic side chain or a basic side chain;
$X^3$ can be C;
$X^4$ can be selected from an amino acid comprising a small hydrophobic side chain;
$X^5$ can be selected from an amino acid comprising a large hydrophobic side chain;
$X^6$ can be selected from an amino acid comprising a large hydrophobic side chain;
$X^7$ can be selected from an amino acid comprising a large hydrophobic side chain;
$X^8$ can be selected from an amino acid;
$X^9$ can be selected from an amino acid comprising an acidic side chain;
$X^{10}$ can be selected from an amino acid comprising a small hydrophobic side chain;
$X^{11}$ can be selected from an amino acid comprising a large hydrophobic side chain;
$X^{12}$ can be selected from an amino acid comprising a large hydrophobic side chain or an acidic side chain;
$X^{13}$ can be C;
$X^{14}$ can be selected from an amino acid comprising a large hydrophobic side chain; and
$X^{15}$ can be selected from an amino acid comprising a large hydrophobic side chain.

In IL-2Rα ligands of Formula (13a)-(13c),
$X^1$ can be selected from A, G, H, K, P, R, S, and T;
$X^2$ can be selected from A, G, H, K, P, R, S, and T;
$X^3$ can be C;
$X^4$ can be selected from A, G, P, S, and T;
$X^5$ can be selected from F, I, L, M, V, W, and Y;
$X^6$ can be selected from F, I, L, M, V, W, and Y;
$X^7$ can be selected from F, I, L, M, V, W, and Y;
$X^8$ can be selected from A, D, E, F, G, H, I, K, L, M, N, P, Q, R, S, T, V, W, and Y;
$X^9$ can be selected from D and E;
$X^{10}$ can be selected from A, G, P, S, and T;
$X^{11}$ can be selected from F, I, L, M, V, W, and Y;
$X^{12}$ can be selected from D, E, F, I, L, M, V, W, and Y;
$X^{13}$ can be C;
$X^{14}$ can be selected from F, I, L, M, V, W, and Y; and
$X^{15}$ can be selected from F, I, L, M, V, W, and Y.

In IL-2Rα ligands of Formula (13a)-(13c), $X^1$ can be selected from S, R, Q, V, A, and G.

In IL-2Rα ligands of Formula (13a)-(13c), $X^2$ can be selected from R, G, A, and S.

In IL-2Rα ligands of Formula (13a)-(13c), $X^3$ can be C.

In IL-2Rα ligands of Formula (13a)-(13c), $X^4$ can be selected from S, T, Q, and H.

In IL-2Rα ligands of Formula (13a)-(13c), $X^5$ can be L.

In IL-2Rα ligands of Formula (13a)-(13c), $X^6$ can be selected from V, Q, A, and R.

In IL-2Rα ligands of Formula (13a)-(13c), $X^7$ can be selected from W and F.

In IL-2Rα ligands of Formula (13a)-(13c), $X^8$ can be selected from T, D, S, L, A, E, and Q.

In IL-2Rα ligands of Formula (13a)-(13c), $X^9$ can be selected from D, G, and E.

In IL-2Rα ligands of Formula (13a)-(13c), $X^{10}$ can be selected from T, S, R, G, A, S, and N.

In IL-2Rα ligands of Formula (13a)-(13c), $X^{11}$ can be W.

In IL-2Rα ligands of Formula (13a)-(13c), $X^{12}$ can be selected from V and E.

In IL-2Rα ligands of Formula (13a)-(13c), $X^{13}$ can be C.

In IL-2Rα ligands of Formula (13a)-(13c), $X^{14}$ can be selected from V and I.

In IL-2Rα ligands of Formula (13a)-(13c), $X^{13}$ can be F.

In IL-2Rα ligands of Formula (13a)-(13c), $X^1$ can be selected from A, G, P, S, and T.

In IL-2Rα ligands of Formula (13a)-(13c), $X^1$ can be selected from H, K, and R.

In IL-2Rα ligands of Formula (13a)-(13c), $X^2$ can be selected from A, G, P, S, and T.

In IL-2Rα ligands of Formula (13a)-(13c), $X^2$ can be selected from H, K, and R.

In IL-2Rα ligands of Formula (13a)-(13c), $X^2$ can be selected from R and G.

In IL-2Rα ligands of Formula (13a)-(13c), $X^3$ can be C.

In IL-2Rα ligands of Formula (13a)-(13c), $X^4$ can be selected from A, G, P, S, and T.

In IL-2Rα ligands of Formula (13a)-(13c), $X^4$ can be selected from S and T.

In IL-2Rα ligands of Formula (13a)-(13c), $X^5$ can be selected from F, I, L, M, V, W, and Y.

In IL-2Rα ligands of Formula (13a)-(13c), $X^5$ can be L.

In IL-2Rα ligands of Formula (13a)-(13c), $X^6$ can be selected from F, I, L, M, V, W, and Y.

In IL-2Rα ligands of Formula (13a)-(13c), $X^6$ can be V.

In IL-2Rα ligands of Formula (13a)-(13c), $X^7$ can be selected from F, I, L, M, V, W, and Y.

In IL-2Rα ligands of Formula (13a)-(13c), $X^7$ can be selected from F, W, and Y.

In IL-2Rα ligands of Formula (13a)-(13c), $X^7$ can be W.

In IL-2Rα ligands of Formula (13a)-(13c), $X^8$ can be selected from A, D, E, F, G, H, I, K, L, M, N, P, Q, R, S, T, V, W, and Y.

In IL-2Rα ligands of Formula (13a)-(13c), $X^8$ can be selected from A, G, P, S, and T.

In IL-2Rα ligands of Formula (13a)-(13c), $X^8$ can be A.

In IL-2Rα ligands of Formula (13a)-(13c), $X^9$ can be selected from D and E.

In IL-2Rα ligands of Formula (13a)-(13c), $X^9$ can be D.

In IL-2Rα ligands of Formula (13a)-(13c), $X^{10}$ can be selected from A, G, P, S, and T.

In IL-2Rα ligands of Formula (13a)-(13c), $X^{10}$ can be S.

In IL-2Rα ligands of Formula (13a)-(13c), $X^{11}$ can be selected from F, I, L, M, V, W, and Y.

In IL-2Rα ligands of Formula (13a)-(13c), $X^{11}$ can be selected from F, W, and Y.

In IL-2Rα ligands of Formula (13a)-(13c), $X^{11}$ can be W.

In IL-2Rα ligands of Formula (13a)-(13c), $X^{12}$ can be selected from F, I, L, M, V, W, and Y.

In IL-2Rα ligands of Formula (13a)-(13c), $X^{12}$ can be selected from D and E.

In IL-2Rα ligands of Formula (13a)-(13c), $X^{12}$ can be selected from V and E.

In IL-2Rα ligands of Formula (13a)-(13c), $X^{12}$ can be V.

In IL-2Rα ligands of Formula (13a)-(13c), $X^{13}$ can be C.

In IL-2Rα ligands of Formula (13a)-(13c), $X^{14}$ can be selected from F, I, L, M, V, W, and Y.

In IL-2Rα ligands of Formula (13a)-(13c), $X^{14}$ can be I.

In IL-2Rα ligands of Formula (13a)-(13c), $X^{15}$ can be F.

In IL-2Rα ligands of Formula (13a)-(13c), $X^2$ can be R, $X^3$ can be C, $X^5$ can be S, $X^6$ can be L, $X^7$ can be V, $X^8$ can be W, $X^{10}$ can be D, $X^{11}$ can be S, $X^{12}$ can be W, $X^{11}$ can be V, $X^{14}$ can be C, $X^{15}$ can be I, and $X^{16}$ can be F.

In IL-2Rα ligands of Formula (13a)-(13c),
$X^1$ can be selected from A, D, E, G, P, S, and T;
$X^2$ can be selected from G and R;
$X^3$ can be C;
$X^4$ can be selected from S and T;
$X^5$ can be L;
$X^6$ can be V;
$X^7$ can be selected from F and W;
$X^8$ can be selected from A, G, P, S, and T;
$X^9$ can be selected from D and E;
$X^{10}$ can be S;
$X^{11}$ can be W;
$X^{12}$ can be V;
$X^{13}$ can be C;
$X^{14}$ can be I; and
$X^{15}$ can be F.

IL-2Rα ligands provided by the present disclosure can comprise an amino acid sequence selected from any one of SEQ ID NO: 152 to SEQ ID NO: 166:

```
                                       SEQ ID NO: 152
       S R C S L V W T D T W V C V F

SEQ ID NO: 153
       S R C T L V F D D S W V C V F

SEQ ID NO: 154
       R G C S L V W S G S W E C I F

SEQ ID NO: 155
       Q A C Q L V W L D S W V C I F
```

```
                                     SEQ ID NO: 156
V G C S L V W T D R W E C I F

SEQ ID NO: 157
S G C S L Q W A D G W V C I F

SEQ ID NO: 158
A R C S L V W D E A W V C I F

SEQ ID NO: 159
R G C S L V W A G S W E C I F

SEQ ID NO: 160
S R C S L V W A E N W V C I F

SEQ ID NO: 161
R R C T L V F L D S W E C I F

SEQ ID NO: 162
R G C T L A W E D S W V C I F

SEQ ID NO: 163
R G C S L R F A E A W E C I F

SEQ ID NO: 164
A S C S L V W Q D S W V C I F

SEQ ID NO: 165
S R C S L V W A D S W V C I F

SEQ ID NO: 166
G R C H L V W S D R W E C I F
```

An IL-2Rα ligand provided by the present disclosure can comprise a truncated amino acid sequence of any one of SEQ ID NO: 149 to SEQ ID NO: 166.

An IL-2Rα ligand provided by the present disclosure can comprise an amino acid sequence selected from any one of SEQ ID NO: 149 to SEQ ID NO: 166, or a truncated amino acid sequence of any one of SEQ ID NO: 149 to SEQ ID NO: 166, wherein the amino acid sequence can independently comprise from 1 to 4 glycines (G) (SEQ ID NO: 1041) on the N-terminus, on the C-terminus, or on both the N- and C-termini.

An IL-2Rα ligand provided by the present disclosure can comprise an amino acid sequence selected from any one of SEQ ID NO: 149 to SEQ ID NO: 166, or a truncated amino acid sequence of any one of SEQ ID NO: 149 to SEQ ID NO: 166, wherein the amino acid sequence comprises one or more amino acid substitutions such as from 1 to 5 amino acid substitutions.

IL-2Rα ligands provided by the present disclosure can comprise the amino acid sequence of Formula (14a) (SEQ ID NO: 167), or the amino acid sequence of Formula (14b) (SEQ ID NO: 168):

$$—X^3—X^4—X^5—X^6—X^7—X^8—X^9—X^{10}—X^{11}—X^{12}— \quad (14a)$$

$$—X^1—C—X^3—X^4—X^5—X^6—X^7—X^8—X^9—X^{10}—X^{11}—X^{12}—C—X^{14}— \quad (14b)$$

wherein, $X^1$ can be selected from an amino acid comprising a small hydrophobic side chain;

$X^2$ can be C;

$X^3$ can be selected from an amino acid comprising a small hydrophobic side chain;

$X^4$ can be selected from an amino acid comprising a large hydrophobic side chain;

$X^5$ can be selected from an amino acid;

$X^6$ can be selected from an amino acid comprising a large hydrophobic side chain;

$X^7$ can be selected from an amino acid comprising an acidic side chain or a polar neutral side chain;

$X^8$ can be selected from an amino acid;

$X^9$ can be selected from an amino acid;

$X^{10}$ can be selected from an amino acid comprising a large hydrophobic side chain;

$X^{11}$ can be selected from an amino acid comprising a large hydrophobic side chain;

$X^{12}$ can be selected from an amino acid comprising a large hydrophobic side chain or an acidic side chain;

$X^{13}$ can be C; and $X^{14}$ can be selected from an amino acid comprising a large hydrophobic side chain.

In IL-2Rα ligands of Formula (14a)-(14b), $X^1$ can be selected from A, G, P, S, and T;

$X^2$ can be C;

$X^3$ can be selected from A, G, P, S, and T;

$X^4$ can be selected from F, I, L, M, V, W, and Y;

$X^5$ can be selected from A, D, E, F, G, H, I, K, L, M, N, P, Q, R, S, T, V, W, and Y;

$X^6$ can be selected from F, I, L, M, V, W, and Y;

$X^7$ can be selected from D, E, N, Q, S, T, and Y;

$X^8$ can be selected from A, D, E, F, G, H, I, K, L, M, N, P, Q, R, S, T, V, W, and Y;

$X^9$ can be selected from A, D, E, F, G, H, I, K, L, M, N, P, Q, R, S, T, V, W, and Y;

$X^{10}$ can be selected from F, I, L, M, V, W, and Y;

$X^{11}$ can be selected from F, I, L, M, V, W, and Y;

$X^{12}$ can be selected from D, E, F, I, L, M, V, W, and Y;

$X^{13}$ can be C; and $X^{14}$ can be selected from F, I, L, M, V, W, and Y.

In IL-2Rα ligands of Formula (14a)-(14b), $X^1$ can be selected from G and S.

In IL-2Rα ligands of Formula (14a)-(14b), $X^2$ can be C.

In IL-2Rα ligands of Formula (14a)-(14b), $X^3$ can be selected from T, S, M, and V.

In IL-2Rα ligands of Formula (14a)-(14b), $X^4$ can be selected from L and V.

In IL-2Rα ligands of Formula (14a)-(14b), $X^5$ can be selected from K, R, M, S, T, and Q.

In IL-2Rα ligands of Formula (14a)-(14b), $X^6$ can be selected from W, R, and F.

In IL-2Rα ligands of Formula (14a)-(14b), $X^7$ can be selected from E, D, Q, N, G, and S.

In IL-2Rα ligands of Formula (14a)-(14b), $X^8$ can be selected from S, G, D, Q, K, and G.

In IL-2Rα ligands of Formula (14a)-(14b), $X^9$ can be selected from P, D, G, F, and V.

In IL-2Rα ligands of Formula (14a)-(14b), $X^{10}$ can be selected from N and W.

In IL-2Rα ligands of Formula (14a)-(14b), $X^{11}$ can be W.

In IL-2Rα ligands of Formula (14a)-(14b), $X^{12}$ can be selected from T, V, H, and E.

In IL-2Rα ligands of Formula (14a)-(14b), $X^{13}$ can be C.

In IL-2Rα ligands of Formula (14a)-(14b), $X^{14}$ can be selected from Y, E, I, and V.

In IL-2Rα ligands of Formula (14a)-(14b), $X^1$ can be G.

In IL-2Rα ligands of Formula (14a)-(14b), $X^2$ can be C.

In IL-2Rα ligands of Formula (14a)-(14b), $X^3$ can be selected from S and T.

In IL-2Rα ligands of Formula (14a)-(14b), $X^3$ can be T.

In IL-2Rα ligands of Formula (14a)-(14b), $X^4$ can be L.

In IL-2Rα ligands of Formula (14a)-(14b), $X^5$ can be selected from A, D, E, F, G, H, I, K, L, M, N, P, Q, R, S, T, V, W, and Y.

In IL-2Rα ligands of Formula (14a)-(14b), $X^6$ can be W.

In IL-2Rα ligands of Formula (14a)-(14b), $X^7$ can be selected from D, E, Q, and N.

In IL-2Rα ligands of Formula (14a)-(14b), $X^8$ can be selected from A, D, E, F, G, H, I, K, L, M, N, P, Q, R, S, T, V, W, and Y.

In IL-2Rα ligands of Formula (14a)-(14b), $X^9$ can be selected from A, D, E, F, G, H, I, K, L, M, N, P, Q, R, S, T, V, W, and Y.

In IL-2Rα ligands of Formula (14a)-(14b), $X^{10}$ can be W.

In IL-2Rα ligands of Formula (14a)-(14b), $X^{11}$ can be W.

In IL-2Rα ligands of Formula (14a)-(14b), $X^{12}$ can be selected from F, I, L, M, V, W, and Y.

In IL-2Rα ligands of Formula (14a)-(14b), $X^{12}$ can be selected from D and E.

In IL-2Rα ligands of Formula (14a)-(14b), $X^{12}$ can be selected from E and V.

In IL-2Rα ligands of Formula (14a)-(14b), $X^{13}$ can be C.

In IL-2Rα ligands of Formula (14a)-(14b), $X^{14}$ can be selected from F, I, L, M, V, W, and Y.

In IL-2Rα ligands of Formula (14a)-(14b), $X^{14}$ can be selected from I and V.

In IL-2Rα ligands of Formula (14a)-(14b), $X^1$ can be G, $X^2$ can be C, $X^3$ can be T, $X^4$ can be L, $X^6$ can be W, $X^{10}$ can be W, $X^{11}$ can be W, and $X^{11}$ can be C.

In IL-2Rα ligands of Formula (14a)-(14b), $X^1$ can be G;
$X^2$ can be C;
$X^3$ can be selected from T and S;
$X^4$ can be L;
$X^5$ can be selected from A, D, E, F, G, H, I, K, L, M, N, P, Q, R, S, T, V, W, and Y;
$X^6$ can be W;
$X^7$ can be selected from D, E, N, Q, S, T, and Y;
$X^8$ can be selected from A, D, E, F, G, H, I, K, L, M, N, P, Q, R, S, T, V, W, and Y;
$X^9$ can be selected from A, D, E, F, G, H, I, K, L, M, N, P, Q, R, S, T, V, W, and Y;
$X^{10}$ can be W;
$X^{11}$ can be W;
$X^{12}$ can be selected from V and E;
$X^{13}$ can be C; and
$X^{14}$ can be selected from F, I, L, M, V, W, and Y.

IL-2Rα ligands provided by the present disclosure can comprise an amino acid sequence selected from any one of SEQ ID NO: 169 to SEQ ID NO: 174:

```
                                    SEQ ID NO: 169
G C T L K W E S P N W T C Y

SEQ ID NO: 170
S C T V R W D G D W W V C E

SEQ ID NO: 171
G C S L M W Q D G W W V C I

SEQ ID NO: 172
G C T L S W N Q G W W H C V

SEQ ID NO: 173
G C M L T R G K F W W E C I

SEQ ID NO: 174
G C V L Q F S G V W W E C V
```

An IL-2Rα ligand provided by the present disclosure can comprise a truncated amino acid sequence of any one of SEQ ID NO: 167 to SEQ ID NO: 174.

An IL-2Rα ligand provided by the present disclosure can comprise an amino acid sequence selected from any one of SEQ ID NO: 167 to SEQ ID NO: 174, or a truncated amino acid sequence of any one of SEQ ID NO: 167 to SEQ ID NO: 174, wherein the amino acid sequence can independently comprise from 1 to 4 glycines (G) (SEQ ID NO: 1041) on the N-terminus, on the C-terminus, or on both the N- and C-termini.

An IL-2Rα ligand provided by the present disclosure can comprise an amino acid sequence selected from any one of SEQ ID NO: 167 to SEQ ID NO: 174, or a truncated amino acid sequence of any one of SEQ ID NO: 167 to SEQ ID NO: 174, wherein the amino acid sequence comprises one or more amino acid substitutions such as from 1 to 5 amino acid substitutions.

IL-2Rα ligands provided by the present disclosure can comprise the amino acid sequence of Formula (15a) (SEQ ID NO: 175), the amino acid sequence of Formula (15b) (SEQ ID NO: 176), or the amino acid sequence of Formula (15c) (SEQ ID NO: 177):

$$-X^4-X^5-X^6-X^7-X^8-X^9-X^{10}-X^{11}-X^{12}-X^{13}- \quad (15a)$$

$$-X^2-C-X^4-X^5-X^6-X^7-X^8-X^9-X^{10}-X^{11}-X^{12}-X^{13}-C-X^{15}- \quad (15b)$$

$$-X^1-X^2-C-X^4-X^5-X^6-X^7-X^8-X^9-X^{10}-X^{11}-X^{12}-X^{13}-C-X^{15}-X^{16}- \quad (15c)$$

wherein, $X^1$ can be selected from an amino acid;
$X^2$ can be selected from an amino acid;
$X^3$ can be C;
$X^4$ can be selected from an amino acid comprising a polar/neutral side chain or a basic side chain;
$X^5$ can be selected from an amino acid comprising a large hydrophobic side chain;
$X^6$ can be selected from an amino acid;
$X^7$ can be selected from an amino acid comprising a polar neutral side chain or a basic side chain;
$X^8$ can be P;
$X^9$ can be G;
$X^{10}$ can be selected from an amino acid;
$X^{11}$ can be selected from an amino acid;
$X^{12}$ can be selected from an amino acid comprising a large hydrophobic side chain;
$X^{13}$ can be selected from an amino acid comprising an acidic side chain or a polar/neutral side chain;
$X^{14}$ can be C;
$X^{15}$ can be selected from an amino acid comprising a large hydrophobic side chain; and
$X^{16}$ can be selected from an amino acid comprising a large hydrophobic side chain.

In IL-2Rα ligands of Formula (15a)-(15c), $X^1$ can be selected from A, D, E, F, G, H, I, K, L, M, N, P, Q, R, S, T, V, W, and Y;
$X^2$ can be selected from A, D, E, F, G, H, I, K, L, M, N, P, Q, R, S, T, V, W, and Y;
$X^3$ can be C;
$X^4$ can be selected from H, K, N, Q, R, S, T, and Y;
$X^5$ can be selected from F, I, L, M, V, W, and Y;
$X^6$ can be selected from A, D, E, F, G, H, I, K, L, M, N, P, Q, R, S, T, V, W, and Y;
$X^7$ can be selected from H, K, N, Q, R, S, T, and Y;
$X^8$ can be P;
$X^9$ can be G;
$X^{10}$ can be selected from A, D, E, F, G, H, I, K, L, M, N, P, Q, R, S, T, V, W, and Y;
$X^{11}$ can be selected from A, D, E, F, G, H, I, K, L, M, N, P, Q, R, S, T, V, W, and Y;

$X^{12}$ can be selected from F, I, L, M, V, W, and Y;
$X^{13}$ can be selected from D, E, N, Q, S, T, and Y;
$X^{14}$ can be C;
$X^{15}$ can be selected from F, I, L, M, V, W, and Y; and
$X^{16}$ can be selected from F, I, L, M, V, W, and Y.

In IL-2Rα ligands of Formula (15a)-(15c), $X^1$ can be selected from Q, A, G, K, L, N, P, Q, S, and T.

In IL-2Rα ligands of Formula (15a)-(15c), $X^2$ can be selected from R, G, K, T, P, A, S, and H.

In IL-2Rα ligands of Formula (15a)-(15c), $X^3$ can be C.

In IL-2Rα ligands of Formula (15a)-(15c), $X^4$ can be selected from Q, M, S, R, T, I, K, R, H, and L.

In IL-2Rα ligands of Formula (15a)-(15c), $X^5$ can be selected from L, P, M, and V.

In IL-2Rα ligands of Formula (15a)-(15c), $X^6$ can be selected from S, L, R, Q, F, W, N, I, and G.

In IL-2Rα ligands of Formula (15a)-(15c), $X^7$ can be selected from K, H, R, W, L, N, F, and V.

In IL-2Rα ligands of Formula (15a)-(15c), $X^8$ can be selected from S, P, T, and L.

In IL-2Rα ligands of Formula (15a)-(15c), $X^9$ can be G.

In IL-2Rα ligands of Formula (15a)-(15c), $X^{10}$ can be selected from G, L, S, D, T, E, M, N, F, H, R, K, and P.

In IL-2Rα ligands of Formula (15a)-(15c), $X^{11}$ can be selected from E, Y, R, G, H, S, I, G, L, W, F, and V.

In IL-2Rα ligands of Formula (15a)-(15c), $X^{12}$ can be selected from L, W, Y, H, and V.

In IL-2Rα ligands of Formula (15a)-(15c), $X^{13}$ can be selected from G, E, V, T, Q, and A.

In IL-2Rα ligands of Formula (15a)-(15c), $X^{14}$ can be C.

In IL-2Rα ligands of Formula (15a)-(15c), $X^{15}$ can be selected from M, I, V, L, W, R, and F.

In IL-2Rα ligands of Formula (15a)-(15c), $X^{16}$ can be selected from F, S, and G.

In IL-2Rα ligands of Formula (15a)-(15c), $X^1$ can be selected from S and T.

In IL-2Rα ligands of Formula (15a)-(15c), $X^2$ can be selected from S, T, R, and K.

In IL-2Rα ligands of Formula (15a)-(15c), $X^3$ can be C.

In IL-2Rα ligands of Formula (15a)-(15c), $X^4$ can be selected from N, Q, S, T, and Y.

In IL-2Rα ligands of Formula (15a)-(15c), $X^4$ can be T.

In IL-2Rα ligands of Formula (15a)-(15c), $X^5$ can be selected from L, M, and V.

In IL-2Rα ligands of Formula (15a)-(15c), $X^5$ can be L.

In IL-2Rα ligands of Formula (15a)-(15c), $X^6$ can be selected from A, D, E, F, G, H, I, K, L, M, N, P, Q, R, S, T, V, W, and Y.

In IL-2Rα ligands of Formula (15a)-(15c), $X^7$ can be selected from N, K, H, and R.

In IL-2Rα ligands of Formula (15a)-(15c), $X^7$ can be N.

In IL-2Rα ligands of Formula (15a)-(15c), $X^8$ can be selected from A, D, E, F, G, H, I, K, L, M, N, P, Q, R, S, T, V, W, and Y.

In IL-2Rα ligands of Formula (15a)-(15c), $X^8$ can be selected from A, G, P, S, and T.

In IL-2Rα ligands of Formula (15a)-(15c), $X^8$ can be P.

In IL-2Rα ligands of Formula (15a)-(15c), $X^9$ can be G.

In IL-2Rα ligands of Formula (15a)-(15c), $X^{10}$ can be selected from A, D, E, F, G, H, I, K, L, M, N, P, Q, R, S, T, V, W, and Y.

In IL-2Rα ligands of Formula (15a)-(15c), $X^{11}$ can be selected from A, D, E, F, G, H, I, K, L, M, N, P, Q, R, S, T, V, W, and Y.

In IL-2Rα ligands of Formula (15a)-(15c), $X^{11}$ can be selected from A, G, P, S, and T.

In IL-2Rα ligands of Formula (15a)-(15c), $X^{11}$ can be G.

In IL-2Rα ligands of Formula (15a)-(15c), $X^{12}$ can be W.

In IL-2Rα ligands of Formula (15a)-(15c), $X^{13}$ can be selected from N, Q, S, T, and Y.

In IL-2Rα ligands of Formula (15a)-(15c), $X^{13}$ can be selected from D and E.

In IL-2Rα ligands of Formula (15a)-(15c), $X^{13}$ can be selected from E and Q.

In IL-2Rα ligands of Formula (15a)-(15c), $X^{13}$ can be E.

In IL-2Rα ligands of Formula (15a)-(15c), $X^{14}$ can be C.

In IL-2Rα ligands of Formula (15a)-(15c), $X^{15}$ can be selected from F, I, L, M, V, W, and Y.

In IL-2Rα ligands of Formula (15a)-(15c), $X^{15}$ can be selected from M, I, V, L, and F.

In IL-2Rα ligands of Formula (15a)-(15c), $X^{15}$ can be selected from I and V.

In IL-2Rα ligands of Formula (15a)-(15c), $X^{16}$ can be F.

In IL-2Rα ligands of Formula (15a)-(15c), $X^3$ can be C, $X^5$ can be L, $X^8$ can be P, $X^9$ can be G, $X^{12}$ can be W, $X^{13}$ can be E, $X^{14}$ can be C, and $X^{16}$ can be F.

In IL-2Rα ligands of Formula (15a)-(15c),
$X^1$ can be selected from A, D, E, F, G, H, I, K, L, M, N, P, Q, R, S, T, V, W, and Y;
$X^2$ can be selected from A, D, E, F, G, H, I, K, L, M, N, P, Q, R, S, T, V, W, and Y;
$X^3$ can be C;
$X^4$ can be selected from N, Q, S, T, and Y;
$X^5$ can be L;
$X^6$ can be selected from A, D, E, F, G, H, I, K, L, M, N, P, Q, R, S, T, V, W, and Y;
$X^7$ can be selected from N, Q, S, T, and Y;
$X^8$ can be P;
$X^9$ can be G;
$X^{10}$ can be selected from A, D, E, F, G, H, I, K, L, M, N, P, Q, R, S, T, V, W, and Y;
$X^{11}$ can be selected from A, G, P, S, and T;
$X^{12}$ can be W;
$X^{13}$ can be selected from E and Q;
$X^{14}$ can be C;
$X^{15}$ can be selected from F, I, L, M, V, W, and Y; and
$X^{16}$ can be F.

IL-2Rα ligands provided by the present disclosure can comprise an amino acid sequence selected from any one of SEQ ID NO: 178 to SEQ ID NO: 195:

```
                                       SEQ ID NO: 178
   Q R C Q L S W S G G E L G C M F

SEQ ID NO: 179
   A G C M L L K P G L Y W E C I F

SEQ ID NO: 180
   A R C S L H H T G S R Y E C I F

SEQ ID NO: 181
   A T C M L R L L G D G W G C V F

SEQ ID NO: 182
   G P C R L S N P G T G W E C I F

SEQ ID NO: 183
   K G C T L Q N P G S G W V C L F

SEQ ID NO: 184
   L A C I L S K P G E H W E C L F

SEQ ID NO: 185
   N G C T S F S S G M S W T C V Y

SEQ ID NO: 186
   N S C I L S N P G L G W Q C V F
```

```
                                   SEQ ID NO: 187
N T C K L F R S G N I W Q C I F

SEQ ID NO: 188
P S C R L W N P G F G W E C I F

SEQ ID NO: 189
Q S C T L Q R L G H L Y Q C W F

SEQ ID NO: 190
S A C T P N W T G R W W E C V F

SEQ ID NO: 191
S K C H L I V S G K F H E C V F

SEQ ID NO: 192
S S C T L F N P G T G W T C V F

SEQ ID NO: 193
S T C R M G N P G G V W G C Y F

SEQ ID NO: 194
T H C L V Q W P G P V V A C R S

SEQ ID NO: 195
T R C R L L K L G S L W E C F G
```

An IL-2Rα ligand provided by the present disclosure can comprise a truncated amino acid sequence of any one of SEQ ID NO: 175 to SEQ ID NO: 195.

An IL-2Rα ligand provided by the present disclosure can comprise an amino acid sequence selected from any one of SEQ ID NO: 175 to SEQ ID NO: 195, or a truncated amino acid sequence of any one of SEQ ID NO: 175 to SEQ ID NO: 195, wherein the amino acid sequence can independently comprise from 1 to 4 glycines (G) (SEQ ID NO: 1041) on the N-terminus, on the C-terminus, or on both the N- and C-termini.

An IL-2Rα ligand provided by the present disclosure can comprise an amino acid sequence selected from any one of SEQ ID NO: 175 to SEQ ID NO: 195, or a truncated amino acid sequence of any one of SEQ ID NO: 175 to SEQ ID NO: 195, wherein the amino acid sequence comprises one or more amino acid substitutions such as from 1 to 5 amino acid substitutions.

IL-2Rα ligands provided by the present disclosure can comprise the amino acid sequence of Formula (16a) (SEQ ID NO: 196), or the amino acid sequence of Formula (16b) (SEQ ID NO: 197):

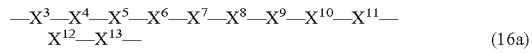

$$-X^3-X^4-X^5-X^6-X^7-X^8-X^9-X^{10}-X^{11}-X^{12}-X^{13}-\quad(16a)$$

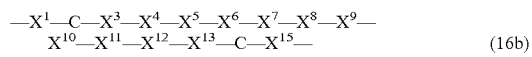

$$-X^1-C-X^3-X^4-X^5-X^6-X^7-X^8-X^9-X^{10}-X^{11}-X^{12}-X^{13}-C-X^{15}-\quad(16b)$$

wherein,
$X^1$ can be selected from an amino acid;
$X^2$ can be C;
$X^3$ can be selected from an amino acid comprising a basic side chain;
$X^4$ can be selected from an amino acid comprising a large hydrophobic side chain;
$X^5$ can be selected from an amino acid comprising a basic side chain or a polar/neutral side chain;
$X^6$ can be selected from an amino acid comprising a basic side chain or a polar/neutral side chain;
$X^7$ can be selected from an amino acid;
$X^8$ can be selected from an amino acid;
$X^9$ can be selected from an amino acid;
$X^{10}$ can be selected from an amino acid;
$X^{11}$ can be selected from an amino acid;
$X^{12}$ can be selected from an amino acid comprising an aromatic side chain or a large hydrophobic side chain;
$X^{13}$ can be selected from an amino acid comprising an acidic side chain;
$X^{14}$ can be C; and
$X^1$ can be selected from an amino acid comprising a large hydrophobic side chain.

In IL-2Rα ligands of Formula (16a)-(16b),
$X^1$ can be selected from A, D, E, F, G, H, I, K, L, M, N, P, Q, R, S, T, V, W, and Y;
$X^2$ can be selected from C;
$X^3$ can be selected from H, K, and R;
$X^4$ can be selected from F, I, L, M, V, W, and Y;
$X^5$ can be selected from H, K, N, Q, R, S, T, and Y;
$X^6$ can be selected from H, K, N, Q, R, S, T, and Y;
$X^7$ can be selected from A, D, E, F, G, H, I, K, L, M, N, P, Q, R, S, T, V, W, and Y;
$X^8$ can be selected from A, D, E, F, G, H, I, K, L, M, N, P, Q, R, S, T, V, W, and Y;
$X^9$ can be selected from A, D, E, F, G, H, I, K, L, M, N, P, Q, R, S, T, V, W, and Y;
$X^{10}$ can be selected from A, D, E, F, G, H, I, K, L, M, N, P, Q, R, S, T, V, W, and Y;
$X^{11}$ can be selected from A, D, E, F, G, H, I, K, L, M, N, P, Q, R, S, T, V, W, and Y;
$X^{12}$ can be selected from F, H, I, L, M, V, W, and Y;
$X^{13}$ can be selected from D and E;
$X^{14}$ can be C; and
$X^{15}$ can be selected from F, I, L, M, V, W, and Y.

In IL-2Rα ligands of Formula (16a)-(16b), $X^1$ can be selected from A, K, N, R, and T.
In IL-2Rα ligands of Formula (16a)-(16b), $X^2$ can be C.
In IL-2Rα ligands of Formula (16a)-(16b), $X^3$ can be selected from W, R, and T.
In IL-2Rα ligands of Formula (16a)-(16b), $X^4$ can be selected from R, L, and V.
In IL-2Rα ligands of Formula (16a)-(16b), $X^5$ can be selected from S, R, Q, K, and H.
In IL-2Rα ligands of Formula (16a)-(16b), $X^6$ can be selected from W, Q, H, K, F, and R.
In IL-2Rα ligands of Formula (16a)-(16b), $X^7$ can be selected from R, M, L, A, D, S, and I.
In IL-2Rα ligands of Formula (16a)-(16b), $X^8$ can be selected from Y, S, P, G, and A.
In IL-2Rα ligands of Formula (16a)-(16b), $X^9$ can be selected from P, R, Y, G, Q, P, and L.
In IL-2Rα ligands of Formula (16a)-(16b), $X^{10}$ can be selected from T, G, P, N, T, N, and A.
In IL-2Rα ligands of Formula (16a)-(16b), $X^{11}$ can be selected from R, G, F, T, G, S, and E.
In IL-2Rα ligands of Formula (16a)-(16b), $X^{12}$ can be selected from T and W.
In IL-2Rα ligands of Formula (16a)-(16b), $X^{13}$ can be selected from F, E, and S.
In IL-2Rα ligands of Formula (16a)-(16b), $X^{14}$ can be C.
In IL-2Rα ligands of Formula (16a)-(16b), $X^{15}$ can be selected from S, L, N, I, and V.
In IL-2Rα ligands of Formula (16a)-(16b), $X^2$ can be C.
In IL-2Rα ligands of Formula (16a)-(16b), $X^3$ can be R.
In IL-2Rα ligands of Formula (16a)-(16b), $X^4$ can be selected from L and V.
In IL-2Rα ligands of Formula (16a)-(16b), $X^5$ can be selected from R, K, and H.
In IL-2Rα ligands of Formula (16a)-(16b), $X^6$ can be selected from R, K, and H.

In IL-2Rα ligands of Formula (16a)-(16b), $X^7$ can be selected from A, D, E, F, G, H, I, K, L, M, N, P, Q, R, S, T, V, W, and Y.

In IL-2Rα ligands of Formula (16a)-(16b), $X^8$ can be selected from A, D, E, F, G, H, I, K, L, M, N, P, Q, R, S, T, V, W, and Y.

In IL-2Rα ligands of Formula (16a)-(16b), $X^8$ can be G.

In IL-2Rα ligands of Formula (16a)-(16b), $X^9$ can be selected from A, D, E, F, G, H, I, K, L, M, N, P, Q, R, S, T, V, W, and Y.

In IL-2Rα ligands of Formula (16a)-(16b), $X^{10}$ can be selected from A, D, E, F, G, H, I, K, L, M, N, P, Q, R, S, T, V, W, and Y.

In IL-2Rα ligands of Formula (16a)-(16b), $X^{11}$ can be selected from A, D, E, F, G, H, I, K, L, M, N, P, Q, R, S, T, V, W, and Y.

In IL-2Rα ligands of Formula (16a)-(16b), $X^{12}$ can be selected from F, I, L, M, V, W, and Y.

In IL-2Rα ligands of Formula (16a)-(16b), $X^{12}$ can be selected from F, W, and Y.

In IL-2Rα ligands of Formula (16a)-(16b), $X^{12}$ can be W.

In IL-2Rα ligands of Formula (16a)-(16b), $X^{13}$ can be E.

In IL-2Rα ligands of Formula (16a)-(16b), $X^{14}$ can be C.

In IL-2Rα ligands of Formula (16a)-(16b), $X^{15}$ can be selected from F, I, L, M, V, W, and Y.

In IL-2Rα ligands of Formula (16a)-(16b), $X^{15}$ can be selected from L, I, and V.

In IL-2Rα ligands of Formula (16a)-(16b), $X^2$ can be C, $X^3$ can be R, $X^{12}$ can be W, $X^{11}$ can be E, and $X^{14}$ can be C.

In IL-2Rα ligands of Formula (16a)-(16b),
$X^2$ can be C;
$X^3$ can be R;
$X^4$ can be selected from F, I, L, M, V, W, and Y;
$X^5$ can be selected from N, Q, S, T, and Y;
$X^6$ can be selected from N, Q, S, T, and Y;
$X^7$ can be selected from A, D, E, F, G, H, I, K, L, M, N, P, Q, R, S, T, V, W, and Y;
$X^8$ can be selected from A, G, P, S, and T;
$X^9$ can be selected from A, D, E, F, G, H, I, K, L, M, N, P, Q, R, S, T, V, W, and Y;
$X^{10}$ can be selected from A, D, E, F, G, H, I, K, L, M, N, P, Q, R, S, T, V, W, and Y;
$X^{11}$ can be selected from A, D, E, F, G, H, I, K, L, M, N, P, Q, R, S, T, V, W, and Y;
$X^{12}$ can be W;
$X^{13}$ can be E;
$X^{14}$ can be C; and
$X^{15}$ can be selected from F, I, L, M, V, W, and Y.

IL-2Rα ligands provided by the present disclosure can comprise an amino acid sequence selected from any one of SEQ ID NO: 189 to SEQ ID NO: 204:

```
                                SEQ ID NO: 198
A C W R S W R Y P T R T F C S

SEQ ID NO: 199
K C R L R Q M S R G G W E C L

SEQ ID NO: 200
N C R V R H L P Y P F W S C L

SEQ ID NO: 201
R C R L Q K A G G N T W E C I

SEQ ID NO: 202
R C T L R F D A Q T G W E C N

SEQ ID NO: 203
T C R L K R S G P N S W E C I

SEQ ID NO: 204
T C T V H R I G L A E W E C V
```

An IL-2Rα ligand provided by the present disclosure can comprise a truncated amino acid sequence of any one of SEQ ID NO: 196 to SEQ ID NO: 204.

An IL-2Rα ligand provided by the present disclosure can comprise an amino acid sequence selected from any one of SEQ ID NO: 196 to SEQ ID NO: 204, or a truncated amino acid sequence of any one of SEQ ID NO: 196 to SEQ ID NO: 204, wherein the amino acid sequence can independently comprise from 1 to 4 glycines (G) (SEQ ID NO: 1041) on the N-terminus, on the C-terminus, or on both the N- and C-termini.

An IL-2Rα ligand provided by the present disclosure can comprise an amino acid sequence selected from any one of SEQ ID NO: 196 to SEQ ID NO: 204, or a truncated amino acid sequence of any one of SEQ ID NO: 196 to SEQ ID NO: 204, wherein the amino acid sequence comprises one or more amino acid substitutions such as from 1 to 5 amino acid substitutions.

IL-2Rα ligands provided by the present disclosure can comprise the amino acid sequence of Formula (17a) (SEQ ID NO: 205), the amino acid sequence of Formula (17b) (SEQ ID NO: 206), or the amino acid sequence of Formula (17c) (SEQ ID NO: 207):

$$-X^4-X^5-X^6-X^7-X^8-X^9-X^{10}-X^{11}-X^{12}-X^{13}- \quad (17a)$$

$$-X^2-C-X^4-X^5-X^6-X^7-X^8-X^9-X^{10}-X^{11}-X^{12}-X^{13}-C-X^{15}- \quad (17b)$$

$$-X^1-X^2-C-X^4-X^5-X^6-X^7-X^8-X^9-X^{10}-X^{11}-X^{12}-X^{13}-CX^{15}-X^{16}- \quad (17c)$$

wherein, $X^1$ can be selected from an amino acid comprising a large hydrophobic side chain;

$X^2$ can be selected from an amino acid comprising a basic side chain;

$X^3$ can be C;

$X^4$ can be selected from an amino acid comprising a basic side chain;

$X^5$ can be selected from an amino acid comprising a basic side chain or an aromatic side chain or a large hydrophobic side chain;

$X^6$ can be selected from an amino acid;

$X^7$ can be selected from an amino acid;

$X^8$ can be P;

$X^9$ can be G;

$X^{10}$ can be selected from an amino acid;

$X^{11}$ can be selected from an amino acid;

$X^{12}$ can be selected from an amino acid;

$X^{13}$ can be selected from an amino acid;

$X^{14}$ can be C;

$X^{15}$ can be selected from an amino acid comprising a large hydrophobic side chain; and $X^{16}$ can be selected from an amino acid comprising a small hydrophobic side chain.

In IL-2Rα ligands of Formula (17a)-(17c), $X^1$ can be selected from F, I, L, M, V, W, and Y;

$X^2$ can be selected from H, K, and R;

$X^3$ can be C;

$X^4$ can be selected from H, K, and R;

$X^5$ can be selected from F, H, I, K, L, M, R, V, W, and Y;

$X^6$ can be selected from A, D, E, F, G, H, I, K, L, M, N, P, Q, R, S, T, V, W, and Y;
$X^7$ can be selected from A, D, E, F, G, H, I, K, L, M, N, P, Q, R, S, T, V, W, and Y;
$X^8$ can be P;
$X^9$ can be G;
$X^{10}$ can be selected from A, D, E, F, G, H, I, K, L, M, N, P, Q, R, S, T, V, W, and Y;
$X^{11}$ can be selected from A, D, E, F, G, H, I, K, L, M, N, P, Q, R, S, T, V, W, and Y;
$X^{12}$ can be selected from A, D, E, F, G, H, I, K, L, M, N, P, Q, R, S, T, V, W, and Y;
$X^{13}$ can be selected from A, D, E, F, G, H, I, K, L, M, N, P, Q, R, S, T, V, W, and Y;
$X^{14}$ can be C;
$X^{15}$ can be selected from F, I, L, M, V, W, and Y; and
$X^{16}$ can be selected from F, I, L, M, V, W, and Y.
In IL-2Rα ligands of Formula (17a)-(17c), $X^1$ can be V.
In IL-2Rα ligands of Formula (17a)-(17c), $X^2$ can be selected from K, R, T, and Y.
In IL-2Rα ligands of Formula (17a)-(17c), $X^3$ can be C.
In IL-2Rα ligands of Formula (17a)-(17c), $X^4$ can be selected from K, F, R, and Y.
In IL-2Rα ligands of Formula (17a)-(17c), $X^5$ can be selected from L, M, V, and R.
In IL-2Rα ligands of Formula (17a)-(17c), $X^6$ can be selected from V, S, A, L, and E.
In IL-2Rα ligands of Formula (17a)-(17c), $X^7$ can be selected from M, E, R, Y, V, and K.
In IL-2Rα ligands of Formula (17a)-(17c), $X^8$ can be P.
In IL-2Rα ligands of Formula (17a)-(17c), $X^9$ can be G.
In IL-2Rα ligands of Formula (17a)-(17c), $X^{10}$ can be selected from S, R, L, Q, V, and G.
In IL-2Rα ligands of Formula (17a)-(17c), $X^{11}$ can be selected from G, V, T, M, and E.
In IL-2Rα ligands of Formula (17a)-(17c), $X^{12}$ can be selected from W, S, W, A, and M.
In IL-2Rα ligands of Formula (17a)-(17c), $X^{13}$ can be selected from A, Y, E, V, and H.
In IL-2Rα ligands of Formula (17a)-(17c), $X^{14}$ can be C.
In IL-2Rα ligands of Formula (17a)-(17c), $X^{14}$ can be selected from H, T, L, V, F, and R.
In IL-2Rα ligands of Formula (17a)-(17c), $X^{14}$ can be selected from F, A, and S.
In IL-2Rα ligands of Formula (17a)-(17c), $X^1$ can be V.
In IL-2Rα ligands of Formula (17a)-(17c), $X^2$ can be R.
In IL-2Rα ligands of Formula (17a)-(17c), $X^3$ can be C.
In IL-2Rα ligands of Formula (17a)-(17c), $X^4$ can be R.
In IL-2Rα ligands of Formula (17a)-(17c), $X^5$ can be selected from F, I, L, M, V, W, and Y.
In IL-2Rα ligands of Formula (17a)-(17c), $X^5$ can be selected from F, W, and Y.
In IL-2Rα ligands of Formula (17a)-(17c), $X^5$ can be selected from H, K, and R.
In IL-2Rα ligands of Formula (17a)-(17c), $X^6$ can be selected from A, D, E, F, G, H, I, K, L, M, N, P, Q, R, S, T, V, W, and Y.
In IL-2Rα ligands of Formula (17a)-(17c), $X^7$ can be selected from A, D, E, F, G, H, I, K, L, M, N, P, Q, R, S, T, V, W, and Y.
In IL-2Rα ligands of Formula (17a)-(17c), $X^8$ can be P.
In IL-2Rα ligands of Formula (17a)-(17c), $X^9$ can be G.
In IL-2Rα ligands of Formula (17a)-(17c), $X^{10}$ can be selected from A, D, E, F, G, H, I, K, L, M, N, P, Q, R, S, T, V, W, and Y.

In IL-2Rα ligands of Formula (17a)-(17c), $X^{11}$ can be selected from A, D, E, F, G, H, I, K, L, M, N, P, Q, R, S, T, V, W, and Y.
In IL-2Rα ligands of Formula (17a)-(17c), $X^{12}$ can be selected from A, D, E, F, G, H, I, K, L, M, N, P, Q, R, S, T, V, W, and Y.
In IL-2Rα ligands of Formula (17a)-(17c), $X^{13}$ can be selected from A, D, E, F, G, H, I, K, L, M, N, P, Q, R, S, T, V, W, and Y.
In IL-2Rα ligands of Formula (17a)-(17c), $X^{14}$ can be C.
In IL-2Rα ligands of Formula (17a)-(17c), $X^{15}$ can be selected from F, I, L, M, V, W, and Y.
In IL-2Rα ligands of Formula (17a)-(17c), $X^{16}$ can be S.
In IL-2Rα ligands of Formula (17a)-(17c), $X^1$ can be V, $X^2$ can be R, $X^3$ can be C, $X^4$ can be R, $X^{14}$ can be C, and $X^{16}$ can be S.
In IL-2Rα ligands of Formula (17a)-(17c),
$X^1$ can be V;
$X^2$ can be R;
$X^3$ can be C;
$X^4$ can be R;
$X^5$ can be selected from H, F, I, K, L, M, R, V, W, and Y;
$X^6$ can be selected from A, D, E, F, G, H, I, K, L, M, N, P, Q, R, S, T, V, W, and Y;
$X^7$ can be selected from A, D, E, F, G, H, I, K, L, M, N, P, Q, R, S, T, V, W, and Y;
$X^8$ can be P;
$X^9$ can be G;
$X^{10}$ can be selected from A, D, E, F, G, H, I, K, L, M, N, P, Q, R, S, T, V, W, and Y;
$X^{11}$ can be selected from A, D, E, F, G, H, I, K, L, M, N, P, Q, R, S, T, V, W, and Y;
$X^{12}$ can be selected from A, D, E, F, G, H, I, K, L, M, N, P, Q, R, S, T, V, W, and Y;
$X^{13}$ can be selected from A, D, E, F, G, H, I, K, L, M, N, P, Q, R, S, T, V, W, and Y;
$X^{14}$ can be C;
$X^{15}$ can be selected from F, I, L, M, V, W, and Y; and
$X^{16}$ can be S.
IL-2Rα ligands provided by the present disclosure can comprise an amino acid sequence selected from any one of SEQ ID NO: 208 to SEQ ID NO: 213:

```
                                    SEQ ID NO: 208
         V K C K L V N P G S G W A C H F

SEQ ID NO: 209
         V R C F M S E P G R V S Y C T A

SEQ ID NO: 210
         V R C R L A R P G L T W E C L S

SEQ ID NO: 211
         V R C R V L Y P G Q M A V C V S

SEQ ID NO: 212
         V T C Y R A V P G V E A Y C F S

SEQ ID NO: 213
         V Y C R R E K P G G E M H C R S
```

An IL-2Rα ligand provided by the present disclosure can comprise a truncated amino acid sequence of any one of SEQ ID NO: 205 to SEQ ID NO: 213.
An IL-2Rα ligand provided by the present disclosure can comprise an amino acid sequence selected from any one of SEQ ID NO: 205 to SEQ ID NO: 213, or a truncated amino acid sequence of any one of SEQ ID NO: 205 to SEQ ID NO: 213, wherein the amino acid sequence can independently comprise from 1 to 4 glycines (G) (SEQ ID NO: 1041) on the N-terminus, on the C-terminus, or on both the N- and C-termini.

An IL-2Rα ligand provided by the present disclosure can comprise an amino acid sequence selected from any one of SEQ ID NO: 205 to SEQ ID NO: 213, or a truncated amino acid sequence of any one of SEQ ID NO: 205 to SEQ ID NO: 213, wherein the amino acid sequence comprises one or more amino acid substitutions such as from 1 to 5 amino acid substitutions.

IL-2Rα ligands provided by the present disclosure can comprise the amino acid sequence of Formula (18a) (SEQ ID NO: 214), the amino acid sequence of Formula (18b) (SEQ ID NO: 215), or the amino acid sequence of Formula (18c) (SEQ ID NO: 216):

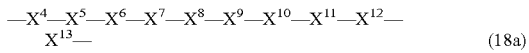
(18a)

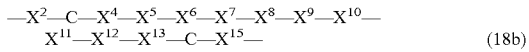
(18b)

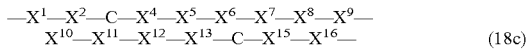
(18c)

wherein, $X^1$ can be selected from an amino acid;
$X^2$ can be selected from an amino acid;
$X^3$ can be C;
$X^4$ can be selected from an amino acid comprising an aromatic side chain or a large hydrophobic side chain;
$X^5$ can be selected from an amino acid comprising a large hydrophobic side chain;
$X^6$ can be selected from an amino acid;
$X^7$ can be selected from an amino acid;
$X^8$ can be P;
$X^9$ can be G;
$X^{10}$ can be selected from an amino acid;
$X^{11}$ can be selected from an amino acid;
$X^{12}$ can be selected from an amino acid;
$X^{13}$ can be selected from an amino acid comprising an aromatic side chain or a large hydrophobic side chain;
$X^{14}$ can be C;
$X^{15}$ can be selected from an amino acid; and
$X^{16}$ can be selected from an amino acid comprising a large hydrophobic side chain.

In IL-2Rα ligands of Formula (18a)-(18c),
$X^1$ can be selected from A, D, E, F, G, H, I, K, L, M, N, P, Q, R, S, T, V, W, and Y;
$X^2$ can be selected from A, D, E, F, G, H, I, K, L, M, N, P, Q, R, S, T, V, W, and Y;
$X^3$ can be C;
$X^4$ can be selected from F, H, I, L, M, V, W, and Y;
$X^5$ can be selected from F, I, L, M, V, W, and Y;
$X^6$ can be selected from A, D, E, F, G, H, I, K, L, M, N, P, Q, R, S, T, V, W, and Y;
$X^7$ can be selected from A, D, E, F, G, H, I, K, L, M, N, P, Q, R, S, T, V, W, and Y;
$X^8$ can be P;
$X^9$ can be G;
$X^{10}$ can be selected from A, D, E, F, G, H, I, K, L, M, N, P, Q, R, S, T, V, W, and Y;
$X^{11}$ can be selected from A, D, E, F, G, H, I, K, L, M, N, P, Q, R, S, T, V, W, and Y;
$X^{12}$ can be selected from A, D, E, F, G, H, I, K, L, M, N, P, Q, R, S, T, V, W, and Y;
$X^{13}$ can be selected from F, H, I, L, M, V, W, and Y;
$X^{14}$ can be C;
$X^{15}$ can be selected from A, D, E, F, G, H, I, K, L, M, N, P, Q, R, S, T, V, W, and Y; and
$X^{16}$ can be selected from F, I, L, M, V, W, and Y.

In IL-2Rα ligands of Formula (18a)-(18c), $X^1$ can be selected from A, H, Q, R, T, and V.
In IL-2Rα ligands of Formula (18a)-(18c), $X^2$ can be selected from T, G, L, D, and K.
In IL-2Rα ligands of Formula (18a)-(18c), $X^3$ can be C.
In IL-2Rα ligands of Formula (18a)-(18c), $X^4$ can be selected from H, T, P, A, F, Q, and Y.
In IL-2Rα ligands of Formula (18a)-(18c), $X^5$ can be selected from L, W, G, I, E, M, and R.
In IL-2Rα ligands of Formula (18a)-(18c), $X^6$ can be selected from L, T, S, M, and N.
In IL-2Rα ligands of Formula (18a)-(18c), $X^7$ can be selected from A, K, D, E, W, T, and S.
In IL-2Rα ligands of Formula (18a)-(18c), $X^8$ can be P.
In IL-2Rα ligands of Formula (18a)-(18c), $X^9$ can be G.
In IL-2Rα ligands of Formula (18a)-(18c), $X^{10}$ can be selected from V, A, S, T, D, Q, and V.
In IL-2Rα ligands of Formula (18a)-(18c), $X^{11}$ can be selected from D, E, W, S, R, and I.
In IL-2Rα ligands of Formula (18a)-(18c), $X^{12}$ can be selected from N, W, G, V, P, and A.
In IL-2Rα ligands of Formula (18a)-(18c), $X^{13}$ can be selected from T, V, P, F, Y, and W.
In IL-2Rα ligands of Formula (18a)-(18c), $X^{14}$ can be C.
In IL-2Rα ligands of Formula (18a)-(18c), $X^{14}$ can be selected from I, S, P, D, H, T, and V.
In IL-2Rα ligands of Formula (18a)-(18c), $X^{14}$ can be selected from F, L, N, I, T, and G.
In IL-2Rα ligands of Formula (18a)-(18c), $X^1$ can be selected from A, D, E, F, G, H, I, K, L, M, N, P, Q, R, S, T, V, W, and Y.
In IL-2Rα ligands of Formula (18a)-(18c), $X^2$ can be selected from A, D, E, F, G, H, I, K, L, M, N, P, Q, R, S, T, V, W, and Y.
In IL-2Rα ligands of Formula (18a)-(18c), $X^3$ can be C.
In IL-2Rα ligands of Formula (18a)-(18c), $X^4$ can be selected from F, H, I, L, M, V, W, and Y.
In IL-2Rα ligands of Formula (18a)-(18c), $X^4$ can be selected from F, W, and Y.
In IL-2Rα ligands of Formula (18a)-(18c), $X^5$ can be selected from F, I, L, M, V, W, and Y.
In IL-2Rα ligands of Formula (18a)-(18c), $X^6$ can be selected from A, D, E, F, G, H, I, K, L, M, N, P, Q, R, S, T, V, W, and Y.
In IL-2Rα ligands of Formula (18a)-(18c), $X^7$ can be selected from A, D, E, F, G, H, I, K, L, M, N, P, Q, R, S, T, V, W, and Y.
In IL-2Rα ligands of Formula (18a)-(18c), $X^8$ can be P.
In IL-2Rα ligands of Formula (18a)-(18c), $X^9$ can be G.
In IL-2Rα ligands of Formula (18a)-(18c), $X^{10}$ can be selected from A, D, E, F, G, H, I, K, L, M, N, P, Q, R, S, T, V, W, and Y.
In IL-2Rα ligands of Formula (18a)-(18c), $X^{11}$ can be selected from A, D, E, F, G, H, I, K, L, M, N, P, Q, R, S, T, V, W, and Y.
In IL-2Rα ligands of Formula (18a)-(18c), $X^{12}$ can be selected from A, D, E, F, G, H, I, K, L, M, N, P, Q, R, S, T, V, W, and Y.
In IL-2Rα ligands of Formula (18a)-(18c), $X^{13}$ can be selected from F, H, I, L, M, V, W, and Y.
In IL-2Rα ligands of Formula (18a)-(18c), $X^{13}$ can be selected from F, W, and Y.
In IL-2Rα ligands of Formula (18a)-(18c), $X^{14}$ can be C.

In IL-2Rα ligands of Formula (18a)-(18c), $X^{15}$ can be selected from A, D, E, F, G, H, I, K, L, M, N, P, Q, R, S, T, V, W, and Y.

In IL-2Rα ligands of Formula (18a)-(18c), $X^{16}$ can be selected from F, I, L, M, V, W, and Y.

In IL-2Rα ligands of Formula (18a)-(18c), $X^3$ can be C, $X^8$ can be P, $X^9$ can be G, and $X^{14}$ can be C.

In IL-2Rα ligands of Formula (18a)-(18c), $X^1$ can be selected from A, D, E, F, G, H, I, K, L, M, N, P, Q, R, S, T, V, W, and Y;

$X^2$ can be selected from A, D, E, F, G, H, I, K, L, M, N, P, Q, R, S, T, V, W, and Y;

$X^3$ can be C;

$X^4$ can be selected from F, H, W, and Y;

$X^5$ can be selected from F, I, L, M, V, W, and Y;

$X^6$ can be selected from A, D, E, F, G, H, I, K, L, M, N, P, Q, R, S, T, V, W, and Y;

$X^7$ can be selected from A, D, E, F, G, H, I, K, L, M, N, P, Q, R, S, T, V, W, and Y;

$X^8$ can be P;

$X^9$ can be G;

$X^{10}$ can be selected from A, D, E, F, G, H, I, K, L, M, N, P, Q, R, S, T, V, W, and Y;

$X^{11}$ can be selected from A, D, E, F, G, H, I, K, L, M, N, P, Q, R, S, T, V, W, and Y;

$X^{12}$ can be selected from A, D, E, F, G, H, I, K, L, M, N, P, Q, R, S, T, V, W, and Y;

$X^{13}$ can be selected from F, H, W, and Y;

$X^{14}$ can be C;

$X^{15}$ can be selected from A, D, E, F, G, H, I, K, L, M, N, P, Q, R, S, T, V, W, and Y; and $X^{16}$ can be selected from F, I, L, M, V, W, and Y.

IL-2Rα ligands provided by the present disclosure can comprise an amino acid sequence selected from any one of SEQ ID NO: 217 to SEQ ID NO: 224:

```
                                     SEQ ID NO: 217
A T C H L L A P G V D N T C I F

SEQ ID NO: 218
H G C T L T K P G A E W V C S F

SEQ ID NO: 219
Q L C P W S D P G S W G P C P L

SEQ ID NO: 220
R D C A G M E P G T S V F C D N

SEQ ID NO: 221
R D C F I L E P G T S V Y C D L

SEQ ID NO: 222
T D C Q E T W P G D R P W C H I

SEQ ID NO: 223
V K C F M S T P G Q I A Y C T T

SEQ ID NO: 224
V K C Y R N S P G V E A Y C V G
```

An IL-2Rα ligand provided by the present disclosure can comprise a truncated amino acid sequence of any one of SEQ ID NO: 214 to SEQ ID NO: 224.

An IL-2Rα ligand provided by the present disclosure can comprise an amino acid sequence selected from any one of SEQ ID NO: 214 to SEQ ID NO: 224, or a truncated amino acid sequence of any one of SEQ ID NO: 214 to SEQ ID NO: 224, wherein the amino acid sequence can independently comprise from 1 to 4 glycines (G) (SEQ ID NO: 1041) on the N-terminus, on the C-terminus, or on both the N- and C-termini.

An IL-2Rα ligand provided by the present disclosure can comprise an amino acid sequence selected from any one of SEQ ID NO: 214 to SEQ ID NO: 224, or a truncated amino acid sequence of any one of SEQ ID NO: 214 to SEQ ID NO: 224, wherein the amino acid sequence comprises one or more amino acid substitutions such as from 1 to 5 amino acid substitutions.

IL-2Rα ligands provided by the present disclosure can comprise the amino acid sequence of Formula (19a) (SEQ ID NO: 225), or the amino acid sequence of Formula (19b) (SEQ ID NO: 226):

$$-X^3-X^4-X^5-X^6-X^7-X^8-X^9-X^{10}-X^{11}-X^{12}- \quad (19a)$$

$$-X^1-C-X^3-X^4-X^5-X^6-X^7-X^8-X^9-X^{10}-X^{11}-X^{12}-C-X^{14}- \quad (19b)$$

wherein, $X^1$ can be selected from an amino acid;

$X^2$ can be C;

$X^3$ can be selected from an amino acid comprising an acidic side chain or a polar/neutral side chain;

$X^4$ can be selected from an amino acid comprising an acidic side chain or a polar/neutral side chain;

$X^5$ can be selected from an amino acid comprising a large hydrophobic side chain;

$X^6$ can be selected from an amino acid comprising a polar/neutral side chain;

$X^7$ can be selected from an amino acid;

$X^8$ can be selected from an amino acid;

$X^9$ can be selected from an amino acid comprising a large hydrophobic side chain;

$X^{10}$ can be selected from an amino acid;

$X^{11}$ can be selected from an amino acid;

$X^{12}$ can be selected from an amino acid;

$X^{13}$ can be C; and $X^{14}$ can be selected from an amino acid.

In IL-2Rα ligands of Formula (19a)-(19b), $X^1$ can be selected from A, D, E, F, G, H, I, K, L, M, N, P, Q, R, S, T, V, W, and Y;

$X^2$ can be C;

$X^3$ can be selected from D, E, N, Q, S, T, and Y;

$X^4$ can be selected from D, E, N, Q, S, T, and Y;

$X^5$ can be selected from F, I, L, M, V, W, and Y;

$X^6$ can be selected from N, Q, S, T, and Y;

$X^7$ can be selected from A, D, E, F, G, H, I, K, L, M, N, P, Q, R, S, T, V, W, and Y;

$X^8$ can be selected from A, D, E, F, G, H, I, K, L, M, N, P, Q, R, S, T, V, W, and Y;

$X^9$ can be selected from F, I, L, M, V, W, and Y;

$X^{10}$ can be selected from A, D, E, F, G, H, I, K, L, M, N, P, Q, R, S, T, V, W, and Y;

$X^{11}$ can be selected from A, D, E, F, G, H, I, K, L, M, N, P, Q, R, S, T, V, W, and Y;

$X^{12}$ can be selected from A, D, E, F, G, H, I, K, L, M, N, P, Q, R, S, T, V, W, and Y;

$X^{13}$ can be C; and $X^{14}$ can be selected from A, D, E, F, G, H, I, K, L, M, N, P, Q, R, S, T, V, W, and Y.

In IL-2Rα ligands of Formula (19a)-(19b), $X^1$ can be selected from D, P, S, T, W, and Y.

In IL-2Rα ligands of Formula (19a)-(19b), $X^2$ can be C.

In IL-2Rα ligands of Formula (19a)-(19b), $X^3$ can be selected from L, Q, M, E, W, and H.

In IL-2Rα ligands of Formula (19a)-(19b), $X^4$ can be selected from D, R, S, E, and L.

In IL-2Rα ligands of Formula (19a)-(19b), $X^5$ can be selected from L, P, F, and V.

In IL-2Rα ligands of Formula (19a)-(19b), $X^6$ can be selected from R, A, K, H, and W.

In IL-2Rα ligands of Formula (19a)-(19b), $X^7$ can be selected from G, E, K, R, D, G, and Q.

In IL-2Rα ligands of Formula (19a)-(19b), $X^8$ can be selected from T, Y, S, M, Q, and D.

In IL-2Rα ligands of Formula (19a)-(19b), $X^9$ can be selected from V, Y, and D.

In IL-2Rα ligands of Formula (19a)-(19b), $X^{10}$ can be selected from G, S, E, N, and Y.

In IL-2Rα ligands of Formula (19a)-(19b), $X^{11}$ can be selected from M, Q, W, V, E, N, R, L, and M.

In IL-2Rα ligands of Formula (19a)-(19b), $X^{12}$ can be selected from V, Q, W, V, E, N, R, L, and M.

In IL-2Rα ligands of Formula (19a)-(19b), $X^{13}$ can be C.

In IL-2Rα ligands of Formula (19a)-(19b), $X^{14}$ can be selected from Q, L, D, N, I, P, and F.

In IL-2Rα ligands of Formula (19a)-(19b), $X^1$ can be selected from A, D, E, F, G, H, I, K, L, M, N, P, Q, R, S, T, V, W, and Y.

In IL-2Rα ligands of Formula (19a)-(19b), $X^2$ can be C.

In IL-2Rα ligands of Formula (19a)-(19b), $X^3$ can be selected from H, N, Q, S, T, and Y.

In IL-2Rα ligands of Formula (19a)-(19b), $X^3$ can be selected from D and E.

In IL-2Rα ligands of Formula (19a)-(19b), $X^3$ can be selected from Q and E.

In IL-2Rα ligands of Formula (19a)-(19b), $X^4$ can be selected from D and E.

In IL-2Rα ligands of Formula (19a)-(19b), $X^5$ can be L.

In IL-2Rα ligands of Formula (19a)-(19b), $X^6$ can be selected from R, H, and K.

In IL-2Rα ligands of Formula (19a)-(19b), $X^7$ can be selected from A, D, E, F, G, H, I, K, L, M, N, P, Q, R, S, T, V, W, and Y.

In IL-2Rα ligands of Formula (19a)-(19b), $X^8$ can be selected from A, D, E, F, G, H, I, K, L, M, N, P, Q, R, S, T, V, W, and Y.

In IL-2Rα ligands of Formula (19a)-(19b), $X^9$ can be Y.

In IL-2Rα ligands of Formula (19a)-(19b), $X^{10}$ can be selected from A, G, P, S, and T.

In IL-2Rα ligands of Formula (19a)-(19b), $X^{11}$ can be selected from A, D, E, F, G, H, I, K, L, M, N, P, Q, R, S, T, V, W, and Y.

In IL-2Rα ligands of Formula (19a)-(19b), $X^{12}$ can be selected from F, I, L, M, V, W, and Y.

In IL-2Rα ligands of Formula (19a)-(19b), $X^{12}$ can be selected from V, L, and M.

In IL-2Rα ligands of Formula (19a)-(19b), $X^{13}$ can be C.

In IL-2Rα ligands of Formula (19a)-(19b), $X^{14}$ can be selected from F, I, L, M, V, W, and Y.

In IL-2Rα ligands of Formula (19a)-(19b), $X^{14}$ can be selected from F, I, and L.

In IL-2Rα ligands of Formula (19a)-(19b), $X^2$ can be C, $X^5$ can be L, and $X^{13}$ can be C.

In IL-2Rα ligands of Formula (19a)-(19b), $X^1$ can be selected from A, D, E, F, G, H, I, K, L, M, N, P, Q, R, S, T, V, W, and Y;

$X^2$ can be C;

$X^3$ can be selected from D, E, N, Q, S, T, and Y;

$X^4$ can be selected from D, E, N, Q, S, T, and Y;

$X^5$ can be L;

$X^6$ can be selected from A, G, H, K, P, S, and T;

$X^7$ can be selected from A, D, E, F, G, H, I, K, L, M, N, P, Q, R, S, T, V, W, and Y;

$X^8$ can be selected from A, D, E, F, G, H, I, K, L, M, N, P, Q, R, S, T, V, W, and Y;

$X^9$ can be selected from F, I, L, M, V, W, and Y;

$X^{10}$ can be selected from A, G, P, S, and T;

$X^{11}$ can be selected from A, D, E, F, G, H, I, K, L, M, N, P, Q, R, S, T, V, W, and Y; and $X^{12}$ can be selected from F, I, L, M, V, W, and Y;

$X^{13}$ can be C; and $X^{14}$ can be selected from F, I, L, M, V, W, and Y.

IL-2Rα ligands provided by the present disclosure can comprise an amino acid sequence selected from any one of SEQ ID NO: 227 to SEQ ID NO: 234:

```
                                SEQ ID NO: 227
D C L D L R G T V G M V C Q

SEQ ID NO: 228
P C Q R L A E Y Y S Q Q C L

SEQ ID NO: 229
S C M D L K G S V G W V C D

SEQ ID NO: 230
T C E S L A K M Y E V E C N

SEQ ID NO: 231
T C E S L A R M Y N E N C I

SEQ ID NO: 232
W C W E P H D Q Y Y V R C P

SEQ ID NO: 233
Y C H D F K G T V G T L C I

SEQ ID NO: 234
G C Q L V W Q D D S Y M C F Y
```

An IL-2Rα ligand provided by the present disclosure can comprise a truncated amino acid sequence of any one of SEQ ID NO: 225 to SEQ ID NO: 234.

An IL-2Rα ligand provided by the present disclosure can comprise an amino acid sequence selected from any one of SEQ ID NO: 225 to SEQ ID NO: 234, or a truncated amino acid sequence of any one of SEQ ID NO: 225 to SEQ ID NO: 234, wherein the amino acid sequence can independently comprise from 1 to 4 glycines (G) (SEQ ID NO: 1041) on the N-terminus, on the C-terminus, or on both the N- and C-termini.

An IL-2Rα ligand provided by the present disclosure can comprise an amino acid sequence selected from any one of SEQ ID NO: 225 to SEQ ID NO: 234, or a truncated amino acid sequence of any one of SEQ ID NO: 225 to SEQ ID NO: 234, wherein the amino acid sequence comprises one or more amino acid substitution such as from 1 to 5 amino acid substitutions.

IL-2Rα ligands provided by the present disclosure can comprise the amino acid sequence of Formula (20a) (SEQ ID NO: 235), or the amino acid sequence of Formula (20b) (SEQ ID NO: 236):

$$—X^3—X^4—X^5—X^6—X^7—X^8—X^9—X^{10}—X^{11}—X^{12}— \quad (20a)$$

$$—X^1—C—X^3—X^4—X^5—X^6—X^7—X^8—X^9—X^{10}—X^{11}—X^{12}—C—X^{14}— \quad (20b)$$

wherein, $X^1$ can be W;

$X^2$ can be C;

$X^3$ can be selected from F, I, L, M, V, W, and Y;

$X^4$ can be G;

$X^5$ can be Q;

$X^6$ can be P;

$X^7$ can be L;

$X^8$ can be selected from F, I, L, M, V, W, and Y;
$X^9$ can be R;
$X^{10}$ can be selected from H, N, Q, F, I, L, M, V, W, and Y;
$X^{11}$ can be G;
$X^{12}$ can be S;
$X^{13}$ can be C; and
$X^{14}$ can be K.

In IL-2Rα ligands of Formula (20a)-(20b), $X^3$ can be selected from I and V.

In IL-2Rα ligands of Formula (20a)-(20b), $X^8$ can be selected from F and Y.

In IL-2Rα ligands of Formula (20a)-(20b), $X^{10}$ can be selected from F, I, L, M, N, Q, S, T, V, W, and Y.

In IL-2Rα ligands of Formula (20a)-(20b), $X^{10}$ can be selected from L and Q.

In IL-2Rα ligands of Formula (20a)-(20b), $X^1$ can be W, $X^2$ can be C, $X^4$ can be G, $X^5$ can be Q, $X^6$ can be P, $X^7$ can be L, $X^9$ can be R, $X^{11}$ can be G, $X^{12}$ can be S, $X^{11}$ can be C, and $X^{14}$ can be K.

In IL-2Rα ligands of Formula (20a)-(20b),
$X^1$ can be W;
$X^2$ can be C;
$X^3$ can be selected from I and V;
$X^4$ can be G;
$X^5$ can be Q;
$X^6$ can be P;
$X^7$ can be L;
$X^8$ can be selected from F and Y;
$X^9$ can be R;
$X^{10}$ can be selected from F, H, I, L, M, N, Q, S, T, V, W, and Y;
$X^{11}$ can be G;
$X^{12}$ can be S;
$X^{13}$ can be C; and
$X^{14}$ can be K.

IL-2Rα ligands provided by the present disclosure can comprise an amino acid sequence selected from an one of SE ID NO: 237 to SE ID NO: 307:

```
                                  SEQ ID NO: 237
W C I G Q P L F R Q G S C K

SEQ ID NO: 238
W C V G Q P L Y R L G S C K

SEQ ID NO: 239
W D Q F Q L G W E A G V A A

SEQ ID NO: 240
F L P W P V Y F S Q V L G G G

SEQ ID NO: 241
Y V M C S A F G C K S I

SEQ ID NO: 242
H V I C S V N G G C R G

SEQ ID NO: 243
I R F C L R S E P T A C W I V

SEQ ID NO: 244
I R C R Y E K Q S G I C L F

SEQ ID NO: 245
G G C S L V W A D S W V C I F

SEQ ID NO: 246
G C S L M W Q D G W W V C I

SEQ ID NO: 247
E W E C R F L P G R R G C S L F

SEQ ID NO: 248
K G C T L Q N P G S G W V C L F

SEQ ID NO: 249
T C R L K R S G P N S W E C I

SEQ ID NO: 250
W C I G Q P L F R Q G S C K

SEQ ID NO: 251
A V S C N S W R C I P W

SEQ ID NO: 252
A V C C D G N S C R R C

SEQ ID NO: 253
F V H C S L M G C W C G

SEQ ID NO: 254
R C L D L G G S V G L V C F

SEQ ID NO: 255
V C F N F R G T V G R H C W

SEQ ID NO: 256
V R C R Q N E P G G A Y W C S S

SEQ ID NO: 257
C V L R E G A E G W E C V W R

SEQ ID NO: 258
C R M M Q G T Y G W T C L F

SEQ ID NO: 259
C I L N D T I Q G W V C I Y

SEQ ID NO: 260
C T L Y R S A P G V W L C I F

SEQ ID NO: 261
C L V F D Q Y G N Y K R R C

SEQ ID NO: 262
I V C C N M F G C H T C R N

SEQ ID NO: 263
Q V C C T S R G C R V C A P V

SEQ ID NO: 264
R V C C S M V G C R S C N L

SEQ ID NO: 265
R V C C T F A G C R V C H K

SEQ ID NO: 266
R V C C T S D G C R G C R Q

SEQ ID NO: 267
T V C C T V Q G C W P C S R

SEQ ID NO: 268
V C C H Q T F G C Y R C K Q

SEQ ID NO: 269
C V V C S A L G C R A C V P R

SEQ ID NO: 270
V W D C F V R G W E A G V A A V G E

SEQ ID NO: 271
L T C L I F K P G T H R H C P V

SEQ ID NO: 272
R Y C S P L I P G S A L G C P R

SEQ ID NO: 273
I R C R L D P P G S Y K T C V F
```

```
                    SEQ ID NO: 274
R G V I C N H A G C R I W Y G

SEQ ID NO: 275
T T Q S C T L R Y C W L L Q

SEQ ID NO: 276
W W I S C L R D L R C L E Y F

SEQ ID NO: 277
R H A C K T W Y R M C I V S

SEQ ID NO: 278
A V S C S R L T G R C H S L

SEQ ID NO: 279
W V A C N R V T G S C R P I

SEQ ID NO: 280
S H G V C C T Q S S C R S C R

SEQ ID NO: 281
W V A C N R L S G C C R P I

SEQ ID NO: 282
H T V C C Q D W G C R S C S G

SEQ ID NO: 283
M A C C T P R G C R P C

SEQ ID NO: 284
R S V C C S S Y G C R A C F G

SEQ ID NO: 285
C K L T C T S S T C S C V F

SEQ ID NO: 286
C M L K C T N A I C E C I F

SEQ ID NO: 287
C R V W C N Q A E C M C I F

SEQ ID NO: 288
S R C S F D V T K Q E C V F

SEQ ID NO: 289
L E C Q P Y R G P L Y Y C Q D

SEQ ID NO: 290
S I C C T P Q L C H S C D G

SEQ ID NO: 291
T T C C T S E G C H K C I T L

SEQ ID NO: 292
C V A C S S D G C S P I I C

SEQ ID NO: 293
A I C S E D E G G E L C C W H

SEQ ID NO: 294
H E I C C G P P G C H S C S V T

SEQ ID NO: 295
L S V C S C P P G Q L Y C M V E

SEQ ID NO: 296
S T W C C L H P G V G E C Q A V

SEQ ID NO: 297
V T Q C F D G P G S F R C C Y Q

SEQ ID NO: 298
R Q C N C L S P G E L V N C Q Q

SEQ ID NO: 299
M V S C T D L G C V V V G G G

SEQ ID NO: 300
V V H C L Q S G C Y S V G S G

SEQ ID NO: 301
T I K C G S S G W C W V E A G

SEQ ID NO: 302
M V S C T D L G C V V V G G G

SEQ ID NO: 303
H E I C C G P P G C H S C S V T

SEQ ID NO: 304
L S V C S C P P G Q L Y C M V E

SEQ ID NO: 305
S T W C C L H P G V G E C Q A V

SEQ ID NO: 306
V T Q C F D G P G S F R C C Y Q

SEQ ID NO: 307
R Q C N C L S P G E L V N C Q Q
```

An IL-2Rα ligand provided by the present disclosure can comprise a truncated amino acid sequence of any one of SEQ ID NO: 235 to SEQ ID NO: 307.

An IL-2Rα ligand provided by the present disclosure can comprise an amino acid sequence selected from any one of SEQ ID NO: 235 to SEQ ID NO: 307, or a truncated amino acid sequence of any one of SEQ ID NO: 235 to SEQ ID NO: 307, wherein the amino acid sequence can independently comprise from 1 to 4 glycines (G) (SEQ ID NO: 1041) on the N-terminus, on the C-terminus, or on both the N- and C-termini.

An IL-2Rα ligand provided by the present disclosure can comprise an amino acid sequence selected from any one of SEQ ID NO: 235 to SEQ ID NO: 307, or a truncated amino acid sequence of any one of SEQ ID NO: 235 to SEQ ID NO: 307, wherein the amino acid sequence comprises one or more amino acid substitution such as from 1 to 5 amino acid substitutions.

IL-2Rα ligands provided by the present disclosure can comprise an amino acid sequence selected from any one of SEQ ID NO: 400 to SEQ ID NO: 423:

```
                    SEQ ID NO: 400
W D D F I L G W E A G V A A V G E V

SEQ ID NO: 401
F L P W P V Y F S Q V L G G R R

SEQ ID NO: 402
Y V M C S A F G C K S I G G

SEQ ID NO: 403
H V I C S V N G G C R G G G

SEQ ID NO: 404
G G I R F C L R S E P T A C W I V G G

SEQ ID NO: 405
G G I R C R Y E K Q S G I C L F G G

SEQ ID NO: 423
G G G G C S L V W A D S W V C I F G G

SEQ ID NO: 406
G G G C S L M W Q D G W W V C I G G

SEQ ID NO: 407
G G E W E C R F L P G R R G C S L F G G

SEQ ID NO: 408
G G K G C T L Q N P G S G W V C L F G G
```

```
                                SEQ ID NO: 409
GGTCRLKRSGPNSWECIGG

SEQ ID NO: 410
GGWCIGQPLFRQGSCKGG

SEQ ID NO: 411
FVLCGLQGCRSGG

SEQ ID NO: 412
FVPWDEYFLQILGG

SEQ ID NO: 413
GGGWVICSALGCPFGG

SEQ ID NO: 414
GGGRRFCLRSEPTACWTVGG

SEQ ID NO: 415
GGGSRCSLVWADSWVCIFGG

SEQ ID NO: 416
GGDWECLFLPGRRGCTLFGG

SEQ ID NO: 417
FIPWDEYFAQLLGG

SEQ ID NO: 418
FVPWDVYFSQILGG

SEQ ID NO: 419
FIPWDEYFKQVLGG

SEQ ID NO: 420
FVPWPEYFLQIMGG

SEQ ID NO: 421
FIPWEEYFSQLLGG

SEQ ID NO: 422
FIPWPEYFSQLLGG
```

An IL-2Rα ligand provided by the present disclosure can comprise a truncated amino acid sequence of any one of SEQ ID NO: 400 to SEQ ID NO: 423.

An IL-2Rα ligand provided by the present disclosure can comprise an amino acid sequence selected from any one of SEQ ID NO: 400 to SEQ ID NO: 423, or a truncated amino acid sequence of any one of SEQ ID NO: 400 to SEQ ID NO: 423, wherein the amino acid sequence can independently comprise from 1 to 4 glycines (G) (SEQ ID NO: 1041) on the N-terminus, on the C-terminus, or on both the N- and C-termini.

An IL-2Rα ligand provided by the present disclosure can comprise an amino acid sequence selected from any one of SEQ ID NO: 400 to SEQ ID NO: 423, or a truncated amino acid sequence of any one of SEQ ID NO: 400 to SEQ ID NO: 423, wherein the amino acid sequence comprises one or more amino acid substitutions such as from 1 to 5 amino acid substitutions.

An IL-2Rα ligand provided by the present disclosure can comprise an amino acid sequence selected from any one of SEQ ID NO: 1 to SEQ ID NO: 307 and SEQ ID NO. 400 to SEQ ID NO: 423.

An IL-2Rα ligand provided by the present disclosure can comprise an amino acid sequence having greater than 70%, greater than 75%, greater than 80%, greater than 85%, greater than 90%, or greater than 95% sequence similarity to any one of SEQ ID NO: 1 to SEQ ID NO: 307 and SEQ ID NO. 400 to SEQ ID NO: 423.

An IL-2Rα ligand provided by the present disclosure can comprise a truncated amino acid sequence of any one of SEQ ID NO: 1 to SEQ ID NO: 307 and SEQ ID NO. 400 to SEQ ID NO: 423.

An IL-2Rα ligand provided by the present disclosure can comprise an amino acid sequence having greater than 70%, greater than 75%, greater than 80%, greater than 85%, greater than 90%, or greater than 95% sequence similarity to a truncated amino acid sequence of any one of SEQ ID NO: 1 to SEQ ID NO: 307 and SEQ ID NO. 400 to SEQ ID NO: 423.

IL-2Rα ligands provided by the present disclosure can comprise an amino acid sequence selected from SEQ ID NO: 1 to SEQ ID NO: 307 independently comprising one or more such as from 1 to 5 or from 1 to 3 of the following conservative substitutions: amino acids having a small hydrophobic side chain comprising alanine (A), glycine (G), proline (P), serine (S) and threonine (T); amino acids having a hydroxyl-containing side chain comprising serine (S) or threonine (T); amino acids having an acidic side chain comprising aspartate (D) and glutamate (E); amino acids having a polar neutral side chain comprising histidine (H), asparagine (N), glutamine (Q), serine (S), threonine (T), and tyrosine (Y); amino acids having a basic side chain comprising arginine (R), lysine (K), or histidine (H); and amino acids having a large hydrophobic side chain comprising isoleucine (I), leucine (L), methionine (M), valine (V), phenylalanine (F), tyrosine (Y), or tryptophan (W).

Small peptidyl IL-2Rα ligands provided by the present disclosure can include naturally amino acids or can be modified to include non-natural amino acids. Because the small peptidyl IL-2Rα ligands can be chemically synthesized, the peptidyl IL-2Rα ligands can be modified using natural and/or non-natural amino acids to optimize potency and efficacy, and to improve metabolic stability. The small peptidyl IL-2Rα ligands also allow such modifications to be made with a low likelihood of inducing immunogenicity. Also, due to their chemical malleability, peptides can be caged to construct a reversibly inactive prodrug using cell-specific environmental triggers such as proteases, or complexes sensitive to low pH. For example, the pH-dependent binding properties of peptides can be optimized by use of non-natural amino acids having sidechain ionizable groups with a pKa in the range of pH 5.0 to pH 8.0. As with proteins, pharmacokinetic-enhancing moieties, such as polyethylene glycol (PEG), can be appended to peptides, either as part of, or independent of, a "caging" strategy. Also, sites on a peptide can be reserved for attaching a variety of cell targeting moieties, such as tumor-specific antibodies and immune cell-specific targeting moieties. These features of peptidyl IL-2Rα ligands can be exploited in the design of optimal therapeutic candidates based on the peptidyl IL-2Rα ligands provided by the present disclosure.

In addition to peptides consisting only of naturally occurring amino acids, peptidomimetics or peptide analogs are also provided. Peptide mimetics can be used to produce an equivalent or enhanced therapeutic effect. Peptidomimetics are structurally similar to a paradigm peptide, for example, an IL-2Rα ligand that has a biological or pharmacological activity, but have one or more peptide linkages optionally replaced by a linkage such as —CH$_2$—NH—, —CH$_2$—S—, —CH$_2$—CH$_2$—, —CH=CH— (cis and trans), —COCH$_2$—, —CH(OH)CH$_2$—, and —CH$_2$SO—, by methods known in the art.

Substitution of one or more amino acids of a consensus sequence with a D-amino acid of the same type, such as D-lysine in place of L-lysine, may be used to generate more stable peptides. In addition, constrained peptides comprising a consensus sequence, or a substantially identical consensus sequence variation may be generated by methods known in the art; for example, by adding internal cysteine residues capable of forming intramolecular disulfide bridges which cyclize the peptide.

One or more amino acids of an IL-2Rα ligand consensus sequence may be replaced with a synthetic or non-naturally occurring amino acid. Synthetic or non-naturally occurring amino acids refer to amino acids which do not naturally occur in vivo but which, nevertheless, can be incorporated into the peptidyl ligands provided by the present disclosure. Suitable examples of synthetic amino acids include the D-α-amino acids of naturally occurring L-α-amino acid as well as non-naturally occurring D- and L-α-amino acids represented by the formula $H_2NCHRCOOH$ where R can be $C_{1-6}$ alkyl, $C_{3-8}$ cycloalkyl, $C_{3-8}$ heterocycloalkyl; an aromatic residue of from 6 to 10 carbon atoms optionally having from 1 to 3 substituents on the aromatic nucleus selected from the group consisting of hydroxyl, lower alkoxy, amino, and carboxyl; -alkylene-Y where alkylene is an alkylene group of from 1 to 7 carbon atoms and Y is selected from a hydroxyl, amino, cycloalkyl, and cycloalkenyl having from 3 to 7 carbon atoms; $C_{6-10}$ aryl, such as from 1 to 3 substituents on the aromatic nucleus selected from the group consisting of hydroxyl, lower alkoxy, amino and carboxyl; heterocyclic of from 3 to 7 carbon atoms and 1 to 2 heteroatoms selected from the group consisting of oxygen, sulfur, and nitrogen; —C(O)R where R is selected from hydrogen, hydroxy, $C_{1-4}$ alkyl, $C_{1-4}$ alkoxy, and $—NR_2$ where each R is independently selected from hydrogen and $C_{1-4}$ alkyl; $—S(O)_nR$ where n is 1 or 2 and R is $C_{1-6}$ alkyl and with the proviso that R does not define a side chain of a naturally occurring amino acid. Examples of synthetic amino acids include amino acids wherein the amino group is separated from the carboxyl group by more than one carbon atom such as b-alanine and g-aminobutyric acid. Other examples of suitable synthetic amino acids include the D-amino acids of naturally occurring L-amino acids, L-1-naphthyl-alanine, L-2-naphthylalanine, L-cyclohexylalanine, L-2-amino isobutyric acid, the sulfoxide and sulfone derivatives of methionine (i.e., $HOOC—(H_2NCH)CH_2CH_2—S(O)_nR^6$) where n and $R_6$ are as defined above as well as the lower alkoxy derivative of methionine (i.e., $HOOC—(H_2NCH)CH_2CH_2OR$ where R is $C_{1-6}$ alkyl and where R does not define a side chain of a naturally occurring amino acid).

IL-2Rα ligands include bioisosteres and isosteres of the IL-2Rα ligands provided by the present disclosure.

An IL-2Rα ligand provided by the present disclosure can have, for example, less than 20 amino acids, less than 15 amino acids, or less than 10 amino acids. For example, an IL-2Rα ligand can have from 5 to 20 amino acids, or from 10 to 15 amino acids.

IL-2Rα ligands of SEQ ID NO: 1 to SEQ ID NO: 307 exhibit an affinity ($IC_{50}$) to the human IL-2Rα subunit of less than 100 μM.

An IL-2Rα ligand provided by the present disclosure can comprise, for example, from 5 to 50 amino acids, from 5 to 40 amino acids, from 5 to 35 amino acids, from 5 to 30 amino acids, from 6 to 25 amino acids, or from 7 to 20 amino acids.

An IL-2Rα ligand provided by the present disclosure can bind to the human IL-2Rα subunit, to a mammalian IL-2Rα subunit, or to both the human IL-2Rα subunit and a mammalian IL-2Rα subunit with an $IC_{50}$, for example, from 1 μM to 100 μM, from 10 μM to 10 μM, from 100 μM to 1 μM, from, 0.001 μM to 1 μM, or from 0.01 μM to 1 μM.

An IL-2Rα ligand provided by the present disclosure can bind to, for example, the human IL-2Rα subunit with an $IC_{50}$ from 0.1 μM to 50 μM.

An IL-2Rα ligand provided by the present disclosure can bind to the human IL-2Rβ subunit and/or human IL-2Rγc subunit with an $IC_{50}$, for example, of greater than 100 μM, greater than 1 mM, greater than 10 mM, or greater than 100 nM.

IL-2Rα ligands and the sub-genuses of IL-2Rα ligands provided by the present disclosure do not include an IL-2Rα ligand having an amino acid sequence selected from SEQ ID NO: 308 to SEQ ID NO: 397.

| | |
|---|---|
| F V R C S A N G C V | SEQ ID NO: 308 |
| S V R C S A S G C V | SEQ ID NO: 309 |
| Y V A C S V S G C V | SEQ ID NO: 310 |
| Y V I C G A S G C V | SEQ ID NO: 311 |
| Y V R C T A I G C V | SEQ ID NO: 312 |
| F V R C S A T G C V | SEQ ID NO: 313 |
| Y V I C S A S G C V | SEQ ID NO: 314 |
| W V R C S A S G C V | SEQ ID NO: 315 |
| F V R C S A S G C V | SEQ ID NO: 316 |
| F V R C T A S G C V | SEQ ID NO: 317 |
| F V R C T S D G C V | SEQ ID NO: 318 |
| Y V R C T A S G C V | SEQ ID NO: 319 |
| F R R C S A S G C V | SEQ ID NO: 320 |
| L R R C S A N G C V | SEQ ID NO: 321 |
| L R R C S A N G C V | SEQ ID NO: 322 |
| F V R C S L I G C V | SEQ ID NO: 323 |
| F V R C N A S G C V | SEQ ID NO: 324 |
| F V R C T R E G C V | SEQ ID NO: 325 |
| F V R C T S D G C V | SEQ ID NO: 326 |
| Y V I C S A S G C V | SEQ ID NO: 327 |
| F V R C T E W G C V | SEQ ID NO: 328 |
| F V R C T A S G C I | SEQ ID NO: 329 |

SEQ ID NO: 330
Y V R C S E S G C V G S S W N A

SEQ ID NO: 331
F V R C S E S G C V G S S W S A

SEQ ID NO: 332
Y V R C S A S G C V G S S W F L

SEQ ID NO: 333
Y V R C S D S G C V G S T W G W

SEQ ID NO: 334
Y V R C S E S G C V G S T W V F

SEQ ID NO: 335
Y V R C S E S G C V G S T W V F

SEQ ID NO: 336
Y V L C A L S G C V G S S W S S

SEQ ID NO: 337
Y V R C G E S G C V G S T W S T

SEQ ID NO: 338
Y V R C S A T G C V G S T W T F

SEQ ID NO: 339
Y V R C G E T G C V G S T W S F

SEQ ID NO: 340
Y V R C G V S G C V G S S W V L

SEQ ID NO: 341
Y V R C G E S G C V G S T W S T

SEQ ID NO: 342
F V R C S E S G C V G S S W S T

SEQ ID NO: 343
Y V R C S E S G C V G S S W W A

SEQ ID NO: 344
Y V R C S V T G C V G S S W S I

SEQ ID NO: 345
Y V R C S V T G C V G S S W S I

SEQ ID NO: 346
Y V R C S E S G C V G S S W S V

SEQ ID NO: 347
F V R C S A D G C V G S S W L Q

SEQ ID NO: 348
Y V R C S A D G C V G S S W I T

SEQ ID NO: 349
Y V R C N P S G C V G S S W S I

SEQ ID NO: 350
Y V R C S V T G C V G S S W S I

SEQ ID NO: 351
Y V R C S E S G C V G S S W S V

SEQ ID NO: 352
F V R C S A N G C V G S T W Q A

SEQ ID NO: 353
Y V R C T E S G C V G S T W T Y

SEQ ID NO: 354
Y V R C S V T G C V G S T W S V

SEQ ID NO: 355
Y V R C S E I G C V G S T W S L

SEQ ID NO: 356
T V R C S A T G C V G S S W V G

SEQ ID NO: 357
Y V R C S A T G C V G S S W V G

SEQ ID NO: 358
F V R C S A S G C V G S S W V G

SEQ ID NO: 359
Y V R C S A D G C V G S T W N L

SEQ ID NO: 360
Y V R S S Q S G C V G S G W V L

SEQ ID NO: 361
Y V A C S E S G C V G S S W S V

SEQ ID NO: 362
F V A C G E L G C V G S S W S I

SEQ ID NO: 363
Y V A C S E S G C V G S S W L A

SEQ ID NO: 364
Y C R C T E S G C V G S T W T Y

SEQ ID NO: 365
F V R C T A I G C V G S S W S V

SEQ ID NO: 366
Y V R C S A D G C V G S S W S A

SEQ ID NO: 367
Y V R C S A S G C V G S S W N Y

SEQ ID NO: 368
Y V L C S A S G C V G S L W T H

SEQ ID NO: 369
Y V R C T D S G C V G S S W H L

SEQ ID NO: 370
Y V A C S E S G C V G S T W I T

SEQ ID NO: 371
Y V A C S E S G C V G S T W T F

SEQ ID NO: 372
Y V R C G A A G C V V S S W V Y

SEQ ID NO: 373
F V R C G A S G C V G S T W G S

SEQ ID NO: 374
Y V A C S E I G C V G S T W S L

SEQ ID NO: 375
Y V A C S E S G C V G S S W T W

SEQ ID NO: 376
Y V A C S V S G C V G S S W S V

SEQ ID NO: 377
Y V R C S E S G C V G S T W T T

SEQ ID NO: 378
Y V R C S E S G C V S S F W S A P W K A

SEQ ID NO: 379
Y V R C S E N G C V G H S W T Q G L R T

SEQ ID NO: 380
Y V R C S E S G C V S Q R P H V L E V W

SEQ ID NO: 381
Y V L C S E R G C V G Q N W A V G K L P

SEQ ID NO: 382
Y V R C S E I G C V G H W S S Y G K H

SEQ ID NO: 383
Y V R C S E N G C V G S S W G R V T L D

```
                                  SEQ ID NO: 384
Y V R C S E S G C V G C E L V W Y F I T

SEQ ID NO: 385
Y V R C S E S G C V G S S W G A V A S I

SEQ ID NO: 386
Y V R C S E S G C V G S S W G A V A S I

SEQ ID NO: 387
Y V R C S E S G C V G S S W S V S P R G

SEQ ID NO: 388
Y V R C G E S G C V S S S W S T M G N S

SEQ ID NO: 389
Y V R C S E N G C V G S S W E H S A I I

SEQ ID NO: 390
Y V R C S E G G C V G S T W T A S Y P N

SEQ ID NO: 391
Y V R C S E S G C V G S T W N G V L S R

SEQ ID NO: 392
Y V R C S E S G C V G S T W N G V L S R

SEQ ID NO: 393
T V R C S Q S G C V G C Q L V W Y F T T

SEQ ID NO: 394
Y V N C S Q S G C V G S T W N G V F S N

SEQ ID NO: 395
Y V A C S E S G C V S V D S S A G A L F

SEQ ID NO: 396
Y V R C N E T G C V G S S W I A A G P F

SEQ ID NO: 397
Y V R C S E S G C V G S T W L F N P W G
```

Compounds provided by the present disclosure comprise at least one IL-2Rα ligand. Compounds can comprise, for example, from 1 to 10 IL-2Rα ligands, from 1 to 6 IL-2Rα ligand, or from 1 to 3 IL-2Rα ligands. Examples of compounds comprising at least one IL-2Rα ligand include peptides and conjugates. Examples of conjugates include one or more IL-2Rα ligands bound to a polypeptide, a macromolecule such as a polyethylene glycol, a fusion protein, or a biological molecule such as an antibody.

Functionally, compounds comprising at least one IL-2Rα ligand can be IL-2Rαβγc agonists, IL-2Rα antagonists, IL-2Rαβ antagonists, IL-2Rαβγc antagonists, IL-2Rαβγc antagonists, diagnostic reagents, imaging reagents, targeting compounds, cytotoxic compounds, and compounds exhibiting dual pharmacology.

Compounds comprising an IL-2Rα ligand provided by the present disclosure can have a molecular weight, for example, from 1,000 to 400,000 Da, from 1,000 to 200,000 Da, from 1,000 to 100,000 Da, from 1,000 Da to 20,000 Da, from 1,500 Da to 15,000 Da, from 2,000 Da to 10,000 Da, or from 5,000 Da to 10,000 Da.

Compounds comprising an IL-2Rα provided by the present disclosure can be attached to one or more moieties that impart a property to the compound that enhances therapeutic efficacy. Examples of properties include potency, aqueous solubility, polarity, lipophilicity, pharmacokinetics, targeting, bioavailability, pH-dependent binding, bioactivity, pharmacodynamics, cellular activity, metabolism, efficacy, reversible incapacitation (caging), selectivity, or a combination of any of the foregoing.

Compounds comprising an IL-2Rα ligand can comprise one or more moieties that are cleavable in vivo. The moiety can be cleavable in a target specific environment such as, for example, by a target specific or target enriched enzyme, or pH. The moiety can be cleavable upon exposure to electromagnetic energy such as visible light or infrared radiation and/or by exposure to thermal energy.

Compounds comprising an IL-2Rα ligand can include a polymer, a peptide, an antibody.

Compounds comprising an IL-2Rα ligand can include a tumor-targeting moiety such as, for example, a tumor-specific antibody, a tumor-specific antibody fragment, a tumor-specific protein, a tumor-specific peptide, a non-peptidyl tumor cell ligand, or a combination of any of the foregoing.

Compounds comprising an IL-2Rα ligand can comprise a caged molecule or molecules. A caged molecule can in effect encapsulate the compound and can serve to prevent bioactivity in certain tissues, for example, to protect peripheral tissues from the toxicity of IL-2Rαβγc activation.

Compounds comprising an IL-2Rα ligand can comprise a moiety, wherein the moiety comprises a small molecule, a peptide, a polymer, or an antibody. The small molecule can be a non-peptidyl molecule. The moiety can exhibit a pharmacological effect. The pharmacological effect can manifest when the moiety is bound to the IL-2Rα and/or after the moiety is cleaved from the compound comprising an IL-2Rα ligand.

Compounds comprising an IL-2Rα ligand can comprise a moiety configured to sustain a circulating reservoir of the compound comprising an IL-2Rα ligand.

Compounds comprising an IL-2Rα ligand can comprise a moiety configured to target the IL-2R-directed immunostimulation of the effector immune cells in the tumor.

Compounds comprising an IL-2Rα ligand can comprise a moiety configured to target specific immune cells such as Treg cells.

The moiety can comprise a compound that is toxic to a cell targeted by the compound comprising an IL-2Rα ligand. A compound comprising an IL-2Rα ligand can target cells having a high expression level of the IL-2Rα subunit such as Treg cells and the compound can comprise a moiety toxic to the cells expressing the IL-2Rα subunit such as Treg cells. The toxic moiety can be cleavable or otherwise activated such as by exposure to electromagnetic radiation. The toxic moiety can be activated by exposure to electromagnetic radiation.

Compounds comprising an IL-2Rα ligand provided by the present disclosure can activate the IL-2 receptor. Compounds comprising an IL-2Rα ligand provided by the present disclosure can inhibit the IL-2 receptor. Certain compounds comprising an IL-2Rα ligand provided by the present disclosure can bind to the IL-2α subunit and prevent other compounds from binding to the IL-2α subunit. Compounds comprising an IL-2Rα ligand can reduce the potency of or interfere with the binding of IL-2R agonists to cells that highly express the IL-2Rα ligand. Compounds comprising an IL-2Rα ligand can reduce the sensitivity of Treg cells to IL-2.

Peptides provided by the present disclosure include at least one IL-2Rα ligand. A peptide can include, for example, less than 50 amino acids, which include the amino acids constituting the IL-2Rα ligand.

A peptide comprising an IL-2Rα ligand can comprise, for example, from 5 to 100 amino acids, from 5 to 80 amino acids, from 5 to 50 amino acids, from 10 to 40 amino acids, from 10 to 30 amino acids, or from 15 to 25 amino acids.

In addition to an IL-2Rα ligand, a peptide can include additional amino acids, for example, for establishing the conformation of an IL-2Rα ligand and/or for coupling the IL-2Rα ligand to other compounds. The additional amino acids can be bonded to the N-terminus and/or to the C-terminus of the IL-2Rα ligand.

Conjugates provided by the present disclosure include at least one IL-2Rα ligand.

A conjugate can comprise a polypeptide.

A polypeptide can be a single chain tandem peptide having two more IL-2Rα ligands. The IL-2Rα ligands can be bonded through amino acid linkers.

An amino acid linker can comprise, for example, more than one amino acid, greater than 5 amino acids, greater than 10 amino acids, greater than 50 amino acids, or greater than 100 amino acids. A peptide linker can comprise, for example, from 1 to 100 amino acids from 3 amino acids to 75 amino acids, from 5 amino acids to 50 amino acids, or from 10 amino acids to 25 amino acids.

For example, in a homodimer, the C-terminus of a first IL-2Rα ligand and the C-terminus of a second IL-2Rα ligand can be attached to the linker; the N-terminus of a first IL-2Rα ligand and the N-terminus of a second IL-2Rα ligand can be attached to the linker; or the C-terminus of a first IL-2Rα ligand and the N-terminus of a second IL-2Rα ligand can be attached to the linker.

A polypeptide comprising an IL-2Rα ligand provided by the present disclosure can comprise, for example, from 5 amino acids to 4,000 amino acids, from 5 amino acids to 3,000 amino acids, from 5 amino acids to 2,500 amino acids, or from 5 amino acids to 2,000 amino acids.

A polypeptide can be a synthetic peptide or a recombinant polypeptide.

A single chain tandem peptide can be a heteromer having at least one IL-2Rα ligand in combination with one or more IL-2Rβ ligands and/or one or more IL-2Rγc ligands. For example, a single chain tandem peptide can comprise an IL-2Rα ligand, an IL-2Rβ ligand, and an IL-2Rγc ligand with amino acid linkers coupling adjacent ligands. A single chain tandem peptide can further include additional amino acids at the N-terminus and/or C-terminus of the polypeptide.

The IL-2Rα and IL-2Rβ ligand and/or IL-2Rγc ligand can be arranged in any order.

Each of the adjacent ligands can independently be coupled through the N-terminus of each ligand, through the C-terminus of each ligand, through the N-terminus and C-terminus of the adjacent ligands, or through the side chains of the ligands and/or linkers.

For example, in a heteromer, the C-terminus of an IL-2Rα ligand can be attached to the linker and the N-terminus of an IL-2Rβ ligand or the N-terminus of an IL-2Rγc ligand can be attached to the linker; the C-terminus of an IL-2Rβ ligand or the N-terminus of an IL-2Rγc ligand can be attached to the linker, or the N-terminus of an IL-2Rα ligand can be attached to the linker. Other examples of suitable linkers include DIG, PEG13, PEG25, PEG1K, PEG2K, PEG3.4K, PEG4K, PEG5K, IDA, IDA-Palm, IDA-Boc, IDA-Ac, IDA-Isovaleric acid, ADA triazine, triazine-Boc, isophthalic acid, 1,3-phenylenediacetic acid, Glu, Asp, D-Glu, D-Asp, 1,4-phenylenediacetic acid, biphenyl diacetic acid, cyclopropylacetic acid, succinic acid, glutaric acid, dodecanedioic acid, suitable aliphatic diacids, suitable aromatic diacids, heteroaromatics, and polyethylene glycols having a molecular weight, for example, from 400 Da to 40,000 Da.

The individual IL-2Rα ligands can be linked in various ways to produce homodimers or homomers, heteromers, that can be evaluated for IL-2R agonist and/or IL-2R antagonist activity. For example, homodimers of IL-2Rα ligands or heteromers of an IL-2Rα ligand with IL-Rβ ligand and/or IL-2Rγc ligand can function as an IL-2R antagonist. Agonist and antagonist activity can depend on heteromers binding simultaneously to both IL-2Rβ and IL-2Rγc subunits to induce proximity and orientation compatible with signaling or inhibition. Several compound characteristics can influence the activity of homodimers or heteromers such as, for example, the linker structure, the linker length, the peptide ligand orientation, the ECD binding site-specificity of the monomeric peptides, and the affinities of each ligand for the respective receptor subunits. IL-2R agonist and IL-2R antagonist activity can depend on increasing the affinity of the IL-2Rα ligand to the IL-2Rα subunit. Induced receptor subunit orientation and the potential for proper intra-cellular alignment and signaling can be, in part, a function of the orientations in which the peptide ligands link to form the heteromer. To determine suitable induced subunit orientations, adjacent IL-2R ligands can be linked in any of four (4) possible orientations such that the C-termini of both subunit binding ligands are coupled through a linker, the N-termini of both subunit binding ligands are coupled through a linker, or the N-terminus of one binding subunit can be bound through the C-terminus of the other binding subunit through a suitable linker. Homomers and heteromers can also be linked through amino acid side chains. Heteromer linkage orientation can be engineered, for example, by synthesizing ligand monomers with the click functionality, i.e., azide or alkyne, and PEG-linker on either the N-terminus or on the C-terminus.

A polypeptide can be a synthetically modified polypeptide comprising one or more IL-2Rα ligands. The modifications can be influence, for example, the activity of the polypeptide or the pharmacokinetics of the polypeptide. Examples include polypeptides incorporating polyethylene glycol moieties or albumin binding moieties.

Compounds comprising an IL-2Rα ligand can be a fusion protein where the fusion partner is from a biological source. An IL-2Rα ligand can be fused to another protein that imparts a desired functionality to the construct. For example, the protein can impart a desired pharmacokinetic profile or to target specific antigens.

Examples of suitable fusion partners include Fc fusion proteins, IgG fusion proteins, human serum albumin (HSA) fusion proteins, other human proteins and mutants and/or variants thereof; and hydrophilic, biodegradable protein polymers. A fusion protein partner can be a naturally occurring protein, a modified-naturally occurring protein, or a synthetic protein.

For example, an IL-2Rα ligand provided by the present disclosure can be fused to a protein that increases the circulating half-life of the compound. Fusion of therapeutic proteins with IgG or IgG Fc domains accomplishes this by increasing the hydrodynamic radius of the protein, thus reducing renal clearance, and through Neonatal Fc Receptor (FcRn)-mediated recycling of the fusion protein, and thereby prolonging the circulating half-life. Other fusion proteins can be designed to modify properties such as the pharmacokinetics, biodistribution, pharmacodynamics, pharmacology, cytotoxicity, and/or targeting.

A fusion protein provided by the present disclosure can comprise a peptide, or multiple tandem peptides provided by the present disclosure linked to one or more fusion protein partners. A fusion protein partner can be linked to the N-terminus and/or the C-terminus of tandem peptides. One or more fusion protein partners can be linked to the N-terminus and/or the C-terminus of tandem peptides. An IL-2Rα ligand can be linked to one or more fusion protein partners, where each of the fusion protein partners can be the same or some of the fusion protein partners can be different than other of the fusion protein partners linked to a peptide.

The amino acid sequence at the junction between an IL-2Rα ligand and a fusion partner protein can be either a direct fusion of the two protein sequences or a fusion with an intervening linker peptide. Linker peptides can be included as spacers between the two protein moieties. Linker peptides can promote proper protein folding and stability of the component protein moieties, improve protein expression, and enable better bioactivity of the component protein moieties. Peptide linkers used in fusion proteins can be designed to be unstructured flexible peptides. Peptide linkers can be, for example, rich in glycine and serine, such as repeats of a sequence such as, for example, GS, GGS, GGGS (SEQ ID NO: 1039), or GGGGS (SEQ ID NO: 1040). A flexible linker peptide with a fully extended β-strand conformation can have an end-to-end length of approximately 3.5 Å per residue. Thus, a linker peptide of 5, 10, 15, 20 or more than 20 residues can have a maximum fully extended length of 17.5 Å, 35 Å, 52.5 Å, 70 Å, 140 Å, or more than 140 Å, respectively.

A linker peptide can facilitate obtaining an appropriate conformation and orientation of individual fusion protein moieties to facilitate the engagement of the IL-2Rα ligand with the IL-2Rα subunit, facilitate binding of the IL-2Rα ligand to the IL-2 receptor, enable fusion protein recycling, and prolong the circulating half-life of the active moiety. Because the factors influencing these interactions are difficult to predict, the requirement for and the proper length of a linker peptide must be empirically tested and determined.

There are multiple options for the design and construction of a fusion protein comprising an IL-2Rα ligand and which can be selected to obtain a compound having the desired biological activity and pharmaceutical characteristics. Design options include, for example, the nature of the IL-2Rα ligand, the choice of the fusion partner protein moiety, the configuration of fusion partners in the fusion protein, and the amino acid sequence at the junction between the IL-2Rα ligand and the fusion partner protein.

In general, preparation of the fusion proteins provided by the present disclosure can be accomplished by recognized recombinant DNA techniques involving, for example, polymerase chain amplification reactions (PCR), preparation of plasmid DNA, cleavage of DNA with restriction enzymes, preparation of oligonucleotides, ligation of DNA, isolation of mRNA, introduction of the DNA into a suitable cell, transformation or transfection of a host, culturing of the host. Additionally, fusion proteins can be isolated and purified using chaotropic agents and well known electrophoretic, centrifugation and chromatographic methods.

Genes encoding fusion proteins provided by the present disclosure involve restriction enzyme digestion and ligation as the basic steps employed to yield DNA encoding the desired fusions. The ends of the DNA fragment may require modification prior to ligation, and this may be accomplished by filling in overhangs, deleting terminal portions of the fragment(s) with nucleases (e.g., ExoIII), site directed mutagenesis, or by adding new base pairs by PCR. Polylinkers and adaptors can be employed to facilitate joining of selected fragments. The expression construct can be assembled in stages employing rounds of restriction, ligation, and transformation of E. coli. Numerous cloning vectors suitable for construction of the expression construct are known in the art. The selection of a cloning vector can be influenced by the gene transfer system selected for introduction of the expression construct into the host cell. At the end of each stage, the resulting construct may be analyzed by restriction, DNA sequence, hybridization and PCR analyses.

Site-directed mutagenesis can be used to introduce specific mutations into the genes encoding the fusion proteins provided by the present disclosure.

Various promoters (transcriptional initiation regulatory region) may be used. The selection of the appropriate promoter can depend on the proposed expression host. Promoters from heterologous sources may be used as long as they are functional in the chosen host.

Various signal sequences may be used to facilitate expression of the fusion proteins. Signal sequences can be selected or designed for efficient secretion and processing in the expression host may also be used. A signal sequence which is homologous to the human IL-2 coding sequence may be used for mammalian cells. The signal sequence may be joined directly through the sequence encoding the signal peptidase cleavage site to the protein coding sequence, or through a short nucleotide bridge.

Nucleic acids encoding a desired fusion protein can be introduced into a host cell by standard techniques for transfecting cells.

Alternatively, one can use synthetic gene construction for all or part of the construction of the fusion proteins. This can entail in vitro synthesis of a designed polynucleotide molecule to encode a polypeptide molecule of interest. Gene synthesis can be performed utilizing a number of techniques, such as the multiplex microchip-based technology and similar technologies wherein oligonucleotides are synthesized and assembled upon photo-programmable microfluidic chips.

Fusion proteins provided by the present disclosure can be isolated from harvested host cells or from the culture medium.

Compounds comprising an IL-2Rα ligand provided by the present disclosure include compounds that act as IL-2Rαβγc agonists.

An IL-2Rαβγc agonist provided by the present disclosure can comprise synthetic peptides or recombinant peptides linked in tandem to create a single chain peptide comprising an IL-2Rα ligand, an IL-2Rβ ligand, and an IL-2Rγc ligand. The ligands can be in any order and can be separated by amino acid linkers. The synthetic peptides can comprise natural amino acids or peptides with natural amino acids and suitable substitutions with unnatural amino acids. IL-2Rαβγc agonists provided by the present disclosure can be a recombinant fusion protein comprising an IL-2Rα ligand, an IL-2Rβ ligand, and IL-2Rγc ligand and fusion partner such as an Fc protein, an IgG protein, human serum albumin or other natural or designed protein, or a hydrophilic, biodegradable protein polymer. An IL-2Rαβγc agonist can comprise one or more IL-2Rα ligands. An IL-2Rαβγc agonist can comprise an IL-2Rα ligand, an IL-2Rβ ligand, and an IL-2Rγc ligand and include one or more moieties selected to modify the pharmacokinetics of the IL-2Rαβγc agonist such as PEG or an albumin binding moiety.

An IL-2Rαβγc agonist can bind to IL-2Rα and activate the IL-2 receptor. An IL-2Rαβγc agonist can bind to IL-2Rα with an $IC_{50}$, for example, less than 100 μM, less than 10 μM, less than 1 μM, less than 100 nM, less than 10 nM, or less than 1 nM. An IL-2Rαβγc agonist can bind to IL-2Rα either competitively or non-competitively with IL-2.

An IL-2Rαβγc agonist comprising an IL-2Rα ligand, an IL-2Rβ ligand, and an IL-2Rγc ligand can be configured to more potently activate cells expressing the IL-2Rα subunit, thereby facilitating the ability to differentially activate IL-2R expressed on the surface of different cell types by controlling dose of the agonist. For example, when incubated with a heteromeric compound comprising an IL-2Rα ligand, IL-2Rβ ligand, and an IL-2Rγc ligand, primary human peripheral blood mononuclear cells (PBMC) expressing the IL-2Rαβγc subunit, phosphorylate transcription 5 (STAT5) under conditions wherein human peripheral blood mononuclear cells (PBMC) expressing only the IL-2Rβγc subunits, do not phosphorylate transcription 5 (STAT5) to the same degree. A heteromer can comprise an IL-2Rα ligand, IL-2Rβ ligand, an IL-2Rγc ligand, and a linker, where the linker is configured such that the heteromer is an agonist for the IL-2 receptor. A linker can comprise a length that facilitates binding of an IL-2Rα ligand, an IL-2Rβ ligand, and an IL-2Rγc ligand to the IL-2 receptor. For example, a linker can have a length from 10 Å to 400 Å, from 10 Å to 300 Å, from 10 Å to 200 Å, 20 Å to 100 Å, from 30 Å to 80 Å, or from 40 Å to 60 Å. A linker can comprise a chemical structure that facilitates simultaneous binding of an IL-2Rα ligand, an IL-2Rβ ligand, an IL-2Rγc ligand to the respective IL-2 receptor subunits. For example, a linker can comprise a peptide or a hydrocarbon.

An IL-2Rαβγc agonist can partially activate the IL-2 receptor. Partial activation refers to a level of activation, that is, for example, less than 75% of maximum activation, less than 50%, less than 25%, less than 10%, or less than 1% of the maximum activation. Maximum activation ($E_{max}$) is the amplitude of cellular signal (activation) achievable at high agonist concentration such as a high concentration of IL-2. Partial IL-2Rαβγc agonists can be effective in modulating the levels of response of IL-2R to activation by the IL-2Rβ and IL-2Rγc subunits among different cell types expressing IL-2R. For example, different cell types are known to vary in expression levels of each of the IL-2R subunits, Rα, Rβ, and Rγc, and to exhibit different sensitivities to IL-2R agonists.

An IL-2R agonist comprising one or more IL-2Rα ligands can exhibit increased binding and potency on cells expressing the IL-2Rα subunit (such as Tregs). Natural IL-2R agonists, or mutants and modified forms of natural IL-2R agonists such as IL-2, can be modified to include additional IL-2Rα ligands to further increase affinity and potency of these agonists on IL-2Rα expressing cells.

An IL-2Rαβγc agonist can comprise an IL-2Rα ligand and modified IL-2Rβ and/or IL-2Rγc ligands. Modified IL-2Rβ and IL-2Rγc ligands can be selected or designed to bind and activate IL-2R, but with low or modest affinity and potency to IL-2R. Such IL-2Rαβγc agonists can have greater differential sensitivity for IL-2R activation between cells that highly express IL-2Rα and cells having a low level of IL-2Rα expression. For examples, between Tregs that have a high expression of IL-2Rα and Teff cells that have a low expression level of IL-2Rα.

An IL-2Rαβγc agonist can comprise one or more IL-2Rα ligands. The presence of multiple IL-2Rα ligands can preferentially increase the potency of the agonists on cells that highly express IL-2Rα compared to cells having low expression levels of IL-2Rα.

An IL-2Rαβγc agonist can comprise a moiety having an additional pharmacological activity other than that mediated by activation of the IL-2 receptor. The pharmacological activity can be an activity that has a therapeutic efficacy that is synergistic with that of the IL-2Rαβγc agonist or the pharmacological activity can be an activity that has a therapeutic efficacy that is not synergistic with that of the IL-2Rαβγc agonist. For example, a moiety or molecule having a useful pharmacological activity can comprise a checkpoint inhibitor.

Compounds provided by the present disclosure include IL-2Rα antagonists. An IL-2Rα antagonist is a compound comprising an IL-2Rα ligand that inhibits binding of IL-2 and mutants and modified forms thereof, to the IL-2Rα subunit and/or diminishes IL-2 activation of the IL-2 receptor.

IL-2Rα antagonists can attenuate the sensitivity of cells expressing the IL-2Rα subunit to activation by IL-2 or mutants and modified forms thereof. Examples of cells expressing the IL-2Rα subunit include Tregs.

IL-2Rα antagonists include compounds having more than one IL-2Rα ligand and can bind competitively or non-competitively with IL-2 to the IL-2 receptor.

IL-2Rα antagonists can comprise one or more IL-2Rα ligands and a moiety having a useful pharmacological activity. The moiety can exhibit a pharmacological activity that is synergistic with IL-2Rα inhibition or is not synergistic with inhibition of the IL-2Rα subunit.

IL-2Rα antagonists further include recombinant fusion proteins.

An IL-2R antagonist can comprise an IL-2Rα ligand only; an IL-2Rα ligand and an IL-2Rβ ligand; an IL-2Rα ligand and an IL-2Rγc ligand; or an IL-2Rα ligand, an IL-2Rβ ligand, and an IL-2Rγc ligand.

IL-2R antagonists include compounds that bind to either the IL-2Rα subunit or to the IL-2Rβ or IL-2Rγc subunit and inhibit activation of the IL-2 receptor.

IL-2R antagonists include compounds that bind to the IL-2Rα subunit and to the IL-2Rβ and/or the IL-2Rγc subunits and inhibit activation of the IL-2 receptor, where the IL-2Rβ and IL-2Rγc ligands are configured to not activate the IL-2 receptor. Such compounds are high affinity antagonists for IL-2R activation and the presence of an IL-2Rα ligand enhances the potency of the IL-2R antagonists.

IL-2R antagonists include compounds comprising the IL-2Rα and/or the IL-2Rβ and/or the IL-2Rγc ligands, which are configured to exhibit partial activation of the IL-2 receptor. These compounds are examples of partial IL-2R agonists. Such compounds are useful for modulating the level of response of cells to IL-2R agonists among cells having different expression levels of IL-2R subunits. Use of the partial IL-2R agonists/antagonists can modulate the response of cells to IL-2R agonists among cells having different expression levels of the IL-2Rα, IL-2Rβ, and/or IL-2Rγc subunits.

An IL-2R antagonist can comprise one or more IL-2Rα ligands. An IL-2R antagonist can be a peptide or a polypeptide, which can be synthetic or recombinant. In addition to one or more IL-2Rα ligands, an IL-2R antagonist can comprise one or more IL-2Rβ ligands and/or one or more IL-2Rγc ligands. The IL-2R ligands can be coupled in any order, in any orientation, and can be coupled with linkers. The linkers can comprise natural and/or unnatural amino acids and/or non-peptidyl structures.

A peptidyl or polypeptidyl IL-2R antagonist can be chemically modified to include, for example, moieties that affect the pharmacokinetics of the IL-2R antagonist such as PEG and albumin-binding moieties.

IL-2R antagonists further include recombinant fusion proteins.

Compounds comprising an IL-2Rα ligand include diagnostic reagents. As a diagnostic agent, a compound comprising an IL-2Rα ligand can be used to detect and/or measure cells expressing the IL-2Rα ligand. The compounds can be used to determine the expression level of the IL-2Rα expression of a cell, or population of cells, or of a tissue. The compounds can be used to assess the binding affinity of the IL-2Rα subunits in a cell or population of cells. The compounds may be used to determine the type of cell, for example, based on IL-2Rα expression levels.

The compounds can be useful for in vitro and in vivo diagnostics.

A diagnostic compound comprising an IL-2Rα ligand can comprise a detectable marker. The detectable marker can be cleavable or non-cleavable.

A detectable marker can comprise, for example, a radiolabel, a fluorescent label, an enzymatic label.

A diagnostic compound comprising an IL-2Rα ligand can be used to measure cells expressing the IL-2Rα subunit and/or the level of expression of cells expressing the IL-2Rα subunit in a biological sample such as a sample of blood of a patient. Measurements can be made, for example, using flow cytometry. The number of cells expressing the IL-2Rα subunit and/or the expression level of the IL-2Rα subunit, when correlated with a disease in a patient or a pharmacologically significant parameter of the disease in a patient can be used to inform treatment of the disease. For example, if a level of expression of the IL-2Rα subunit is above or below a therapeutically meaningful threshold for a particular disease, a compound comprising an IL-2Rα ligand provided by the present disclosure can be administered to the patient to treat the disease.

Compounds comprising an IL-2Rα ligand can be attached to a solid support. Based on their ability to bind to the IL-2Rα subunit, the compounds can be used as reagents for detecting IL-2Rα subunits, for example, on living cells, fixed cells, in biological fluids, in tissue homogenates, in purified, and natural in biological materials. In addition, based on their ability to bind the IL-2Rα subunit, the peptides of the present invention can be used, for example, in in situ staining, FACS (fluorescence-activated cell sorting), Western blotting, and ELISA. In addition, compounds provided by the present disclosure can be used in receptor purification, or in purifying cells expressing IL-2Rα subunit on the cell surface.

Compounds comprising an IL-2Rα ligand provided by the present disclosure can also be used as reagents for various medical research and diagnostic uses. Such uses include, for example, use as a calibration standard for quantitating the activities of candidate IL-2R agonists or IL-2R antagonists in functional assays; use to maintain the proliferation and growth of IL-2-dependent cell lines; (3) use in structural analysis of the IL-2-receptor through co-crystallization; use to investigate the mechanism of IL-2 signal transduction/receptor activation; and other research and diagnostic applications wherein the IL-2-receptor is implicated.

Assessing single patient response to therapy and qualifying a patient for optimal therapy are among the greatest challenges of modern healthcare and relate to trends in personalized medicine. A compound comprising an IL-2Rα ligand can have target selectivity for diseases in which cells associated with the etiology of the disease express the IL-2Rα ligand. For example, a compound comprising an IL-2Rα ligand radiolabeled for positron emission tomography (PET) or single photon emission computed tomography (SPECT) can be used to predict the targeting of the treatment based on a single-study, case-by-case patient analysis thus excluding subjects that are expected not to benefit from treatment with a therapeutic compound affecting the activity of the IL-2Rα subunit. PET/SPECT scans using radiolabeled a compound comprising an IL-2Rα ligand, once correlated to the concentration of a compound comprising an IL-2Rα ligand can provide a three-dimensional distribution map, which can then be used for macroscopic dose calculations.

Compounds comprising an IL-2Rα ligand can comprise one or more imaging agents. The IL-2Rα ligand can direct and localize the compound to cells, populations of cells, and tissue expressing the IL-2Rα subunit. The imaging compounds can comprise one or more imaging agents such as radiolabels, fluorescent labels, enzymatic labels, or PET imaging agents.

The imaging agents can be used to determine the number of cells expressing the IL-2Rα subunit, the expression level of cells expressing the IL-2Rα subunit, or properties of the IL-2Rα subunit such as the affinity of the IL-2Rα subunit to a particular IL-2Rα ligand and/or compound comprising an IL-2Rα ligand. The imaging agents can be used, for example, to evaluate cancer cells expressing the IL-2Rα receptor, or to evaluate Treg and/or Teff cells.

The label can be detected to determine a biodistribution of the compound in a patient or to assess the potential for therapeutic efficacy. For examples, tumors expressing high levels of the IL-2R receptor and/or the IL-2Rα subunit may be attractive targets for compounds comprising an IL-2Rα ligand provided by the present disclosure.

The imaging agents can be used to evaluate cells expressing the IL-2Rα subunit before therapy, during therapy, and/or following therapy.

Imaging agents comprising an IL-2Rα ligand can further comprise a moiety capable of binding to a cell surface and in particular to a protein expressed on the cell surface. The protein can be indicative of a certain cell type and is referred to as a cell surface marker. Imaging agents comprising both an IL-2Rα ligand and a cell surface marker can be used to assess cells, a population of cells, and/or a tissue expressing both the IL-2Rα subunit and the cell surface marker. Assessment can include determining the number of cells expressing both the IL-2Rα subunit and the cell surface marker, the expression levels of the IL-2Rα subunit and the cell surface marker, and/or the affinity of the imaging agent to the IL-2Rα subunit and/or the cell surface marker.

Cells expressing both the IL-2Rα subunit and the cell surface marker can be, for example, Tregs and/or activated Teff cells.

The imaging agents can be used to evaluate cells expressing the IL-2Rα subunit and the cell surface marker before therapy, during therapy, and/or following therapy.

As a practical example, T cell infiltration of tumor lesions is a known prognostic factor in several tumor types and is used as a treatment mechanism in some of these tumor types. For example, in metastatic melanoma, treatment with immune checkpoint inhibitors induces clinical benefit in about 30-50% of the patients. Tumor-infiltrating T cells express the IL-2 receptor on their surface. Therefore, these T cells can be visualized by molecular imaging with a compound comprising an IL-2Rα ligand and a radiolabel such as a PET tracer.

As another example, IL-2 is synthesized and secreted by activated T lymphocytes, especially $CD8^+$ CTL and $CD4^+$ Th1 lymphocytes. T lymphocyte activation is observed in many types of inflammatory diseases, such as inflammatory degenerative diseases, graft rejection, tumor inflammation, organ-specific autoimmune diseases, and adipose inflammatory insulin resistance. IL-2 binds with high affinity to the cell membrane IL-2 receptor, which is mainly expressed on the cell surface of activated T lymphocytes. PET imaging of activated T lymphocytes by a radiolabeled compound comprising an IL-2Rα ligand therefore provides an in vivo, dynamic approach in studying the immune-cell infiltration in these inflammatory diseases.

Compounds comprising IL-2Rα ligands can comprise a cell-specific targeting moiety or molecule.

A cell-specific targeting moiety can comprise a moiety that has an affinity for a component on the surface of a cell such as a receptor, a protein, or an epitope. A moiety can comprise, for example, a ligand or an antibody having an affinity to a cell surface component.

The targeting moiety can direct and concentrate compounds comprising an IL-2Rα ligand at the cells, population of cells, or tissue targeted by the targeting moiety.

The targeting moiety can enhance the potency of IL-2R agonism or IL-2R antagonism for the cells or population of cells being targeted.

The targeting moiety can provide a differential response to IL-2R agonism or to IL-2R antagonism between the cells being targeted and the cells not being targeted by the targeting moiety.

The targeting moiety can provide a differential response to IL-2R agonism or IL-2R antagonism between cells having a high expression level of the targeted component and cells having a lower expression level of the targeted component.

Compounds comprising an IL-2Rα ligand can further comprise a bioactive moiety or a bioactive molecule. A compound comprising an IL-2Rα ligand can be used to deliver the bioactive moiety or bioactive molecule to cells, to a population of cells, or to a tissue expressing the IL-2Rα subunit.

The bioactive moiety or molecule can be non-cleavable and capable of exerting a biological activity when bound to the compound comprising an IL-2Rα ligand.

The bioactive moiety or molecule can be cleavable. The moiety can be cleavable by any suitable mechanism such as by pH, enzymatic, thermal, and/or electromagnetic mechanisms. Electromagnetic mechanisms include, for example, exposing the compounds to infrared, visible, or ultraviolet radiation, where the bioactive moiety is attached to the compounds comprising an IL-2Rα ligand through a photolabile moiety capable of being cleaved by the radiation.

The bioactive molecule can be non-cleavable but otherwise activatable, such as for example, activatable by exposure to electromagnetic radiation.

IL-2Rα ligands can be selected to have enhanced binding to the IL-2Rα subunit at a certain pH. For example, a pH-selective IL-2Rα ligand can have a greater affinity to the IL-2Rα subunit at low pH commensurate with that of a solid tumor microenvironment. Compounds comprising low-pH selective IL-2Rα ligands can be used to preferentially target cells in low pH environments expressing the IL-2Rα subunit compared to cells in normal pH environments associated with healthy tissue.

Thus, compounds comprising selective IL-2Rα ligands such as pH-selective IL-2Rα ligands can be used to deliver bioactive moieties and molecules to cells targeted by the selective IL-2Rα ligands.

A bioactive moiety or bioactive molecule can itself be selective for a particular cell population. For example, a bioactive moiety or bioactive molecule can exhibit a greater or lesser affinity, potency, and/or activity at the cell being targeted by a selective or IL-2Rα ligand. For example, the bioactive moiety or molecule can exhibit greater bioactivity in a low pH tumor microenvironment when targeted by a pH-selective IL-2Rα ligand. In this example, the bioactive moiety is directed to cells located in the low-pH tumor microenvironment that express the IL-2Rα subunit by the pH-selective IL-2Rα ligand. Thus, the activity of the pH-selective bioactive moiety is enhanced in the low-pH tumor microenvironment.

Compounds comprising an IL-2Rα ligand can further comprise a cytotoxic moiety or molecule. Such compounds can be used to deliver a cytotoxic compound to a cell expressing the IL-2Rα subunit such as Tregs. The cytotoxic moiety or molecule can exert cytotoxicity when bound to the compound or can be cleavable and the moiety or molecule can be cytotoxic when released from the compound; or the cytotoxic moiety can be activated by electromagnetic radiation.

The cytotoxic moiety or molecule can be used to deplete cells expressing the IL-2Rα ligand being targeted.

IL-2Rα ligand-containing cytotoxic compounds can have more than one IL-2Rα subunit and thereby can exhibit a higher affinity and/or selectivity to cells, populations of cells, and tissue that highly express the IL-2Rα subunit compared to cells having a lower expression level of the IL-2Rα subunit.

IL-2Rα ligand-containing cytotoxic compounds can further include a cell surface targeting component. Such cytotoxic compounds can exhibit enhanced efficacy to cells, populations of cells, and tissue expressing both the IL-2Rα subunit and the surface target component.

Examples of suitable cytotoxic molecules include anti-microtubule agents, alkylating agents, and DNA minor groove binding agents.

These therapeutic strategies for targeting IL-2Rα expressing cells with cytotoxic compounds have been demonstrated.

As an example, denileukin diftitox (DAB-IL-2, Ontak) is a diphtheria-toxin-based fusion protein that depletes CD25-positive cells including regulatory T cells and has been approved for the treatment of persistent or recurrent cutaneous T cell lymphoma. Significant toxicities of the drug include acute hypersensitivity, vascular leak syndrome and impaired immune function. The latter two toxicities are due to nonspecific binding of immunotoxin to macrophages and activated lymphocytes. A modified immunotoxin was developed to the efficacy and reduce the toxicity. A modified diphtheria toxin (DT) served as the cytotoxic moiety and IL-2 served as the targeting moiety for targeting cancer cells that overexpress the IL-2 receptor. T cells, B cells, macrophages and natural killer cells express the IL-2Rβ and IL-2Rγc subunits, whereas the IL-2Rα subunit is uniquely expressed on cancer cells and activated T cells. Targeting the IL-2Rα subunit eliminated toxicity.

Cytotoxicity of this recombinant protein was observed to be more than denileukin diftitox for cells with higher IL-2Rα expression whereas in cells expressing both IL-2Rα subunit and the IL-2Rβ subunit, cytotoxicity varies from cell line to cell line. The immunotoxin exhibited comparable efficacy to denileukin diftitox and was more specifically targeted to cells expressing the IL-2Rα subunit. The fusion protein depletes IL-2Rα-positive cells including Tregs and has been approved for the treatment of persistent or recurrent cutaneous T cell lymphoma.

Another example of an IL-2Rα-targeted cytotoxic compound is $^{90}$Y-daclizumab, an anti-CD25 monoclonal antibody for treating relapsed Hodgkin's lymphoma. Using the anti-CD25 monoclonal antibody, daclizumab was directed toward nonmalignant T cells expressing the IL-2Rα subunit, rather than the tumor cells. $^{90}$Y provided strong β emissions that killed antigen-non-expressing tumor cells at a distance by a crossfire effect. Furthermore, the strong Pirradiation killed normal cells in the tumor microenvironment that nurture the malignant cells in the lymphomatous mass and thereby provided meaningful treatment of the Hodgkin's lymphoma.

Compounds comprising an IL-2Rα ligand can further comprise a moiety having a useful pharmacological activity.

The pharmacological moiety can function synergistically with IL-2R agonist activity or synergistically with IL-2R antagonist activity, or the pharmacological moiety may not exhibit synergism with activity of the IL-2Rα subunit.

Examples of suitable pharmacological moieties include antibodies and antibody fragments that are inhibitors of checkpoint molecules, pro-apoptotic and anti-apoptotic molecules, cytotoxic molecules, agonists of chemokine, antagonists of chemokine, cytokine, growth factor and other cell surface rectors, and ligands and inhibitors of cell surface adhesion molecules such as integrins.

Peptides provided by the present disclosure can be synthesized by methods known in the art, for example, by using standard solid phase techniques.

A peptide comprising an IL-2Rα ligand provided by the present disclosure can be modified, for example, by phosphorylation, and by other methods known in the art. Thus, the peptides provided by the disclosure can also serve as a basis to prepare peptide mimetics with similar biological activity.

A variety of techniques are available for constructing peptide mimetics with the same or similar desired biological activity as a corresponding peptide but with more favorable activity than the peptide with respect to solubility, stability, and susceptibility to hydrolysis and proteolysis.

Pharmaceutical compositions provided by the present disclosure comprise a compound comprising an IL-2Rα ligand.

Pharmaceutical compositions provided by the present disclosure can comprise a therapeutically effective amount of a compound comprising an IL-2Rα ligand or a pharmaceutically acceptable salt thereof together with a suitable amount of one or more pharmaceutically acceptable vehicles so as to provide a composition for administration to a patient. Suitable pharmaceutical vehicles and methods of preparing pharmaceutical compositions are known.

A pharmaceutical composition can comprise a therapeutically effective amount of one or more compounds comprising an IL-2Rα ligand.

A compound comprising an IL-2Rα ligand and/or pharmaceutical composition thereof can be used in an amount effective to achieve an intended purpose. For example, for use to treat a disease such as cancer or an autoimmune disease, a compound comprising an IL-2Rα ligand and/or pharmaceutical compositions thereof, can be administered a therapeutically effective amount for treating the cancer or the autoimmune disease.

The amount of a compound comprising an IL-2Rα ligand and/or pharmaceutical composition thereof that will be effective in the treatment of a particular disease can depend on, among other factors, the patient being treated, the severity of the disease, the etiology of the disease, the manner of administration and the judgment of the prescribing physician, and can be determined by standard clinical techniques known in the art.

A therapeutically effective dose of a compound comprising an IL-2Rα ligand and/or pharmaceutical composition thereof can provide a therapeutic benefit without causing substantial toxicity. Toxicity of a compound comprising an IL-2Rα ligand and/or pharmaceutical compositions thereof may be determined using standard pharmaceutical procedures. The dose ratio between toxic and therapeutic effect is the therapeutic index. A compound comprising an IL-2Rα ligand and/or pharmaceutical composition thereof can exhibit a high therapeutic index in treating a disease such as cancer or an autoimmune disease. A dose of a compound comprising an IL-2Rα ligand and/or pharmaceutical composition thereof can be within a range of circulating concentrations that include an effective dose with minimal toxicity.

A dose of a compound comprising an IL-2Rα ligand provided by the present disclosure and appropriate dosing intervals may be selected to maintain a sustained therapeutically effective concentration of the compound comprising an IL-2Rα ligand provided by the present disclosure in the blood of a patient, and in certain embodiments, without exceeding a minimum adverse concentration.

Pharmaceutical compositions provided by the present disclosure may further comprise one or more pharmaceutically active compounds in addition to a compound comprising an IL-2Rα ligand provided by the present disclosure. Such compounds may be provided, for example, to treat the disease being treated with a compound comprising an IL-2Rα ligand or to treat a disease, disorder, or condition other than the disease being treated with the compound comprising an IL-2Rα ligand, to treat a side-effect caused by administering the compound comprising an IL-2Rα ligand, to augment the efficacy of the a compound comprising an IL-2Rα ligand, and/or to modulate the activity of the compound comprising an IL-2Rα ligand.

A compound comprising an IL-2Rα ligand provided by the present disclosure may be used in combination with at least one other therapeutic agent. A compound comprising an IL-2Rα ligand may be administered to a patient together with another compound for treating the disease. The at least one other therapeutic agent may be a different compound comprising an IL-2Rα ligand. A compound comprising an IL-2Rα ligand and the at least one other therapeutic agent may act additively or synergistically. The at least one additional therapeutic agent may be included in the same pharmaceutical composition or vehicle comprising the compound comprising an IL-2Rα ligand or may be in a separate pharmaceutical composition or vehicle. Accordingly, methods provided by the present disclosure further include, in addition to administering a compound comprising an IL-2Rα ligand, administering one or more therapeutic agents effective for treating the disease being treated by the compound comprising an IL-2Rα ligand or a different disease. Methods provided by the present disclosure include administration of a compound comprising an IL-2Rα ligand and one or more other therapeutic agents provided that the combined administration does not inhibit the therapeutic efficacy of the compound comprising an IL-2Rα ligand and/or does not produce adverse combination effects. A pharmaceutical composition comprising a compound comprising an IL-2Rα ligand provided by the present disclosure may be administered with one or more substances, for example, to enhance, modulate and/or control release, bioavailability, therapeutic efficacy, therapeutic potency, and/or stability, of the compound comprising an IL-2Rα ligand. For example, a pharmaceutical composition comprising a compound comprising an IL-2Rα ligand can be co-administered with an active agent having pharmacological effects that enhance the therapeutic efficacy of the compound comprising an IL-2Rα ligand.

Compounds comprising an IL-2Rα ligand provided by the present disclosure or a pharmaceutical composition thereof may be included in a kit that may be used to administer the compound to a patient for therapeutic purposes. A kit may include a pharmaceutical composition comprising a compound comprising an IL-2Rα ligand provided by the present disclosure suitable for administration to a patient and instructions for administering the pharmaceutical composition to the patient. The kit can be a kit, for example for treating cancer or a kit for treating an autoimmune disease. A kit for use in treating cancer or an autoimmune disease in a patient can comprise a compound comprising an IL-2Rα ligand provided by the present disclosure, a pharmaceutically acceptable vehicle for administering the compound, and instructions for administering the compound to a patient.

The pharmaceutical compositions can be included in a container, pack, or dispenser together with instructions for administration. Instructions supplied with a kit may be printed and/or supplied, for example, as an electronic-readable medium, a video cassette, an audiotape, a flash memory device, or may be published on an internet web site or distributed to a patient and/or health care provider as an electronic communication.

Compounds comprising an IL-2Rα ligand provided by the present disclosure may be used for treating cancer in a patient. The cancer can be, for example, a solid tumor or a metastasis.

A compound comprising an IL-2Rα ligand provided by the present disclosure or a pharmaceutical composition thereof may be administered to treat a cancer known to be treated by activation or inhibition of the IL-2R receptor. Compounds comprising an IL-2Rα ligand provided by the present disclosure or a pharmaceutical composition thereof may be administered to treat a cancer known to be treated by activation or inhibition of the IL-2Rβγc subunits and where simultaneous activation of the IL-2Rα subunit enhances therapeutic efficacy, modulates therapeutic efficacy, enhances selective therapeutic efficacy, and/or minimizes unwanted side effects.

Compounds comprising an IL-2Rα ligand provided by the present disclosure or a pharmaceutical composition thereof can be used to treat, for example, one or more of the following cancers: acute lymphoblastic leukemia, acute myeloid leukemia, adrenocortical carcinoma, appendix cancer, astrocytoma, atypical teratoid/rhabdoid tumor, basal cell carcinoma (nonmelanoma), B-cell lymphoma, bladder cancer, bone cancer, brain and spinal cord tumors, brain stem cancer, brain tumor, breast cancer, bronchial tumors, Burkitt lymphoma, carcinoid tumor, carcinoma of head and neck, central nervous system embryonal tumors, cerebellar astrocytoma, cerebral astrocytoma/malignant glioma, cervical cancer, chordoma, chronic lymphocytic leukemia, chronic myelogenous leukemia, colorectal cancer, craniopharyngioma, cutaneous T-cell lymphoma, desmoplastic small round cell tumor, ductal carcinoma, dye cancer, endocrine pancreas tumors (islet cell tumors), endometrial cancer, ependymoblastoma, esophageal cancer, esthesioneuroblastoma, Ewing family of tumors, extracranial germ cell tumor, extrahepatic bile duct cancer, gallbladder cancer, gastric cancer, gastrointestinal carcinoid tumor, gastrointestinal stromal tumor, gestational trophoblastic tumor, glioblastoma, glioma, hairy cell leukemia, head and neck cancer, heart cancer, hematopoetic tumors of the lymphoid lineage, hepatocellular cancer, Hodgkin lymphoma, hypopharyngeal cancer, hypothalamic and visual pathway glioma, IDs-related lymphoma, intraocular melanoma, islet cell tumors, Kaposi sarcoma, kidney cancer, Langerhans cell histiocytosis, laryngeal cancer, leukemia, lip and oral cavity cancer, male breast cancer, malignant fibrous histiocytoma, malignant germ cell tumors, malignant mesothelioma, medulloblastoma, melanoma, Merkel cell carcinoma, mesothelioma, mouth cancer, multiple endocrine neoplasia syndrome, multiple myeloma, mycosis fungoides, myelodysplastic, myeloproliferative neoplasms, nasal cavity and paranasal sinus cancer, nasopharyngeal cancer, neuroblastoma, non-Hodgkin lymphoma, non-small cell lung cancer, oral cancer, oropharyngeal cancer, osteosarcoma, ovarian cancer, ovarian epithelial cancer, ovarian germ cell tumor, ovarian low malignant potential tumor, pancreatic cancer, pancreatic neuroendocrine tumors (islet cell tumors), papillomatosis, paraganglioma, paranasal sinus and nasal cavity cancer, parathyroid cancer, penile cancer, pharyngeal cancer, pheochromocytoma, pineal parenchymal tumors, pineoblastoma and supratentorial primitive neuroectodermal tumors, pituitary tumor, plasma cell neoplasm/multiple myeloma, pleuropulmonary blastoma, pregnancy and breast cancer, primary central nervous system lymphoma, primary liver cancer, primary metastatic squamous neck cancer with occult, prostate cancer, rectal cancer, renal cell cancer, renal pelvis and ureter, respiratory tract carcinoma, retinoblastoma, rhabdomyosarcoma, salivary gland cancer, sarcoma, Sézary syndrome, skin cancer, skin cancer, small intestine cancer, soft tissue sarcoma, squamous cell carcinoma (non-melanoma), stomach cancer, supratentorial primitive neuroectodermal tumors, T-cell lymphoma, testicular cancer, throat cancer, thymoma and thymic carcinoma, thyroid cancer, transitional cell cancer, urethral cancer, uterine sarcoma, vaginal cancer, visual pathway and hypothalamic glioma, vulvar cancer, Waldenström macroglobulinemia, Wilms tumor, and systemic and central metastases of any of the foregoing.

A compound comprising an IL-2Rα ligand or a pharmaceutical composition comprising a compound comprising an IL-2Rα ligand may be administered in conjunction with an agent known or believed to be effective in treating cancer in a patient, such as the same cancer being treated with the compound comprising an IL-2Rα ligand.

A compound comprising an IL-2Rα ligand or a pharmaceutical composition thereof may be administered in conjunction with a chemotherapeutic agent, such as, for example, N-acetyl cysteine (NAC), adriamycin, alemtuzumab, amifostine, arsenic trioxide, ascorbic acid, bendamustine, bevacizumab, bortezomib, busulfan, buthionine sulfoxime, carfilzomib, carmustine, clofarabine, cyclophosphamide, cyclosporine, cytarabine, dasatinib, datinomycin, defibrotide, dexamethasone, docetaxel, doxorubicin, etoposide, filgrastim, floxuridine, fludarabine, gemcitabine, interferon alpha, ipilimumab, lenalidomide, leucovorin, melphalan, mycofenolate mofetil, paclitaxel, palifermin, panobinostat, pegfilrastim, prednisolone, prednisone, revlimid, rituximab, sirolimus, sodium 2-mercaptoethane sulfonate (MESNA), sodium thiosulfate, tacrolimus, temozolomide, thalidomide, thioguanine, thiotepa, topotecan, velcade, or a combination of any of the foregoing.

A compound comprising an IL-2Rα ligand and/or pharmaceutical composition thereof can be used in combination therapy with other chemotherapeutic agents including one or more antimetabolites such as folic acid analogs; pyrimidine analogs such as fluorouracil, floxuridine, and cytosine arabinoside; purine analogs such as mercaptopurine, thiogunaine, and pentostatin; natural products such as vinblastine, vincristine, etoposide, tertiposide, dactinomycin, daunorubicin, doxorubicin, bleomycin, mithamycin, mitomycin C, L-asparaginase, and interferon alpha; platinum coordination complexes such as cis-platinum, and carboplatin; mitoxantrone; hydroxyurea; procarbazine; hormones and antagonists such as prednisone, hydroxyprogesterone caproate, medroxyprogesterone acetate, megestrol acetate, diethylstilbestrol, ethinyl estradiol, tamoxifen, testosterone propionate, fluoxymesterone, flutamide, and leuprolide, anti-angiogenesis agents or inhibitors such as angiostatin, retinoic acids, paclitaxel, estradiol derivatives, and thiazolopyrimidine derivatives; apoptosis prevention agents; triptolide; colchicine; luliconazole; and radiation therapy.

A compound comprising an IL-2Rα ligand or a pharmaceutical composition comprising compound comprising an IL-2Rα ligand may be administered in conjunction with one or more chemotherapeutic agents, such as, for example, abarelix, abiraterone, abiraterone acetate, n-acetyl cysteine, aclarubicin hydrochloride, adriamycin, adenine, afatinib, afatinib dimaleate, alemtuzumab, alendronate sodium, alitretinoin, allopurinol sodium, altretamine, amifostine, aminoglutethimide, aminolevulinic acid, amrubicin, amsacrine, anastrozole, angiostatin, apremilast, aprepitant, arsenic trioxide, ascorbic acid, 1-asparaginase, azacitidine, azathioprine sodium, bazedoxifene (serm), belinostat, bendamustine hcl, o6-benzylguanine (o6-bg), bevacizumab, bexarotene, bicalutamide, biricodar, bleomycin sulfate, bortezomib, bosutinib, brivudine, buserelin, busulfan, buthionine sulfoximine, cabazitaxel, cabozantinib, capecitabine, carboplatin, carboquone, carfilzomib, carmofur, carmustine, ceritinib, chlorambucil, cisplatin, cladribine, clodronate disodium, clofarabine, crizotinib, cyclophosphamide, cyclosporine, cytarabine, cytosine arabinoside, dabrafenib, dacarbazine, dactinomycin, dasatinib, datinomycin, daunorubicin, decitabine, defribrotide, degarelix acetate, dexamethasone, dexrazoxane hydrochloride, diaziquone, diethyl stilbestrol, docetaxel, doxifluridine, doxorubicin hydrochloride, doxorubicin free base, dromostanolone propionate, dutasteride, eltrombopag, enzalutamide, epirubicin hydrochloride, eribulin mesylate, erlotinib hydrochloride, estramustine phosphate sodium, ethinyl estradiol, etoposide phosphate, etoposide, everolimus, exemestane, fentanyl, filgrastim, fingolimod, floxuridine, fludarabine phosphate, fluorouracil, fluoxymesterone, flutamide, formestane, formylmelphalan, fosaprepitant, fotemustine, fulvestrant, gefitinib, gemcitabine hydrochloride, gemcitabine free base, glutathione, glyciphosphoramide, glyfosfin, goserelin acetate, granisetron hydrochloride, heptaplatin, hexyl 5-aminolevulinate, histrelin acetate, hydroxyprogesterone caproate, hydroxyurea, ibandronate sodium, ibrutinib, icotinib, idarubicin HCl, idelalisib, idoxuridine, ifosfamide, interferon alpha, imatinib mesylate, imiquimod, ingenol mebutate, ipilimumab, irinotecan hydrochloride, ixabepilone, lanreotide acetate, lapatinib free base, lapatinib ditosylate, lasofoxifene, lenalidomide, letrozole, leucovorin calcium, leuprolide acetate, levamisole hydrochloride, levoleucovorin calcium, iobenguane, lobaplatin, lomustine, maropitant, masoprocol, mechlorethamine hydrochloride, megestrol acetate, medroxyprogesterone acetate, melphalan hydrochloride, mercaptopurine, mercaptoethane sulfonate sodium, methotrexate, methoxsalen, methyl aminolevulinate, methylene blue, methylisoindigotin, mifamurtide, miltefosine, miriplatin, mithamycin, mitobronitol, mitomycin C, mitotane, mitoxantrone hydrochloride, mycophenolate mofetil, nabiximols, nafarelin, nandrolone, nedaplatin, nelarabine, netupitant, nilotinib, nilutamide, nimustine, nintedanib, nocodazole, octreotide, olaparib, omacetaxine mepesuccinate, ondansetron hydrochloride, oxaliplatin, paclitaxel, palbociclib, palifermin, palonosetron hydrochloride, pamidronate disodium, panobinostat, pasireotide, pazopanib hydrochloride, pegfilrastim, pemetrexed disodium, pentostatin, peplomycin, pipobroman, pirarubicin, plerixafor, plicamycin, pomalidomide, ponatinib, porfimer sodium, porfiromycin, pralatrexate, prednimustine, prednisolone, prednisone, procarbazine hydrochloride, quinagolide hydrochloride, raloxifene, raltitrexed, radotinib, ranimustine, retinoic acids, revlimide, rituxinab, romidepsin, ruxolitinib, ruxolitinib phosphate, semustine, sirolimus, sodium thiosulfate, sorafenib free base, sorafenib tosylate, streptozocin, sufentanil, sunitinib, tacrolimus, talaporfin sodium, tamibarotene, tamoxifen citrate, tapentadol, temoporfin, temozolomide, temsirolimus, teniposide, teriflunomide, tertiposide, testolactone, testosterone propionate, thalidomide, thioguanine, thiotepa, thymalfasin, toceranib phosphate, topotecan hydrochloride, toremifene citrate, trabectedin, trametinib, tretinoin, trilostane, triptorelin, tropisetron, uramustine, valrubicin, vandetanib, vedotin, vemurafenib, verteporfin, vinblastine, vincristine sulfate, vincristine free base, vindesine, vinorelbine tartrate, vorinostat, and zoledronic acid.

Compounds provided by the present disclosure can be useful in treating autoimmune diseases. Autoimmune diseases are defined as human diseases in which the immune system attacks its own proteins, cells, and tissues. A comprehensive listing and review of autoimmune diseases can be found, for example, in *The Autoimmune Diseases* (Rose and Mackay, 2014, Academic Press).

Examples of autoimmune diseases include Addison's disease, agammaglobulinemia, alopecia areata, amyloidosis, ankylosing spondylitis, anti-GBM/anti-TBN nephritis, antiphospholipid syndrome, autoimmune angioedema, autoimmune dysautonomia, autoimmune encephalomyelitis, autoimmune hepatitis, autoimmune inner ear disease, autoimmune myocarditis, autoimmune pancreatitis, autoimmune retinopathy, autoimmune urticaria, axonal and neuronal neuropathy, Balo disease, Bechet's disease, benign mucosal pemphigoid, bullous pemphigoid, Castleman disease, celiac disease, Chagas disease, chronic inflammatory demyelinating polyneuropathy, chronic recurrent multifocal osteomyelitis, Churg-Strauss, cicatricial pemphigoid, Cogan's syndrome, cold agglutinin disease, congenital heart block, Coxsackie myocarditts, CREST syndrome, Crohn's disease, dermatitis herpetiformis, dermatomyositis, Devic's disease, discoid lupus, Dressler's syndrome, endometriosis, eosinophilic esophagitis, eosinophilic fasciitis, erythema nodosum, essential mixed cryoglobulinemia, Evans syndrome, fibromyalgia, fibrosing alveolitis, giant cell arteritis, giant cell myocarditis, glomerulonephritis, Goodpasture's syndrome, granulomatosis with polyangiitis, Graves' disease, Guillain-Barre syndrome, Hashimoto thyroiditis, hemolytic anemia, Henoch-Schonlein purpura, herpes gestationis or pemphigoid gestationis, hypogammaglobulinemia, IgA nephropathy, IgG4-related sclerosing disease, immune thrombocytopenic purpura, inclusion body myositis, interstitial cystitis, juvenile arthritis, juvenile diabetes, juvenile myositis, Kawasaki disease, Lambert-Eaton syndrome, leukocytoclastic vasculitis, lichen planus, lichen sclerosis, ligneous conjunctivitis, linear IgA disease, lupus, Lyme disease chronic, Meniere's diseases, microscopic polyangiitis, mixed connective tissue disease, Mooren's ulcer, Mucha-Habermann disease, multiple sclerosis, myasthenia gravis, myositis, narcolepsy, neuromyelitis, optica, neutropenia, ocular cicatricial pemphigoid, optic neuritis, palindromic rheumatism, PANDAS, paraneoplastic cerebellar degeneration, paroxysmal nocturnal hemoglobinuria, Parry Romberg syndrome, pars planitis, Parsonage-Turner syndrome, pemphigus, peripheral neuropathy, perivenous encephalomyelitis, pernicious anemia, POEMS syndrome, polyarteritis nodosa, polyglandular syndromes, polymyalgia rheumatica, polymyositis, postmyocardial infarction syndrome, postpericardiotomy syndrome, primary biliary cirrhosis, primary sclerosing cholangitis, progesterone dermatitis, psoriasis, psoriatic arthritis, pure red cell aplasia, pyoderma gangrenosum, Raynaud's phenomenon, reactive arthritis, reflex sympathetic dystrophy, relapsing polychondritis, restless legs syndrome, retroperitoneal fibrosis, rheumatic fever, rheumatoid arthritis, sarcoidosis, Schmidt syndrome, scleritis, scleroderma, Sjogren's syndrome, sperm and testicular autoimmunity, stiff person syndrome, subacute bacterial endocarditis, Susac's syndrome, sympathetic ophthalmia, Takayasu's arteritis, temporal arteritis, thrombocytopenic purpura, Tolosa-Hunt syndrome, transverse myelitis, Type 1 diabetes, ulcerative colitis, undifferentiated connective tissue disease, uveitis, vasculitis, vitiligo, and Wegener's granulomatosis.

A compound comprising an IL-2Rα ligand or a pharmaceutical composition comprising a compound comprising an IL-2Rα ligand may be administered in conjunction with an agent known or believed to be effective in treating an autoimmune disease in a patient.

A compound comprising an IL-2Rα ligand or a pharmaceutical composition comprising a compound comprising an IL-2Rα ligand may be administered in conjunction with an IL-15 agonist for treating an autoimmune disease. For example, a suitable IL-15 agonist is disclosed in PCT International Publication No. WO 2017/062832 A1 and in PCT International Publication No. WO 2015/153753 A1.

Compounds comprising an IL-2Rα ligand provided by the present disclosure and pharmaceutical compositions thereof may be administered to a patient to treat a disease associated with the activation, proliferation, metabolism, and/or differentiation of T-cells.

Compounds comprising an IL-2Rα ligand provided by the present disclosure and pharmaceutical compositions thereof may be administered to a patient to treat an organ transplant.

Compounds comprising an IL-2Rα ligand provided by the present disclosure and pharmaceutical compositions thereof may be administered to treat an inflammatory disease.

A compound comprising an IL-2Rα ligand or a pharmaceutical composition comprising a compound comprising an IL-2Rα ligand may be administered in conjunction with an agent known or believed to interfere with cell proliferation.

A compound comprising an IL-2Rα ligand or a pharmaceutical composition comprising a compound comprising an IL-2Rα ligand may be administered in conjunction with an agent known or believed to interfere with metabolism. A compound comprising an IL-2Rα ligand or a pharmaceutical composition comprising a compound comprising an IL-2Rα ligand may be administered in conjunction with an agent known or believed to interfere with mitochondrial metabolism. A compound comprising an IL-2Rα ligand or a pharmaceutical composition comprising a compound comprising an IL-2Rα ligand may be administered in conjunction with an agent known or believed to be an anti-metabolite. A compound comprising an IL-2Rα ligand or a pharmaceutical composition comprising a compound comprising an IL-2Rα ligand may be administered in conjunction with an agent known or believed to interfere RNA transcription. A compound comprising an IL-2Rα ligand or a pharmaceutical composition comprising a compound comprising an IL-2Rα ligand may be administered in conjunction with an agent known or believed to interfere with RNA translation. A compound comprising an IL-2Rα ligand or a pharmaceutical composition comprising a compound comprising an IL-2Rα ligand may be administered in conjunction with an agent known or believed to interfere with protein synthesis. A compound comprising an IL-2Rα ligand or a pharmaceutical composition comprising a compound comprising an IL-2Rα ligand may be administered in conjunction with an agent known or believed to interfere with synthesis of precursors for DNA synthesis and replication. A compound comprising an IL-2Rα ligand or a pharmaceutical composition comprising a compound comprising an IL-2Rα ligand may be administered in conjunction with an agent known or believed to interfere with purine synthesis. A compound comprising an IL-2Rα ligand or a pharmaceutical composition comprising a compound comprising an IL-2Rα ligand may be administered in conjunction with an agent known or believed to interfere with nucleoside synthesis. A compound comprising an IL-2Rα ligand or a pharmaceutical composition comprising a compound comprising an IL-2Rα ligand may be administered in conjunction with an agent known or believed to interact with mTOR. A compound comprising an IL-2Rα ligand or a pharmaceutical composition comprising a compound comprising an IL-2Rα ligand may be administered in conjunction with an agent known or believed to interact be an mTOR inhibitor. A compound comprising an IL-2Rα ligand or a pharmaceutical composition comprising compound comprising an IL-2Rα ligand may be administered in conjunction with an agent known or believed to interfere with cell cycle checkpoints.

A compound comprising an IL-2Rα ligand or a pharmaceutical composition comprising a compound comprising an IL-2Rα ligand may be administered in conjunction with a checkpoint inhibitor including CTLA-4 inhibitors such as ipilimumab, PD1 inhibitors such as pembrolizumab and cemiplimab, and PD-LI inhibitors such as atezolizumab, avelumab, and durvalumab. A compound comprising an IL-2Rα ligand or a pharmaceutical composition comprising a compound comprising an IL-2Rα ligand may be administered in conjunction with an immunomodulator such as CD137/4-1BB, CD27, GIYR, and/or OC40.

A compound comprising an IL-2Rα ligand or a pharmaceutical composition comprising a compound comprising an IL-2Rα ligand may be administered in conjunction with an agent known or believed to be cytotoxic. A compound comprising an IL-2Rα ligand or a pharmaceutical composition comprising a compound comprising an IL-2Rα ligand may be administered in conjunction with an agent known or believed to be cytostatic. A compound comprising an IL-2Rα ligand or a pharmaceutical composition comprising a compound comprising an IL-2Rα ligand may be administered in conjunction with an agent known or believed to cause DNA damage. A compound comprising an IL-2Rα ligand or a pharmaceutical composition comprising a compound comprising an IL-2Rα ligand may be administered in conjunction with an agent known or believed to cause cell cycle arrest. A compound comprising an IL-2Rα ligand or a pharmaceutical composition comprising a compound comprising an IL-2Rα ligand may be administered in conjunction with an agent known or believed to cause mitotic catastrophe.

A compound comprising an IL-2Rα ligand or a pharmaceutical composition comprising a compound comprising an IL-2Rα ligand may be administered in conjunction with an agent known or believed to modulate drug resistance. A compound comprising an IL-2Rα ligand or a pharmaceutical composition comprising a compound comprising an IL-2Rα ligand may be administered in conjunction with an agent known or believed to reduce multi-drug resistance. A compound comprising an IL-2Rα ligand or a pharmaceutical composition comprising a compound comprising an IL-2Rα ligand may be administered in conjunction with an agent known or believed to interact with membrane proteins. A compound comprising an IL-2Rα ligand or a pharmaceutical composition comprising a compound comprising an IL-2Rα ligand may be administered in conjunction with an agent known or believed to interact with plasma membrane proteins. A compound comprising an IL-2Rα ligand or a pharmaceutical composition comprising a compound comprising an IL-2Rα ligand may be administered in conjunction with an agent known or believed to interact with nuclear membrane proteins. A compound comprising an IL-2Rα ligand or a pharmaceutical composition comprising a compound comprising an IL-2Rα ligand may be administered in conjunction with an agent known or believed to interact with major vault protein or proteins. A compound comprising an IL-2Rα ligand or a pharmaceutical composition comprising a compound comprising an IL-2Rα ligand may be administered in conjunction with an agent known or believed to interact with gen products of the MVP (major vault protein) gene.

A compound comprising an IL-2Rα ligand or a pharmaceutical composition comprising a compound comprising an IL-2Rα ligand may be administered in conjunction with an agent known or believed to modulate glutathione concentration. A compound comprising an IL-2Rα ligand or a pharmaceutical composition comprising a compound comprising an IL-2Rα ligand may be administered in conjunction with an agent known or believed to modulate glutathione concentration within cells. A compound comprising an IL-2Rα ligand or a pharmaceutical composition comprising a compound comprising an IL-2Rα ligand may be administered in conjunction with an agent known or believed to decrease glutathione concentration within cells. A compound comprising an IL-2Rα ligand or a pharmaceutical composition comprising a compound comprising an IL-2Rα ligand may be administered in conjunction with an agent known or believed to reduce glutathione uptake into cells. A compound comprising an IL-2Rα ligand or a pharmaceutical composition comprising a compound comprising an IL-2Rα ligand may be administered in conjunction with an agent known or believed to reduce glutathione synthesis. A compound comprising an IL-2Rα ligand or a pharmaceutical composition comprising a compound comprising an IL-2Rα ligand may be administered in conjunction with an agent known or believed to reduce glutathione synthesis within cells.

A compound comprising an IL-2Rα ligand or a pharmaceutical composition comprising a compound comprising an IL-2Rα ligand may be administered in conjunction with an agent known or believed to interfere with neovascularization. A compound comprising an IL-2Rα ligand or a pharmaceutical composition comprising a compound comprising an IL-2Rα ligand may be administered in conjunction with an agent known or believed to reduce neovascularization. A compound comprising an IL-2Rα ligand or a pharmaceutical composition comprising a compound comprising an IL-2Rα ligand may be administered in conjunction with an agent known or believed to promote neovascularization.

A compound comprising an IL-2Rα ligand or a pharmaceutical composition comprising a compound comprising an IL-2Rα ligand may be administered in conjunction with an agent known or believed to interfere with hormone homeostasis. A compound comprising an IL-2Rα ligand or a pharmaceutical composition comprising a compound comprising an IL-2Rα ligand may be administered in conjunction with an agent known or believed to interfere with hormone synthesis. A compound comprising an IL-2Rα ligand or a pharmaceutical composition comprising a compound comprising an IL-2Rα ligand may be administered in conjunction with an agent known or believed to interfere with hormone receptor binding. A compound comprising an IL-2Rα ligand or a pharmaceutical composition comprising a compound comprising an IL-2Rα ligand may be administered in conjunction with an agent known or believed to interfere with hormone signal transduction.

A compound comprising an IL-2Rα ligand or a pharmaceutical composition comprising a compound comprising an IL-2Rα ligand may be administered in conjunction with an agent known or believed to interfere with growth factor homeostasis. A compound comprising an IL-2Rα ligand or a pharmaceutical composition comprising a compound comprising an IL-2Rα ligand may be administered in conjunction with an agent known or believed to interfere with growth factor synthesis. A compound comprising an IL-2Rα ligand or a pharmaceutical composition comprising a compound comprising an IL-2Rα ligand may be administered in conjunction with an agent known or believed to interfere with growth factor receptor expression. A compound comprising an IL-2Rα ligand or a pharmaceutical composition comprising a compound comprising an IL-2Rα ligand may be administered in conjunction with an agent known or believed to interfere with growth factor binding to growth factor receptors. A compound comprising an IL-2Rα ligand or a pharmaceutical composition comprising a compound comprising an IL-2Rα ligand may be administered in conjunction with an agent known or believed to interfere with growth factors binding to growth factor receptors. A compound comprising an IL-2Rα ligand or a pharmaceutical composition comprising a compound comprising an IL-2Rα ligand may be administered in conjunction with an agent known or believed to interfere with growth factor receptor signal transduction. A compound comprising an IL-2Rα ligand or a pharmaceutical composition comprising a compound comprising an IL-2Rα ligand may be administered in conjunction with an agent known or believed to interfere with the Hedgehog (Hh) signaling. A compound comprising an IL-2Rα ligand or a pharmaceutical composition comprising a compound comprising an IL-2Rα ligand can be administered in conjunction with an agent known or believed to inhibit the Hedgehog pathway signaling. A compound comprising an IL-2Rα ligand or a pharmaceutical composition comprising a compound comprising an IL-2Rα ligand may be administered in conjunction with an agent known or believed to inhibit ALK (anaplastic lymphoma kinase) pathway signaling. A compound comprising an IL-2Rα ligand or a pharmaceutical composition comprising a compound comprising an IL-2Rα ligand may be administered in conjunction with an agent known or believed to inhibit non-homologous end joining (NHEJ) is a pathway.

A compound comprising an IL-2Rα ligand or a pharmaceutical composition comprising a compound comprising an IL-2Rα ligand may be administered in conjunction with one or more agents known or believed to be a VEGFR (vascular endothelial growth factor receptor) inhibitor, a RTK (receptor tyrosine kinase) inhibitor, a sodium channel current blocker, aFAK (focal adhesion kinase) inhibitor, a GLI (glioma-associated oncogene) inhibitor, a GLI1 inhibitor, a GLI2 inhibitor, a GLI3 inhibitor, a MAPK (mitogen-activated protein kinase) inhibitor, a MAPK/ERK pathway (also known as Ras-Raf-MEK-ERK pathways) inhibitor, a MEK1 inhibitor, a MEK2 inhibitor, a MEK5 inhibitor, a MEK5/

ERK5 inhibitor, aRTA (renal tubular acidosis) inhibitor, a ALK (anaplastic lymphoma kinase) inhibitor, Aa LK kinase inhibitor, a nuclear translocation inhibitor, a PORCN (porcupine) inhibitor, a 5-ARI (5α-reductase inhibitor), topoisomerase inhibitor, a Ras (rat sarcoma) inhibitor, a K-ras inhibitor, a CERK (ceramide kinase) inhibitor, a PKB (protein kinase B, also known as AKT) inhibitor, a AKT1 inhibitor, EZH2 (enhacer of zeste homolog 2) inhibitor, a BET (bromodomain and extraterminal domain motif) inhibitor, a SYK (apleen tyrosine kinase) inhibitor, JAK (janus kinase) inhibitors, a SYK/JAK inhibitor, a IDO (indoleamine-pyrrole 2,3-dioxygenase) inhibitor, a IDO1 inhibitor, a RXR (retinoic X receptors) activating agent, a selectively RXR activating agent, a p-glycoprotein inhibitor, a ERK inhibitor, a PI3K (phosphatidylinositol-4,5-bisphosphate 3-kinase) inhibitor, a BRD (bromodomain-containing protein) inhibitor, a BRD2 inhibitor, a BRD3 inhibitor, a BRD4 inhibitor, a BRDT (bromodomain testis-specific protein) inhibitor, a reverse transcriptase inhibitor, a NRT (nucleoside analog reverse-transcriptase) inhibitor, a PIM (proviral integrations of moloney virus) inhibitor, a EGFR (epidermal growth factor receptor) inhibitor, a photosensitizer, a radiosensitizer, a ROS (proto-oncogene, receptor tyrosine kinase) inhibitor, a ROS1 (proto-oncogene 1) inhibitor, a CK (caseine kinase) inhibitor, a CK2 inhibitor, a Bcr-Abl (breakpoint cluster region—Abelson proto-oncogene) tyrosine-kinase inhibitor such as dasatinib, a microtubule stabilizing agent, a microtubule depolymerisation/disassembly inhibitor, a DNA intercalator, an androgen receptor antagonist, a chemoprotective agents, a HDAC (histone deacetylase) inhibitor, a DPP (dipeptidyl pepdidase) inhibitor, a DPP-4 inhibitor, BTK (Bruton's tyrosine kinase) inhibitor, a kinase inhibitor such as imatinib, a tyrosine kinase inhibitor such as nilotinib, a ARP (poly (ADP-ribose) polymerase) inhibitor, a CDK (cyclin-dependent kinase) inhibitor, a CDK4 inhibitor, a CDK6 inhibitor, a CDK4/6 inhibitor, a HIF1α (hypoxia-inducible factor 1-α) inhibitor, a DNA ligase inhibitor, a DNA ligase IV inhibitor, a NHEJ (non-homologous end joining) inhibitor, a DNA ligase IV, a NHEJ inhibitor and a RAF inhibitor, a TKI and a RAF inhibitor, a TKI and RAF inhibitor such as sorafenib, a PDT (photodynamic therapy) sensitizer, an ATR (ataxia telangiectasia- and Rad3-related protein kinase) inhibitor, or a combination of any of the foregoing.

A compound comprising an IL-2Rα ligand or a pharmaceutical composition comprising a IL-2Rα ligand may be administered in conjunction with one or more chemotherapeutic agents, such as, for example, a VEGFR inhibitor such as fruquintinib, motesanib/AMG-706, vatalanib; a RTK inhibitor such as ponatinib; a sodium channel blocker such as GS967; a FAK inhibitor such as TAE226; a GLI1 and GLI2 inhibitor such as GANT61, a MEK inhibitor such as binimetinib; a RTA inhibitor such as linifanib; an ALK inhibitor such as brigstinib; bromopyruvic acid; a DNA alkylating agent such as thiotepa; nuclear translocations factors such as JSH-23; a PORCn inhibitor such as Wnt-C59; a 5α-reductase inhibitor such as dutasteride; a topoisomerase inhibitor such as carubicin; a RAS inhibitor such as Kobe0065; a CerK inhibitor such as NVP-231; an AKT inhibitor such as uprosertib; a EZH2 inhibitor such as GSK-503; a BET bromodomain inhibitor such as OTX015; a MEK5/ERK5 inhibitor such as BIX02189; a Syl/JAK inhibitor such as cerdulatinib; an IDO1 inhibitor such as NLG919; a retinoic X receptor activating agent such as bexsrotene; a PGP inhibitor such as acotiamide or actoti-amide HCl; an Erk inhibitor such SCH772984; a PI3K inhibitor such as gedatolisib; a JAK inhibitor such as rux-olitinib; an AKT inhibitor such as afuresertib or afuresertib HCl; an ALK1 inhibitor such as ceritinib; an HDAC inhibitor such as abexinostat; a DPP inhibitor such as oamarigliptin; an EGFR inhibitor such as gefittinib; an EZH2 inhibitor such as GSK126; a BTK inhibitor such as ibrutinib; a kinase inhibitor such as imatinin HCl; an IDO inhibitor such as INCB024360; a DNA crosslinker such as mitomycin C; a tyrosine kinase inhibitor such as nilotinib, a PARP inhibitor such as olaparib; a tubulin stabilization promoter such as paclitaxel; a CDK4/6 inhibitor such as palbociclib; a RTK inhibitor such as sunitinib; a PDT sensitizer such as tslsporfin; a p-glycoprotein inhibitor such as tariquidar; an ATR inhibitor such as VE-822; an HDAC inhibitor such as PCI-24781; a DPP inhibitor such as omarigliptin; an EGFR inhibitor such as gefinib; an EZH2 inhibitor such as GSK126; a BTK inhibitor such as irbrutinib; an IDO inhibitor such as INCB024360; or a combination of any of the foregoing.

An IL-2Rα binding compound provided by the present disclosure can be used as a vaccine adjuvant.

IL-2Rα binding compounds provided by the present disclosure can be useful when combined with certain vaccines, including cancer neo-antigen vaccines. Mutations in tumor DNA produce new protein sequences that are foreign to the body. Vaccines can be designed to specifically activate a patient's immune system with respect to tumor-specific neoantigens. When administered in combination with a neo-antigen vaccine, IL-2Rα binding compounds provided by the present disclosure can expand and proliferate neo-antigen-specific T-cells in the tumor microenvironment and thereby drive maximal expansion of vaccine-induced neoantigen-specific T-cells for the treatment of cancer.

IL-2Rα ligands and IL-2Rα constructs provided by the present disclosure can be used as adjuvants. An adjuvant refers to a compound that enhances the efficacy of a vaccine without directly participating in the protective immunity. For example, an IL-2Rα binding compound provided by the present disclosure can be used in conjunction with a cancer vaccine.

IL-2Rα ligands and IL-2Rα ligand constructs provided by the present disclosure can be useful for cell therapy when engineered to be expressed on the membrane surface of cells that also express the IL-2Rα subunit. Adoptive immunotherapy using NK cells or using re-targeted chimeric antigen receptor (CAR) T-cells is currently being studied as a treatment for neoplasms and viral infections. One challenge with these cell therapies is the suboptimal sustained survival of the infused cells.

DNA encoding an IL-2Rα binding compound fused to a membrane protein in such away that the IL-2Rα binding compound is expressed on the extracellular surface of a cell can be constructed using standard techniques. When the fusion protein comprising the IL-2Rα binding compound is expressed, IL-7 receptors on the cell can become activated leading to long-term persistence of the cell.

DNA encoding an IL-2Rα binding compound can be incorporated into a cell and can be configured to produce an IL-2Rα binding compound provided by the present disclosure. The IL-2Rα binding compound can be secreted from the cell and can interact with the secreting cells (i.e., autocrine signaling) and/or cells in the vicinity of the secreting cell (i.e., paracrine signaling). A secreted IL-2Rα binding compound provided by the present disclosure can be an IL-2R agonist and can be designed to localize near the secreting cell.

An IL-2Rα binding compound provided by the present disclosure can be used to expand non-regulatory T-cells within a patient or within a biological sample. Methods of increasing the ratio of non-regulatory T-cells to Treg cells can comprise contacting a population of T-cells with an effective amount of an IL-2Rα binding compound. The ratio can be measured by determining the ratio of CD3+FOXP3+ cells to CD3+FOXP3-cells within the population of T-cells. A typical Treg frequency in human blood is 5% to 10% of the total CD4+CD3+ T-cells, however, in certain diseases this percentage may be lower or higher.

An IL-2Rα binding compound can be used to expand NK cells. NK cells modified with chimeric antigen receptors (CARs), which redirect immune cell activity to target cancer cells have been demonstrated to exhibit improved antitumor responses. CARs can comprise an antibody-derived extracellular domain, which binds to the desired tumor-associated antigen (TAA) and triggers an intracellular signaling cascade to activate the immune cell against the target cells.

NK cells can be genetically engineered for enhanced expression of one or more tumor targeting receptors such as NKG2D with membrane-bound IL-2Rα binding compound, which can prolong the persistence and potency of the NK cells.

CAR T-cells can be genetically engineered to co-express a tethered form of an IL-2Rα binding compound provided by the present disclosure to support in vivo persistence and maintenance of an immature state of differentiation and to exhibit in vivo antitumor activity.

IL-2Rα binding compounds provided by the present disclosure can also be utilized as commercial reagents for various medical research and diagnostic uses. Such uses include, for example, (1) use as a calibration standard for quantitating the activities of candidate IL-2R agonists in a variety of functional assays; (2) use to maintain the proliferation and growth of IL-7-dependent cell lines; (3) use in structural analysis of IL-2R through co-crystallization; (4) use to investigate the mechanism of IL-2R signal transduction/receptor activation; and (5) other research and diagnostic applications where IL-2R is activated or such activation is conveniently calibrated against a known quantity of an IL-2R agonist.

Aspects of the present invention include nucleic acids encoding for an IL-2Rα binding compound provided by the present disclosure.

A nucleic acid or isolated polynucleotide encoding an IL-2Rα provided by the present disclosure can be incorporated into expression vectors depending in part on the host cells used to produce the IL-2Rα binding compound. Generally, the nucleic acids can be operably linked to any number of regulatory elements such as, for example, promoters, origin of replication, selectable markers, ribosomal binding sites, and/or inducers. The expression vectors can be extra-chromosomal or integrating vectors.

The nucleic acids and/or expression can be transformed into any number of different types of host cells including mammalian, bacterial, yeast, insect and/or fungal cells, with mammalian cells such as CHO cells.

A nucleic acid encoding an IL-2Rα binding compound can comprise a first nucleic acid sequence encoding an IL-2Rα ligand; a second nucleic acid sequence encoding a peptidyl ligand linker; and a third nucleic acid sequence encoding an IL-2Rα ligand, an Rye ligand, and/or a construct partner.

A nucleic acid encoding an IL-2Rα ligand fusion protein can comprise a first nucleic acid sequence encoding the IL-2Rα ligand provided by the present disclosure; and a second nucleic acid sequence encoding a fusion partner. A nucleic acid encoding an IL-2Rα ligand fusion protein can comprise a nucleic acid encoding an IL-2Rα ligand and the fusion partner. A nucleic acid encoding an IL-2Rα ligand fusion protein can further comprise a nucleic acid segment encoding a construct linker and a nucleic acid encoding an IL-2Rα ligand fusion protein can comprise a nucleic acid encoding an IL-2Rα ligand, the fusion partner, and the construct linker.

The fusion partner can comprise, for example, HSA, an Fc-fragment, an IgG, an antibody directed to a cell-specific antigen, and an antibody directed to a cell-specific receptor.

A nucleic acid encoding an IL-2Rα fusion protein can further comprise a nucleic acid encoding a peptidyl linker, where the peptidyl linker is configured to bind the IL-2Rα ligand to the fusion partner.

A nucleic acid provided by the present disclosure can encode a fusion protein comprising an IL-2Rα ligand, and a linker binding the C-terminus of the IL-2Rα ligand to HSA.

A nucleic acid provided by the present disclosure can encode a fusion protein comprising a dimeric Fc-Fragment of IgG1, IgG2, or IgG4, an IL-2Rα ligand, and a linker binding the N-terminus of an IL-2Rα ligand to the C-terminus of one CH3 domain of the dimeric Fc-fragment.

A nucleic acid provided by the present disclosure can encode a fusion protein comprising a dimeric Fc-Fragment of IgG1, IgG2, or IgG4, two IL-2Rα ligands, and a linker binding the N-terminus of each of the two IL-2Rα ligands to the C-terminus of each CH3 domain of the dimeric Fc-fragment.

A nucleic acid provided by the present disclosure can encode a fusion protein comprising a heavy chain of an immunoglobulin molecule such as IgG1, IgG2, or IgG4, an IL-2Rα ligand, and a Fc linker bonding the N-terminus of the IL-2Rα ligand to the C-terminus of the Fc region.

A nucleic acid provided by the present disclosure can encode for an IL-2Rα ligand comprising an amino acid sequence of any one of SEQ ID NOS: 1-307 and 400-423, or can encode for an amino acid sequence comprising an amino acid sequence having greater than 60%, greater than 70%, greater than 80%, greater than 85%, greater than 90%, or greater than 95% sequence similarity to any one of SEQ ID NOS: 1-307 and 400-423.

A nucleic acid provided by the present disclosure can encode for a homomeric IL-2Rα ligand comprising two or more IL-2Rα ligands provided by the present disclosure.

Aspects of the invention further include a host cell comprising an expression vector comprising a nucleic acid encoding an IL-2Rα ligand or an IL-2Rα binding compound provided by the present disclosure.

Methods provided by the present disclosure include methods of making an IL-2Rα ligand or an IL-2Rα binding compound provided by the present disclosure, comprising culturing a host cell, wherein the host cell comprises an expression vector comprising a nucleic acid encoding an IL-2Rα ligand or an IL-2Rα binding compound provided by the present disclosure, under conditions where the IL-2Rα ligand or the IL-2Rα binding compound is expressed, and recovering the expressed IL-2Rα ligand or IL-2Rα binding compound.

EXAMPLES

The following examples describe in detail methods used for determining the activity of peptides comprising the IL-2Rα subunit. It will be apparent to those skilled in the art that many modifications, both to materials and methods, may be practiced without departing from the scope of the disclosure.

Example 1

Phage Display pIII Library Panning Against Fc-Fusions on Magnetic Beads (Acid Elution)
Library Panning Procedure Fifty (50) µL of Protein G Dynabeads® (Invitrogen) was used for each library sample. After resuspending the stock bottle, the desired volume of beads was transferred to a sterile microfuge tube and applied to the magnet.

With the beads on a magnet, the supernatant was removed, and the beads were washed with 1 mL of PT buffer (1×PBS, 0.05% Tween®-20).

The supernatant was removed and 1 mL of PBS+1% BSA+0.05% Tween®-20 was added and mixed at 25° C. for at least 1 hour to block the beads.

A tube was applied to the magnet and the blocking solution was removed. For each library to be tested, 5 µg of a Fc-fused receptor of interest was added to each library sample for each round to bring the total volume to at least 400 µL. The samples were mixed at 25° C. for at least 1 h. The sample was applied to the magnet and the supernatant was removed.

Two-hundred 200 µL of PT buffer was added for each 50 µL of bead. The sample was thoroughly mixed and 200 µL aliquots were transferred into tubes that were pre-labeled for each library to be screened. An additional 500 µL of PT was added to each tube, the samples mixed, and then applied to the magnet. A total of 700 µL/tube was used for the wash.

The wash was removed and 500 µL of 250 nM Fc blocking peptide diluted in PBT (PBS+0.5% BSA+0.05% Tween®-20) was added to each sample. The stock concentration was 25 µM (100×). The samples were incubated at 4° C. for at least 30 min while rotating. Following the incubation, the samples were applied to the magnet and the blocking peptide solution was removed prior to adding the libraries. One (1) mL aliquots of the libraries removed from the −20° C. freezer. One-hundred (100 µL of 10×BT buffer (5% BSA, 0.5% Tween®-20 in 1×PBS) was added to each tube and vortexed. Eleven (11) µL of Fc blocking peptide was added to each library sample and vortexed. The library samples were transferred to pre-labeled tubes containing beads. The samples were then incubated at 4° C. on the rotator for at least 2 h. For the additional rounds of screening, 1 mL aliquots of the amplification from the previous round from each library was used. Fc blocking peptide was then added at the concentration indicated in step 6 (10 µL blocking peptide).

The beads were recovered with the magnet and the phage solution removed. The beads were washed 2× with 1 mL of PT buffer. Five-hundred (500) µL of PT buffer was added and the suspension was transferred to a clean tube. The beads were recovered on the magnet and the final wash removed.

Four-hundred seventy-five (475) µL of phage elution buffer was added to each well (0.2 M glycine-HCL, pH 2.2, 1 mg/mL BSA). The samples were incubated at 25° C. for 10 min on the rotator. The beads were recovered on the magnet and the eluted phage transferred to a clean tube.

Twenty-five (25) µL of neutralization buffer (2M Tris Base) was added to the 475 µL of elution. The neutralized samples were maintained at 4° C. until the TG1 cells were ready amplification. The samples were stored at −20° C. after screening. Fifty (50) L (about 10% of the total volume) was transferred to a 1.5 mL microfuge tube and store at −20° C. for use in deep sequencing.

Example 2

TG1 Culture and Library Amplification

Afresh T G1 (or OmniMax) culture was grown for about 1 to 1.5 h after adding the libraries to the beads. 2X-YT medium (10 mL) was placed into a 50 mL Falcon® tube. Two-hundred (200) µL of the TG1 overnight was added to the falcon tube. 2X-YT medium (600 µL) was placed in a cuvette for OD600 blank. The culture was grown at 250 rpm and 37° C., taking the first OD measurement after 60 min. The TG1 cells should be in log phase at the time of use with an OD600 of 0.5-0.7.

Eluted phage (400 µL to 450 µL) was added to 1 mL of the TG1 cells at an OD600 of 0.5-0.7 in a 50 mL Falcon® tube. The phage and TG1 cells were incubated at 37° C. for 30 min without shaking. About 50 µL to 100 µL was set aside for titering and characterization.

2YT medium (10.5 mL) was added to 12 µL of carbenicillin (carb) (100 mg/mL to make 100 µg/mL) and 24 µL of 50% glucose (to make 0.1% glucose) and the cells incubated while shaking at 37° C. at 250 rpm for 1 h.

M13K07 helper phage ($5 \times 10^{10}$ pfu, 24 µL of the stock, $2 \times 10^2$ pfu/mL) was then added and swirled to mix. The phage and cells were incubated at 37° C. for 30 min without shaking.

Kanamycin was diluted to 3 mg/mL and arabinose to 2.4% in 2YT medium/Carbenicillin-100/0.1% glucose and 100 µL was added to each amplification. The mixture was incubated overnight at 37° C. and 250 rpm.

The culture was transferred to a 50 mL high-speed VWR centrifuge tube and centrifuged at 8,000 g for 15 min at 4° C. in a JSP-F50C centrifuge to pellet the cells.

The supernatant was transferred to a 50 mL high-speed VWR centrifuge tube and 0.2 volumes of PEG/NaCl (multiply the volume by 0.25 mL to 3 mL PEG/NaCl for 12 mL amplification) was added, mixed, and incubated on ice for 30 minutes.

The cells were then centrifuged at 10,500 g for 15 min at 4° C. in a JSP-F50C centrifuge. The supernatant was removed, and the phage pellet was resuspended in a total of 1 mL of PBT (1×PBS, 0.05% Tween® 20, 0.5% BSA) by pipetting.

The sample was transferred to an Eppendorf tube, vortexed, and centrifuged at 12,000 rpm for 30 sec. The supernatant was transferred to a clean Eppendorf tube and stored at 4° C. This amplified phage sample (250-500 µL) was used for the next round of screening.

Example 3

Preparation of Cultures from Individual Colonies

Ninety-six (96) wells of a deep well plate were filled with 1 mL of 2YT broth/Ampicillin-50/0.1% glucose. Ninety-six (96) colonies were placed into the wells using P20 tips. The tips were left in the wells to mark the position. The tips were removed using a multi-channel pipette after the entire plate was completed. The plate was covered with a breathable film.

The inoculated plate(s) were incubated in a shaker at 37° C. until the cultures became turbid, typically within 4 h at 250 rpm.

The plate(s) was removed from the Incubator and 50 μL of the culture from each well was removed to another deep well block designated as the "Archive Block" containing 1 mL of 2YT broth/Ampicillin-50/0.1% glucose. The plate(s) were covered with a breathable film and incubated overnight at 37° C. and 250 rpm.

After incubating overnight, M13K07 helper phage was added to $2 \times 10^{10}$ pfu/mL in 2YT broth/Ampicillin-50/0.1% glucose (make 6.0 mL per block). Fifty (50) μL of the diluted M13K07 was added to each culture well in the deep well block. The deep well block was covered with breathable film and incubated for 30 min at 37° C. and 250 rpm.

Kanamycin was diluted to 0.5 mg/ml and arabinose to 0.4% in 2YT broth/Ampicillin-50/0.1% glucose (make 6.0 ml per block) and 50 μL was added to each well. The plate was covered with a breathable film and incubated overnight at 37° C. and 250 rpm.

The "Archive Block" culture was removed from the incubator and 50 μL was transferred to a 96-well plate containing 50 μL of 50% glycerol. The plate was sealed with foil and stored at −80° C. The remaining culture in the block was covered with a foil seal and stored at 4° C.

The block was centrifuged and inoculated with M13K07 at 4000 rpm for 15 min. While avoiding the bacterial pellet, 850 μL of the phage supernatant was transferred to a fresh deep well plate, covered with a foil seal, and stored at 4° C.

Example 4

ELISA Protocol for Fc-Fusions

For each block to be assayed, a 1×96 well ELISA plate was coated with Fc-fusion (1 μg/mL in PBS) at 50 μL/well. The wells were incubated at 25° C. for at least 1 h.

The Fc-fusion was removed from each well. Three-hundred (300) μL of blocking buffer (1×PBS, 1% BSA) was added to each well of a receptor-coated plate. Also, 300 μL of the blocking buffer was added to a separate uncoated 96-well ELISA plate to be used as the negative control. Both plates were covered with film and left at 37° C. for 1 h or overnight at 4° C.

The plate was washed 4 times with PT (1×PBS, 0.05% Tween® 20) buffer.

Fifty (50) μL of PBT was added to each well. Fifty (50) μL of the phage supernatant from the block was added to each well and incubated at 4° C. for 1 h.

The plates were washed 4 times with cold PT.

To each well 100 μL of anti-M13-HRP antibody diluted 1:5000 in cold PBT was added. The wells were incubated for 1 h at 4° C.

The plates were then washed 4 times with cold PT.

Fifty (50) μL of TMB was then added to each well, and the wells were incubated for 1-10 min at 25° C. Fifty (50) μL of a "stop" solution was added and the plate read at 450 nm.

Example 5

Evaluation of Peptide Heteromer Ability to Activate IL-2 Responsive Cells

Following the identification of peptidyl ligands that exhibit IL-2Rα binding activity, compounds will be identified that exhibit IL-2R agonist, IL-2R antagonist activity, and/or IL-2R binding activity. This can involve assessing the ability of the peptide to polymerize the IL-2Rαβγc subunits and to signal in cell-based assays. Polymerization is a necessary, but not sufficient, step in the activation of IL-2 receptor signaling. To assess agonist activity in cell-based assays, IL-2 responsive cell lines will be tested for an indicator of IL-2 signaling, phosphorylation of STAT5. Compounds that exhibit IL-2R agonist activity in these cell lines will then be tested in primary human peripheral blood mononuclear cells (PBMC) for IL-2R agonism, and for the desired selectivity favoring activation of cell types expressing IL-2Rβγc subunits.

Polymerization potential will be assessed using a β-Gal complementation system in which a portion of the intracellular domains of each respective IL-2 receptor subunit is replaced with functionally complementary fragments of β-Gal, which regain catalytic activity when brought into sufficiently proximity. Cells expressing these constructs generate β-Gal activity, with an EC50 of about 26 nM, when treated with IL-2 (see DiscoverX product specifications). Candidate compounds will be scored for induction of STAT5 phosphorylation in two cell lines: (1) CTLL-2 cells, a mouse cytotoxic T-lymphocyte line that expresses all three IL-2 receptor subunits, and which are responsive to IL-2Rβγc-biased variants as well as wild type IL-2; and (2) TF-1β cells derived from the human erythroleukemia line TF-1, which naturally express only IL-2Rγc, and are engineered to be IL-2 responsive by transfection of IL-2Rβ. TF-1β will be constructed and IL-2R subunit expression levels in both cell lines will be verified by QPCR and FACS analysis.

Compounds will be tested in both cell lines. Dose response assays will be conducted to determine EC50 of the test compounds and to compare the test compounds with IL-2 as an indicator of IL-2Rβγc receptor bias. To further characterize subunit bias, a parallel assay will be run in the presence of a neutralizing antibody to the human IL-2Rβ subunit.

As a control to confirm that positive compounds are acting through stimulation of the IL-2 receptor, the assay will also be done with cells treated with neutralizing anti-huIL-2Rα antibody. To determine that compound activity is not due to contamination with cytokines, test compounds will be treated with neutralizing antibodies (R&D Systems) against the natural IL-2Rβγc agonists, IL-2 and IL-15.

Compounds exhibiting IL-2R agonist activity in the cell lines will be tested on human primary immune cells, PBMCs, collected from individual donors (commercially available from Lonza and others), and in some cases on purified CD4+CD8+ cells (Lonza). A substantial fraction of PBMCs from normal donors are responsive to IL-2. To assess IL-2 agonist activity of the test compounds, cells will be exposed to the compounds or IL-2 and scored for STAT5 phosphorylation by western blot analysis. As a control to confirm that positive compounds are acting through direct stimulation of the IL-2 receptor, the assay will also be done with cells treated with neutralizing anti-huRα antibody.

Those compounds exhibiting STAT5 activation of PBMCs will be subjected to a follow-on assay designed to assess subunit bias of the compounds compared to IL-2. This assay will involve determining a dose response of the test compounds and IL-2 (1 to 1000 I) over 30 min, scored by a FACS-based protocol allowing detection of both intracellular pSTAT5 as an indicator of IL-2R activation, and cell surface CD25, the IL-2Rβ subunit. Cells expressing the three IL-2R subunits, IL-2Rαβγc, bind IL-2 with very high affinity (about 10 μM) and are therefore sensitive to low concentrations of IL-2; whereas cells expressing only IL-2Rβγc (about 1 nM affinity) require exposure to substantially higher IL-2 levels for activation. Because compounds provided by the present disclosure are selected for binding to the IL-2Rα the potency of the compounds comprising an IL-2Rα ligand is expected to be correlated with the level of expression of IL-2Rα on cells; and comparison of response profiles of cells treated with compounds provided by the present disclosure or treated with IL-2 should reveal any bias.

Example 6

Identified Peptides

Stochastic libraries with each library containing approximately 10 billion independent recombinants, with each clone potentially displaying a unique peptide sequence have been screened for binding to the human IL-2Rα subunit. In screening these initial libraries against the IL-2Rα subunit extracellular domain (ECD), unique peptide clones were identified and confirmed as ligands of IL-2Rα. These IL-2Rα ligands can be grouped into sequence families that exhibit a clear consensus sequence.

Example 7

Chemical Synthesis of IL-2Rα.Ligands

2-Cholorotrityl resin (1 g, 1.5 mmole/g, from Anaspec) was washed with DMF (2×), and then allowed to stand in 50 mL DMF for 10 min. The swollen resin was treated with an activated solution of Fmoc-glycine prepared from 5 eq. of amino acid and 5 eq. of HATU dissolved at 0.5M in DMF, followed by the addition of 10 eq. of DIEA, and the mixture gently stirred for 30 min at 25° C. The resin was washed (DMF, THF, DCM, and MeOH) and dried to yield the Fmoc-protected resin. Fmoc groups were then removed by gently shaking the resin with 30% piperidine in DMF for 20 min, followed by washing (DMF, THF, DCM, and MeOH), and drying. The resin was then subjected to repeated cycles of Fmoc-amino acid couplings with HATU activation and Fmoc removal with piperidine to build a desired amino acid sequence. Except for examples with four cysteine residues in the sequence, standard 95% TFA-labile amino acid side chain protecting groups were used. With compounds with four cysteines, the two cysteine residues proximal to the resin, Trt protection was used, and for the two cysteine residues distal to the resin, Acm protection was used. After Fmoc removal from the final amino acid of the dimer sequence, in some cases the terminal amine groups were acylated with acetic anhydride (10 eq.) and DIEA (20 eq.) in DMF for 20 min, followed by washing as described above.

The completed peptide was cleaved from the resin by suspension in a solution of TFA (95 vol %), water (2.5 vol %), and triisopropylsilane (2.5 vol %) for 3 h at 25° C. The TFA solution was cooled to 5° C. and poured into Et₂O to precipitate the peptide. Filtration and drying under reduced pressure gave the desired peptide. Purification via preparative HPLC with a C18 column afforded the pure peptide with the two C-terminal thiol groups in a reduced state. This peptide was dissolved in 20% DMSO/water (1 mg dry weight peptide/mL) and allowed to stand at 25° C. for 36 h, and then purified by reverse phase HPLC to provide the peptide with the two C-terminal thiols linked by a disulfide bridge. In compounds containing four cysteines, the two N-terminal Acm-protected cysteine residues were then deprotected by dissolving 0.1 mmole of peptide in 25 mL of 50% acetic acid/H₂O and 2.5 mL of 1M HCl and adding 5 mL of 0.1M iodine (in glacial acetic acid; 5 eq.) dropwise with stirring under a nitrogen atmosphere. The deprotection/oxidation reaction was allowed to proceed for 2 h at 25° C. with frequent monitoring (analytical HPLC) to ensure complete reaction. The reaction was stopped by addition of ice-cooled diethyl ether (9 volume eq.). The resulting solution was cooled on dry ice (3 min), the ether solution carefully decanted, and the resulting light-yellow solid purified by preparative reverse phase HPLC (95%) to yield the final IL-2Rα ligand or peptide having an IL-2Rα ligand.

IL-2Rα ligands having SEQ ID NO: 400 to SEQ ID NO: 423 were synthesized.

ASPECTS OF THE INVENTION

The invention is further defined by the following aspects.

Aspect 1. An IL-2Rα ligand, wherein the IL-2Rα ligand binds to the human IL-2Rα subunit with an $IC_{50}$ of less than 100 μM.

Aspect 2. The IL-2Rα ligand of aspect 1, wherein the IL-2Rα ligand comprises from 5 to 30 amino acids.

Aspect 3. The IL-2Rα ligand of any one of aspects 1 to 2, wherein the IL-2Rα ligand binds to the human IL-2Rα subunit with an $IC_{50}$ from 1 μM to 100 μM.

Aspect 4. The IL-2Rα ligand of any one of aspects 1 to 2, wherein the IL-2Rα ligand binds to the human IL-2Rα subunit with an $IC_{50}$ from 0.1 μM to 50 μM.

Aspect 5. The IL-2Rα ligand of any one of aspects 1 to 2, wherein the IL-2Rα ligand binds to the human IL-2Rα subunit with an $IC_{50}$ of less than 100 μM.

Aspect 6. The IL-2Rα ligand of any one of aspects 1 to 2, wherein the IL-2Rα ligand binds to a mammalian IL-2Rα subunit with an $IC_{50}$ of less than 100 μM.

Aspect 7. The IL-2Rα ligand of any one of aspects 1 to 6, wherein the IL-2Rα ligand comprises the amino acid sequence of Formula (1) (SEQ ID NO: 1):

$$-X^1-X^2-X^3-X^4-X^5-X^6-X^7-X^8-X^9-X^{10}-X^{11}-X^{12}- \quad (1)$$

wherein, $X^1$ is selected from an amino acid comprising a large hydrophobic side chain or an aromatic side chain;

$X^2$ is selected from an amino acid comprising a large hydrophobic side chain;

$X^3$ is selected from an amino acid;

$X^4$ is selected from an amino acid comprising a large hydrophobic side chain;

$X^5$ is selected from an amino acid comprising a small hydrophobic side chain or a polar/neutral side chain;

$X^6$ is selected from an amino acid comprising a large hydrophobic side chain;

$X^7$ is selected from an amino acid comprising a large hydrophobic side chain;

$X^8$ is selected from an amino acid comprising a large hydrophobic side chain;

$X^9$ is selected from an amino acid comprising a small hydrophobic side chain;

$X^{10}$ is selected from an amino acid comprising a polar/neutral side chain;

$X^{11}$ is selected from an amino acid comprising a large hydrophobic side chain; and $X^{12}$ is selected from an amino acid comprising a large hydrophobic side chain.

Aspect 8. The IL-2Rα ligand of aspect 7, wherein $X^1$ is selected from F, H, I, L, M, V, W, and Y.

Aspect 9. The IL-2Rα ligand of any one of aspects 7 to 8, wherein $X^2$ is selected from F, I, L, M, V, W, and Y.

Aspect 10. The IL-2Rα ligand of any one of aspects 7 to 9, wherein $X^3$ is selected from A, D, E, F, G, H, I, K, L, M, N, P, Q, R, S, T, V, W, and Y.

Aspect 11. The IL-2Rα ligand of any one of aspects 7 to 10, wherein $X^4$ is selected from F, I, L, M, V, W, and Y.

Aspect 12. The IL-2Rα ligand of any one of aspects 7 to 11, wherein $X^5$ is selected from H, N, Q, Y, A, G, P, S, and T.

Aspect 13. The IL-2Rα ligand of any one of aspects 7 to 12, wherein $X^6$ is selected from F, I, L, M, V, W, and Y.

Aspect 14. The IL-2Rα ligand of any one of aspects 7 to 13, wherein $X^7$ is selected from F, I, L, M, V, W, and Y.

Aspect 15. The IL-2Rα ligand of any one of aspects 7 to 14, wherein $X^8$ is selected from F, I, L, M, V, W, and Y.

Aspect 16. The IL-2Rα ligand of any one of aspects 7 to 15, wherein $X^9$ is selected from A, G, P, S, and T.

Aspect 17. The IL-2Rα ligand of any one of aspects 7 to 16, wherein $X^{10}$ is selected from H, N, Q, S, T, and Y.

Aspect 18. The IL-2Rα ligand of any one of aspects 7 to 177, wherein $X^{11}$ is selected from F, I, L, M, V, W, and Y.

Aspect 19. The IL-2Rα ligand of any one of aspects 7 to 18, wherein $X^{12}$ is selected from F, I, L, M, V, W, and Y.

Aspect 20. The IL-2Rα ligand of any one of aspects 7 to 19, wherein $X^1$ is selected from L, W, and F.

Aspect 21. The IL-2Rα ligand of any one of aspects 7 to 20, wherein $X^2$ is selected from D, A, L, and V.

Aspect 22. The IL-2Rα ligand of any one of aspects 7 to 21, wherein $X^3$ is selected from L, V, H, P, and E.

Aspect 23. The IL-2Rα ligand of any one of aspects 7 to 22, wherein $X^4$ is selected from T, D, and W.

Aspect 24. The IL-2Rα ligand of any one of aspects 7 to 23, wherein $X^5$ is selected from Y, W, P, and Q.

Aspect 25. The IL-2Rα ligand of any one of aspects 7 to 24, wherein $X^6$ is selected from D, S, V, and A.

Aspect 26. The IL-2Rα ligand of any one of aspects 7 to 25, wherein $X^7$ is selected from E and Y.

Aspect 27. The IL-2Rα ligand of any one of aspects 7 to 26, wherein $X^8$ is selected from L and F.

Aspect 28. The IL-2Rα ligand of any one of aspects 7 to 27, wherein $X^9$ is selected from L, R, and S.

Aspect 29. The IL-2Rα ligand of any one of aspects 7 to 28, wherein $X^{10}$ is selected from A, R, and Q.

Aspect 30. The IL-2Rα ligand of any one of aspects 7 to 29, wherein $X^{11}$ is selected from C, R, V, and M.

Aspect 31. The IL-2Rα ligand of any one of aspects 7 to 30, wherein $X^{12}$ is selected from T, L, and M.

Aspect 32. The IL-2Rα ligand of any one of aspects 7 to 31, wherein $X^1$ is F.

Aspect 33. The IL-2Rα ligand of any one of aspects 7 to 32, wherein $X^2$ is selected from L and V.

Aspect 34. The IL-2Rα ligand of any one of aspects 7 to 33, wherein $X^3$ is selected from A, D, E, F, G, H, I, K, L, M, N, P, Q, R, S, T, V, W, and Y.

Aspect 35. The IL-2Rα ligand of any one of aspects 7 to 34, wherein $X^4$ is W.

Aspect 36. The IL-2Rα ligand of any one of aspects 7 to 35, wherein $X^5$ is P.

Aspect 37. The IL-2Rα ligand of any one of aspects 7 to 36, wherein $X^6$ is V.

Aspect 38. The IL-2Rα ligand of any one of aspects 7 to 37, wherein $X^7$ is Y.

Aspect 39. The IL-2Rα ligand of any one of aspects 7 to 38, wherein $X^8$ is F.

Aspect 40. The IL-2Rα ligand of any one of aspects 7 to 39, wherein $X^9$ is S.

Aspect 41. The IL-2Rα ligand of any one of aspects 7 to 40, wherein $X^{10}$ is Q.

Aspect 42. The IL-2Rα ligand of any one of aspects 7 to 41, wherein $X^{11}$ is selected from N and V.

Aspect 43. The IL-2Rα ligand of any one of aspects 7 to 42, wherein $X^{12}$ is selected from L and M.

Aspect 44. The IL-2Rα ligand of aspect 7, wherein $X^1$ is F, $X^4$ is W, $X^5$ is P, $X^6$, is V, $X^7$ is Y, $X^8$ is F, $X^9$ is S, and $X^{10}$ is Q.

Aspect 45. The IL-2Rα ligand of aspect 7,
$X^1$ is F;
$X^2$ is selected from F, H, I, L, M, V, W, and Y;
$X^3$ is selected from A, D, E, F, G, H, I, K, L, M, N, P, Q, R, S, T, V, W, and Y;
$X^4$ is W;
$X^5$ is selected from H, N, Q, Y, A, G, P, S, and T;
$X^6$ is V;
$X^7$ is Y;
$X^8$ is F;
$X^9$ is S;
$X^{10}$ is Q;
$X^{11}$ is selected from F, I, L, M, V, W, and Y; and
$X^{12}$ is selected from F, I, L, M, V, W, and Y.

Aspect 46. The IL-2Rα ligand of aspect 7, wherein the IL-2Rα ligand comprises an amino acid sequence selected from any one of SEQ ID NO: 2 to SEQ ID NO: 6:

```
                                        SEQ ID NO: 2
        L D L T Y D E L L A C T

SEQ ID NO: 3
        W A Y D W S C F R R R L

SEQ ID NO: 4
        F L H W P V Y F C Q V M

SEQ ID NO: 5
        F L P W P V Y F S Q V L

SEQ ID NO: 6
        F V E W Q A Y F S Q M M
```

Aspect 47. The IL-2Rα ligand of any one of aspects 7 to 46, wherein,
the amino acid sequence independently comprises from 1 to 4 glycines (G) (SEQ ID NO: 1041) on the N-terminus, on the C-terminus, or on both the N- and C-termini;
the amino acid sequence comprises a truncated amino acid sequence; or
the amino acid sequence comprises a truncated amino acid sequence, wherein the truncated amino acid sequence independently comprises from 1 to 4 glycines (G) (SEQ ID NO: 1041) on the N-terminus, on the C-terminus, or on both the N- and C-termini.

Aspect 48. The IL-2Rα ligand of aspects 46 to 47, wherein from 1 to 5 of the amino acids is independently substituted with another amino acid.

Aspect 49. The IL-2Rα ligand of any one of aspects 1 to 6, wherein the IL-2Rα ligand comprises the amino acid sequence of Formula (2) (SEQ ID NO: 7):

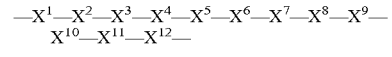

(2)

wherein,
$X^1$ is selected from an amino acid comprising a large hydrophobic side chain;
$X^2$ is selected from an amino acid comprising a large hydrophobic side chain;
$X^3$ is selected from an amino acid comprising a small hydrophobic side chain;

$X^4$ is selected from an amino acid comprising a large hydrophobic side chain;

$X^5$ is selected from an amino acid comprising an acidic side chain;

$X^6$ is selected from an amino acid comprising an acidic side chain;

$X^7$ is selected from an amino acid comprising a large hydrophobic side chain;

$X^8$ is selected from an amino acid comprising a large hydrophobic side chain;

$X^9$ is selected from an amino acid;

$X^{10}$ is selected from an amino acid comprising a polar/neutral side chain;

$X^{11}$ is selected from an amino acid comprising a large hydrophobic side chain; and $X^{12}$ is selected from an amino acid comprising a large hydrophobic side chain.

Aspect 50. The IL-2Rα ligand of aspect 49, wherein $X^1$ is selected from F, I, L, M, V, W, and Y.

Aspect 51. The IL-2Rα ligand of any one of aspects 49 to 50, wherein $X^2$ is selected from F, I, L, M, V, W, and Y.

Aspect 52. The IL-2Rα ligand of any one of aspects 49 to 51, wherein $X^3$ is selected from A, G, P, S, and T.

Aspect 53. The IL-2Rα ligand of any one of aspects 49 to 52, wherein $X^4$ is selected from F, I, L, M, V, W, and Y.

Aspect 54. The IL-2Rα ligand of any one of aspects 49 to 53, wherein $X^6$ is selected from D and E.

Aspect 55. The IL-2Rα ligand of any one of aspects 49 to 54, wherein $X^7$ is selected from F, I, L, M, V, W, and Y.

Aspect 56. The IL-2Rα ligand of any one of aspects 49 to 55, wherein $X^8$ is selected from F, I, L, M, V, W, and Y.

Aspect 57. The IL-2Rα ligand of any one of aspects 49 to 56, wherein $X^9$ is selected from A, D, E, F, G, H, I, K, L, M, N, P, Q, R, S, T, V, W, and Y.

Aspect 58. The IL-2Rα ligand of any one of aspects 49 to 57, wherein $X^{10}$ is selected from H, N, Q, S, T, and Y.

Aspect 59. The IL-2Rα ligand of any one of aspects 49 to 58, wherein $X^{11}$ is selected from F, I, L, M, V, W, and Y.

Aspect 60. The IL-2Rα ligand of any one of aspects 49 to 59, wherein $X^{12}$ is selected from F, I, L, M, V, W, and Y.

Aspect 61. The IL-2Rα ligand of any one of aspects 49 to 60, wherein $X^1$ is F.

Aspect 62. The IL-2Rα ligand of any one of aspects 49 to 61, wherein $X^2$ is selected from I, L, and V.

Aspect 63. The IL-2Rα ligand of any one of aspects 49 to 62, wherein $X^3$ is P.

Aspect 64. The IL-2Rα ligand of any one of aspects 49 to 63, wherein $X^4$ is W.

Aspect 65. The IL-2Rα ligand of any one of aspects 49 to 64, wherein $X^5$ is selected from P, D, and E.

Aspect 66. The IL-2Rα ligand of any one of aspects 49 to 65, wherein $X^6$ is selected from V and E.

Aspect 67. The IL-2Rα ligand of any one of aspects 49 to 66, wherein $X^7$ is Y.

Aspect 68. The IL-2Rα ligand of any one of aspects 49 to 67, wherein $X^8$ is F.

Aspect 69. The IL-2Rα ligand of any one of aspects 49 to 68, wherein $X^9$ is selected from S, A, K, and L.

Aspect 70. The IL-2Rα ligand of any one of aspects 49 to 69, wherein $X^{10}$ is Q.

Aspect 71. The IL-2Rα ligand of any one of aspects 49 to 70, wherein $X^{11}$ is selected from V, I, and L.

Aspect 72. The IL-2Rα ligand of any one of aspects 49 to 71, wherein $X^{12}$ is selected from L and M.

Aspect 73. The IL-2Rα ligand of any one of aspects 49 to 72, wherein $X^1$ is F.

Aspect 74. The IL-2Rα ligand of any one of aspects 49 to 73, wherein $X^2$ is selected from L and V.

Aspect 75. The IL-2Rα ligand of any one of aspects 49 to 74, wherein $X^3$ is P.

Aspect 76. The IL-2Rα ligand of any one of aspects 49 to 75, wherein $X^4$ is W.

Aspect 77. The IL-2Rα ligand of any one of aspects 49 to 76, wherein $X^5$ is D.

Aspect 78. The IL-2Rα ligand of any one of aspects 49 to 77, wherein $X^6$ is E.

Aspect 79. The IL-2Rα ligand of any one of aspects 49 to 78, wherein $X^7$ is Y.

Aspect 80. The IL-2Rα ligand of any one of aspects 49 to 79, wherein $X^8$ is F.

Aspect 81. The IL-2Rα ligand of any one of aspects 49 to 80, wherein $X^9$ is selected from A, D, E, F, G, H, I, K, L, M, N, P, Q, R, S, T, V, W, and Y.

Aspect 82. The IL-2Rα ligand of any one of aspects 49 to 80, wherein $X^9$ is S.

Aspect 83. The IL-2Rα ligand of any one of aspects 49 to 82, wherein $X^{10}$ is Q.

Aspect 84. The IL-2Rα ligand of any one of aspects 49 to 83, wherein $X^{11}$ is selected from I, L, and V.

Aspect 85. The IL-2Rα ligand of any one of aspects 49 to 84, wherein $X^{12}$ is L.

Aspect 86. The IL-2Rα ligand of aspect 49, wherein $X^1$ is F, $X^3$ is P, $X^4$ is W, $X^5$ is D, $X^6$, is E, $X^7$ is Y, $X^8$ is F, $X^{10}$ is Q, and $X^{12}$ is L.

Aspect 87. The IL-2Rα ligand of aspect 49, wherein, $X^1$ is F;

$X^2$ is selected from F, I, L, M, V, W, and Y;

$X^3$ is P;

$X^4$ is W;

$X^5$ is selected from D and P;

$X^6$ is E;

$X^7$ is Y;

$X^8$ is F;

$X^9$ is selected from A, D, E, F, G, H, I, K, L, M, N, P, Q, R, S, T, V, W, and Y;

$X^{10}$ is Q;

$X^{11}$ is selected from F, I, L, M, V, W, and Y; and $X^{12}$ is L.

Aspect 88. The IL-2Rα ligand of aspect 49, wherein the IL-2Rα ligand comprises an amino acid sequence selected from any one of SEQ ID NO: 8 to SEQ ID NO: 15:

```
                                        SEQ ID NO: 8
        F I P W D E Y F A Q L L

SEQ ID NO: 9
        F I P W D E Y F K Q V L

SEQ ID NO: 10
        F V P W D V Y F S Q I L

SEQ ID NO: 11
        F I P W D E Y F K Q V L

SEQ ID NO: 12
        F V P W P E Y F L Q I M

SEQ ID NO: 13
        F I P W E E Y F S Q L L

SEQ ID NO: 14
        F I P W P E Y F S Q L L

SEQ ID NO: 15
        F V P W D E Y F L Q I L
```

Aspect 89. The IL-2Rα ligand of any one of aspects 49 to 88, wherein,
the amino acid sequence independently comprises from 1 to 4 glycines (G) (SEQ ID NO: 1041) on the N-terminus, on the C-terminus, or on both the N- and C-termini;
the amino acid sequence comprises a truncated amino acid sequence; or
the amino acid sequence comprises a truncated amino acid sequence, wherein the truncated amino acid sequence independently comprises from 1 to 4 glycines (G) (SEQ ID NO: 1041) on the N-terminus, on the C-terminus, or on both the N- and C-termini.

Aspect 90. The IL-2Rα ligand of any one of aspects 88 to 89, wherein from 1 to 5 of the amino acids is independently substituted with another amino acid.

Aspect 91. The IL-2Rα ligand of any one of aspects 1 to 6, wherein the IL-2Rα ligand comprises the amino acid sequence of Formula (3a) (SEQ ID NO: 16), the amino acid sequence of Formula (3b) (SEQ ID NO: 17), or the amino acid sequence of Formula (3c) (SEQ ID NO: 18):

  (3a)

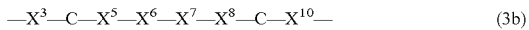  (3b)

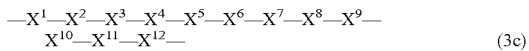  (3c)

wherein,
$X^1$ is selected from an amino acid comprising a large hydrophobic side chain;
$X^2$ is selected from an amino acid comprising a large hydrophobic side chain;
$X^3$ is selected from an amino acid;
$X^4$ is C;
$X^5$ is selected from an amino acid comprising a small hydrophobic side chain;
$X^6$ is selected from an amino acid;
$X^7$ is selected from an amino acid;
$X^8$ is selected from amino acid comprising a small hydrophobic side chain;
$X^9$ is C;
$X^{10}$ is selected from an amino acid comprising a basic side chain or a polar/neutral side chain;
$X^{11}$ is selected from an amino acid comprising a small hydrophobic side chain; and
$X^{12}$ is selected from an amino acid.

Aspect 92. The IL-2Rα ligand of aspect 91, wherein $X^1$ is selected from F, I, L, M, V, W, and Y.

Aspect 93. The IL-2Rα ligand of any one of aspects 91 to 92, wherein $X^2$ is selected from F, I, L, M, V, W, and Y.

Aspect 94. The IL-2Rα ligand of any one of aspects 91 to 93, wherein $X^3$ is selected from A, D, E, F, G, H, I, K, L, M, N, P, Q, R, S, T, V, W, and Y.

Aspect 95. The IL-2Rα ligand of any one of aspects 91 to 94, wherein $X^4$ is C.

Aspect 96. The IL-2Rα ligand of any one of aspects 91 to 95, wherein $X^5$ is selected from A, G, P, S, and T.

Aspect 97. The IL-2Rα ligand of any one of aspects 91 to 96, wherein $X^6$ is selected from A, D, E, F, G, H, I, K, L, M, N, P, Q, R, S, T, V, W, and Y.

Aspect 98. The IL-2Rα ligand of any one of aspects 91 to 97, wherein $X^7$ is selected from A, D, E, F, G, H, I, K, L, M, N, P, Q, R, S, T, V, W, and Y.

Aspect 99. The IL-2Rα ligand of any one of aspects 91 to 98, wherein $X^8$ is selected from A, G, P, S, and T.

Aspect 100. The IL-2Rα ligand of any one of aspects 91 to 99, wherein $X^9$ is C.

Aspect 101. The IL-2Rα ligand of any one of aspects 91 to 100, wherein $X^{10}$ is selected from H, K, N, Q, R, S, T, and Y.

Aspect 102. The IL-2Rα ligand of any one of aspects 91 to 101, wherein $X^{11}$ is selected from A, G, P, S, and T.

Aspect 103. The IL-2Rα ligand of any one of aspects 91 to 102, wherein $X^{12}$ is selected from A, D, E, F, G, H, I, K, L, M, N, P, Q, R, S, T, V, W, and Y.

Aspect 104. The IL-2Rα ligand of any one of aspects 91 to 103, wherein $X^1$ is selected from Y and W.

Aspect 105. The IL-2Rα ligand of any one of aspects 91 to 104, wherein $X^2$ is V.

Aspect 106. The IL-2Rα ligand of any one of aspects 91 to 105, wherein $X^3$ is selected from M and I.

Aspect 107. The IL-2Rα ligand of any one of aspects 91 to 106, wherein $X^4$ is C.

Aspect 108. The IL-2Rα ligand of any one of aspects 91 to 107, wherein $X^5$ is S.

Aspect 109. The IL-2Rα ligand of any one of aspects 91 to 108, wherein $X^6$ is A.

Aspect 110. The IL-2Rα ligand of any one of aspects 91 to 109, wherein $X^7$ is F, L, V, and M.

Aspect 111. The IL-2Rα ligand of any one of aspects 91 to 110, wherein $X^8$ is G.

Aspect 112. The IL-2Rα ligand of any one of aspects 91 to 111, wherein $X^9$ is C.

Aspect 113. The IL-2Rα ligand of any one of aspects 91 to 112, wherein $X^{10}$ is selected from K and R.

Aspect 114. The IL-2Rα ligand of any one of aspects 91 to 113, wherein $X^{11}$ is selected from S, P, and A.

Aspect 115. The IL-2Rα ligand of any one of aspects 91 to 114, wherein $X^{12}$ is selected from I, L, M, F, and W.

Aspect 116. The IL-2Rα ligand of any one of aspects 91 to 115, wherein $X^1$ is selected from F, I, L, M, V, W, and Y.

Aspect 117. The IL-2Rα ligand of any one of aspects 91 to 116, wherein $X^2$ is V.

Aspect 118. The IL-2Rα ligand of any one of aspects 91 to 117, wherein $X^3$ is selected from F, I, L, M, V, W, and Y.

Aspect 119. The IL-2Rα ligand of any one of aspects 91 to 118, wherein $X^4$ is C.

Aspect 120. The IL-2Rα ligand of any one of aspects 91 to 119, wherein $X^5$ is G.

Aspect 121. The IL-2Rα ligand of any one of aspects 91 to 120, wherein $X^6$ is selected from A, D, E, F, G, H, I, K, L, M, N, P, Q, R, S, T, V, W, and Y.

Aspect 122. The IL-2Rα ligand of any one of aspects 91 to 121, wherein $X^7$ is selected from A, D, E, F, G, H, I, K, L, M, N, P, Q, R, S, T, V, W, and Y.

Aspect 123. The IL-2Rα ligand of any one of aspects 91 to 122, wherein $X^8$ is G.

Aspect 124. The IL-2Rα ligand of any one of aspects 91 to 123, wherein $X^9$ is C.

Aspect 125. The IL-2Rα ligand of any one of aspects 91 to 124, wherein $X^{10}$ is R.

Aspect 126. The IL-2Rα ligand of any one of aspects 91 to 125, wherein $X^{11}$ is S.

Aspect 127. The IL-2Rα ligand of any one of aspects 91 to 126, wherein $X^{12}$ is selected from F, I, L, M, V, W, and Y.

Aspect 128. The IL-2Rα ligand of any one of aspects 91 to 126, wherein $X^{12}$ is V.

Aspect 129. The IL-2Rα ligand of aspect 91, wherein $X^2$ is V, $X^4$ is C, $X^5$ is G, $X^8$ is G,
$X^9$ is C, $X^{10}$ is R, and $X^{11}$ is S.

Aspect 130. The IL-2Rα ligand of aspect 91, wherein,
$X^1$ is selected from F, I, L, M, V, W, and Y;
$X^2$ is V;
$X^3$ is selected from F, I, L, M, V, W, and Y;

X⁴ is C;
X⁵ is G;
X⁶ is selected from A, D, E, F, G, H, I, K, L, M, N, P, Q, R, S, T, V, W, and Y;
X⁷ is selected from A, D, E, F, G, H, I, K, L, M, N, P, Q, R, S, T, V, W, and Y;
X⁸ is G;
X⁹ is C;
X¹⁰ is R;
X¹¹ is S; and
X¹² is selected from F, I, L, M, V, W, and Y.

Aspect 131. The IL-2Rα ligand of aspect 91, wherein the IL-2Rα ligand comprises an amino acid sequence selected from any one of SEQ ID NO: 19 to SEQ ID NO: 24:

F V L C G L Q G C R G S    SEQ ID NO: 19

K V I C G W D G C R    SEQ ID NO: 20

L V F C G K N G C H S G    SEQ ID NO: 21

V V L C T P K G C R S A    SEQ ID NO: 22

Y V M C S A F G C K S I    SEQ ID NO: 23

F V H C T L L G C W S G    SEQ ID NO: 24

Aspect 132. The IL-2Rα ligand of any one of aspects 91 to 131, wherein,
the amino acid sequence independently comprises from 1 to 4 glycines (G) (SEQ ID NO: 1041) on the N-terminus, on the C-terminus, or on both the N- and C-termini;
the amino acid sequence comprises a truncated amino acid sequence; or
the amino acid sequence comprises a truncated amino acid sequence, wherein the truncated amino acid sequence independently comprises from 1 to 4 glycines (G) (SEQ ID NO: 1041) on the N-terminus, on the C-terminus, or on both the N- and C-termini.

Aspect 133. The IL-2Rα ligand of any one of aspects 131 to 132, wherein from 1 to 5 of the amino acids is independently substituted with another amino acid.

Aspect 134. The IL-2Rα ligand of any one of aspects 1 to 6, wherein the IL-2Rα ligand comprises the amino acid sequence of Formula (4a) (SEQ ID NO: 25), the amino acid sequence of Formula (4b) (SEQ ID NO: 26), the amino acid sequence of Formula (4c) (SEQ ID NO: 27), or the amino acid sequence of Formula (4d) (SEQ ID NO: 28):

—X⁵—X⁶—X⁷—X⁸—X⁹— (4a)

—X³—C—X⁵—X⁶—X⁷—X⁸—C—X¹⁰— (4b)

—X²—X³—C—X⁵—X⁶—X⁷—X⁸—C—X¹⁰— X¹¹— (4c)

—X¹—X²—X³—X⁴—X⁵—X⁶—X⁷—X⁸—X⁹— X¹⁰—X¹¹—X¹²— (4d)

wherein,
X¹ is selected from an amino acid comprising a large hydrophobic side chain;
X² is selected from an amino acid comprising a large hydrophobic side chain;
X³ is selected from an amino acid comprising a large hydrophobic side chain;
X⁴ is C;
X⁵ is selected from an amino acid comprising a small hydrophobic side chain;
X⁶ is selected from an amino acid comprising a small hydrophobic side chain;
X⁷ is selected from an amino acid comprising a large hydrophobic side chain;
X⁸ is selected from an amino acid comprising a small hydrophobic side chain;
X⁹ is C;
X¹⁰ is selected from an amino acid comprising a basic side chain;
X¹¹ is selected from an amino acid comprising a small hydrophobic side chain; and
X¹² is selected from an amino acid comprising a large hydrophobic side chain.

Aspect 135. The IL-2Rα ligand of aspect 134, wherein X¹ is selected from F, I, L, M, V, W, and Y.
Aspect 136. The IL-2Rα ligand of any one of aspects 134 to 135, wherein X² is selected from F, I, L, M, V, W, and Y.
Aspect 137. The IL-2Rα ligand of any one of aspects 134 to 136, wherein X³ is selected from F, I, L, M, V, W, and Y.
Aspect 138. The IL-2Rα ligand of any one of aspects 134 to 137, wherein X⁴ is C.
Aspect 139. The IL-2Rα ligand of any one of aspects 134 to 138, wherein X⁵ is selected from A, G, P, S, and T.
Aspect 140. The IL-2Rα ligand of any one of aspects 134 to 139, wherein X⁶ is selected from A, G, P, S, and T.
Aspect 141. The IL-2Rα ligand of any one of aspects 134 to 140, wherein X⁷ is selected from F, I, L, M, V, W, and Y.
Aspect 142. The IL-2Rα ligand of any one of aspects 134 to 141, wherein X⁸ is selected from A, G, P, S, and T.
Aspect 143. The IL-2Rα ligand of any one of aspects 134 to 142, wherein X⁹ is C.
Aspect 144. The IL-2Rα ligand of any one of aspects 134 to 143, wherein X¹⁰ is selected from H, K, and R.
Aspect 145. The IL-2Rα ligand of any one of aspects 134 to 144, wherein X¹¹ is selected from A, G, P, S, and T.
Aspect 146. The IL-2Rα ligand of any one of aspects 134 to 145, wherein X¹² is selected from F, I, L, M, V, W, and Y.
Aspect 147. The IL-2Rα ligand of any one of aspects 134 to 146, wherein X¹ is selected from Y and W.
Aspect 148. The IL-2Rα ligand of any one of aspects 134 to 147, wherein X² is V.
Aspect 149. The IL-2Rα ligand of any one of aspects 134 to 148, wherein X³ is selected from M and I.
Aspect 150. The IL-2Rα ligand of any one of aspects 134 to 149, wherein X⁴ is C.
Aspect 151. The IL-2Rα ligand of any one of aspects 134 to 150, wherein X⁵ is S.
Aspect 152. The IL-2Rα ligand of any one of aspects 134 to 151, wherein X⁶ is A.
Aspect 153. The IL-2Rα ligand of any one of aspects 134 to 152, wherein X⁷ is selected from F, L, V, and M.
Aspect 154. The IL-2Rα ligand of any one of aspects 134 to 153, wherein X⁸ is G.
Aspect 155. The IL-2Rα ligand of any one of aspects 134 to 154, wherein X⁹ is C.
Aspect 156. The IL-2Rα ligand of any one of aspects 134 to 155, wherein X¹⁰ is selected from R and K.
Aspect 157. The IL-2Rα ligand of any one of aspects 134 to 156, wherein X¹¹ is selected from S, P, and A.
Aspect 158. The IL-2Rα ligand of any one of aspects 134 to 157, wherein X¹² is selected from I, M, F, and W.
Aspect 159. The IL-2Rα ligand of any one of aspects 134 to 158, wherein X¹ is W.

Aspect 160. The IL-2Rα ligand of any one of aspects 134 to 159, wherein $X^2$ is V.

Aspect 161. The IL-2Rα ligand of any one of aspects 134 to 160, wherein $X^3$ is I.

Aspect 162. The IL-2Rα ligand of any one of aspects 134 to 161, wherein $X^4$ is C.

Aspect 163. The IL-2Rα ligand of any one of aspects 134 to 162, wherein $X^5$ is S Aspect 164. The IL-2Rα ligand of any one of aspects 134 to 163, wherein $X^6$ is A.

Aspect 165. The IL-2Rα ligand of any one of aspects 134 to 164, wherein $X^7$ is selected from F, I, L, M, V, W, and Y.

Aspect 166. The IL-2Rα ligand of any one of aspects 134 to 165, wherein $X^8$ is G.

Aspect 167. The IL-2Rα ligand of any one of aspects 134 to 166, wherein $X^9$ is C.

Aspect 168. The IL-2Rα ligand of any one of aspects 134 to 167, wherein $X^{10}$ is R.

Aspect 169. The IL-2Rα ligand of any one of aspects 134 to 168, wherein $X^{11}$ is S.

Aspect 170. The IL-2Rα ligand of any one of aspects 134 to 169, wherein $X^{12}$ is selected from F, I, L, M, V, W, and Y.

Aspect 171. The IL-2Rα ligand of aspect 134, wherein $X^1$ is W, $X^2$ is V, $X^3$ is I, $X^4$ is C, $X^5$ is S, $X^6$ is A, $X^8$ is G, $X^9$ is C, $X^{10}$ is R, and $X^{11}$ is S.

Aspect 172. The IL-2Rα ligand of aspect 134, wherein,
$X^1$ is W;
$X^2$ is V;
$X^3$ is I;
$X^4$ is C;
$X^5$ is S;
$X^6$ is A;
$X^7$ is selected from F, I, L, M, V, W, and Y.
$X^8$ is G;
$X^9$ is C;
$X^{10}$ is selected from R and K;
$X^{11}$ is S; and
$X^{12}$ is selected from F, I, L, M, V, W, and Y.

Aspect 173. The IL-2Rα ligand of aspect 134, wherein the IL-2Rα ligand comprises an amino acid sequence selected from any one of SEQ ID NO: 29 to SEQ ID NO: 36:

```
                      SEQ ID NO: 29
W V I C S A L G C R S L

SEQ ID NO: 30
W V I C S A L G C R S M

SEQ ID NO: 31
W V I C S A V G C R P F

SEQ ID NO: 32
W V I C S A M G C R S I

SEQ ID NO: 33
W V I C S A L G C R S I

SEQ ID NO: 34
W V I C S A F G C R S M

SEQ ID NO: 35
W V I C S A L G C R P F

SEQ ID NO: 36
W V I C S A L G C K A W
```

Aspect 174. The IL-2Rα ligand of any one of aspects 134 to 173, wherein,
the amino acid sequence independently comprises from 1 to 4 glycines (G) (SEQ ID NO: 1041) on the N-terminus, on the C-terminus, or on both the N- and C-termini;
the amino acid sequence comprises a truncated amino acid sequence; or
the amino acid sequence comprises a truncated amino acid sequence, wherein the truncated amino acid sequence independently comprises from 1 to 4 glycines (G) (SEQ ID NO: 1041) on the N-terminus, on the C-terminus, or on both the N- and C-termini.

Aspect 175. The IL-2Rα ligand of any one of aspects 173 to 174, wherein from 1 to 5 of the amino acids is independently substituted with another amino acid.

Aspect 176. The IL-2Rα ligand of any one of aspects 1 to 6, wherein the IL-2Rα ligand comprises the amino acid sequence of Formula (5a) (SEQ ID NO: 37), the amino acid sequence of Formula (5b) (SEQ ID NO: 38), the amino acid sequence of Formula (5c) (SEQ ID NO: 39), or the amino acid sequence of Formula (5d) (SEQ ID NO: 40):

$$-X^5-X^6-X^7-X^8-X^9- \quad (5a)$$

$$-X^3-C-X^5-X^6-X^7-X^8-X^9-C-X^{11}- \quad (5b)$$

$$-X^3-C-X^5-X^6-X^7-X^8-X^9-C-X^{11}-$$
$$X^{12}- \quad (5c)$$

$$-X^1-X^2-X^3-X^4-X^5-X^6-X^7-X^8-X^9-$$
$$X^{10}-X^{11}-X^{12}- \quad (5d)$$

wherein,
$X^1$ is selected from an amino acid comprising an aromatic side chain or a large hydrophobic side chain;
$X^2$ is selected from an amino acid comprising a large hydrophobic side chain;
$X^3$ is selected from an amino acid comprising a large hydrophobic side chain;
$X^4$ is C;
$X^5$ is selected from an amino acid comprising a small hydrophobic side chain or an acidic side chain;
$X^6$ is selected from an amino acid;
$X^7$ is selected from an amino acid;
$X^8$ is selected from an amino acid;
$X^9$ is selected from an amino acid comprising a small hydrophobic side chain;
$X^{10}$ is C;
$X^{11}$ is selected from an amino acid comprising a basic side chain; and
$X^{12}$ is selected from an amino acid.

Aspect 177. The IL-2Rα ligand of aspect 176, wherein $X^1$ is selected from F, H, I, L, M, V, W, and Y.

Aspect 178. The IL-2Rα ligand of any one of aspects 176 to 177, wherein $X^2$ is selected from F, I, L, M, V, W, and Y.

Aspect 179. The IL-2Rα ligand of any one of aspects 176 to 178, wherein $X^3$ is selected from F, I, L, M, V, W, and Y.

Aspect 180. The IL-2Rα ligand of any one of aspects 176 to 179, wherein $X^4$ is C.

Aspect 181. The IL-2Rα ligand of any one of aspects 176 to 180, wherein $X^5$ is selected from A, G, H, K, P, R, S, and T.

Aspect 182. The IL-2Rα ligand of any one of aspects 176 to 181, wherein $X^6$ is selected from A, D, E, F, G, H, I, K, L, M, N, P, Q, R, S, T, V, W, and Y.

Aspect 183. The IL-2Rα ligand of any one of aspects 176 to 182, wherein $X^7$ is selected from A, D, E, F, G, H, I, K, L, M, N, P, Q, R, S, T, V, W, and Y.

Aspect 184. The IL-2Rα ligand of any one of aspects 176 to 183, wherein $X^8$ is selected from A, D, E, F, G, H, I, K, L, M, N, P, Q, R, S, T, V, W, and Y.

Aspect 185. The IL-2Rα ligand of any one of aspects 176 to 184, wherein $X^9$ is selected from A, G, P, S, and T.

Aspect 186. The IL-2Rα ligand of any one of aspects 176 to 185, wherein $X^{10}$ is C.

Aspect 187. The IL-2Rα ligand of any one of aspects 176 to 186, wherein $X^{11}$ is selected from H, K, and R.

Aspect 188. The IL-2Rα ligand of any one of aspects 176 to 187, wherein $X^{12}$ is selected from A, D, E, F, G, H, I, K, L, M, N, P, Q, R, S, T, V, W, and Y.

Aspect 189. The IL-2Rα ligand of any one of aspects 176 to 188, wherein $X^1$ is selected from F, H, W, and Y.

Aspect 190. The IL-2Rα ligand of any one of aspects 176 to 189, wherein $X^2$ is V.

Aspect 191. The IL-2Rα ligand of any one of aspects 176 to 190, wherein $X^3$ is selected from F, I, L, M, V, W, and Y.

Aspect 192. The IL-2Rα ligand of any one of aspects 176 to 191, wherein $X^4$ is selected from F, K, L, V, W, and H.

Aspect 193. The IL-2Rα ligand of any one of aspects 176 to 192, wherein $X^5$ is V.

Aspect 194. The IL-2Rα ligand of any one of aspects 176 to 193, wherein $X^5$ is selected from L, F, M, H, T, A, and I.

Aspect 195. The IL-2Rα ligand of any one of aspects 176 to 194, wherein $X^5$ is C.

Aspect 196. The IL-2Rα ligand of any one of aspects 176 to 195, wherein $X^6$ is selected from G, T, S, R, and K.

Aspect 197. The IL-2Rα ligand of any one of aspects 176 to 196, wherein $X^6$ is selected from L, W, K, P, A, N, W, and V.

Aspect 198. The IL-2Rα ligand of any one of aspects 176 to 197, wherein $X^7$ is selected from Q, D, N, K, F, L, R, G, and D.

Aspect 199. The IL-2Rα ligand of any one of aspects 176 to 198, wherein $X^8$ is selected from G, N, Y, H, and G.

Aspect 200. The IL-2Rα ligand of any one of aspects 176 to 199, wherein $X^9$ is G.

Aspect 201. The IL-2Rα ligand of any one of aspects 176 to 200, wherein $X^{10}$ is C.

Aspect 202. The IL-2Rα ligand of any one of aspects 176 to 201, wherein $X^{11}$ is selected from G, S, R, T, and Y.

Aspect 203. The IL-2Rα ligand of any one of aspects 176 to 202, wherein $X^{12}$ is selected from S, G, A, I, G, P, R, and S.

Aspect 204. The IL-2Rα ligand of any one of aspects 176 to 203, wherein $X^1$ is selected from F, W, and Y.

Aspect 205. The IL-2Rα ligand of any one of aspects 176 to 204, wherein $X^2$ is V.

Aspect 206. The IL-2Rα ligand of any one of aspects 176 to 205, wherein $X^3$ is selected from F, I, L, M, V, W, and Y.

Aspect 207. The IL-2Rα ligand of any one of aspects 176 to 206, wherein $X^4$ is C.

Aspect 208. The IL-2Rα ligand of any one of aspects 176 to 207, wherein $X^5$ is selected from A, G, P, S, and T.

Aspect 209. The IL-2Rα ligand of any one of aspects 176 to 208, wherein $X^5$ is selected from H, K, and R.

Aspect 210. The IL-2Rα ligand of any one of aspects 176 to 209, wherein $X^5$ is S.

Aspect 211. The IL-2Rα ligand of any one of aspects 176 to 210, wherein $X^6$ is selected from F, I, L, M, V, W, and Y.

Aspect 212. The IL-2Rα ligand of any one of aspects 176 to 211, wherein $X^6$ is W.

Aspect 213. The IL-2Rα ligand of any one of aspects 176 to 212, wherein $X^7$ is selected from A, D, E, F, G, H, I, K, L, M, N, P, Q, R, S, T, V, W, and Y.

Aspect 214. The IL-2Rα ligand of any one of aspects 176 to 213, wherein $X^8$ is selected from A, D, E, F, G, H, I, K, L, M, N, P, Q, R, S, T, V, W, and Y.

Aspect 215. The IL-2Rα ligand of any one of aspects 176 to 214, wherein $X^9$ is G.

Aspect 216. The IL-2Rα ligand of any one of aspects 176 to 215, wherein $X^{10}$ is C.

Aspect 217. The IL-2Rα ligand of any one of aspects 176 to 216, wherein $X^{11}$ is R.

Aspect 218. The IL-2Rα ligand of any one of aspects 176 to 217, wherein $X^{12}$ is selected from A, D, E, F, G, H, I, K, L, M, N, P, Q, R, S, T, V, W, and Y.

Aspect 219. The IL-2Rα ligand of aspect 176, wherein $X^2$ is V, $X^4$ is C, $X^5$ is S, $X^9$ is G, $X^{10}$ is C, and $X^{11}$ is R.

Aspect 220. The IL-2Rα ligand of aspect 176, wherein,
$X^1$ is selected from F, H, I, L, M, V, W, and Y;
$X^2$ is V;
$X^3$ is selected from F, I, L, M, V, W, and Y;
$X^4$ is C;
$X^5$ is S;
$X^6$ is selected from F, I, L, M, V, W, and Y;
$X^7$ is selected from A, D, E, F, G, H, I, K, L, M, N, P, Q, R, S, T, V, W, and Y;
$X^8$ is selected from A, D, E, F, G, H, I, K, L, M, N, P, Q, R, S, T, V, W, and Y;
$X^9$ is G;
$X^{10}$ is C;
$X^{11}$ is R; and
$X^{12}$ is selected from A, D, E, F, G, H, I, K, L, M, N, P, Q, R, S, T, V, W, and Y.

Aspect 221. The IL-2Rα ligand of aspect 176, wherein the IL-2Rα ligand comprises an amino acid sequence selected from any one of SEQ ID NO: 41 to SEQ ID NO: 45:

```
                                      SEQ ID NO: 41
    Y V L C S N R N G C R P

SEQ ID NO: 42
    Y V T C R W G Y G C T R

SEQ ID NO: 43
    W V A C S W D H G C R S

SEQ ID NO: 44
    H V I C S V N G G C R G

SEQ ID NO: 45
    W V X C K P L H G C Y G
```

Aspect 222. The IL-2Rα ligand of any one of aspects 176 to 221, wherein,
the amino acid sequence independently comprises from 1 to 4 glycines (G) (SEQ ID NO: 1041) on the N-terminus, on the C-terminus, or on both the N- and C-termini;
the amino acid sequence comprises a truncated amino acid sequence; or
the amino acid sequence comprises a truncated amino acid sequence, wherein the truncated amino acid sequence independently comprises from 1 to 4 glycines (G) (SEQ ID NO: 1041) on the N-terminus, on the C-terminus, or on both the N- and C-termini.

Aspect 223. The IL-2Rα ligand of any one of aspects 221 to 222, wherein from 1 to 5 of the amino acids is independently substituted with another amino acid.

Aspect 224. The IL-2Rα ligand of any one of aspects 1 to 6, wherein the IL-2Rα ligand comprises the amino acid sequence of Formula (6a) (SEQ ID NO: 46), the amino acid sequence of Formula (6b) (SEQ ID NO: 47), the amino acid sequence of Formula (6c) (SEQ ID NO: 48), or the amino acid sequence of Formula (6d) (SEQ ID NO: 49):

$$-X^5-X^6-X^7-X^8-X^9-X^{10}-X^{11}- \tag{6a}$$

$$-X^3-C-X^5-X^6-X^7-X^8-X^9-X^{10}-X^{11}-C-X^{13}- \quad (6b)$$

$$-X^2-X^3-C-X^5-X^6-X^7-X^8-X^9-X^{10}-X^{11}-C-X^{13}-X^{14}- \quad (6c)$$

$$-X^1-X^2-X^3-X^4-X^5-X^6-X^7-X^8-X^9-X^{10}-X^{11}-X^{12}-X^{13}-X^{14}-X^{15}- \quad (6d)$$

wherein, $X^1$ is selected from an amino acid;
$X^2$ is selected from an amino acid;
$X^3$ is selected from an amino acid comprising a large hydrophobic side chain or an aromatic side chain;
$X^4$ is C;
$X^5$ is selected from an amino acid comprising a large hydrophobic side chain;
$X^6$ is selected from an amino acid comprising a basic side chain;
$X^7$ is selected from an amino acid comprising a small hydrophobic side chain or a polar neutral side chain;
$X^8$ is selected from an amino acid comprising an acidic side chain;
$X^9$ is selected from an amino acid comprising a small hydrophobic side chain;
$X^{10}$ is selected from an amino acid;
$X^{11}$ is selected from an amino acid comprising a small hydrophobic side chain;
$X^{12}$ is C;
$X^{13}$ is selected from an amino acid comprising an aromatic side chain or a large hydrophobic side chain;
$X^{14}$ is selected from an amino acid comprising a small hydrophobic side chain or a polar neutral side chain; and
$X^{15}$ is selected from an amino acid.

Aspect 225. The IL-2Rα ligand of aspect 224, wherein,
$X^1$ is selected from A, D, E, F, G, H, I, K, L, M, N, P, Q, R, S, T, V, W, and Y;
$X^2$ is selected from A, D, E, F, G, H, I, K, L, M, N, P, Q, R, S, T, V, W, and Y;
$X^3$ is selected from F, H, I, L, M, V, W, and Y;
$X^4$ is C;
$X^5$ is selected from F, I, L, M, V, W, and Y;
$X^6$ is selected from H, K, and R;
$X^7$ is selected from A, G, H, N, P, Q, S, T, and Y;
$X^8$ is selected from D and E;
$X^9$ is selected from A, G, P, S, and T;
$X^{10}$ is selected from A, D, E, F, G, H, I, K, L, M, N, P, Q, R, S, T, V, W, and Y;
$X^{11}$ is selected from A, G, P, S, and T;
$X^{12}$ is C;
$X^{13}$ is selected from F, H, I, L, M, V, W, and Y;
$X^{14}$ is selected from A, G, H, N, P, Q, S, T, and Y; and
$X^{15}$ is selected from any A, D, E, F, G, H, I, K, L, M, N, P, Q, R, S, T, V, W, and Y.

Aspect 226. The IL-2Rα ligand f any one of aspects 224 to 225, wherein $X^1$ is selected from E, K, R, T, and L.
Aspect 227. The IL-2Rα ligand of any one of aspects 224 to 226, wherein $X^2$ is selected from Q, Y, V, K, and R.
Aspect 228. The IL-2Rα ligand of any one of aspects 224 to 227, wherein $X^3$ is selected from F, W, V, and L.
Aspect 229. The IL-2Rα ligand of any one of aspects 224 to 228, wherein $X^4$ is C.
Aspect 230. The IL-2Rα ligand of any one of aspects 224 to 229, wherein $X^5$ is L.
Aspect 231. The IL-2Rα ligand of any one of aspects 224 to 230, wherein $X^6$ is selected from V, R, A, and K.
Aspect 232. The IL-2Rα ligand of any one of aspects 224 to 231, wherein $X^7$ is S.
Aspect 233. The IL-2Rα ligand of any one of aspects 224 to 232, wherein $X^8$ is selected from D and E.
Aspect 234. The IL-2Rα ligand of any one of aspects 224 to 233, wherein $X^9$ is P.
Aspect 235. The IL-2Rα ligand of any one of aspects 224 to 234, wherein $X^{10}$ is selected from M, D, N, M Q, and T.
Aspect 236. The IL-2Rα ligand of any one of aspects 224 to 235, wherein $X^{11}$ is selected from A and S.
Aspect 237. The IL-2Rα ligand of any one of aspects 224 to 236, wherein $X^{12}$ is C.
Aspect 238. The IL-2Rα ligand of any one of aspects 224 to 237, wherein $X^{13}$ is selected from F and W.
Aspect 239. The IL-2Rα ligand of any one of aspects 224 to 238, wherein $X^{14}$ is selected from S, A, and I.
Aspect 240. The IL-2Rα ligand of any one of aspects 224 to 239, wherein $X^{15}$ is selected from L, T, M, and V.
Aspect 241. The IL-2Rα ligand of any one of aspects 224 to 240, wherein $X^1$ is selected from A, D, E, F, G, H, I, K, L, M, N, P, Q, R, S, T, V, W, and Y.
Aspect 242. The IL-2Rα ligand of any one of aspects 224 to 241, wherein $X^2$ is selected from A, D, E, F, G, H, I, K, L, M, N, P, Q, R, S, T, V, W, and Y.
Aspect 243. The IL-2Rα ligand of any one of aspects 224 to 242, wherein $X^3$ is selected from F, W, and Y.
Aspect 244. The IL-2Rα ligand of any one of aspects 224 to 243, wherein $X^4$ is C.
Aspect 245. The IL-2Rα ligand of any one of aspects 224 to 244, wherein $X^5$ is L.
Aspect 246. The IL-2Rα ligand of any one of aspects 224 to 245, wherein $X^6$ is selected from H, K, and R.
Aspect 247. The IL-2Rα ligand of any one of aspects 224 to 246, wherein $X^7$ is S.
Aspect 248. The IL-2Rα ligand of any one of aspects 224 to 247, wherein $X^8$ is selected from D and E.
Aspect 249. The IL-2Rα ligand of any one of aspects 224 to 248, wherein $X^9$ is P.
Aspect 250. The IL-2Rα ligand of any one of aspects 224 to 249, wherein $X^{10}$ is selected from A, D, E, F, G, H, I, K, L, M, N, P, Q, R, S, T, V, W, and Y.
Aspect 251. The IL-2Rα ligand of any one of aspects 224 to 250, wherein $X^{11}$ is A.
Aspect 252. The IL-2Rα ligand of any one of aspects 224 to 251, wherein $X^{12}$ is C.
Aspect 253. The IL-2Rα ligand of any one of aspects 224 to 252, wherein $X^{13}$ is selected from F, W, and Y.
Aspect 254. The IL-2Rα ligand of any one of aspects 224 to 252, wherein $X^{13}$ is W.
Aspect 255. The IL-2Rα ligand of any one of aspects 224 to 254, wherein $X^{14}$ is S.
Aspect 256. The IL-2Rα ligand of any one of aspects 224 to 255, wherein $X^{15}$ is selected from A, D, E, F, G, H, I, K, L, M, N, P, Q, R, S, T, V, W, and Y.
Aspect 257. The IL-2Rα ligand of aspect 224, wherein $X^4$ is C, $X^5$ is L, $X^7$ is S, $X^8$ is E, $X^9$ is P, $X^{11}$ is A, $X^{12}$ is C, $X^{12}$ is W, and $X^{14}$ is S.
Aspect 258. The IL-2Rα ligand of aspect 224, wherein,
$X^1$ is selected from A, D, E, F, G, H, I, K, L, M, N, P, Q, R, S, T, V, W, and Y;
$X^2$ is selected from A, D, E, F, G, H, I, K, L, M, N, P, Q, R, S, T, V, W, and Y;
$X^3$ is selected from F, H, I, L, M, V, W, and Y;
$X^4$ is C;
$X^5$ is L;
$X^6$ is selected from H, K, and R;
$X^7$ is S;
$X^8$ is E;
$X^9$ is P;

$X^{10}$ is selected from A, D, E, F, G, H, I, K, L, M, N, P, Q, R, S, T, V, W, and Y;
$X^{11}$ is A;
$X^{12}$ is C;
$X^{11}$ is W;
$X^{14}$ is S; and
$X^{15}$ is selected from A, D, E, F, G, H, I, K, L, M, N, P, Q, R, S, T, V, W, and Y.

Aspect 259. The IL-2Rα ligand of aspect 224, wherein the IL-2Rα ligand comprises an amino acid sequence selected from any one of SEQ ID NO: 50 to SEQ ID NO: 54:

```
                                        SEQ ID NO: 50
         E Q F C L V S D P M A C W S L

SEQ ID NO: 51
         K Y W C L R S E P D A C F A T

SEQ ID NO: 52
         R V Y C L A S E P N S C W S T

SEQ ID NO: 53
         T K L C L K S E P Q A C W S M

SEQ ID NO: 54
         I R F C L R S E P T A C W I V
```

Aspect 260. The IL-2Rα ligand of any one of aspects 224 to 259, wherein, the amino acid sequence independently comprises from 1 to 4 glycines (G) (SEQ ID NO: 1041) on the N-terminus, on the C-terminus, or on both the N- and C-termini;

the amino acid sequence comprises a truncated amino acid sequence; or the amino acid sequence comprises a truncated amino acid sequence, wherein the truncated amino acid sequence independently comprises from 1 to 4 glycines (G) (SEQ ID NO: 1041) on the N-terminus, on the C-terminus, or on both the N- and C-termini.

Aspect 261. The IL-2Rα ligand of any one of aspects 259 to 260, wherein from 1 to 5 of the amino acids is independently substituted with another amino acid.

Aspect 262. The IL-2Rα ligand of any one of aspects 1 to 6, wherein the IL-2Rα ligand comprises the amino acid sequence of Formula (7a) (SEQ ID NO: 55), the amino acid sequence of Formula (7b) (SEQ ID NO: 56), the amino acid sequence of Formula (7c) (SEQ ID NO: 57), or the amino acid sequence of Formula (7d) (SEQ ID NO: 58):

$$-X^5-X^6-X^7-X^8-X^9-X^{10}-X^{11}- \quad (7a)$$

$$-X^3-C-X^5-X^6-X^7-X^8-X^9-X^{10}-X^{11}-C-X^{13}- \quad (7b)$$

$$-X^2-X^3-C-X^5-X^6-X^7-X^8-X^9-X^{10}-X^{11}-C-X^{13}-X^{14}- \quad (7c)$$

$$-X^1-X^2-X^3-X^4-X^5-X^6-X^7-X^8-X^9-X^{10}-X^{11}-X^{12}-X^{13}-X^{14}-X^{15}- \quad (7d)$$

wherein,
$X^1$ is selected from a basic amino acid;
$X^2$ is selected from a basic amino acid;
$X^3$ is selected from an amino acid comprising a large hydrophobic side chain;
$X^4$ is C;
$X^5$ is selected from an amino acid comprising a large hydrophobic side chain;
$X^6$ is selected from an amino acid comprising a basic side chain;
$X^7$ is selected from an amino acid comprising a small hydrophobic side chain or a polar neutral side chain;
$X^8$ is selected from an amino acid comprising a large hydrophobic side chain;
$X^9$ is selected from an amino acid comprising a small hydrophobic side chain;
$X^{10}$ is selected from an amino acid comprising a small hydrophobic side chain or a polar neutral side chain;
$X^{11}$ is selected from an amino acid comprising a small hydrophobic side chain;
$X^{12}$ is C;
$X^{13}$ is selected from an amino acid comprising an aromatic side chain or a large hydrophobic side chain;
$X^{14}$ is selected from an amino acid comprising a small hydrophobic side chain or a polar neutral side chain; and
$X^{15}$ is selected from an amino acid comprising a large hydrophobic side chain.

Aspect 263. The IL-2Rα ligand of aspect 262, wherein,
$X^1$ is selected from K, and R;
$X^2$ is selected from H, K, and R;
$X^3$ is selected from F, I, L, M, V, W, and Y;
$X^4$ is C;
$X^5$ is selected from F, I, L, M, V, W, and Y;
$X^6$ is selected from H, K, and R;
$X^7$ is selected from A, G, H, N, P, Q, S, T, and Y;
$X^8$ is selected from F, I, L, M, V, W, and Y;
$X^9$ is selected from A, G, P, S, and T;
$X^{10}$ is selected from A, G, H, N, P, Q, S, T, and Y;
$X^{11}$ is selected from A, G, P, S, and T;
$X^{12}$ is C;
$X^{13}$ is selected from F, H, I, L, M, V, W, and Y;
$X^{14}$ is selected from A, G, H, N, P, Q, S, T, and Y; and
$X^{15}$ is selected from F, I, L, M, V, W, and Y.

Aspect 264. The IL-2Rα ligand of any one of aspects 262 to 263, wherein $X^1$ is selected from A, D, E, F, G, H, I, K, L, M, N, P, Q, R, S, T, V, W, and Y.

Aspect 265. The IL-2Rα ligand of any one of aspects 262 to 264, wherein $X^2$ is selected from A, D, E, F, G, H, I, K, L, M, N, P, Q, R, S, T, V, W, and Y.

Aspect 266. The IL-2Rα ligand of any one of aspects 262 to 265, wherein $X^3$ is selected from F, I, L, M, V, W, and Y.

Aspect 267. The IL-2Rα ligand of any one of aspects 262 to 266, wherein $X^4$ is C.

Aspect 268. The IL-2Rα ligand of any one of aspects 262 to 267, wherein $X^5$ is selected from F, I, L, M, V, W, and Y.

Aspect 269. The IL-2Rα ligand of any one of aspects 262 to 268, wherein $X^5$ is L.

Aspect 270. The IL-2Rα ligand of any one of aspects 262 to 269, wherein $X^6$ is selected from H, K, and R.

Aspect 271. The IL-2Rα ligand of any one of aspects 262 to 270, wherein $X^7$ is selected from A, G, P, S, and T.

Aspect 272. The IL-2Rα ligand of any one of aspects 262 to 271, wherein $X^7$ is selected from H, N, Q, S, T, and Y.

Aspect 273. The IL-2Rα ligand of any one of aspects 262 to 272, wherein $X^7$ is S.

Aspect 274. The IL-2Rα ligand of any one of aspects 262 to 273, wherein $X^8$ is selected from D and E.

Aspect 275. The IL-2Rα ligand of any one of aspects 262 to 274, wherein $X^9$ is P.

Aspect 276. The IL-2Rα ligand of any one of aspects 262 to 275, wherein $X^{10}$ is selected from A, D, E, F, G, H, I, K, L, M, N, P, Q, R, S, T, V, W, and Y.

Aspect 277. The IL-2Rα ligand of any one of aspects 262 to 276, wherein $X^{11}$ is A.

Aspect 278. The IL-2Rα ligand of any one of aspects 262 to 277, wherein $X^{12}$ is C.

Aspect 279. The IL-2Rα ligand of any one of aspects 262 to 278, wherein $X^{13}$ is W.

Aspect 280. The IL-2Rα ligand of any one of aspects 262 to 279, wherein $X^{14}$ is S.

Aspect 281. The IL-2Rα ligand of any one of aspects 262 to 280, wherein $X^{15}$ is selected from A, D, E, F, G, H, I, K, L, M, N, P, Q, R, S, T, V, W, and Y.

Aspect 282. The IL-2Rα ligand of any one of aspects 262 to 281, wherein $X^1$ is R.

Aspect 283. The IL-2Rα ligand of any one of aspects 262 to 282, wherein $X^2$ is R.

Aspect 284. The IL-2Rα ligand of any one of aspects 262 to 283, wherein $X^3$ is F.

Aspect 285. The IL-2Rα ligand of any one of aspects 262 to 284, wherein $X^4$ is C.

Aspect 286. The IL-2Rα ligand of any one of aspects 262 to 285, wherein $X^5$ is L.

Aspect 287. The IL-2Rα ligand of any one of aspects 262 to 286, wherein $X^6$ is R.

Aspect 288. The IL-2Rα ligand of any one of aspects 262 to 287, wherein $X^7$ is S.

Aspect 289. The IL-2Rα ligand of any one of aspects 262 to 288, wherein $X^8$ is E.

Aspect 290. The IL-2Rα ligand of any one of aspects 262 to 289, wherein $X^9$ is P.

Aspect 291. The IL-2Rα ligand of any one of aspects 262 to 290, wherein $X^{10}$ is T.

Aspect 292. The IL-2Rα ligand of any one of aspects 262 to 291, wherein $X^{11}$ is A.

Aspect 293. The IL-2Rα ligand of any one of aspects 262 to 292, wherein $X^{12}$ is C.

Aspect 294. The IL-2Rα ligand of any one of aspects 262 to 293, wherein $X^{13}$ is W.

Aspect 295. The IL-2Rα ligand of any one of aspects 262 to 294, wherein $X^{14}$ is T.

Aspect 296. The IL-2Rα ligand of any one of aspects 262 to 295, wherein $X^{15}$ is V.

Aspect 297. The IL-2Rα ligand of aspect 262, wherein $X^1$ is R, $X^2$ is R, $X^3$ is F, $X^4$ is C, $X^5$ is L, $X^6$, is R, $X^7$ is S, X is E, $X^9$ is P, $X^{10}$ is T, $X^{11}$ is A, $X^{12}$ is C, $X^{11}$ is W, and $X^{15}$ is V.

Aspect 298. The IL-2Rα ligand of aspect 262, wherein, $X^1$ is selected from K and R;

$X^2$ is R;

$X^3$ is F;

$X^4$ is C;

$X^5$ is L;

$X^6$ is R;

$X^7$ is S;

$X^8$ is E;

$X^9$ is P;

$X^{10}$ is T;

$X^{11}$ is A;

$X^{12}$ is C;

$X^{13}$ is W;

$X^{14}$ is T; and $X^{15}$ is V.

Aspect 299. The IL-2Rα ligand of aspect 262, wherein the IL-2Rα ligand comprises an amino acid sequence selected from any one of SEQ ID NO: 59 to SEQ ID NO: 68:

SEQ ID NO: 59
R R F C L R S E P T A C W I V

SEQ ID NO: 60
K L F C L R S G D R A C W V V

-continued

SEQ ID NO: 61
M R F C L R S E P T A C W T V

SEQ ID NO: 62
R R F C L R S E P T A C W D V

SEQ ID NO: 63
R R F C L R S D P T A C W I V

SEQ ID NO: 64
K R F C L R S E P T A C W T V

SEQ ID NO: 65
R R F C L R S E P M A C W T V

SEQ ID NO: 66
R R F C L R S E P T A C W T V

SEQ ID NO: 67
R R F C L R S E P A A C W F V

SEQ ID NO: 68
R R F C L R S E P T A C W Y V

Aspect 300. The IL-2Rα ligand of any one of aspects 262 to 299, wherein, the amino acid sequence independently comprises from 1 to 4 glycines (G) (SEQ ID NO: 1041) on the N-terminus, on the C-terminus, or on both the N- and C-termini;

the amino acid sequence comprises a truncated amino acid sequence; or the amino acid sequence comprises a truncated amino acid sequence, wherein the truncated amino acid sequence independently comprises from 1 to 4 glycines (G) (SEQ ID NO: 1041) on the N-terminus, on the C-terminus, or on both the N- and C-termini.

Aspect 301. The IL-2Rα ligand of any one of aspects 299 to 300, wherein from 1 to 5 of the amino acids is independently substituted with another amino acid.

Aspect 302. The IL-2Rα ligand of any one of aspects 1 to 6, wherein the IL-2Rα ligand comprises the amino acid sequence of Formula (8a) (SEQ ID NO: 69), the amino acid sequence of Formula (8b) (SEQ ID NO: 70), or the amino acid sequence of Formula (8c) (SEQ ID NO: 71):

$$—X^4—X^5—X^6—X^7—X^8—X^9—X^{10}—X^{11}— \quad (8a)$$

$$—X^2—C—X^4—X^5—X^6—X^7—X^8—X^9—X^{10}—X^{11}—C—X^{13}— \quad (8b)$$

$$—X^1—X^2—X^3—X^4—X^5—X^6—X^7—X^8—X^9—X^{10}—X^{11}—X^{12}—X^{13}—X^{14}— \quad (8c)$$

wherein, $X^1$ is selected from an amino acid;

$X^2$ is selected from an amino acid comprising a basic side chain;

$X^3$ is C;

$X^4$ is selected from an amino acid comprising a large hydrophobic side chain or a basic side chain;

$X^5$ is selected from an amino acid;

$X^6$ is selected from an amino acid comprising an acidic side chain;

$X^7$ is selected from an amino acid;

$X^8$ is selected from an amino acid;

$X^9$ is selected from an amino acid;

$X^{10}$ is selected from an amino acid comprising a small hydrophobic side chain;

$X^{11}$ is selected from an amino acid;

$X^{12}$ is C;

$X^{13}$ is selected from an amino acid comprising a large hydrophobic side chain; and $X^{14}$ is selected from an amino acid comprising a large hydrophobic side chain.

Aspect 303. The IL-2Rα ligand of aspect 302, wherein,
$X^1$ is selected from A, D, E, F, G, H, I, K, L, M, N, P, Q, R, S, T, V, W, and Y;
$X^2$ is selected from H, K, and R;
$X^3$ is C;
$X^4$ is selected from F, H, I, K, L, M, R, V, W, and Y;
$X^5$ is selected from A, D, E, F, G, H, I, K, L, M, N, P, Q, R, S, T, V, W, and Y;
$X^6$ is selected from D and E;
$X^7$ is selected from A, D, E, F, G, H, I, K, L, M, N, P, Q, R, S, T, V, W, and Y;
$X^8$ is selected from A, D, E, F, G, H, I, K, L, M, N, P, Q, R, S, T, V, W, and Y;
$X^9$ is selected from A, D, E, F, G, H, I, K, L, M, N, P, Q, R, S, T, V, W, and Y;
$X^{10}$ is selected from A, G, P, S, and T;
$X^{11}$ is selected from A, D, E, F, G, H, I, K, L, M, N, P, Q, R, S, T, V, W, and Y;
$X^{12}$ is C;
$X^{13}$ is selected from F, I, L, M, V, W, and Y; and
$X^{14}$ is selected from F, I, L, M, V, W, and Y.

Aspect 304. The IL-2Rα ligand of any one of aspects 302 to 303, wherein $X^1$ is selected from R, I, L, M, N, S, T, V, and D.

Aspect 305. The IL-2Rα ligand of any one of aspects 302 to 304, wherein $X^2$ is selected from S, K, R, H, G, and F.

Aspect 306. The IL-2Rα ligand of any one of aspects 302 to 305, wherein $X^3$ is C.

Aspect 307. The IL-2Rα ligand of any one of aspects 302 to 306, wherein $X^4$ is selected from N, R, I, T, V, L, and D.

Aspect 308. The IL-2Rα ligand of any one of aspects 302 to 307, wherein $X^5$ is selected from R, V, L, M, V, G, Y, I, F, and T.

Aspect 309. The IL-2Rα ligand of any one of aspects 302 to 308, wherein $X^5$ is selected from Y, L, E, D, S, I, Y, D, and R.

Aspect 310. The IL-2Rα ligand of any one of aspects 302 to 308, wherein $X^6$ is selected from Y, L, E, D, S, and R.

Aspect 311. The IL-2Rα ligand of any one of aspects 302 to 310, wherein $X^7$ is selected from G, E, K, T, P, W, L, Y, G, S, and R.

Aspect 312. The IL-2Rα ligand of any one of aspects 302 to 311, wherein $X^8$ is selected from I, A, Q, R, S R, L, N, P, A, I, R, D, and W.

Aspect 313. The IL-2Rα ligand of any one of aspects 302 to 312, wherein $X^9$ is selected from W, G, S, D, R, L, F, P, A, and T.

Aspect 314. The IL-2Rα ligand of any one of aspects 302 to 313, wherein $X^{10}$ is selected from G, T, E, W, Q, R, and Y.

Aspect 315. The IL-2Rα ligand of any one of aspects 302 to 314, wherein $X^{11}$ is selected from H, P, I, T, H, A, S, F, and Y.

Aspect 316. The IL-2Rα ligand of any one of aspects 302 to 315, wherein $X^{12}$ is C.

Aspect 317. The IL-2Rα ligand of any one of aspects 302 to 316, wherein $X^{13}$ is selected from D, V, L, I, Y, I, R, H, T, I, and W.

Aspect 318. The IL-2Rα ligand of any one of aspects 302 to 317, wherein $X^{14}$ is selected from T, S, F, and I.

Aspect 319. The IL-2Rα ligand of any one of aspects 302 to 318, wherein $X^1$ is selected from R, I, L, M, N, S, T, V, and D.

Aspect 320. The IL-2Rα ligand of any one of aspects 302 to 319, wherein $X^2$ is selected from S, K, R, H, G, and F.

Aspect 321. The IL-2Rα ligand of any one of aspects 302 to 320, wherein $X^3$ is C.

Aspect 322. The IL-2Rα ligand of any one of aspects 302 to 321, wherein $X^4$ is selected from F, I, L, M, V, W, and Y.

Aspect 323. The IL-2Rα ligand of any one of aspects 302 to 321, wherein $X^4$ is selected from H, K, and R.

Aspect 324. The IL-2Rα ligand of any one of aspects 302 to 323, wherein $X^5$ is selected from Y, L, E, D, S, I, Y, D, and R.

Aspect 325. The IL-2Rα ligand of any one of aspects 302 to 324, wherein $X^6$ is selected from Y, L, E, D, S, and R.

Aspect 326. The IL-2Rα ligand of any one of aspects 302 to 324, wherein $X^6$ is selected from D and E.

Aspect 327. The IL-2Rα ligand of any one of aspects 302 to 326, wherein $X^7$ is selected from G, E, K, T, P, W, L, Y, G, S, and R.

Aspect 328. The IL-2Rα ligand of any one of aspects 302 to 327, wherein $X^8$ is selected from I, A, Q, R, S R, L, N, P, A, I, R, D, and W.

Aspect 329. The IL-2Rα ligand of any one of aspects 302 to 328, wherein $X^9$ is selected from W, G, S, D, R, L, F, P, A, and T.

Aspect 330. The IL-2Rα ligand of any one of aspects 302 to 329, wherein $X^{10}$ is selected from G, T, E, W, Q, R, and Y.

Aspect 331. The IL-2Rα ligand of any one of aspects 302 to 329, wherein $X^{10}$ is G.

Aspect 332. The IL-2Rα ligand of any one of aspects 302 to 331, wherein $X^{11}$ is selected from H, P, I, T, H, A, S, F, and Y.

Aspect 333. The IL-2Rα ligand of any one of aspects 302 to 332, wherein $X^{12}$ is C.

Aspect 334. The IL-2Rα ligand of any one of aspects 302 to 333, wherein $X^{13}$ is selected from F, I, L, M, V, W, and Y.

Aspect 335. The IL-2Rα ligand of any one of aspects 302 to 334, wherein $X^{14}$ is F.

Aspect 336. The IL-2Rα ligand of aspect 302, wherein $X^2$ is R, $X^3$ is C, $X^6$, is D, $X^{10}$ is G, $X^{12}$ is C, and $X^{14}$ is F.

Aspect 337. The IL-2Rα ligand of aspect 302, wherein,
$X^1$ is selected from A, D, E, F, G, H, I, K, L, M, N, P, Q, R, S, T, V, W, and Y;
$X^2$ is R;
$X^3$ is C;
$X^4$ is selected from F, H, I, K, L, M, R, V, W, and Y;
$X^5$ is selected from A, D, E, F, G, H, I, K, L, M, N, P, Q, R, S, T, V, W, and Y;
$X^6$ is D;
$X^7$ is selected from A, D, E, F, G, H, I, K, L, M, N, P, Q, R, S, T, V, W, and Y;
$X^8$ is selected from A, D, E, F, G, H, I, K, L, M, N, P, Q, R, S, T, V, W, and Y;
$X^9$ is selected from A, D, E, F, G, H, I, K, L, M, N, P, Q, R, S, T, V, W, and Y;
$X^{10}$ is G;
$X^{11}$ is selected from A, D, E, F, G, H, I, K, L, M, N, P, Q, R, S, T, V, W, and Y;
$X^{12}$ is C;
$X^{13}$ is selected from F, I, L, M, V, W, and Y; and
$X^{14}$ is F.

Aspect 338. The IL-2Rα ligand of aspect 302, wherein the IL-2Rα ligand comprises an amino acid sequence selected from any one of SEQ ID NO: 72 to SEQ ID NO: 86:

SEQ ID NO: 72
R S C N R Y G I W G H C D T

-continued

```
                                    SEQ ID NO: 73
I K C R V L E A G T P C V F

SEQ ID NO: 74
I R C R Y E K Q S G I C L F

SEQ ID NO: 75
L R C R L D T R D G T C R F

SEQ ID NO: 76
M R C I L S P S R E H C L F

SEQ ID NO: 77
N H C T M D W R L G A C I F

SEQ ID NO: 78
S G C R L S L L D G H C Y F

SEQ ID NO: 79
S K C V Y D Y N F G T C I F

SEQ ID NO: 80
S R C V M S L Q L G A C I F

SEQ ID NO: 81
T R C T V I G P P W S C R F

SEQ ID NO: 82
V F C I G Y G A A Q S C H S

SEQ ID NO: 83
V R C L Y D S I T R T C T F

SEQ ID NO: 84
V S C K I D R R S G S C L F

SEQ ID NO: 85
V S C R F R P D L G F C I F

SEQ ID NO: 86
D R C D T R T W G Y Y C W I
```

Aspect 339. The IL-2Rα ligand of any one of aspects 302 to 338, wherein, the amino acid sequence independently comprises from 1 to 4 glycines (G) (SEQ ID NO: 1041) on the N-terminus, on the C-terminus, or on both the N- and C-termini;

the amino acid sequence comprises a truncated amino acid sequence; or the amino acid sequence comprises a truncated amino acid sequence, wherein the truncated amino acid sequence independently comprises from 1 to 4 glycines (G) (SEQ ID NO: 1041) on the N-terminus, on the C-terminus, or on both the N- and C-termini.

Aspect 340. The IL-2Rα ligand of any one of aspects 338 to 339, wherein from 1 to 5 of the amino acids is independently substituted with another amino acid.

Aspect 341. The IL-2Rα ligand of any one of aspects 1 to 6, wherein the IL-2Rα ligand comprises the amino acid sequence of Formula (9a) (SEQ ID NO: 87), the amino acid sequence of Formula (9b) (SEQ ID NO: 88), the amino acid sequence of Formula (9c) (SEQ ID NO: 89), or the amino acid sequence of Formula (9d) (SEQ ID NO: 90):

$$-X^5-X^6-X^7-X^8-X^9-X^{10}-X^{11}-X^{12}- \quad (9a)$$

$$-X^3-C-X^5-X^6-X^7-X^8-X^9-X^{10}-X^{11}-X^{12}-C-X^{14}- \quad (9b)$$

$$-X^2-X^3-C-X^5-X^6-X^7-X^8-X^9-X^{10}-X^{11}-X^{12}-C-X^{14}-X^{15}- \quad (9c)$$

$$-X^1-X^2-X^3-X^4-X^5-X^6-X^7-X^8-X^9-X^{10}-X^{11}-X^{12}-X^{13}-X^{14}-X^{15}-X^{16}- \quad (9d)$$

wherein, $X^1$ is selected from an amino acid;

$X^2$ is selected from an amino acid comprising a large hydrophobic side chain;

$X^3$ is selected from an amino acid comprising a large hydrophobic side chain or an acidic side chain;

$X^4$ is C;

$X^5$ is selected from an amino acid comprising a large hydrophobic side chain or a basic side chain;

$X^6$ is selected from an amino acid comprising a large hydrophobic side chain;

$X^7$ is selected from an amino acid;

$X^8$ is selected from an amino acid comprising a small hydrophobic side chain;

$X^9$ is selected from an amino acid comprising a small hydrophobic side chain;

$X^{10}$ is selected from an amino acid comprising a large hydrophobic side chain or a basic side chain;

$X^{11}$ is selected from an amino acid comprising a basic side chain or an acidic side chain;

$X^{12}$ is selected from an amino acid comprising a small hydrophobic side chain or a polar neutral side chain;

$X^{13}$ is C;

$X^{14}$ is selected from an amino acid;

$X^{15}$ is selected from an amino acid; and $X^{16}$ is selected from an amino acid.

Aspect 342. The IL-2Rα ligand of aspect 341, wherein, $X^1$ is selected from A, D, E, F, G, H, I, K, L, M, N, P, Q, R, S, T, V, W, and Y;

$X^2$ is selected from F, I, L, M, V, W, and Y;

$X^3$ is selected from D, E, F, I, L, M, V, W, and Y;

$X^4$ is C;

$X^5$ is selected from F, H, I, K, L, M, R, V, W, and Y;

$X^6$ is selected from F, I, L, M, V, W, and Y;

$X^7$ is selected from A, D, E, F, G, H, I, K, L, M, N, P, Q, R, S, T, V, W, and Y;

$X^8$ is selected from A, G, P, S, and T;

$X^9$ is selected from A, G, P, S, and T;

$X^{10}$ is selected from F, H, I, K, L, M, R, V, W, and Y;

$X^{11}$ is selected from D, E, H, K, and R;

$X^{12}$ is selected from A, G, H, N, P, Q, S, T, and Y;

$X^{13}$ is C;

$X^{14}$ is selected from A, D, E, F, G, H, I, K, L, M, N, P, Q, R, S, T, V, W, and Y;

$X^{15}$ is selected from A, D, E, F, G, H, I, K, L, M, N, P, Q, R, S, T, V, W, and Y; and $X^{16}$ is selected from A, D, E, F, G, H, I, K, L, M, N, P, Q, R, S, T, V, W, and Y.

Aspect 343. The IL-2Rα ligand of any one of aspects 341 to 342, wherein $X^1$ is selected from G, E, F, K, P, Q, R, S, and V.

Aspect 344. The IL-2Rα ligand of any one of aspects 341 to 343, wherein $X^2$ is selected from S, W, I, F, L, and R.

Aspect 345. The IL-2Rα ligand of any one of aspects 341 to 344, wherein $X^3$ is selected from R, E, I, V, S, N, F, L, and M.

Aspect 346. The IL-2Rα ligand of any one of aspects 341 to 345, wherein $X^4$ is C.

Aspect 347. The IL-2Rα ligand of any one of aspects 341 to 346, wherein $X^5$ is selected from Y, R, V, T, E, I, and K.

Aspect 348. The IL-2Rα ligand of any one of aspects 341 to 347, wherein $X^6$ is selected from W, F, Y, L, H, I, T, S, and V.

Aspect 349. The IL-2Rα ligand of any one of aspects 341 to 348, wherein $X^7$ is selected from D, L, S, D, V, Y, S, Q, I, R, M, G, and A.

Aspect 350. The IL-2Rα ligand of any one of aspects 341 to 349, wherein $X^8$ is P.

Aspect 351. The IL-2Rα ligand of any one of aspects 341 to 350, wherein $X^9$ is G.

Aspect 352. The IL-2Rα ligand of any one of aspects 341 to 351, wherein $X^{10}$ is selected from R, S, T, N, R, V, L, H, W, and Y.

Aspect 353. The IL-2Rα ligand of any one of aspects 341 to 352, wherein $X^{11}$ is selected from E, R, H, G, E, K, Q, and V.

Aspect 354. The IL-2Rα ligand of any one of aspects 341 to 353, wherein $X^{12}$ is selected from V, G, S, A, and W.

Aspect 355. The IL-2Rα ligand of any one of aspects 341 to 354, wherein $X^{13}$ is C.

Aspect 356. The IL-2Rα ligand of any one of aspects 341 to 355, wherein $X^{14}$ is selected from I, S, R, W, H, V, K, T, R, G, and P.

Aspect 357. The IL-2Rα ligand of any one of aspects 341 to 356, wherein $X^{15}$ is selected from F, L, M, S, W, T, A, and R.

Aspect 358. The IL-2Rα ligand of any one of aspects 341 to 357, wherein $X^{16}$ is selected from K, F, V, I, F, M, L, Q, T, and N.

Aspect 359. The IL-2Rα ligand of any one of aspects 341 to 358, wherein $X^1$ is selected from A, D, E, F, G, H, I, K, L, M, N, P, Q, R, S, T, V, W, and Y.

Aspect 360. The IL-2Rα ligand of any one of aspects 341 to 359, wherein $X^2$ is selected from F, W, and Y.

Aspect 361. The IL-2Rα ligand of any one of aspects 341 to 360, wherein $X^3$ is W.

Aspect 362. The IL-2Rα ligand of any one of aspects 341 to 361, wherein $X^4$ is C.

Aspect 363. The IL-2Rα ligand of any one of aspects 341 to 362, wherein $X^5$ is selected from F, I, L, M, V, W, and Y.

Aspect 364. The IL-2Rα ligand of any one of aspects 341 to 362, wherein $X^5$ is selected from D and E.

Aspect 365. The IL-2Rα ligand of any one of aspects 341 to 364, wherein $X^6$ is selected from F, I, L, M, V, W, and Y.

Aspect 366. The IL-2Rα ligand of any one of aspects 341 to 364, wherein $X^6$ is selected from F, W, and Y.

Aspect 367. The IL-2Rα ligand of any one of aspects 341 to 366, wherein $X^7$ is selected from A, D, E, F, G, H, I, K, L, M, N, P, Q, R, S, T, V, W, and Y.

Aspect 368. The IL-2Rα ligand of any one of aspects 341 to 367, wherein $X^8$ is P.

Aspect 369. The IL-2Rα ligand of any one of aspects 341 to 368, wherein $X^9$ is G.

Aspect 370. The IL-2Rα ligand of any one of aspects 341 to 369, wherein $X^{10}$ is selected from F, I, L, M, V, W, and Y.

Aspect 371. The IL-2Rα ligand of any one of aspects 341 to 369, wherein $X^{10}$ is selected from F, W, and Y.

Aspect 372. The IL-2Rα ligand of any one of aspects 341 to 371, wherein $X^{10}$ is selected from H, K, and R.

Aspect 373. The IL-2Rα ligand of any one of aspects 341 to 372, wherein $X^{11}$ is selected from H, K, and R.

Aspect 374. The IL-2Rα ligand of any one of aspects 341 to 372, wherein $X^{11}$ is selected from D and E.

Aspect 375. The IL-2Rα ligand of any one of aspects 341 to 374, wherein $X^{12}$ is selected from A, G, P, S, and T.

Aspect 376. The IL-2Rα ligand of any one of aspects 341 to 374, wherein $X^{12}$ is selected from N, Q, S, T, and Y.

Aspect 377. The IL-2Rα ligand of any one of aspects 341 to 376, wherein $X^{13}$ is C.

Aspect 378. The IL-2Rα ligand of any one of aspects 341 to 377, wherein $X^{14}$ is selected from A, D, E, F, G, H, I, K, L, M, N, P, Q, R, S, T, V, W, and Y.

Aspect 379. The IL-2Rα ligand of any one of aspects 341 to 378, wherein $X^{15}$ is selected from A, D, E, F, G, H, I, K, L, M, N, P, Q, R, S, T, V, W, and Y.

Aspect 380. The IL-2Rα ligand of any one of aspects 341 to 379, wherein $X^{16}$ is selected from A, D, E, F, G, H, I, K, L, M, N, P, Q, R, S, T, V, W, and Y.

Aspect 381. The IL-2Rα ligand of any one of aspects 341 to 379, wherein $X^{16}$ is selected from F, I, L, M, V, W, and Y.

Aspect 382. The IL-2Rα ligand of any one of aspects 341 to 379, wherein $X^{16}$ is selected from F, W, and Y.

Aspect 383. The IL-2Rα ligand of aspect 341, wherein $X^2$ is W, $X^3$ is E, $X^4$ is C, $X^5$ is R, $X^8$ is P, $X^9$ is G, $X^{10}$ is R, $X^1$ is R, $X^{12}$ is G, and $X^{11}$ is C.

Aspect 384. The IL-2Rα ligand of aspect 341, wherein,
$X^1$ is selected from A, D, E, F, G, H, I, K, L, M, N, P, Q, R, S, T, V, W, and Y;
$X^2$ is W;
$X^3$ is E;
$X^4$ is C;
$X^5$ is R;
$X^6$ is selected from F, H, I, L, M, V, W, and Y;
$X^7$ is selected from A, D, E, F, G, H, I, K, L, M, N, P, Q, R, S, T, V, W, and Y;
$X^8$ is P;
$X^9$ is G
$X^{10}$ is R;
$X^{11}$ is R;
$X^{12}$ is G;
$X^{13}$ is C;
$X^{14}$ is selected from A, D, E, F, G, H, I, K, L, M, N, P, Q, R, S, T, V, W, and Y;
$X^{15}$ is selected from A, D, E, F, G, H, I, K, L, M, N, P, Q, R, S, T, V, W, and Y; and
$X^{16}$ is selected from A, D, E, F, G, H, I, K, L, M, N, P, Q, R, S, T, V, W, and Y.

Aspect 385. The IL-2Rα ligand of aspect 341, wherein the IL-2Rα ligand comprises an amino acid sequence selected from any one of SEQ ID NO: 91 to SEQ ID NO: 104:

```
                                    SEQ ID NO: 91
    G S R C Y W D P G R E V C I F K

SEQ ID NO: 92
    E W E C R F L P G R R G C S L F

SEQ ID NO: 93
    F W E C V Y S P G S R G C R M V

SEQ ID NO: 94
    G F R C T Y D P G T H S C W S I

SEQ ID NO: 95
    K W I C R L V P G N G A C H S F

SEQ ID NO: 96
    P W V C E H Y P G R R G C V L M

SEQ ID NO: 97
    Q W S C V F S P G V R G C K L V

SEQ ID NO: 98
    R F I C R I Q P G R E G C W S L

SEQ ID NO: 99
    R W E C I Y I P G R K G C T L Q

SEQ ID NO: 100
    S L N C K T R P G L R W C T W T

SEQ ID NO: 101
    S W E C V Y M P G H Q G C R L F
```

```
                                        SEQ ID NO: 102
            V R F C R S G P G W V S C G T Q

SEQ ID NO: 103
            V R L C R V G P G Y E S C P A N

SEQ ID NO: 104
            V R M C Y V A P G Y V S C P R M
```

Aspect 386. The IL-2Rα ligand of any one of aspects 341 to 385, wherein, the amino acid sequence independently comprises from 1 to 4 glycines (G) (SEQ ID NO: 1041) on the N-terminus, on the C-terminus, or on both the N- and C-termini;

the amino acid sequence comprises a truncated amino acid sequence; or the amino acid sequence comprises a truncated amino acid sequence, wherein the truncated amino acid sequence independently comprises from 1 to 4 glycines (G) (SEQ ID NO: 1041) on the N-terminus, on the C-terminus, or on both the N- and C-termini.

Aspect 387. The IL-2Rα ligand of any one of aspects 385 to 386, wherein from 1 to 5 of the amino acids is independently substituted with another amino acid.

Aspect 388. The IL-2Rα ligand of any one of aspects 1 to 6, wherein the IL-2Rα ligand comprises the amino acid sequence of Formula (10a) (SEQ ID NO: 105), the amino acid sequence of Formula (10b) (SEQ ID NO: 106), the amino acid sequence of Formula (10c) (SEQ ID NO: 107), or the amino acid sequence of Formula (10d) (SEQ ID NO: 108):

$$-X^5-X^6-X^7-X^8-X^9-X^{10}-X^{11}-X^{12}- \quad (10a)$$

$$-X^3-C-X^5-X^6-X^7-X^8-X^9-X^{10}-X^{11}-X^{12}-C-X^{14}- \quad (10b)$$

$$-X^2-X^3-C-X^5-X^6-X^7-X^8-X^9-X^{10}-X^{11}-X^{12}-C-X^{14}-X^{15}- \quad (10c)$$

$$-X^1-X^2-X^3-X^4-X^5-X^6-X^7-X^8-X^9-X^{10}-X^{11}-X^{12}-X^{13}-X^{14}-X^{15}-X^{16}- \quad (10d)$$

wherein, $X^1$ is selected from an amino acid comprising an acidic side chain;

$X^2$ is selected from an amino acid comprising a large hydrophobic side chain;

$X^3$ is selected from an amino acid comprising an acidic side chain;

$X^4$ is C;

$X^5$ is selected from an amino acid comprising a large hydrophobic side chain;

$X^6$ is selected from an amino acid comprising a large hydrophobic side chain;

$X^7$ is selected from an amino acid comprising a large hydrophobic side chain;

$X^8$ is selected from an amino acid comprising a small hydrophobic side chain;

$X^9$ is selected from an amino acid comprising a small hydrophobic side chain;

$X^{10}$ is selected from an amino acid comprising a basic side chain;

$X^{11}$ is selected from an amino acid comprising a basic side chain;

$X^{12}$ is selected from an amino acid comprising a small hydrophobic side chain;

$X^{13}$ is C;

$X^{14}$ is selected from an amino acid comprising a small hydrophobic side chain or a polar neutral side chain;

$X^{15}$ is selected from an amino acid comprising a large hydrophobic side chain; and $X^{16}$ is selected from an amino acid comprising a large hydrophobic side chain.

Aspect 389. The IL-2Rα ligand of aspect 388, wherein, $X^1$ is selected from A, D, E, F, G, H, I, K, L, M, N, P, Q, R, S, T, V, W, and Y;

$X^2$ is selected from F, I, L, M, V, W, and Y;

$X^3$ is selected from D and E;

$X^4$ is C;

$X^5$ is selected from F, I, L, M, V, W, and Y;

$X^6$ is selected from F, I, L, M, V, W, and Y;

$X^7$ is selected from F, I, L, M, V, W, and Y;

$X^8$ is selected from A, G, P, S, and T;

$X^9$ is selected from A, G, P, S, and T;

$X^{10}$ is selected from H, K, and R;

$X^{11}$ is selected from H, K, and R;

$X^{12}$ is selected from A, G, P, S, and T;

$X^{13}$ is C;

$X^{14}$ is selected from A, G, H, N, P, Q, S, T, and Y;

$X^{15}$ is selected from F, I, L, M, V, W, and Y; and $X^{16}$ is selected from F, I, L, M, V, W, and Y.

Aspect 390. The IL-2Rα ligand of any one of aspects 388 to 389, wherein $X^1$ is selected from N, D, E, A, V, and T.

Aspect 391. The IL-2Rα ligand of any one of aspects 388 to 390, wherein $X^2$ is selected from W and Y.

Aspect 392. The IL-2Rα ligand of any one of aspects 388 to 391, wherein $X^3$ is selected from E, H, and D.

Aspect 393. The IL-2Rα ligand of any one of aspects 388 to 392, wherein $X^4$ is C.

Aspect 394. The IL-2Rα ligand of any one of aspects 388 to 393, wherein $X^5$ is selected from I, 1, W, and V.

Aspect 395. The IL-2Rα ligand of any one of aspects 388 to 394, wherein $X^6$ is selected from F and I.

Aspect 396. The IL-2Rα ligand of any one of aspects 388 to 395, wherein $X^7$ is selected from S, L, and M.

Aspect 397. The IL-2Rα ligand of any one of aspects 388 to 396, wherein $X^8$ is P.

Aspect 398. The IL-2Rα ligand of any one of aspects 388 to 397, wherein $X^9$ is G.

Aspect 399. The IL-2Rα ligand of any one of aspects 388 to 398, wherein $X^{10}$ is selected from R and H.

Aspect 400. The IL-2Rα ligand of any one of aspects 388 to 399, wherein $X^{11}$ is selected from R and K.

Aspect 401. The IL-2Rα ligand of any one of aspects 388 to 400, wherein $X^{12}$ is G.

Aspect 402. The IL-2Rα ligand of any one of aspects 388 to 401, wherein $X^{13}$ is C.

Aspect 403. The IL-2Rα ligand of any one of aspects 388 to 402, wherein $X^{14}$ is selected from S, L, T, and F.

Aspect 404. The IL-2Rα ligand of any one of aspects 388 to 403, wherein $X^{15}$ is selected from L and G.

Aspect 405. The IL-2Rα ligand of any one of aspects 388 to 404, wherein $X^{16}$ is selected from F, M, T, and I.

Aspect 406. The IL-2Rα ligand of any one of aspects 388 to 405, wherein $X^1$ is selected from D and E.

Aspect 407. The IL-2Rα ligand of any one of aspects 388 to 406, wherein $X^2$ is W.

Aspect 408. The IL-2Rα ligand of any one of aspects 388 to 407, wherein $X^3$ is selected from D and E.

Aspect 409. The IL-2Rα ligand of any one of aspects 388 to 408, wherein $X^4$ is C.

Aspect 410. The IL-2Rα ligand of any one of aspects 388 to 409, wherein $X^5$ is selected from F, I, L, M, V, W, and Y.

Aspect 411. The IL-2Rα ligand of any one of aspects 388 to 409, wherein $X^5$ is selected from I and L.

Aspect 412. The IL-2Rα ligand of any one of aspects 388 to 411, wherein $X^6$ is F.

Aspect 413. The IL-2Rα ligand of any one of aspects 388 to 412, wherein $X^7$ is selected from L and M.

Aspect 414. The IL-2Rα ligand of any one of aspects 388 to 413, wherein $X^8$ is P.

Aspect 415. The IL-2Rα ligand of any one of aspects 388 to 414, wherein $X^9$ is G.

Aspect 416. The IL-2Rα ligand of any one of aspects 388 to 415, wherein $X^{10}$ is selected from H and R.

Aspect 417. The IL-2Rα ligand of any one of aspects 388 to 416, wherein $X^{11}$ is selected from K and R.

Aspect 418. The IL-2Rα ligand of any one of aspects 388 to 417, wherein $X^{12}$ is G.

Aspect 419. The IL-2Rα ligand of any one of aspects 388 to 418, wherein $X^{13}$ is C.

Aspect 420. The IL-2Rα ligand of any one of aspects 388 to 419, wherein $X^{14}$ is selected from S and T.

Aspect 421. The IL-2Rα ligand of any one of aspects 388 to 420, wherein $X^{15}$ is L.

Aspect 422. The IL-2Rα ligand of any one of aspects 388 to 421, wherein $X^{16}$ is selected from F and M.

Aspect 423. The IL-2Rα ligand of aspect 388, wherein,
$X^1$ is D;
$X^2$ is W;
$X^3$ is E;
$X^4$ is C;
$X^5$ is L;
$X^6$ is F;
$X^7$ is L;
$X^8$ is P;
$X^9$ is G;
$X^{10}$ is selected from H and R;
$X^{11}$ is selected from K and R;
$X^{12}$ is G;
$X^{13}$ is C;
$X^{14}$ is T;
$X^{15}$ is L; and
$X^{16}$ is F.

Aspect 424. The IL-2Rα ligand of aspect 388, wherein the IL-2Rα ligand comprises an amino acid sequence selected from any one of SEQ ID NO: 109 to SEQ ID NO: 121:

```
                                         SEQ ID NO: 109
    N W E C I F S P G R R G C S L T

SEQ ID NO: 110
    D W E C L F L P G R R G C L L F

SEQ ID NO: 111
    E W E C L F M P G R R G C L L M

SEQ ID NO: 112
    A W E C L F L P G H R G C S L F

SEQ ID NO: 113
    E W E C L F L P G R K G C T L F

SEQ ID NO: 114
    D W E C I F L P G R R G C T L F

SEQ ID NO: 115
    V Y E C L F M P G R K G C F G M

SEQ ID NO: 116
    E W E C W F L P G R R G C T L I

SEQ ID NO: 117
    D W H C L F L P G H R G C T L F

SEQ ID NO: 118
    D W E C L F L P G R R G C T L F

SEQ ID NO: 119
    Y W E C V F M P G H R G C S L I

SEQ ID NO: 120
    T W D C L F L P G R R G C T L M

SEQ ID NO: 121
    N W E C I F S P G R R G C S L T
```

Aspect 425. The IL-2Rα ligand of any one of aspects 388 to 424, wherein,
the amino acid sequence independently comprises from 1 to 4 glycines (G) (SEQ ID NO: 1041) on the N-terminus, on the C-terminus, or on both the N- and C-termini;
the amino acid sequence comprises a truncated amino acid sequence; or
the amino acid sequence comprises a truncated amino acid sequence, wherein the truncated amino acid sequence independently comprises from 1 to 4 glycines (G) (SEQ ID NO: 1041) on the N-terminus, on the C-terminus, or on both the N- and C-termini.

Aspect 426. The IL-2Rα ligand of any one of aspects 424 to 425, wherein from 1 to 5 of the amino acids is independently substituted with another amino acid.

Aspect 427. The IL-2Rα ligand of any one of aspects 1 to 6, wherein the IL-2Rα ligand comprises the amino acid sequence of Formula (11a) (SEQ ID NO: 122), the amino acid sequence of Formula (11b) (SEQ ID NO: 123), the amino acid sequence of Formula (11c) (SEQ ID NO: 124), or the amino acid sequence of Formula (11d) (SEQ ID NO: 125):

$$—X^5—X^6—X^7—X^8—X^9—X^{10}—X^{11}—X^{12}— \quad (11a)$$

$$—X^3—C—X^5—X^6—X^7—X^8—X^9—X^{10}—X^{11}—X^{12}—C—X^{14}— \quad (11b)$$

$$—X^2—X^3—C—X^5—X^6—X^7—X^8—X^9—X^{10}—X^{11}—X^{12}—C—X^{14}—X^{15}— \quad (11c)$$

$$—X^1—X^2—X^3—X^4—X^5—X^6—X^7—X^8—X^9—X^{10}—X^{11}—X^{12}—X^{13}—X^{14}—X^{15}—X^{16}— \quad (11d)$$

wherein,
$X^1$ is selected from an amino acid;
$X^2$ is selected from an amino acid;
$X^3$ is selected from an amino acid;
$X^4$ is C;
$X^5$ is selected from an amino acid comprising an acidic side chain;
$X^6$ is selected from an amino acid
$X^7$ is selected from an amino acid comprising an acidic side chain or an aromatic side chain;
$X^8$ is selected from an amino acid comprising a small hydrophobic side chain;
$X^9$ is selected from an amino acid comprising a small hydrophobic side chain;
$X^{10}$ is selected from an amino acid comprising an aromatic chain;
$X^{11}$ is selected from an amino acid;
$X^{12}$ is selected from an amino acid;
$X^{13}$ is C;
$X^{14}$ is selected from an amino acid;
$X^{15}$ is selected from an amino acid comprising a large hydrophobic side chain; and $X^{16}$ is selected from an amino acid comprising a large hydrophobic side chain.

Aspect 428. The IL-2Rα ligand of aspect 427, wherein, $X^1$ is selected from A, D, E, F, G, H, I, K, L, M, N, P, Q, R, S, T, V, W, and Y;

$X^2$ is selected from A, D, E, F, G, H, I, K, L, M, N, P, Q, R, S, T, V, W, and Y;

$X^3$ is selected from A, D, E, F, G, H, I, K, L, M, N, P, Q, R, S, T, V, W, and Y;

$X^4$ is C;

$X^5$ is selected from D and E;

$X^6$ is selected from A, D, E, F, G, H, I, K, L, M, N, P, Q, R, S, T, V, W, and Y;

$X^7$ is selected from D, E, F, H, W, and Y;

$X^8$ is selected from A, G, P, S, and T;

$X^9$ is selected from A, G, P, S, and T;

$X^{10}$ is selected from F, H, W, and Y;

$X^{11}$ is selected from A, D, E, F, G, H, I, K, L, M, N, P, Q, R, S, T, V, W, and Y $X^{12}$ is selected from A, D, E, F, G, H, I, K, L, M, N, P, Q, R, S, T, V, W, and Y;

$X^{13}$ is C;

$X^{14}$ is selected from A, D, E, F, G, H, I, K, L, M, N, P, Q, R, S, T, V, W, and Y;

$X^{15}$ is selected from F, I, L, M, V, W, and Y; and $X^{16}$ is selected from F, I, L, M, V, W, and Y.

Aspect 429. The IL-2Rα ligand of any one of aspects 427 to 428, wherein $X^1$ is selected from A, E, F, G, K, R, T, Y, and W.

Aspect 430. The IL-2Rα ligand of any one of aspects 427 to 429, wherein $X^2$ is selected from G, T, K, Q, S, L, Q, R, and A.

Aspect 431. The IL-2Rα ligand of any one of aspects 427 to 430, wherein $X^3$ is selected from F, Y, W, and H.

Aspect 432. The IL-2Rα ligand of any one of aspects 427 to 430, wherein $X^3$ is selected from G, W, P, L, R, F, M, V, S, and P.

Aspect 433. The IL-2Rα ligand of any one of aspects 427 to 432, wherein $X^4$ is C.

Aspect 434. The IL-2Rα ligand of any one of aspects 427 to 433, wherein $X^5$ is selected from K, D, Y, T, Y, Q, F, L, and S.

Aspect 435. The IL-2Rα ligand of any one of aspects 427 to 434, wherein $X^6$ is selected from L, D, F, Y, W, N, D, M, V, D, L, and Y.

Aspect 436. The IL-2Rα ligand of any one of aspects 427 to 435, wherein $X^7$ is selected from N, H, F, D, N, S, L, and Y.

Aspect 437. The IL-2Rα ligand of any one of aspects 427 to 436, wherein $X^8$ is P.

Aspect 438. The IL-2Rα ligand of any one of aspects 427 to 437, wherein $X^9$ is G.

Aspect 439. The IL-2Rα ligand of any one of aspects 427 to 438, wherein $X^{10}$ is selected from T, H, L, S, Q, R, N, Y, W, V, S, and H.

Aspect 440. The IL-2Rα ligand of any one of aspects 427 to 439, wherein $X^{11}$ is selected from Q, W, P, D, E, S, P, E, H, G, R, and G.

Aspect 441. The IL-2Rα ligand of any one of aspects 427 to 440, wherein $X^{12}$ is selected from V, S, R, I, A, D, S, E, Y, and G.

Aspect 442. The IL-2Rα ligand of any one of aspects 427 to 441, wherein $X^{13}$ is C.

Aspect 443. The IL-2Rα ligand of any one of aspects 427 to 442, wherein $X^{14}$ is selected from S, E, T, V, I, D, Q, W, P, I, and Y.

Aspect 444. The IL-2Rα ligand of any one of aspects 427 to 443, wherein $X^{15}$ is selected from F, M, W, I, V, T, N, L, and S.

Aspect 445. The IL-2Rα ligand of any one of aspects 427 to 444, wherein $X^{16}$ is selected from Y, V, I, L, S, K, E, and R.

Aspect 446. The IL-2Rα ligand of any one of aspects 427 to 445, wherein $X^4$ is C.

Aspect 447. The IL-2Rα ligand of any one of aspects 427 to 446, wherein $X^5$ is D.

Aspect 448. The IL-2Rα ligand of any one of aspects 427 to 447, wherein $X^7$ is selected from D and H.

Aspect 449. The IL-2Rα ligand of any one of aspects 427 to 448, wherein $X^8$ is P.

Aspect 450. The IL-2Rα ligand of any one of aspects 427 to 449, wherein $X^9$ is G.

Aspect 451. The IL-2Rα ligand of any one of aspects 427 to 450, wherein $X^{10}$ is selected from F, H, W, and Y.

Aspect 452. The IL-2Rα ligand of any one of aspects 427 to 451, wherein $X^{13}$ is C.

Aspect 453. The IL-2Rα ligand of any one of aspects 427 to 452, wherein $X^{15}$ is selected from F, M, I, W, V, and L.

Aspect 454. The IL-2Rα ligand of any one of aspects 427 to 453, wherein $X^{16}$ is selected from Y, V, I, and L.

Aspect 455. The IL-2Rα ligand of aspect 427, wherein, $X^1$ is selected from A, D, E, F, G, H, I, K, L, M, N, P, Q, R, S, T, V, W, and Y;

$X^2$ is selected from A, D, E, F, G, H, I, K, L, M, N, P, Q, R, S, T, V, W, and Y;

$X^3$ is selected from A, D, E, F, G, H, I, K, L, M, N, P, Q, R, S, T, V, W, and Y;

$X^4$ is C;

$X^5$ is selected from D and E;

$X^6$ is selected from A, D, E, F, G, H, I, K, L, M, N, P, Q, R, S, T, V, W, and Y;

$X^7$ is selected from D, E, H, F, W, and Y;

$X^8$ is P;

$X^9$ is G;

$X^{10}$ is selected from H, F, W, and Y;

$X^{11}$ is selected from A, D, E, F, G, H, I, K, L, M, N, P, Q, R, S, T, V, W, and Y;

$X^{12}$ is selected from A, D, E, F, G, H, I, K, L, M, N, P, Q, R, S, T, V, W, and Y;

$X^{13}$ is C;

$X^{14}$ is selected from A, D, E, F, G, H, I, K, L, M, N, P, Q, R, S, T, V, W, and Y;

$X^{15}$ is selected from F, I, L, M, V, W, and Y; and $X^{16}$ is selected from F, I, L, M, V, W, and Y.

Aspect 456. The IL-2Rα ligand of aspect 427, wherein the IL-2Rα ligand comprises an amino acid sequence selected from any one of SEQ ID NO: 126 to SEQ ID NO: 140:

```
                                      SEQ ID NO: 126
    A G W C K L N P G T Q V C S F Y

SEQ ID NO: 127
    E T P C D L H P G H W S C S M V

SEQ ID NO: 128
    F F L C D D F P G L P R C E W I

SEQ ID NO: 129
    G L R C Y F D P G S Q I C T F L

SEQ ID NO: 130
    G Q R C T Y D P G Q D A C V F S
```

GSRCYWDPGREVCIFK (SEQ ID NO: 131)

KLWCQNNPGNSICDMY (SEQ ID NO: 132)

KSWCFDHPGYPICQFY (SEQ ID NO: 133)

RLFCLMNPGPPDCWIY (SEQ ID NO: 134)

RQFCLVSPGYEDCWFV (SEQ ID NO: 135)

TRMCFDDPGWHSCPVV (SEQ ID NO: 136)

TRWCSLHPGVGECVTL (SEQ ID NO: 137)

TTVCDYHPGSRYCINE (SEQ ID NO: 138)

YASCTYLPGHRGCTLV (SEQ ID NO: 139)

WLPCDDYPGHGYCYSR (SEQ ID NO: 140)

Aspect 457. The IL-2Rα ligand of any one of aspects 427 to 456, wherein,
the amino acid sequence independently comprises from 1 to 4 glycines (G) (SEQ ID NO: 1041) on the N-terminus, on the C-terminus, or on both the N- and C-termini;
the amino acid sequence comprises a truncated amino acid sequence; or
the amino acid sequence comprises a truncated amino acid sequence, wherein the truncated amino acid sequence independently comprises from 1 to 4 glycines (G) (SEQ ID NO: 1041) on the N-terminus, on the C-terminus, or on both the N- and C-termini.

Aspect 458. The IL-2Rα ligand of any one of aspects 456 to 457, wherein from 1 to 5 of the amino acids is independently substituted with another amino acid.

Aspect 459. The IL-2Rα ligand of any one of aspects 1 to 6, wherein the IL-2Rα ligand comprises the amino acid sequence of Formula (12a) (SEQ ID NO: 141), the amino acid sequence of Formula (12b) (SEQ ID NO: 142), or the amino acid sequence of Formula (12c) (SEQ ID NO: 143):

$$-X^4-X^5-X^6-X^7-X^8-X^9-X^{10}-X^{11}-X^{12}- \quad (12a)$$

$$-X^2-C-X^4-X^5-X^6-X^7-X^8-X^9-X^{10}-X^{11}-X^{12}-C-X^{14}- \quad (12b)$$

$$-X^1-X^2-X^3-X^4-X^5-X^6-X^7-X^8-X^9-X^{10}-X^{11}-X^{12}-X^{13}-X^{14}-X^{15}-X^{16}- \quad (12c)$$

wherein,
$X^1$ is selected from an amino acid;
$X^2$ is selected from an amino acid;
$X^3$ is C;
$X^4$ is selected from an amino acid;
$X^5$ is selected from an amino acid comprising a large hydrophobic side chain;
$X^6$ is selected from an amino acid;
$X^7$ is selected from an amino acid;
$X^8$ is selected from an amino acid;
$X^9$ is selected from an amino acid comprising an acidic side chain, a small hydrophobic side chain, or a polar neutral side chain;
$X^{10}$ is selected from an amino acid;
$X^{11}$ is selected from an amino acid comprising a large hydrophobic side chain;
$X^{12}$ is selected from an amino acid comprising a large hydrophobic side chain;
$X^{13}$ is C;
$X^{14}$ is selected from an amino acid comprising a large hydrophobic side chain; and
$X^{15}$ is selected from an amino acid comprising a large hydrophobic side chain;
$X^{16}$ is selected from an amino acid.

Aspect 471. The IL-2Rα ligand of aspect 459, wherein,
$X^1$ is selected from A, D, E, F, G, H, I, K, L, M, N, P, Q, R, S, T, V, W, and Y;
$X^2$ is selected from A, D, E, F, G, H, I, K, L, M, N, P, Q, R, S, T, V, W, and Y;
$X^3$ is C;
$X^4$ is selected from A, D, E, F, G, H, I, K, L, M, N, P, Q, R, S, T, V, W, and Y;
$X^5$ is selected from F, I, L, M, V, W, and Y;
$X^6$ is selected from A, D, E, F, G, H, I, K, L, M, N, P, Q, R, S, T, V, W, and Y;
$X^7$ is selected from A, D, E, F, G, H, I, K, L, M, N, P, Q, R, S, T, V, W, and Y;
$X^8$ is selected from A, D, E, F, G, H, I, K, L, M, N, P, Q, R, S, T, V, W, and Y;
$X^9$ is selected from A, D, E, G, H, N, P, Q, S, T, and Y;
$X^{10}$ is selected from A, D, E, F, G, H, I, K, L, M, N, P, Q, R, S, T, V, W, and Y;
$X^{11}$ is selected from F, I, L, M, V, W, and Y;
$X^{12}$ is selected from F, I, L, M, V, W, and Y;
$X^{13}$ is C;
$X^{14}$ is selected from F, I, L, M, V, W, and Y; and
$X^{15}$ is selected from F, I, L, M, V, W, and Y.

Aspect 461. The IL-2Rα ligand of any one of aspects 459 to 460, wherein $X^1$ is selected from S, N, Q, R, and G.

Aspect 462. The IL-2Rα ligand of any one of aspects 459 to 461, wherein $X^2$ is selected from A, H, R, and G.

Aspect 463. The IL-2Rα ligand of any one of aspects 459 to 462, wherein $X^3$ is C.

Aspect 464. The IL-2Rα ligand of any one of aspects 459 to 463, wherein $X^4$ is selected from Q, T, N, M, and S.

Aspect 465. The IL-2Rα ligand of any one of aspects 459 to 464, wherein $X^5$ is selected from L and R.

Aspect 466. The IL-2Rα ligand of any one of aspects 459 to 465, wherein $X^6$ is selected from K, S, R, and V.

Aspect 467. The IL-2Rα ligand of any one of aspects 459 to 466, wherein $X^7$ is selected from W, K, and L.

Aspect 468. The IL-2Rα ligand of any one of aspects 459 to 467, wherein $X^8$ is selected from D, T, L, Q, and A.

Aspect 469. The IL-2Rα ligand of any one of aspects 459 to 468, wherein $X^9$ is selected from E, Y, D, and P.

Aspect 470. The IL-2Rα ligand of any one of aspects 459 to 469, wherein $X^{10}$ is selected from G, P, A, E, and S.

Aspect 471. The IL-2Rα ligand of any one of aspects 459 to 470, wherein $X^{11}$ is selected from W and L.

Aspect 472. The IL-2Rα ligand of any one of aspects 459 to 471, wherein $X^{12}$ is selected from T, V, I, and A.

Aspect 473. The IL-2Rα ligand of any one of aspects 459 to 472, wherein $X^{13}$ is C.

Aspect 474. The IL-2Rα ligand of any one of aspects 459 to 473, wherein $X^{14}$ is selected from L, V, Q, and I.

Aspect 475. The IL-2Rα ligand of any one of aspects 459 to 474, wherein $X^{15}$ is selected from F and A.

Aspect 476. The IL-2Rα ligand of any one of aspects 459 to 475, wherein $X^1$ is selected from A, D, E, F, G, H, I, K, L, M, N, P, Q, R, S, T, V, W, and Y.

Aspect 477. The IL-2Rα ligand of any one of aspects 459 to 476, wherein $X^2$ is selected from A, D, E, F, G, H, I, K, L, M, N, P, Q, R, S, T, V, W, and Y.

Aspect 478. The IL-2Rα ligand of any one of aspects 459 to 477, wherein $X^3$ is C.

Aspect 479. The IL-2Rα ligand of any one of aspects 459 to 478, wherein $X^4$ is selected from A, D, E, F, G, H, I, K, L, M, N, P, Q, R, S, T, V, W, and Y.

Aspect 480. The IL-2Rα ligand of any one of aspects 459 to 479, wherein $X^5$ is L.

Aspect 481. The IL-2Rα ligand of any one of aspects 459 to 480, wherein $X^6$ is selected from A, D, E, F, G, H, I, K, L, M, N, P, Q, R, S, T, V, W, and Y.

Aspect 482. The IL-2Rα ligand of any one of aspects 459 to 481, wherein $X^7$ is selected from A, D, E, F, G, H, I, K, L, M, N, P, Q, R, S, T, V, W, and Y.

Aspect 483. The IL-2Rα ligand of any one of aspects 459 to 482, wherein $X^8$ is selected from A, D, E, F, G, H, I, K, L, M, N, P, Q, R, S, T, V, W, and Y.

Aspect 484. The IL-2Rα ligand of any one of aspects 459 to 483, wherein $X^9$ is selected from D and E.

Aspect 485. The IL-2Rα ligand of any one of aspects 459 to 484, wherein $X^{10}$ is selected from A, D, E, F, G, H, I, K, L, M, N, P, Q, R, S, T, V, W, and Y.

Aspect 486. The IL-2Rα ligand of any one of aspects 459 to 485, wherein $X^{11}$ is selected from F, I, L, M, V, W, and Y.

Aspect 487. The IL-2Rα ligand of any one of aspects 459 to 485, wherein $X^{11}$ is W.

Aspect 488. The IL-2Rα ligand of any one of aspects 459 to 487, wherein $X^{12}$ is selected from F, I, L, M, V, W, and Y.

Aspect 489. The IL-2Rα ligand of any one of aspects 459 to 488, wherein $X^{13}$ is C.

Aspect 490. The IL-2Rα ligand of any one of aspects 459 to 489, wherein $X^{14}$ is selected from F, I, L, M, V, W, and Y.

Aspect 491. The IL-2Rα ligand of any one of aspects 459 to 490, wherein $X^{15}$ is F.

Aspect 492. The IL-2Rα ligand of aspect 459, wherein $X^3$ is C, $X^5$ is L, $X^9$ is D or E, $X^{11}$ is W, $X^{13}$ is C, and $X^{15}$ is F.

Aspect 493. The IL-2Rα ligand of aspect 459, wherein, $X^1$ is selected from A, D, E, F, G, H, I, K, L, M, N, P, Q, R, S, T, V, W, and Y;

$X^2$ is selected from A, D, E, F, G, H, I, K, L, M, N, P, Q, R, S, T, V, W, and Y;
$X^3$ is C;
$X^4$ is selected from A, D, E, F, G, H, I, K, L, M, N, P, Q, R, S, T, V, W, and Y;
$X^5$ is L;
$X^6$ is selected from A, D, E, F, G, H, I, K, L, M, N, P, Q, R, S, T, V, W, and Y;
$X^7$ is selected from A, D, E, F, G, H, I, K, L, M, N, P, Q, R, S, T, V, W, and Y;
$X^8$ is selected from A, D, E, F, G, H, I, K, L, M, N, P, Q, R, S, T, V, W, and Y;
$X^9$ is selected from D and E;
$X^{10}$ is selected from A, D, E, F, G, H, I, K, L, M, N, P, Q, R, S, T, V, W, and Y:
$X^{11}$ is selected from F, I, L, M, V, W, and Y;
$X^{12}$ is selected from F, I, L, M, V, W, and Y;
$X^{13}$ is C;

$X^{14}$ is selected from F, I, L, M, V, W, and Y; and $X^{15}$ is F.

Aspect 494. The IL-2Rα ligand of aspect 459, wherein $X^3$ is C, $X^5$ is L, $X^{11}$ is W, $X^{11}$ is C, and $X^1$ is F.

Aspect 495. The IL-2Rα ligand of aspect 459, wherein the IL-2Rα ligand comprises an amino acid sequence selected from any one of SEQ ID NO: 144 to SEQ ID NO: 148:

```
                        SEQ ID NO: 144
S A C Q L K W D E G W T C L F

SEQ ID NO: 145
N H C T L S K T Y P W V C V F

SEQ ID NO: 146
Q R C N R S L L D A L I C Q A

SEQ ID NO: 147
R G C M L R L Q P E L A C V F

SEQ ID NO: 148
G G C S L V W A D S W V C I F
```

Aspect 496. The IL-2Rα ligand of any one of aspects 459 to 495, wherein, the amino acid sequence independently comprises from 1 to 4 glycines (G) (SEQ ID NO: 1041) on the N-terminus, on the C-terminus, or on both the N- and C-termini;

the amino acid sequence comprises a truncated amino acid sequence; or the amino acid sequence comprises a truncated amino acid sequence, wherein the truncated amino acid sequence independently comprises from 1 to 4 glycines (G) (SEQ ID NO: 1041) on the N-terminus, on the C-terminus, or on both the N- and C-termini.

Aspect 497. The IL-2Rα ligand of any one of aspects 495 to 496, wherein from 1 to 5 of the amino acids is independently substituted with another amino acid.

Aspect 498. The IL-2Rα ligand of any one of aspects 1 to 6, wherein the IL-2Rα ligand comprises the amino acid sequence of Formula (13a) (SEQ ID NO: 149), the amino acid sequence of Formula (13b) (SEQ ID NO: 150), or the amino acid sequence of Formula (13c) (SEQ ID NO: 151):

$$-X^4-X^5-X^6-X^7-X^8-X^9-X^{10}-X^{11}-X^{12}- \quad (13a)$$

$$-X^2-C-X^4-X^5-X^6-X^7-X^8-X^9-X^{10}-X^{11}-X^{12}-C-X^{14}- \quad (13b)$$

$$-X^1-X^2-X^3-X^4-X^5-X^6-X^7-X^8-X^9-X^{10}-X^{11}-X^{12}-X^{13}-X^{14}-X^{15}- \quad (13c)$$

wherein, $X^1$ is selected from an amino acid comprising a small hydrophobic side chain or a basic side chain;

$X^2$ is selected from an amino acid comprising a small hydrophobic side chain or a basic side chain;

$X^3$ is C;

$X^4$ is selected from an amino acid comprising a small hydrophobic side chain;

$X^5$ is selected from an amino acid comprising a large hydrophobic side chain;

$X^6$ is selected from an amino acid comprising a large hydrophobic side chain;

$X^7$ is selected from an amino acid comprising a large hydrophobic side chain;

$X^8$ is selected from an amino acid;

$X^9$ is selected from an amino acid comprising an acidic side chain;

$X^{10}$ is selected from an amino acid comprising a small hydrophobic side chain;

$X^{11}$ is selected from an amino acid comprising a large hydrophobic side chain;

$X^{12}$ is selected from an amino acid comprising a large hydrophobic side chain or an acidic side chain;

$X^{13}$ is C;

$X^{14}$ is selected from an amino acid comprising a large hydrophobic side chain; and $X^{15}$ is selected from an amino acid comprising a large hydrophobic side chain.

Aspect 499. The IL-2Rα ligand of aspect 498, wherein,
$X^1$ is selected from A, G, H, K, P, R, S, and T;
$X^2$ is selected from A, G, H, K, P, R, S, and T;
$X^3$ is C;
$X^4$ is selected from A, G, P, S, and T;
$X^5$ is selected from F, I, L, M, V, W, and Y;
$X^6$ is selected from F, I, L, M, V, W, and Y;
$X^7$ is selected from F, I, L, M, V, W, and Y;
$X^8$ is selected from A, D, E, F, G, H, I, K, L, M, N, P, Q, R, S, T, V, W, and Y;
$X^9$ is selected from D and E;
$X^{10}$ is selected from A, G, P, S, and T;
$X^{11}$ is selected from F, I, L, M, V, W, and Y;
$X^{12}$ is selected from D, E, F, I, L, M, V, W, and Y;
$X^{13}$ is C;
$X^{14}$ is selected from F, I, L, M, V, W, and Y; and
$X^{15}$ is selected from F, I, L, M, V, W, and Y.

Aspect 500. The IL-2Rα ligand of any one of aspects 498 to 499, wherein $X^1$ is selected from S, R, Q, V, A, and G.

Aspect 501. The IL-2Rα ligand of any one of aspects 498 to 500, wherein $X^2$ is selected from R, G, A, and S.

Aspect 502. The IL-2Rα ligand of any one of aspects 498 to 501, wherein $X^3$ is C.

Aspect 503. The IL-2Rα ligand of any one of aspects 498 to 502, wherein $X^4$ is selected from S, T, Q, and H.

Aspect 504. The IL-2Rα ligand of any one of aspects 498 to 503, wherein $X^5$ is L.

Aspect 505. The IL-2Rα ligand of any one of aspects 498 to 504, wherein $X^6$ is selected from V, Q, A, and R.

Aspect 506. The IL-2Rα ligand of any one of aspects 498 to 505, wherein $X^7$ is selected from W and F.

Aspect 507. The IL-2Rα ligand of any one of aspects 498 to 506, wherein $X^8$ is selected from T, D, S, L, A, E, and Q.

Aspect 508. The IL-2Rα ligand of any one of aspects 498 to 507, wherein $X^9$ is selected from D, G, and E.

Aspect 509. The IL-2Rα ligand of any one of aspects 498 to 507, wherein $X^{10}$ is selected from T, S, R, G, A, S, and N.

Aspect 510. The IL-2Rα ligand of any one of aspects 498 to 508, wherein $X^{11}$ is W.

Aspect 511. The IL-2Rα ligand of any one of aspects 498 to 510, wherein $X^{12}$ is selected from V and E.

Aspect 512. The IL-2Rα ligand of any one of aspects 498 to 511, wherein $X^{13}$ is C.

Aspect 513. The IL-2Rα ligand of any one of aspects 498 to 512, wherein $X^{14}$ is selected from V and I.

Aspect 514. The IL-2Rα ligand of any one of aspects 498 to 513, wherein $X^{15}$ is F.

Aspect 515. The IL-2Rα ligand of any one of aspects 498 to 514, wherein $X^1$ is selected from A, G, P, S, and T.

Aspect 516. The IL-2Rα ligand of any one of aspects 498 to 514, wherein $X^1$ is selected from H, K, and R.

Aspect 517. The IL-2Rα ligand of any one of aspects 498 to 516, wherein $X^2$ is selected from A, G, P, S, and T.

Aspect 518. The IL-2Rα ligand of any one of aspects 498 to 516, wherein $X^2$ is selected from H, K, and R.

Aspect 519. The IL-2Rα ligand of any one of aspects 498 to 518, wherein $X^2$ is selected from R and G.

Aspect 520. The IL-2Rα ligand of any one of aspects 498 to 519, wherein $X^3$ is C.

Aspect 521. The IL-2Rα ligand of any one of aspects 498 to 520, wherein $X^4$ is selected from A, G, P, S, and T.

Aspect 522. The IL-2Rα ligand of any one of aspects 498 to 520, wherein $X^4$ is selected from S and T.

Aspect 523. The IL-2Rα ligand of any one of aspects 498 to 522, wherein $X^5$ is selected from F, I, L, M, V, W, and Y.

Aspect 524. The IL-2Rα ligand of any one of aspects 498 to 522, wherein $X^5$ is L.

Aspect 525. The IL-2Rα ligand of any one of aspects 498 to 524, wherein $X^6$ is selected from F, I, L, M, V, W, and Y.

Aspect 526. The IL-2Rα ligand of any one of aspects 498 to 524, wherein $X^6$ is V.

Aspect 527. The IL-2Rα ligand of any one of aspects 498 to 526, wherein $X^7$ is selected from F, I, L, M, V, W, and Y.

Aspect 528. The IL-2Rα ligand of any one of aspects 498 to 526, wherein $X^7$ is selected from F, W, and Y.

Aspect 529. The IL-2Rα ligand of any one of aspects 498 to 526, wherein $X^7$ is W.

Aspect 530. The IL-2Rα ligand of any one of aspects 498 to 529, wherein $X^8$ is selected from A, D, E, F, G, H, I, K, L, M, N, P, Q, R, S, T, V, W, and Y.

Aspect 531. The IL-2Rα ligand of any one of aspects 498 to 530, wherein $X^8$ is selected from A, G, P, S, and T.

Aspect 532. The IL-2Rα ligand of any one of aspects 498 to 530, wherein $X^8$ is A.

Aspect 533. The IL-2Rα ligand of any one of aspects 498 to 532, wherein $X^9$ is selected from D and E.

Aspect 534. The IL-2Rα ligand of any one of aspects 498 to 532, wherein $X^9$ is D.

Aspect 535. The IL-2Rα ligand of any one of aspects 498 to 534, wherein $X^{10}$ is selected from A, G, P, S, and T.

Aspect 536. The IL-2Rα ligand of any one of aspects 498 to 534, wherein $X^{10}$ is S.

Aspect 537. The IL-2Rα ligand of any one of aspects 498 to 536, wherein $X^{11}$ is selected from F, I, L, M, V, W, and Y.

Aspect 538. The IL-2Rα ligand of any one of aspects 498 to 536, wherein $X^{11}$ is selected from F, W, and Y.

Aspect 539. The IL-2Rα ligand of any one of aspects 498 to 536, wherein $X^{11}$ is W.

Aspect 540. The IL-2Rα ligand of any one of aspects 498 to 539, wherein $X^{12}$ is selected from F, I, L, M, V, W, and Y.

Aspect 541. The IL-2Rα ligand of any one of aspects 498 to 540, wherein $X^{12}$ is selected from D and E.

Aspect 542. The IL-2Rα ligand of any one of aspects 498 to 540, wherein $X^{12}$ is selected from V and E.

Aspect 543. The IL-2Rα ligand of any one of aspects 498 to 540, wherein $X^{12}$ is V.

Aspect 544. The IL-2Rα ligand of any one of aspects 498 to 543, wherein $X^{13}$ is C.

Aspect 545. The IL-2Rα ligand of any one of aspects 498 to 544, wherein $X^{14}$ is selected from F, I, L, M, V, W, and Y.

Aspect 546. The IL-2Rα ligand of any one of aspects 498 to 544, wherein $X^{14}$ is I.

Aspect 547. The IL-2Rα ligand of any one of aspects 498 to 546, wherein $X^{15}$ is F.

Aspect 548. The IL-2Rα ligand of aspect 498, wherein $X^2$ is R, $X^3$ is C, $X^5$ is S, $X^6$ is L, $X^7$ is V, $X^8$ is W, $X^{10}$ is D, $X^{11}$ is S, $X^{12}$ is W, $X^{13}$ is V, $X^{14}$ is C, $X^{15}$ is I, and $X^{16}$ is F.

Aspect 549. The IL-2Rα ligand of aspect 498, wherein,
$X^1$ is selected from A, D, E, G, P, S, and T;
$X^2$ is selected from G and R;
$X^3$ is C;
$X^4$ is selected from S and T;
$X^5$ is L;
$X^6$ is V;
$X^7$ is selected from F and W;
$X^8$ is selected from A, G, P, S, and T;
$X^9$ is selected from D and E;
$X^{10}$ is S;
$X^{11}$ is W;
$X^{12}$ is V;
$X^{13}$ is C;

$X^{14}$ is I; and
$X^{15}$ is F.

Aspect 550. The IL-2Rα ligand of aspect 498, wherein the IL-2Rα ligand comprises an amino acid sequence selected from any one of SEQ ID NO: 152 to SEQ ID NO: 166:

```
                                    SEQ ID NO: 152
S R C S L V W T D T W V C V F

SEQ ID NO: 153
S R C T L V F D D S W V C V F

SEQ ID NO: 154
R G C S L V W S G S W E C I F

SEQ ID NO: 155
Q A C Q L V W L D S W V C I F

SEQ ID NO: 156
V G C S L V W T D R W E C I F

SEQ ID NO: 157
S G C S L Q W A D G W V C I F

SEQ ID NO: 158
A R C S L V W D E A W V C I F

SEQ ID NO: 159
R G C S L V W A G S W E C I F

SEQ ID NO: 160
S R C S L V W A E N W V C I F

SEQ ID NO: 161
R R C T L V F L D S W E C I F

SEQ ID NO: 162
R G C T L A W E D S W V C I F

SEQ ID NO: 163
R G C S L R F A E A W E C I F

SEQ ID NO: 164
A S C S L V W Q D S W V C I F

SEQ ID NO: 165
S R C S L V W A D S W V C I F

SEQ ID NO: 166
G R C H L V W S D R W E C I F
```

Aspect 551. The IL-2Rα ligand of any one of aspects 498 to 550, wherein, the amino acid sequence independently comprises from 1 to 4 glycines (G) (SEQ ID NO: 1041) on the N-terminus, on the C-terminus, or on both the N- and C-termini;

the amino acid sequence comprises a truncated amino acid sequence; or the amino acid sequence comprises a truncated amino acid sequence, wherein the truncated amino acid sequence independently comprises from 1 to 4 glycines (G) (SEQ ID NO: 1041) on the N-terminus, on the C-terminus, or on both the N- and C-termini.

Aspect 552. The IL-2Rα ligand of any one of aspects 550 to 551, wherein from 1 to 5 of the amino acids is independently substituted with another amino acid.

Aspect 553. The IL-2Rα ligand of any one of aspects 1 to 6, wherein the IL-2Rα ligand comprises the amino acid sequence of Formula (14a) (SEQ ID NO: 167), or the amino acid sequence of Formula (14b) (SEQ ID NO: 168):

$$-X^3-X^4-X^5-X^6-X^7-X^8-X^9-X^{10}-X^{11}-X^{12}- \quad (14a)$$

$$-X^1-C-X^3-X^4-X^5-X^6-X^7-X^8-X^9-X^{10}-X^{11}-X^{12}-C-X^{14}- \quad (14b)$$

wherein,
$X^1$ is selected from an amino acid comprising a small hydrophobic side chain;
$X^2$ is C;
$X^3$ is selected from an amino acid comprising a small hydrophobic side chain;
$X^4$ is selected from an amino acid comprising a large hydrophobic side chain;
$X^5$ is selected from an amino acid;
$X^6$ is selected from an amino acid comprising a large hydrophobic side chain;
$X^7$ is selected from an amino acid comprising an acidic side chain or a polar neutral side chain;
$X^8$ is selected from an amino acid;
$X^9$ is selected from an amino acid;
$X^{10}$ is selected from an amino acid comprising a large hydrophobic side chain;
$X^{11}$ is selected from an amino acid comprising a large hydrophobic side chain;
$X^{12}$ is selected from an amino acid comprising a large hydrophobic side chain or an acidic side chain;
$X^{13}$ is C; and
$X^{14}$ is selected from an amino acid comprising a large hydrophobic side chain.

Aspect 554. The IL-2Rα ligand of aspect 553, wherein,
$X^1$ is selected from A, G, P, S, and T;
$X^2$ is C;
$X^3$ is selected from A, G, P, S, and T;
$X^4$ is selected from F, I, L, M, V, W, and Y;
$X^5$ is selected from A, D, E, F, G, H, I, K, L, M, N, P, Q, R, S, T, V, W, and Y;
$X^6$ is selected from F, I, L, M, V, W, and Y;
$X^7$ is selected from D, E, N, Q, S, T, and Y;
$X^8$ is selected from A, D, E, F, G, H, I, K, L, M, N, P, Q, R, S, T, V, W, and Y;
$X^9$ is selected from A, D, E, F, G, H, I, K, L, M, N, P, Q, R, S, T, V, W, and Y;
$X^{10}$ is selected from F, I, L, M, V, W, and Y;
$X^{11}$ is selected from F, I, L, M, V, W, and Y;
$X^{11}$ is selected from D, E, F, I, L, M, V, W, and Y;
$X^{13}$ is C; and
$X^{14}$ is selected from F, I, L, M, V, W, and Y.

Aspect 555. The IL-2Rα ligand of any one of aspects 553 to 554, wherein $X^1$ is selected from G and S.

Aspect 556. The IL-2Rα ligand of any one of aspects 553 to 555, wherein $X^2$ is C.

Aspect 557. The IL-2Rα ligand of any one of aspects 553 to 556, wherein $X^3$ is selected from T, S, M, and V.

Aspect 558. The IL-2Rα ligand of any one of aspects 553 to 557, wherein $X^4$ is selected from L and V.

Aspect 559. The IL-2Rα ligand of any one of aspects 553 to 558, wherein $X^5$ is selected from K, R, M, S, T, and Q.

Aspect 560. The IL-2Rα ligand of any one of aspects 553 to 559, wherein $X^6$ is selected from W, R, and F.

Aspect 561. The IL-2Rα ligand of any one of aspects 553 to 560, wherein $X^7$ is selected from E, D, Q, N, G, and S.

Aspect 562. The IL-2Rα ligand of any one of aspects 553 to 561, wherein $X^8$ is selected from S, G, D, Q, K, and G.

Aspect 563. The IL-2Rα ligand of any one of aspects 553 to 562, wherein $X^9$ is selected from P, D, G, F, and V.

Aspect 564. The IL-2Rα ligand of any one of aspects 553 to 563, wherein $X^{10}$ is selected from N and W.

Aspect 565. The IL-2Rα ligand of any one of aspects 553 to 564, wherein $X^{11}$ is W.

Aspect 566. The IL-2Rα ligand of any one of aspects 553 to 565, wherein $X^{12}$ is selected from T, V, H, and E.

Aspect 567. The IL-2Rα ligand of any one of aspects 553 to 566, wherein $X^{13}$ is C.

Aspect 568. The IL-2Rα ligand of any one of aspects 553 to 567, wherein $X^{14}$ is selected from Y, E, I, and V.

Aspect 569. The IL-2Rα ligand of any one of aspects 553 to 568, wherein $X^1$ is G.

Aspect 570. The IL-2Rα ligand of any one of aspects 553 to 569, wherein $X^2$ is C.

Aspect 571. The IL-2Rα ligand of any one of aspects 553 to 570, wherein $X^3$ is selected from S and T.

Aspect 572. The IL-2Rα ligand of any one of aspects 553 to 570, wherein $X^3$ is T.

Aspect 573. The IL-2Rα ligand of any one of aspects 553 to 572, wherein $X^4$ is L.

Aspect 574. The IL-2Rα ligand of any one of aspects 553 to 573, wherein $X^5$ is selected from A, D, E, F, G, H, I, K, L, M, N, P, Q, R, S, T, V, W, and Y.

Aspect 575. The IL-2Rα ligand of any one of aspects 553 to 574, wherein $X^6$ is W.

Aspect 576. The IL-2Rα ligand of any one of aspects 553 to 575, wherein $X^7$ is selected from D, E, Q, and N.

Aspect 577. The IL-2Rα ligand of any one of aspects 553 to 576, wherein $X^8$ is selected from A, D, E, F, G, H, I, K, L, M, N, P, Q, R, S, T, V, W, and Y.

Aspect 578. The IL-2Rα ligand of any one of aspects 553 to 577, wherein $X^9$ is selected from A, D, E, F, G, H, I, K, L, M, N, P, Q, R, S, T, V, W, and Y.

Aspect 579. The IL-2Rα ligand of any one of aspects 553 to 578, wherein $X^{10}$ is W.

Aspect 580. The IL-2Rα ligand of any one of aspects 553 to 579, wherein $X^{11}$ is W.

Aspect 581. The IL-2Rα ligand of any one of aspects 553 to 580, wherein $X^{12}$ is selected from F, I, L, M, V, W, and Y.

Aspect 582. The IL-2Rα ligand of any one of aspects 553 to 581, wherein $X^{12}$ is selected from D and E.

Aspect 583. The IL-2Rα ligand of any one of aspects 553 to 581, wherein $X^{12}$ is selected from E and V.

Aspect 584. The IL-2Rα ligand of any one of aspects 553 to 583, wherein $X^{13}$ is C.

Aspect 585. The IL-2Rα ligand of any one of aspects 553 to 584, wherein $X^{14}$ is selected from F, I, L, M, V, W, and Y.

Aspect 586. The IL-2Rα ligand of any one of aspects 553 to 584, wherein $X^{14}$ is selected from I and V.

Aspect 587. The IL-2Rα ligand of aspect 553, wherein $X^1$ is G, $X^2$ is C, $X^3$ is T, $X^4$ is L, $X^6$ is W, $X^{10}$ is W, $X^{11}$ is W, and $X^{11}$ is C.

Aspect 588. The IL-2Rα ligand of aspect 553, wherein,
$X^1$ is G;
$X^2$ is C;
$X^3$ is selected from T and S;
$X^4$ is L;
$X^5$ is selected from A, D, E, F, G, H, I, K, L, M, N, P, Q, R, S, T, V, W, and Y;
$X^6$ is W;
$X^7$ is selected from D, E, N, Q, S, T, and Y;
$X^8$ is selected from A, D, E, F, G, H, I, K, L, M, N, P, Q, R, S, T, V, W, and Y;
$X^9$ is selected from A, D, E, F, G, H, I, K, L, M, N, P, Q, R, S, T, V, W, and Y;
$X^{10}$ is W;
$X^{11}$ is W;
$X^{12}$ is selected from V and E;
$X^{13}$ is C; and
$X^{14}$ is selected from F, I, L, M, V, W, and Y.

Aspect 589. The IL-2Rα ligand of aspect 553, wherein the IL-2Rα ligand comprises an amino acid sequence selected from any one of SEQ ID NO: 169 to SEQ ID NO: 174:

SEQ ID NO: 169 G C T L K W E S P N W T C Y
SEQ ID NO: 170 S C T V R W D G D W W V C E
SEQ ID NO: 171 G C S L M W Q D G W W V C I
SEQ ID NO: 172 G C T L S W N Q G W W H C V
SEQ ID NO: 173 G C M L T R G K F W W E C I
SEQ ID NO: 174 G C V L Q F S G V W W E C V

Aspect 590. The IL-2Rα ligand of any one of aspects 553 to 589, wherein, the amino acid sequence independently comprises from 1 to 4 glycines (G) (SEQ ID NO: 1041) on the N-terminus, on the C-terminus, or on both the N- and C-termini;

the amino acid sequence comprises a truncated amino acid sequence; or the amino acid sequence comprises a truncated amino acid sequence, wherein the truncated amino acid sequence independently comprises from 1 to 4 glycines (G) (SEQ ID NO: 1041) on the N-terminus, on the C-terminus, or on both the N- and C-termini.

Aspect 591. The IL-2Rα ligand of any one of aspects 589 to 590, wherein from 1 to 5 of the amino acids is independently substituted with another amino acid.

Aspect 592. The IL-2Rα ligand of any one of aspects 1 to 6, wherein the IL-2Rα ligand comprises the amino acid sequence of Formula (15a) (SEQ ID NO: 175), the amino acid sequence of Formula (15b) (SEQ ID NO: 176), or the amino acid sequence of Formula (15c) (SEQ ID NO: 177):

$$—X^4—X^5—X^6—X^7—X^8—X^9—X^{10}—X^{11}—X^{12}—X^{13}— \quad (15a)$$

$$—X^2—C—X^4—X^5—X^6—X^7—X^8—X^9—X^{10}—X^{11}—X^{12}—X^{13}—C—X^{15}— \quad (15b)$$

$$—X^1—X^2—C—X^4—X^5—X^6—X^7—X^8—X^9—X^{10}—X^{11}—X^{12}—X^{13}—C—X^{15}—X^{16}— \quad (15c)$$

wherein, $X^1$ is selected from an amino acid;

$X^2$ is selected from an amino acid;

$X^3$ is C;

$X^4$ is selected from an amino acid comprising a polar/neutral side chain or a basic side chain;

$X^5$ is selected from an amino acid comprising a large hydrophobic side chain;

$X^6$ is selected from an amino acid;

$X^7$ is selected from an amino acid comprising a polar neutral side chain or a basic side chain;

$X^8$ is P;

$X^9$ is G;

$X^{10}$ is selected from an amino acid;

$X^{11}$ is selected from an amino acid;

$X^{12}$ is selected from an amino acid comprising a large hydrophobic side chain;

$X^{13}$ is selected from an amino acid comprising an acidic side chain or a polar/neutral side chain;

$X^{14}$ is C;

$X^{15}$ is selected from an amino acid comprising a large hydrophobic side chain; and $X^{16}$ is selected from an amino acid comprising a large hydrophobic side chain.

Aspect 593. The IL-2Rα ligand of aspect 592, wherein, $X^1$ is selected from A, D, E, F, G, H, I, K, L, M, N, P, Q, R, S, T, V, W, and Y;

$X^2$ is selected from A, D, E, F, G, H, I, K, L, M, N, P, Q, R, S, T, V, W, and Y;

$X^3$ is C;

$X^4$ is selected from H, K, N, Q, R, S, T, and Y;

$X^5$ is selected from F, I, L, M, V, W, and Y;

$X^6$ is selected from A, D, E, F, G, H, I, K, L, M, N, P, Q, R, S, T, V, W, and Y;

$X^7$ is selected from H, K, N, Q, R, S, T, and Y;

$X^8$ is P;

$X^9$ is G;

$X^{10}$ is selected from A, D, E, F, G, H, I, K, L, M, N, P, Q, R, S, T, V, W, and Y;

$X^{11}$ is selected from A, D, E, F, G, H, I, K, L, M, N, P, Q, R, S, T, V, W, and Y;

$X^{12}$ is selected from F, I, L, M, V, W, and Y;

$X^{13}$ is selected from D, E, N, Q, S, T, and Y;

$X^{14}$ is C;

$X^{15}$ is selected from F, I, L, M, V, W, and Y; and $X^{16}$ is selected from F, I, L, M, V, W, and Y.

Aspect 594. The IL-2Rα ligand of any one of aspects 592 to 593, wherein $X^1$ is selected from Q, A, G, K, L, N, P, Q, S, and T.

Aspect 595. The IL-2Rα ligand of any one of aspects 592 to 594, wherein $X^2$ is selected from R, G, K, T, P, A, S, and H.

Aspect 596. The IL-2Rα ligand of any one of aspects 592 to 595, wherein $X^3$ is C.

Aspect 597. The IL-2Rα ligand of any one of aspects 592 to 596, wherein $X^4$ is selected from Q, M, S, R, T, I, K, R, H, and L.

Aspect 598. The IL-2Rα ligand of any one of aspects 592 to 597, wherein $X^5$ is selected from L, P, M, and V.

Aspect 599. The IL-2Rα ligand of any one of aspects 592 to 598, wherein $X^6$ is selected from S, L, R, Q, F, W, N, I, and G.

Aspect 600. The IL-2Rα ligand of any one of aspects 592 to 599, wherein $X^7$ is selected from K, H, R, W, L, N, F, and V.

Aspect 601. The IL-2Rα ligand of any one of aspects 592 to 600, wherein $X^8$ is selected from S, P, T, and L.

Aspect 602. The IL-2Rα ligand of any one of aspects 592 to 601, wherein $X^9$ is G.

Aspect 603. The IL-2Rα ligand of any one of aspects 592 to 602, wherein $X^{10}$ is selected from G, L, S, D, T, E, M, N, F, H, R, K, and P.

Aspect 604. The IL-2Rα ligand of any one of aspects 592 to 603, wherein $X^{11}$ is selected from E, Y, R, G, H, S, I, G, L, W, F, and V.

Aspect 605. The IL-2Rα ligand of any one of aspects 592 to 604, wherein $X^{12}$ is selected from L, W, Y, H, and V.

Aspect 606. The IL-2Rα ligand of any one of aspects 592 to 605, wherein $X^{13}$ is selected from G, E, V, T, Q, and A.

Aspect 607. The IL-2Rα ligand of any one of aspects 592 to 606, wherein $X^{14}$ is C.

Aspect 608. The IL-2Rα ligand of any one of aspects 592 to 607, wherein $X^{15}$ is selected from M, I, V, L, W, R, and F.

Aspect 609. The IL-2Rα ligand of any one of aspects 592 to 609, wherein $X^{16}$ is selected from F, S, and G.

Aspect 610. The IL-2Rα ligand of any one of aspects 592 to 609, wherein $X^1$ is selected from S and T.

Aspect 611. The IL-2Rα ligand of any one of aspects 592 to 610, wherein $X^2$ is selected from S, T, R, and K.

Aspect 612. The IL-2Rα ligand of any one of aspects 592 to 611, wherein $X^3$ is C.

Aspect 613. The IL-2Rα ligand of any one of aspects 592 to 612, wherein $X^4$ is selected from N, Q, S, T, and Y.

Aspect 614. The IL-2Rα ligand of any one of aspects 592 to 612, wherein $X^4$ is T.

Aspect 615. The IL-2Rα ligand of any one of aspects 592 to 614, wherein $X^5$ is selected from L, M, and V.

Aspect 616. The IL-2Rα ligand of any one of aspects 592 to 614, wherein $X^5$ is L.

Aspect 617. The IL-2Rα ligand of any one of aspects 592 to 616, wherein $X^6$ is selected from A, D, E, F, G, H, I, K, L, M, N, P, Q, R, S, T, V, W, and Y.

Aspect 618. The IL-2Rα ligand of any one of aspects 592 to 617, wherein $X^7$ is selected from N, K, H, and R.

Aspect 619. The IL-2Rα ligand of any one of aspects 592 to 617, wherein $X^7$ is N.

Aspect 620. The IL-2Rα ligand of any one of aspects 592 to 619, wherein $X^8$ is selected from A, D, E, F, G, H, I, K, L, M, N, P, Q, R, S, T, V, W, and Y.

Aspect 621. The IL-2Rα ligand of any one of aspects 592 to 620, wherein $X^8$ is selected from A, G, P, S, and T.

Aspect 622. The IL-2Rα ligand of any one of aspects 592 to 620, wherein $X^8$ is P.

Aspect 623. The IL-2Rα ligand of any one of aspects 592 to 622, wherein $X^9$ is G.

Aspect 624. The IL-2Rα ligand of any one of aspects 592 to 623, wherein $X^{10}$ is selected from A, D, E, F, G, H, I, K, L, M, N, P, Q, R, S, T, V, W, and Y.

Aspect 625. The IL-2Rα ligand of any one of aspects 592 to 624, wherein $X^{11}$ is selected from A, D, E, F, G, H, I, K, L, M, N, P, Q, R, S, T, V, W, and Y.

Aspect 626. The IL-2Rα ligand of any one of aspects 592 to 625, wherein $X^{11}$ is selected from A, G, P, S, and T.

Aspect 627. The IL-2Rα ligand of any one of aspects 592 to 625, wherein $X^{11}$ is G.

Aspect 628. The IL-2Rα ligand of any one of aspects 592 to 627, wherein $X^{12}$ is W.

Aspect 629. The IL-2Rα ligand of any one of aspects 592 to 628, wherein $X^{13}$ is selected from N, Q, S, T, and Y.

Aspect 630. The IL-2Rα ligand of any one of aspects 592 to 628, wherein $X^{13}$ is selected from D and E.

Aspect 631. The IL-2Rα ligand of any one of aspects 592 to 628, wherein $X^{13}$ is selected from E and Q.

Aspect 632. The IL-2Rα ligand of any one of aspects 592 to 628, wherein $X^{13}$ is E.

Aspect 633. The IL-2Rα ligand of any one of aspects 592 to 632, wherein $X^{14}$ is C.

Aspect 634. The IL-2Rα ligand of any one of aspects 592 to 633, wherein $X^{15}$ is selected from F, I, L, M, V, W, and Y.

Aspect 635. The IL-2Rα ligand of any one of aspects 592 to 633, wherein $X^{15}$ is selected from M, I, V, L, and F.

Aspect 636. The IL-2Rα ligand of any one of aspects 592 to 633, wherein $X^{15}$ is selected from I and V.

Aspect 637. The IL-2Rα ligand of any one of aspects 592 to 636, wherein $X^{16}$ is F.

Aspect 638. The IL-2Rα ligand of aspect 592, wherein $X^3$ is C, $X^5$ is L, $X^8$ is P, $X^9$ is G, $X^{12}$ is W, $X^{11}$ is E, $X^{14}$ is C, and $X^{16}$ is F.

Aspect 639. The IL-2Rα ligand of aspect 592, wherein, $X^1$ is selected from A, D, E, F, G, H, I, K, L, M, N, P, Q, R, S, T, V, W, and Y;

$X^2$ is selected from A, D, E, F, G, H, I, K, L, M, N, P, Q, R, S, T, V, W, and Y;

$X^3$ is C;

$X^4$ is selected from N, Q, S, T, and Y;

$X^5$ is L;

$X^6$ is selected from A, D, E, F, G, H, I, K, L, M, N, P, Q, R, S, T, V, W, and Y;

$X^7$ is selected from N, Q, S, T, and Y;

$X^8$ is P;

$X^9$ is G;

$X^{10}$ is selected from A, D, E, F, G, H, I, K, L, M, N, P, Q, R, S, T, V, W, and Y;

$X^{11}$ is selected from A, G, P, S, and T;

$X^{12}$ is W;
$X^{13}$ is selected from E and Q;
$X^{14}$ is C;
$X^{15}$ is selected from F, I, L, M, V, W, and Y; and
$X^{16}$ is F.

Aspect 640. The IL-2Rα ligand of aspect 592, wherein the IL-2Rα ligand comprises an amino acid sequence selected from any one of SEQ ID NO: 178 to SEQ ID NO: 195:

```
                                              SEQ ID NO: 178
Q R C Q L S W S G G E L G C M F

SEQ ID NO: 179
A G C M L L K P G L Y W E C I F

SEQ ID NO: 180
A R C S L H H T G S R Y E C I F

SEQ ID NO: 181
A T C M L R L L G D G W G C V F

SEQ ID NO: 182
G P C R L S N P G T G W E C I F

SEQ ID NO: 183
K G C T L Q N P G S G W V C L F

SEQ ID NO: 184
L A C I L S K P G E H W E C L F

SEQ ID NO: 185
N G C T L S F S G M S W T C V Y

SEQ ID NO: 186
N S C I L S N P G L G W Q C V F

SEQ ID NO: 187
N T C K L F R S G N I W Q C I F

SEQ ID NO: 188
P S C R L W N P G F G W E C I F

SEQ ID NO: 189
Q S C T L Q R L G H L Y Q C W F

SEQ ID NO: 190
S A C T P N W T G R W W E C V F

SEQ ID NO: 191
S K C H L I V S G K F H E C V F

SEQ ID NO: 192
S S C T L F N P G T G W T C V F

SEQ ID NO: 193
S T C R M G N P G G V W G C Y F

SEQ ID NO: 194
T H C L V Q W P G P V V A C R S

SEQ ID NO: 195
T R C R L L K L G S L W E C F G
```

Aspect 641. The IL-2Rα ligand of any one of aspects 592 to 640, wherein, the amino acid sequence independently comprises from 1 to 4 glycines (G) (SEQ ID NO: 1041) on the N-terminus, on the C-terminus, or on both the N- and C-termini;

the amino acid sequence comprises a truncated amino acid sequence; or the amino acid sequence comprises a truncated amino acid sequence, wherein the truncated amino acid sequence independently comprises from 1 to 4 glycines (G) (SEQ ID NO: 1041) on the N-terminus, on the C-terminus, or on both the N- and C-termini.

Aspect 642. The IL-2Rα ligand of any one of aspects 640 to 641, wherein from 1 to 5 of the amino acids is independently substituted with another amino acid.

Aspect 643. The IL-2Rα ligand of any one of aspects 1 to 6, wherein the IL-2Rα ligand comprises the amino acid sequence of Formula (16a) (SEQ ID NO: 196), or the amino acid sequence of Formula (16b) (SEQ ID NO: 197):

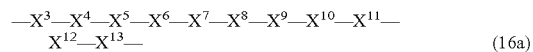

$$—X^3—X^4—X^5—X^6—X^7—X^8—X^9—X^{10}—X^{11}—X^{12}—X^{13}— \quad (16a)$$

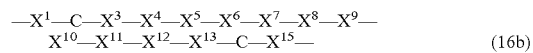

$$—X^1—C—X^3—X^4—X^5—X^6—X^7—X^8—X^9—X^{10}—X^{11}—X^{12}—X^{13}—C—X^{15}— \quad (16b)$$

wherein, $X^1$ is selected from an amino acid;

$X^2$ is C;

$X^3$ is selected from an amino acid comprising a basic side chain;

$X^4$ is selected from an amino acid comprising a large hydrophobic side chain;

$X^5$ is selected from an amino acid comprising a basic side chain or a polar/neutral side chain;

$X^6$ is selected from an amino acid comprising a basic side chain or a polar/neutral side chain;

$X^7$ is selected from an amino acid;

$X^8$ is selected from an amino acid;

$X^9$ is selected from an amino acid;

$X^{10}$ is selected from an amino acid;

$X^{11}$ is selected from an amino acid;

$X^{12}$ is selected from an amino acid comprising an aromatic side chain or a large hydrophobic side chain;

$X^{13}$ is selected from an amino acid comprising an acidic side chain;

$X^{14}$ is C; and $X^{15}$ is selected from an amino acid comprising a large hydrophobic side chain.

Aspect 644. The IL-2Rα ligand of aspect 643, wherein, $X^1$ is selected from A, D, E, F, G, H, I, K, L, M, N, P, Q, R, S, T, V, W, and Y;

$X^2$ is selected from C;

$X^3$ is selected from H, K, and R;

$X^4$ is selected from F, I, L, M, V, W, and Y;

$X^5$ is selected from H, K, N, Q, R, S, T, and Y;

$X^6$ is selected from H, K, N, Q, R, S, T, and Y;

$X^7$ is selected from A, D, E, F, G, H, I, K, L, M, N, P, Q, R, S, T, V, W, and Y;

$X^8$ is selected from A, D, E, F, G, H, I, K, L, M, N, P, Q, R, S, T, V, W, and Y;

$X^9$ is selected from A, D, E, F, G, H, I, K, L, M, N, P, Q, R, S, T, V, W, and Y;

$X^{10}$ is selected from A, D, E, F, G, H, I, K, L, M, N, P, Q, R, S, T, V, W, and Y;

$X^{11}$ is selected from A, D, E, F, G, H, I, K, L, M, N, P, Q, R, S, T, V, W, and Y;

$X^{12}$ is selected from F, H, I, L, M, V, W, and Y;

$X^{13}$ is selected from D and E;

$X^{14}$ is C; and $X^{15}$ is selected from F, I, L, M, V, W, and Y.

Aspect 645. The IL-2Rα ligand of any one of aspects 643 to 644, wherein $X^1$ is selected from A, K, N, R, and T.

Aspect 646. The IL-2Rα ligand of any one of aspects 643 to 645, wherein $X^2$ is C.

Aspect 647. The IL-2Rα ligand of any one of aspects 643 to 646, wherein $X^3$ is selected from W, R, and T.

Aspect 648. The IL-2Rα ligand of any one of aspects 643 to 647, wherein $X^4$ is selected from R, L, and V.

Aspect 649. The IL-2Rα ligand of any one of aspects 643 to 648, wherein $X^5$ is selected from S, R, Q, K, and H.

Aspect 650. The IL-2Rα ligand of any one of aspects 643 to 649, wherein $X^6$ is selected from W, Q, H, K, F, and R.

Aspect 651. The IL-2Rα ligand of any one of aspects 643 to 650, wherein $X^7$ is selected from R, M, L, A, D, S, and I.

Aspect 652. The IL-2Rα ligand of any one of aspects 643 to 651, wherein $X^8$ is selected from Y, S, P, G, and A.

Aspect 653. The IL-2Rα ligand of any one of aspects 643 to 652, wherein $X^9$ is selected from P, R, Y, G, Q, P, and L.

Aspect 654. The IL-2Rα ligand of any one of aspects 643 to 653, wherein $X^{10}$ is selected from T, G, P, N, T, N, and A.

Aspect 655. The IL-2Rα ligand of any one of aspects 643 to 654, wherein $X^{11}$ is selected from R, G, F, T, G, S, and E.

Aspect 656. The IL-2Rα ligand of any one of aspects 643 to 655, wherein $X^{12}$ is selected from T and W.

Aspect 657. The IL-2Rα ligand of any one of aspects 643 to 656, wherein $X^{13}$ is selected from F, E, and S.

Aspect 658. The IL-2Rα ligand of any one of aspects 643 to 657, wherein $X^{14}$ is C.

Aspect 659. The IL-2Rα ligand of any one of aspects 643 to 658, wherein $X^{15}$ is selected from S, L, N, I, and V.

Aspect 660. The IL-2Rα ligand of any one of aspects 643 to 659, wherein $X^2$ is C.

Aspect 661. The IL-2Rα ligand of any one of aspects 643 to 660, wherein $X^3$ is R.

Aspect 662. The IL-2Rα ligand of any one of aspects 643 to 661, wherein $X^4$ is selected from L and V.

Aspect 663. The IL-2Rα ligand of any one of aspects 643 to 662, wherein $X^5$ is selected from R, K, and H.

Aspect 664. The IL-2Rα ligand of any one of aspects 643 to 663, wherein $X^6$ is selected from R, K, and H.

Aspect 665. The IL-2Rα ligand of any one of aspects 643 to 664, wherein $X^7$ is selected from A, D, E, F, G, H, I, K, L, M, N, P, Q, R, S, T, V, W, and Y.

Aspect 666. The IL-2Rα ligand of any one of aspects 643 to 665, wherein $X^8$ is selected from A, D, E, F, G, H, I, K, L, M, N, P, Q, R, S, T, V, W, and Y.

Aspect 667. The IL-2Rα ligand of any one of aspects 643 to 665, wherein $X^8$ is G.

Aspect 668. The IL-2Rα ligand of any one of aspects 643 to 667, wherein $X^9$ is selected from A, D, E, F, G, H, I, K, L, M, N, P, Q, R, S, T, V, W, and Y.

Aspect 669. The IL-2Rα ligand of any one of aspects 643 to 668, wherein $X^{10}$ is selected from A, D, E, F, G, H, I, K, L, M, N, P, Q, R, S, T, V, W, and Y.

Aspect 670. The IL-2Rα ligand of any one of aspects 643 to 669, wherein $X^{11}$ is selected from A, D, E, F, G, H, I, K, L, M, N, P, Q, R, S, T, V, W, and Y.

Aspect 671. The IL-2Rα ligand of any one of aspects 643 to 670, wherein $X^{12}$ is selected from F, I, L, M, V, W, and Y.

Aspect 672. The IL-2Rα ligand of any one of aspects 643 to 670, wherein $X^{12}$ is selected from F, W, and Y.

Aspect 673. The IL-2Rα ligand of any one of aspects 643 to 670, wherein $X^{12}$ is W.

Aspect 674. The IL-2Rα ligand of any one of aspects 643 to 673, wherein $X^{13}$ is E.

Aspect 675. The IL-2Rα ligand of any one of aspects 643 to 674, wherein $X^{14}$ is C.

Aspect 676. The IL-2Rα ligand of any one of aspects 643 to 675, wherein $X^{15}$ is selected from F, I, L, M, V, W, and Y.

Aspect 677. The IL-2Rα ligand of any one of aspects 643 to 675, wherein $X^{15}$ is selected from L, I, and V.

Aspect 678. The IL-2Rα ligand of aspect 643, wherein $X^2$ is C, $X^3$ is R, $X^{12}$ is W, $X^{13}$ is E, and $X^{14}$ is C.

Aspect 679. The IL-2Rα ligand of aspect 643, wherein,
$X^2$ is C;
$X^3$ is R;
$X^4$ is selected from F, I, L, M, V, W, and Y;
$X^5$ is selected from N, Q, S, T, and Y;
$X^6$ is selected from N, Q, S, T, and Y;
$X^7$ is selected from A, D, E, F, G, H, I, K, L, M, N, P, Q, R, S, T, V, W, and Y;
$X^8$ is selected from A, G, P, S, and T;
$X^9$ is selected from A, D, E, F, G, H, I, K, L, M, N, P, Q, R, S, T, V, W, and Y;
$X^{10}$ is selected from A, D, E, F, G, H, I, K, L, M, N, P, Q, R, S, T, V, W, and Y;
$X^{11}$ is selected from A, D, E, F, G, H, I, K, L, M, N, P, Q, R, S, T, V, W, and Y;
$X^{12}$ is W;
$X^{13}$ is E;
$X^{14}$ is C; and
$X^{15}$ is selected from F, I, L, M, V, W, and Y.

Aspect 680. The IL-2Rα ligand of aspect 643, wherein the IL-2Rα ligand comprises an amino acid sequence selected from any one of SEQ ID NO: 198 to SEQ ID NO: 204:

```
                                          SEQ ID NO: 198
          A C W R S W R Y P T R T F C S

SEQ ID NO: 199
          K C R L R Q M S R G G W E C L

SEQ ID NO: 200
          N C R V R H L P Y P F W S C L

SEQ ID NO: 201
          R C R L Q K A G G N T W E C I

SEQ ID NO: 202
          R C T L R F D A Q T G W E C N

SEQ ID NO: 203
          T C R L K R S G P N S W E C I

SEQ ID NO: 204
          T C T V H R I G L A E W E C V
```

Aspect 681. The IL-2Rα ligand of any one of aspects 643 to 680, wherein,
the amino acid sequence independently comprises from 1 to 4 glycines (G) (SEQ ID NO: 1041) on the N-terminus, on the C-terminus, or on both the N- and C-termini;
the amino acid sequence comprises a truncated amino acid sequence; or
the amino acid sequence comprises a truncated amino acid sequence, wherein the truncated amino acid sequence independently comprises from 1 to 4 glycines (G) (SEQ ID NO: 1041) on the N-terminus, on the C-terminus, or on both the N- and C-termini.

Aspect 682. The IL-2Rα ligand of any one of aspects 680 to 681, wherein from 1 to 5 of the amino acids is independently substituted with another amino acid.

Aspect 683. The IL-2Rα ligand of any one of aspects 1 to 6, wherein the IL-2Rα ligand comprises the amino acid sequence of Formula (17a) (SEQ ID NO: 205), the amino acid sequence of Formula (17b) (SEQ ID NO: 206), or the amino acid sequence of Formula (17c) (SEQ ID NO: 207):

$$-X^4-X^5-X^6-X^7-X^8-X^9-X^{10}-X^{11}-X^{12}-X^{13}- \quad (17a)$$

$$-X^2-C-X^4-X^5-X^6-X^7-X^8-X^9-X^{10}-X^{11}-X^{12}-X^{13}-C-X^{15}- \quad (17b)$$

$$-X^1-X^2-C-X^4-X^5-X^6-X^7-X^8-X^9-X^{10}-X^{11}-X^{12}-X^{13}-CX^{15}-X^{16}- \quad (17c)$$

wherein,
$X^1$ is selected from an amino acid comprising a large hydrophobic side chain;

$X^2$ is selected from an amino acid comprising a basic side chain;
$X^3$ is C;
$X^4$ is selected from an amino acid comprising a basic side chain;
$X^5$ is selected from an amino acid comprising a basic side chain or an aromatic side chain or a large hydrophobic side chain;
$X^6$ is selected from an amino acid;
$X^7$ is selected from an amino acid;
$X^8$ is P;
$X^9$ is G;
$X^{10}$ is selected from an amino acid;
$X^{11}$ is selected from an amino acid;
$X^{12}$ is selected from an amino acid;
$X^{13}$ is selected from an amino acid;
$X^{14}$ is C;
$X^{15}$ is selected from an amino acid comprising a large hydrophobic side chain; and
$X^{16}$ is selected from an amino acid comprising a small hydrophobic side chain.

Aspect 684. The IL-2Rα ligand of aspect 683, wherein,
$X^1$ is selected from F, I, L, M, V, W, and Y;
$X^2$ is selected from H, K, and R;
$X^3$ is C;
$X^4$ is selected from H, K, and R;
$X^5$ is selected from F, H, I, K, L, M, R, V, W, and Y;
$X^6$ is selected from A, D, E, F, G, H, I, K, L, M, N, P, Q, R, S, T, V, W, and Y;
$X^7$ is selected from A, D, E, F, G, H, I, K, L, M, N, P, Q, R, S, T, V, W, and Y;
$X^8$ is P;
$X^9$ is G;
$X^{10}$ is selected from A, D, E, F, G, H, I, K, L, M, N, P, Q, R, S, T, V, W, and Y;
$X^{11}$ is selected from A, D, E, F, G, H, I, K, L, M, N, P, Q, R, S, T, V, W, and Y;
$X^{12}$ is selected from A, D, E, F, G, H, I, K, L, M, N, P, Q, R, S, T, V, W, and Y;
$X^{13}$ is selected from A, D, E, F, G, H, I, K, L, M, N, P, Q, R, S, T, V, W, and Y;
$X^{14}$ is C;
$X^{15}$ is selected from F, I, L, M, V, W, and Y; and
$X^{16}$ is selected from F, I, L, M, V, W, and Y.

Aspect 685. The IL-2Rα ligand of any one of aspects 683 to 684, wherein $X^1$ is V.

Aspect 686. The IL-2Rα ligand of any one of aspects 683 to 685, wherein $X^2$ is selected from K, R, T, and Y.

Aspect 687. The IL-2Rα ligand of any one of aspects 683 to 686, wherein $X^3$ is C.

Aspect 688. The IL-2Rα ligand of any one of aspects 683 to 687, wherein $X^4$ is selected from K, F, R, and Y.

Aspect 689. The IL-2Rα ligand of any one of aspects 683 to 688, wherein $X^5$ is selected from L, M, V, and R.

Aspect 690. The IL-2Rα ligand of any one of aspects 683 to 689, wherein $X^6$ is selected from V, S, A, L, and E.

Aspect 691. The IL-2Rα ligand of any one of aspects 683 to 690, wherein $X^7$ is selected from M, E, R, Y, V, and K.

Aspect 692. The IL-2Rα ligand of any one of aspects 683 to 691, wherein $X^8$ is P.

Aspect 693. The IL-2Rα ligand of any one of aspects 683 to 692, wherein $X^9$ is G.

Aspect 694. The IL-2Rα ligand of any one of aspects 683 to 693, wherein $X^{10}$ is selected from S, R, L, Q, V, and G.

Aspect 695. The IL-2Rα ligand of any one of aspects 683 to 694, wherein $X^{11}$ is selected from G, V, T, M, and E.

Aspect 696. The IL-2Rα ligand of any one of aspects 683 to 695, wherein $X^{12}$ is selected from W, S, W, A, and M.

Aspect 697. The IL-2Rα ligand of any one of aspects 683 to 696, wherein $X^{13}$ is selected from A, Y, E, V, and H.

Aspect 698. The IL-2Rα ligand of any one of aspects 683 to 697, wherein $X^{14}$ is C.

Aspect 699. The IL-2Rα ligand of any one of aspects 683 to 697, wherein $X^{14}$ is selected from H, T, L, V, F, and R.

Aspect 700. The IL-2Rα ligand of any one of aspects 683 to 697, wherein $X^{14}$ is selected from F, A, and S.

Aspect 701. The IL-2Rα ligand of any one of aspects 683 to 700, wherein $X^1$ is V.

Aspect 702. The IL-2Rα ligand of any one of aspects 683 to 701, wherein $X^2$ is R.

Aspect 703. The IL-2Rα ligand of any one of aspects 683 to 702, wherein $X^3$ is C.

Aspect 704. The IL-2Rα ligand of any one of aspects 683 to 703, wherein $X^4$ is R.

Aspect 705. The IL-2Rα ligand of any one of aspects 683 to 704, wherein $X^5$ is selected from F, I, L, M, V, W, and Y.

Aspect 706. The IL-2Rα ligand of any one of aspects 683 to 704, wherein $X^5$ is selected from F, W, and Y.

Aspect 707. The IL-2Rα ligand of any one of aspects 683 to 704, wherein $X^5$ is selected from H, K, and R.

Aspect 708. The IL-2Rα ligand of any one of aspects 683 to 707, wherein $X^6$ is selected from A, D, E, F, G, H, I, K, L, M, N, P, Q, R, S, T, V, W, and Y.

Aspect 709. The IL-2Rα ligand of any one of aspects 683 to 708, wherein $X^7$ is selected from A, D, E, F, G, H, I, K, L, M, N, P, Q, R, S, T, V, W, and Y.

Aspect 710. The IL-2Rα ligand of any one of aspects 683 to 709, wherein $X^8$ is P.

Aspect 711. The IL-2Rα ligand of any one of aspects 683 to 710, wherein $X^9$ is G.

Aspect 712. The IL-2Rα ligand of any one of aspects 683 to 711, wherein $X^{10}$ is selected from A, D, E, F, G, H, I, K, L, M, N, P, Q, R, S, T, V, W, and Y.

Aspect 713. The IL-2Rα ligand of any one of aspects 683 to 712, wherein $X^{11}$ is selected from A, D, E, F, G, H, I, K, L, M, N, P, Q, R, S, T, V, W, and Y.

Aspect 714. The IL-2Rα ligand of any one of aspects 683 to 713, wherein $X^{12}$ is selected from A, D, E, F, G, H, I, K, L, M, N, P, Q, R, S, T, V, W, and Y.

Aspect 715. The IL-2Rα ligand of any one of aspects 683 to 714, wherein $X^{13}$ is selected from A, D, E, F, G, H, I, K, L, M, N, P, Q, R, S, T, V, W, and Y.

Aspect 716. The IL-2Rα ligand of any one of aspects 683 to 715, wherein $X^{14}$ is C.

Aspect 717. The IL-2Rα ligand of any one of aspects 683 to 716, wherein $X^{15}$ is selected from F, I, L, M, V, W, and Y.

Aspect 718. The IL-2Rα ligand of any one of aspects 683 to 717, wherein $X^{16}$ is S.

Aspect 719. The IL-2Rα ligand of aspect 683, wherein $X^1$ is V, $X^2$, is R, $X^3$ is C, $X^4$ is R, $X^{14}$ is C, and $X^{16}$ is S.

Aspect 720. The IL-2Rα ligand of aspect 683, wherein,
$X^1$ is V;
$X^2$ is R;
$X^3$ is C;
$X^4$ is R;
$X^5$ is selected from H, F, I, K, L, M, R, V, W, and Y;
$X^6$ is selected from A, D, E, F, G, H, I, K, L, M, N, P, Q, R, S, T, V, W, and Y;
$X^7$ is selected from A, D, E, F, G, H, I, K, L, M, N, P, Q, R, S, T, V, W, and Y;
$X^8$ is P;
$X^9$ is G;

$X^{10}$ is selected from A, D, E, F, G, H, I, K, L, M, N, P, Q, R, S, T, V, W, and Y;

$X^{11}$ is selected from A, D, E, F, G, H, I, K, L, M, N, P, Q, R, S, T, V, W, and Y;

$X^{12}$ is selected from A, D, E, F, G, H, I, K, L, M, N, P, Q, R, S, T, V, W, and Y;

$X^{13}$ is selected from A, D, E, F, G, H, I, K, L, M, N, P, Q, R, S, T, V, W, and Y;

$X^{14}$ is C;

$X^{15}$ is selected from F, I, L, M, V, W, and Y; and $X^{16}$ is S.

Aspect 721. The IL-2Rα ligand of aspect 683, wherein the IL-2Rα ligand comprises an amino acid sequence selected from any one of SEQ ID NO: 208 to SEQ ID NO: 213:

```
                                         SEQ ID NO: 208
V  K  C  K  L  V  N  P  G  S  G  W  A  C  H  F

SEQ ID NO: 209
V  R  C  F  M  S  E  P  G  R  V  S  Y  C  T  A

SEQ ID NO: 210
V  R  C  R  L  A  R  P  G  L  T  W  E  C  L  S

SEQ ID NO: 211
V  R  C  R  V  L  Y  P  G  Q  M  A  V  C  V  S

SEQ ID NO: 212
V  T  C  Y  R  A  V  P  G  V  E  A  Y  C  F  S

SEQ ID NO: 213
V  Y  C  R  R  E  K  P  G  G  E  M  H  C  R  S
```

Aspect 722. The IL-2Rα ligand of any one of aspects 683 to 721, wherein, the amino acid sequence independently comprises from 1 to 4 glycines (G) (SEQ ID NO: 1041) on the N-terminus, on the C-terminus, or on both the N- and C-termini;

the amino acid sequence comprises a truncated amino acid sequence; or the amino acid sequence comprises a truncated amino acid sequence, wherein the truncated amino acid sequence independently comprises from 1 to 4 glycines (G) (SEQ ID NO: 1041) on the N-terminus, on the C-terminus, or on both the N- and C-termini.

Aspect 723. The IL-2Rα ligand of any one of aspects 721 to 722, wherein from 1 to 5 of the amino acids is independently substituted with another amino acid.

Aspect 724. The IL-2Rα ligand of any one of aspects 1 to 6, wherein the IL-2Rα ligand comprises the amino acid sequence of Formula (18a) (SEQ ID NO: 214), the amino acid sequence of Formula (18b) (SEQ ID NO: 215), or the amino acid sequence of Formula (18c) (SEQ ID NO: 216):

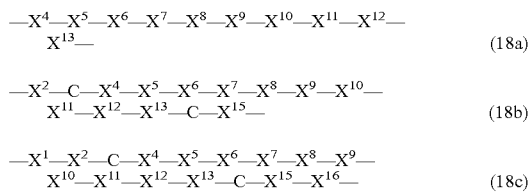

$$-X^4-X^5-X^6-X^7-X^8-X^9-X^{10}-X^{11}-X^{12}-X^{13}- \quad (18a)$$

$$-X^2-C-X^4-X^5-X^6-X^7-X^8-X^9-X^{10}-X^{11}-X^{12}-X^{13}-C-X^{15}- \quad (18b)$$

$$-X^1-X^2-C-X^4-X^5-X^6-X^7-X^8-X^9-X^{10}-X^{11}-X^{12}-X^{13}-C-X^{15}-X^{16}- \quad (18c)$$

wherein, $X^1$ is selected from an amino acid;

$X^2$ is selected from an amino acid;

$X^3$ is C;

$X^4$ is selected from an amino acid comprising an aromatic side chain or a large hydrophobic side chain;

$X^5$ is selected from an amino acid comprising a large hydrophobic side chain;

$X^6$ is selected from an amino acid;

$X^7$ is selected from an amino acid;

$X^8$ is P;

$X^9$ is G;

$X^{10}$ is selected from an amino acid;

$X^{11}$ is selected from an amino acid;

$X^{12}$ is selected from an amino acid;

$X^{13}$ is selected from an amino acid comprising an aromatic side chain or a large hydrophobic side chain;

$X^{14}$ is C;

$X^{15}$ is selected from an amino acid; and $X^{16}$ is selected from an amino acid comprising a large hydrophobic side chain.

Aspect 725. The IL-2Rα ligand of aspect 724, wherein, $X^1$ is selected from A, D, E, F, G, H, I, K, L, M, N, P, Q, R, S, T, V, W, and Y;

$X^2$ is selected from A, D, E, F, G, H, I, K, L, M, N, P, Q, R, S, T, V, W, and Y;

$X^3$ is C;

$X^4$ is selected from F, H, I, L, M, V, W, and Y;

$X^5$ is selected from F, I, L, M, V, W, and Y;

$X^6$ is selected from A, D, E, F, G, H, I, K, L, M, N, P, Q, R, S, T, V, W, and Y;

$X^7$ is selected from A, D, E, F, G, H, I, K, L, M, N, P, Q, R, S, T, V, W, and Y;

$X^8$ is P;

$X^9$ is G;

$X^{10}$ is selected from A, D, E, F, G, H, I, K, L, M, N, P, Q, R, S, T, V, W, and Y;

$X^{11}$ is selected from A, D, E, F, G, H, I, K, L, M, N, P, Q, R, S, T, V, W, and Y;

$X^{12}$ is selected from A, D, E, F, G, H, I, K, L, M, N, P, Q, R, S, T, V, W, and Y;

$X^{13}$ is selected from F, H, I, L, M, V, W, and Y;

$X^{14}$ is C;

$X^{15}$ is selected from A, D, E, F, G, H, I, K, L, M, N, P, Q, R, S, T, V, W, and Y; and $X^{16}$ is selected from F, I, L, M, V, W, and Y.

Aspect 726. The IL-2Rα ligand of any one of aspects 724 to 725, wherein $X^1$ is selected from A, H, Q, R, T, and V.

Aspect 727. The IL-2Rα ligand of any one of aspects 724 to 726, wherein $X^2$ is selected from T, G, L, D, and K.

Aspect 728. The IL-2Rα ligand of any one of aspects 724 to 727, wherein $X^3$ is C.

Aspect 729. The IL-2Rα ligand of any one of aspects 724 to 728, wherein $X^4$ is selected from H, T, P, A, F, Q, and Y.

Aspect 730. The IL-2Rα ligand of any one of aspects 724 to 729, wherein $X^5$ is selected from L, W, G, I, E, M, and R.

Aspect 731. The IL-2Rα ligand of any one of aspects 724 to 730, wherein $X^6$ is selected from L, T, S, M, and N.

Aspect 732. The IL-2Rα ligand of any one of aspects 724 to 731, wherein $X^7$ is selected from A, K, D, E, W, T, and S.

Aspect 733. The IL-2Rα ligand of any one of aspects 724 to 732, wherein $X^8$ is P.

Aspect 734. The IL-2Rα ligand of any one of aspects 724 to 733, wherein $X^9$ is G.

Aspect 735. The IL-2Rα ligand of any one of aspects 724 to 734, wherein $X^{10}$ is selected from V, A, S, T, D, Q, and V.

Aspect 736. The IL-2Rα ligand of any one of aspects 724 to 735, wherein $X^{11}$ is selected from D, E, W, S, R, and I.

Aspect 737. The IL-2Rα ligand of any one of aspects 724 to 736, wherein $X^{12}$ is selected from N, W, G, V, P, and A.

Aspect 738. The IL-2Rα ligand of any one of aspects 724 to 737, wherein $X^{13}$ is selected from T, V, P, F, Y, and W.

Aspect 739. The IL-2Rα ligand of any one of aspects 724 to 738, wherein $X^{14}$ is C.

Aspect 740. The IL-2Rα ligand of any one of aspects 724 to 738, wherein $X^{14}$ is selected from I, S, P, D, H, T, and V.

Aspect 741. The IL-2Rα ligand of any one of aspects 724 to 738, wherein $X^{14}$ is selected from F, L, N, I, T, and G.

Aspect 742. The IL-2Rα ligand of any one of aspects 724 to 741, wherein $X^1$ is selected from A, D, E, F, G, H, I, K, L, M, N, P, Q, R, S, T, V, W, and Y.

Aspect 743. The IL-2Rα ligand of any one of aspects 724 to 742, wherein $X^2$ is selected from A, D, E, F, G, H, I, K, L, M, N, P, Q, R, S, T, V, W, and Y.

Aspect 744. The IL-2Rα ligand of any one of aspects 724 to 743, wherein $X^3$ is C.

Aspect 745. The IL-2Rα ligand of any one of aspects 724 to 744, wherein $X^4$ is selected from F, H, I, L, M, V, W, and Y.

Aspect 746. The IL-2Rα ligand of any one of aspects 724 to 744, wherein $X^4$ is selected from F, W, and Y.

Aspect 747. The IL-2Rα ligand of any one of aspects 724 to 746, wherein $X^5$ is selected from F, I, L, M, V, W, and Y.

Aspect 748. The IL-2Rα ligand of any one of aspects 724 to 747, wherein $X^6$ is selected from A, D, E, F, G, H, I, K, L, M, N, P, Q, R, S, T, V, W, and Y.

Aspect 749. The IL-2Rα ligand of any one of aspects 724 to 748, wherein $X^7$ is selected from A, D, E, F, G, H, I, K, L, M, N, P, Q, R, S, T, V, W, and Y.

Aspect 750. The IL-2Rα ligand of any one of aspects 724 to 749, wherein $X^8$ is P.

Aspect 751. The IL-2Rα ligand of any one of aspects 724 to 750, wherein $X^9$ is G.

Aspect 752. The IL-2Rα ligand of any one of aspects 724 to 751, wherein $X^{10}$ is selected from A, D, E, F, G, H, I, K, L, M, N, P, Q, R, S, T, V, W, and Y.

Aspect 753. The IL-2Rα ligand of any one of aspects 724 to 752, wherein $X^{11}$ is selected from A, D, E, F, G, H, I, K, L, M, N, P, Q, R, S, T, V, W, and Y.

Aspect 754. The IL-2Rα ligand of any one of aspects 724 to 753, wherein $X^{12}$ is selected from A, D, E, F, G, H, I, K, L, M, N, P, Q, R, S, T, V, W, and Y.

Aspect 755. The IL-2Rα ligand of any one of aspects 724 to 754, wherein $X^{13}$ is selected from F, H, I, L, M, V, W, and Y.

Aspect 756. The IL-2Rα ligand of any one of aspects 724 to 754, wherein $X^{13}$ is selected from F, W, and Y.

Aspect 757. The IL-2Rα ligand of any one of aspects 724 to 756, wherein $X^{14}$ is C.

Aspect 758. The IL-2Rα ligand of any one of aspects 724 to 757, wherein $X^{15}$ is selected from A, D, E, F, G, H, I, K, L, M, N, P, Q, R, S, T, V, W, and Y.

Aspect 759. The IL-2Rα ligand of any one of aspects 724 to 758, wherein $X^{16}$ is selected from F, I, L, M, V, W, and Y.

Aspect 760. The IL-2Rα ligand of aspect 724, wherein $X^3$ is C, $X^8$ is P, $X^9$ is G, and $X^{14}$ is C.

Aspect 761. The IL-2Rα ligand of aspect 724, wherein,
$X^1$ is selected from A, D, E, F, G, H, I, K, L, M, N, P, Q, R, S, T, V, W, and Y;
$X^2$ is selected from A, D, E, F, G, H, I, K, L, M, N, P, Q, R, S, T, V, W, and Y;
$X^3$ is C;
$X^4$ is selected from F, H, W, and Y;
$X^5$ is selected from F, I, L, M, V, W, and Y;
$X^6$ is selected from A, D, E, F, G, H, I, K, L, M, N, P, Q, R, S, T, V, W, and Y;
$X^7$ is selected from A, D, E, F, G, H, I, K, L, M, N, P, Q, R, S, T, V, W, and Y;
$X^8$ is P;
$X^9$ is G;
$X^{10}$ is selected from A, D, E, F, G, H, I, K, L, M, N, P, Q, R, S, T, V, W, and Y;
$X^{11}$ is selected from A, D, E, F, G, H, I, K, L, M, N, P, Q, R, S, T, V, W, and Y;
$X^{12}$ is selected from A, D, E, F, G, H, I, K, L, M, N, P, Q, R, S, T, V, W, and Y;
$X^{13}$ is selected from F, H, W, and Y;
$X^{14}$ is C;
$X^{15}$ is selected from A, D, E, F, G, H, I, K, L, M, N, P, Q, R, S, T, V, W, and Y; and
$X^{16}$ is selected from F, I, L, M, V, W, and Y.

Aspect 762. The IL-2Rα ligand of aspect 724, wherein the IL-2Rα ligand comprises an amino acid sequence selected from any one of SEQ ID NO: 217 to SEQ ID NO: 224:

```
                                      SEQ ID NO: 217
    A T C H L L A P G V D N T C I F

SEQ ID NO: 218
    H G C T L T K P G A E W V C S F

SEQ ID NO: 219
    Q L C P W S D P G S W G P C P L

SEQ ID NO: 220
    R D C A G M E P G T S V F C D N

SEQ ID NO: 221
    R D C F I L E P G T S V Y C D L

SEQ ID NO: 222
    T D C Q E T W P G D R P W C H I

SEQ ID NO: 223
    V K C F M S T P G Q I A Y C T T

SEQ ID NO: 224
    V K C Y R N S P G V E A Y C V G
```

Aspect 763. The IL-2Rα ligand of any one of aspects 724 to 762, wherein,
the amino acid sequence independently comprises from 1 to 4 glycines (G) (SEQ ID NO: 1041) on the N-terminus, on the C-terminus, or on both the N- and C-termini;
the amino acid sequence comprises a truncated amino acid sequence; or
the amino acid sequence comprises a truncated amino acid sequence, wherein the truncated amino acid sequence independently comprises from 1 to 4 glycines (G) (SEQ ID NO: 1041) on the N-terminus, on the C-terminus, or on both the N- and C-termini.

Aspect 764. The IL-2Rα ligand of any one of aspects 762 to 763, wherein from 1 to 5 of the amino acids is independently substituted with another amino acid.

Aspect 765. The IL-2Rα ligand of any one of aspects 1 to 6, wherein the IL-2Rα ligand comprises the amino acid sequence of Formula (19a) (SEQ ID NO: 225), or the amino acid sequence of Formula (19b) (SEQ ID NO: 226):

$$—X^3—X^4—X^5—X^6—X^7—X^8—X^9—X^{10}—X^{11}—X^{12}— \quad (19a)$$

$$—X^1—C—X^3—X^4—X^5—X^6—X^7—X^8—X^9—X^{10}—X^{11}—X^{12}—C—X^{14}— \quad (19b)$$

wherein,
$X^1$ is selected from an amino acid;
$X^2$ is C;
$X^3$ is selected from an amino acid comprising an acidic side chain or a polar/neutral side chain;
$X^4$ is selected from an amino acid comprising an acidic side chain or a polar/neutral side chain;

X⁵ is selected from an amino acid comprising a large hydrophobic side chain;
X⁶ is selected from an amino acid comprising a polar/neutral side chain;
X⁷ is selected from an amino acid;
X⁸ is selected from an amino acid;
X⁹ is selected from an amino acid comprising a large hydrophobic side chain;
X¹⁰ is selected from an amino acid;
X¹¹ is selected from an amino acid;
X¹² is selected from an amino acid;
X¹³ is C; and
X¹⁴ is selected from an amino acid.

Aspect 766. The IL-2Rα ligand of aspect 765, wherein,
X¹ is selected from A, D, E, F, G, H, I, K, L, M, N, P, Q, R, S, T, V, W, and Y;
X² is C;
X³ is selected from D, E, N, Q, S, T, and Y;
X⁴ is selected from D, E, N, Q, S, T, and Y;
X⁵ is selected from F, I, L, M, V, W, and Y;
X⁶ is selected from N, Q, S, T, and Y;
X⁷ is selected from A, D, E, F, G, H, I, K, L, M, N, P, Q, R, S, T, V, W, and Y;
X⁸ is selected from A, D, E, F, G, H, I, K, L, M, N, P, Q, R, S, T, V, W, and Y;
X⁹ is selected from F, I, L, M, V, W, and Y;
X¹⁰ is selected from A, D, E, F, G, H, I, K, L, M, N, P, Q, R, S, T, V, W, and Y;
X¹¹ is selected from A, D, E, F, G, H, I, K, L, M, N, P, Q, R, S, T, V, W, and Y;
X¹² is selected from A, D, E, F, G, H, I, K, L, M, N, P, Q, R, S, T, V, W, and Y;
X¹³ is C; and
X¹⁴ is selected from A, D, E, F, G, H, I, K, L, M, N, P, Q, R, S, T, V, W, and Y.

Aspect 767. The IL-2Rα ligand of any one of aspects 765 to 766, wherein X¹ is selected from D, P, S, T, W, and Y.

Aspect 768. The IL-2Rα ligand of any one of aspects 765 to 767, wherein X² is C.

Aspect 769. The IL-2Rα ligand of any one of aspects 765 to 768, wherein X³ is selected from L, Q, M, E, W, and H.

Aspect 770. The IL-2Rα ligand of any one of aspects 765 to 769, wherein X⁴ is selected from D, R, S, E, and L.

Aspect 771. The IL-2Rα ligand of any one of aspects 765 to 770, wherein X⁵ is selected from L, P, F, and V.

Aspect 772. The IL-2Rα ligand of any one of aspects 765 to 771, wherein X⁶ is selected from R, A, K, H, and W.

Aspect 773. The IL-2Rα ligand of any one of aspects 765 to 772, wherein X⁷ is selected from G, E, K, R, D, G, and Q.

Aspect 774. The IL-2Rα ligand of any one of aspects 765 to 773, wherein X⁸ is selected from T, Y, S, M, Q, and D.

Aspect 775. The IL-2Rα ligand of any one of aspects 765 to 774, wherein X⁹ is selected from V, Y, and D.

Aspect 776. The IL-2Rα ligand of any one of aspects 765 to 775, wherein X¹⁰ is selected from G, S, E, N, and Y.

Aspect 777. The IL-2Rα ligand of any one of aspects 765 to 776, wherein X¹¹ is selected from M, Q, W, V, E, N, R, L, and M.

Aspect 778. The IL-2Rα ligand of any one of aspects 765 to 777, wherein X¹² is selected from V, Q, W, V, E, N, R, L, and M.

Aspect 779. The IL-2Rα ligand of any one of aspects 765 to 778, wherein X¹³ is C.

Aspect 780. The IL-2Rα ligand of any one of aspects 765 to 779, wherein X¹⁴ is selected from Q, L, D, N, I, P, and F.

Aspect 781. The IL-2Rα ligand of any one of aspects 765 to 780, wherein X¹ is selected from A, D, E, F, G, H, I, K, L, M, N, P, Q, R, S, T, V, W, and Y.

Aspect 782. The IL-2Rα ligand of any one of aspects 765 to 781, wherein X² is C.

Aspect 783. The IL-2Rα ligand of any one of aspects 765 to 782, wherein X³ is selected from H, N, Q, S, T, and Y.

Aspect 784. The IL-2Rα ligand of any one of aspects 765 to 783, wherein X³ is selected from D and E.

Aspect 785. The IL-2Rα ligand of any one of aspects 765 to 783, wherein X³ is selected from Q and E.

Aspect 786. The IL-2Rα ligand of any one of aspects 765 to 785, wherein X⁴ is selected from D and E.

Aspect 787. The IL-2Rα ligand of any one of aspects 765 to 786, wherein X⁵ is L.

Aspect 788. The IL-2Rα ligand of any one of aspects 765 to 787, wherein X⁶ is selected from R, H, and K.

Aspect 789. The IL-2Rα ligand of any one of aspects 765 to 788, wherein X⁷ is selected from A, D, E, F, G, H, I, K, L, M, N, P, Q, R, S, T, V, W, and Y.

Aspect 790. The IL-2Rα ligand of any one of aspects 765 to 789, wherein X⁸ is selected from A, D, E, F, G, H, I, K, L, M, N, P, Q, R, S, T, V, W, and Y.

Aspect 791. The IL-2Rα ligand of any one of aspects 765 to 790, wherein X⁹ is Y.

Aspect 792. The IL-2Rα ligand of any one of aspects 765 to 791, wherein X¹⁰ is selected from A, G, P, S, and T.

Aspect 793. The IL-2Rα ligand of any one of aspects 765 to 792, wherein X¹¹ is selected from A, D, E, F, G, H, I, K, L, M, N, P, Q, R, S, T, V, W, and Y.

Aspect 794. The IL-2Rα ligand of any one of aspects 765 to 793, wherein X¹² is selected from F, I, L, M, V, W, and Y.

Aspect 795. The IL-2Rα ligand of any one of aspects 765 to 793, wherein X¹² is selected from V, L, and M.

Aspect 796. The IL-2Rα ligand of any one of aspects 765 to 795, wherein X¹³ is C.

Aspect 797. The IL-2Rα ligand of any one of aspects 765 to 796, wherein X¹⁴ is selected from F, I, L, M, V, W, and Y.

Aspect 798. The IL-2Rα ligand of any one of aspects 765 to 796, wherein X¹⁴ is selected from F, I, and L.

Aspect 799. The IL-2Rα ligand of any one of aspects 765 to 766, wherein X² is C, X⁵ is L, and X¹ is C.

Aspect 800. The IL-2Rα ligand of aspect 765, wherein,
X¹ is selected from A, D, E, F, G, H, I, K, L, M, N, P, Q, R, S, T, V, W, and Y;
X² is C;
X³ is selected from D, E, N, Q, S, T, and Y;
X⁴ is selected from D, E, N, Q, S, T, and Y;
X⁵ is L;
X⁶ is selected from A, G, H, K, P, S, and T;
X⁷ is selected from A, D, E, F, G, H, I, K, L, M, N, P, Q, R, S, T, V, W, and Y;
X⁸ is selected from A, D, E, F, G, H, I, K, L, M, N, P, Q, R, S, T, V, W, and Y;
X⁹ is selected from F, I, L, M, V, W, and Y;
X¹⁰ is selected from A, G, P, S, and T;
X¹¹ is selected from A, D, E, F, G, H, I, K, L, M, N, P, Q, R, S, T, V, W, and Y; and
X¹² is selected from F, I, L, M, V, W, and Y;
X¹³ is C; and
X¹⁴ is selected from F, I, L, M, V, W, and Y.

Aspect 801. The IL-2Rα ligand of aspect 765, wherein the IL-2Rα ligand comprises an amino acid sequence selected from any one of SEQ ID NO: 227 to SEQ ID NO: 234:
SEQ ID NO: 227 D C L D L R G T V G M V C Q
SEQ ID NO: 228 P C Q R L A E Y Y S Q Q C L
SEQ ID NO: 229 S C M D L K G S V G W V C D SEQ ID NO: 230 T C E S L A K M Y E V E C N
SEQ ID NO: 231 T C E S L A R M Y N E N C I
SEQ ID NO: 232 W C W E P H D Q Y Y V R C P
SEQ ID NO: 233 Y C H D F K G T V G T L C I
SEQ ID NO: 234 G C Q L V W Q D D S Y M C F Y Aspect 802. The IL-2Rα ligand of any one of aspects 765 to 801, wherein,
the amino acid sequence independently comprises from 1 to 4 glycines (G) (SEQ ID NO: 1041) on the N-terminus, on the C-terminus, or on both the N- and C-termini;
the amino acid sequence comprises a truncated amino acid sequence; or
the amino acid sequence comprises a truncated amino acid sequence, wherein the truncated amino acid sequence independently comprises from 1 to 4 glycines (G) (SEQ ID NO: 1041) on the N-terminus, on the C-terminus, or on both the N- and C-termini.

Aspect 803. The IL-2Rα ligand of any one of aspects 801 to 802, wherein from 1 to 5 of the amino acids is independently substituted with another amino acid.

Aspect 804. The IL-2Rα ligand of any one of aspects 1 to 6, wherein the IL-2Rα ligand comprises the amino acid sequence of Formula (20a) (SEQ ID NO: 235), or the amino acid sequence of Formula (20b) (SEQ ID NO: 236):

$$-X^3-X^4-X^5-X^6-X^7-X^8-X^9-X^{10}-X^{11}-X^{12}- \quad (20a)$$

$$-X^1-C-X^3-X^4-X^5-X^6-X^7-X^8-X^9-X^{10}-X^{11}-X^{12}-C-X^{14}- \quad (20b)$$

wherein,
$X^1$ is W;
$X^2$ is C;
$X^3$ is selected from F, I, L, M, V, W, and Y;
$X^4$ is G;
$X^5$ is Q;
$X^6$ is P;
$X^7$ is L;
$X^8$ is selected from F, I, L, M, V, W, and Y;
$X^9$ is R;
$X^{10}$ is selected from H, N, Q, F, I, L, M, V, W, and Y;
$X^{11}$ is G;
$X^{12}$ is S;
$X^{13}$ is C; and
$X^{14}$ is K.

Aspect 805. The IL-2Rα ligand of aspect 804, wherein $X^3$ is selected from I and V.

Aspect 806. The IL-2Rα ligand of any one of aspects 804 to 805, wherein $X^8$ is selected from F and Y.

Aspect 807. The IL-2Rα ligand of any one of aspects 804 to 806, wherein $X^{10}$ is selected from F, I, L, M, N, Q, S, T, V, W, and Y.

Aspect 808. The IL-2Rα ligand of any one of aspects 804 to 807, wherein $X^{10}$ is selected from L and Q.

Aspect 809. The IL-2Rα ligand of aspect 804, wherein $X^1$ is W, $X^2$ is C, $X^4$ is G, $X^5$ is Q, $X^6$ is P, $X^7$ is L, $X^9$ is R, $X^{11}$ is G, $X^{12}$ is 5S, $X^{11}$ is C, and $X^{14}$ is K.

Aspect 810. The IL-2Rα ligand of aspect 804, wherein,
$X^1$ is W;
$X^2$ is C;
$X^3$ is selected from I and V;
$X^4$ is G;
$X^5$ is Q;
$X^6$ is P;
$X^7$ is L;
$X^8$ can be selected from F and Y;
$X^9$ is R;
$X^{10}$ is selected from F, H, I, L, M, N, Q, S, T, V, W, and Y;
$X^{11}$ is G;
$X^{12}$ is S;
$X^{13}$ is C; and
$X^{14}$ is K.

Aspect 811. The IL-2Rα ligand of aspect 804, wherein the IL-2Rα ligand comprises an amino acid sequence selected from any one of SEQ ID NO: 237 to SEQ ID NO: 307:

```
                                        SEQ ID NO: 237
W C I G Q P L F R Q G S C K

SEQ ID NO: 238
W C V G Q P L Y R L G S C K

SEQ ID NO: 239
W D Q F Q L G W E A G V A A

SEQ ID NO: 240
F L P W P V Y F S Q V L G G G

SEQ ID NO: 241
Y V M C S A F G C K S I

SEQ ID NO: 242
H V I C S V N G G C R G

SEQ ID NO: 243
I R F C L R S E P T A C W I V

SEQ ID NO: 244
I R C R Y E K Q S G I C L F

SEQ ID NO: 245
G G C S L V W A D S W V C I F

SEQ ID NO: 246
G C S L M W Q D G W W V C I

SEQ ID NO: 247
E W E C R F L P G R R G C S L F

SEQ ID NO: 248
K G C T L Q N P G S G W V C L F

SEQ ID NO: 249
T C R L K R S G P N S W E C I

SEQ ID NO: 250
W C I G Q P L F R Q G S C K

SEQ ID NO: 251
A V S C N S W R C I P W

SEQ ID NO: 252
A V C C D G N S C R R C

SEQ ID NO: 253
F V H C S L M G C W C G

SEQ ID NO: 254
R C L D L G G S V G L V C F

SEQ ID NO: 255
V C F N F R G T V G R H C W

SEQ ID NO: 256
V R C R Q N E P G G A Y W C S S

SEQ ID NO: 257
C V L R E G A E G W E C V W R

SEQ ID NO: 258
C R M M Q G T Y G W T C L F

SEQ ID NO: 259
C I L N D T I Q G W V C I Y
```

-continued

SEQ ID NO: 260
C T L Y R S A P G V W L C I F

SEQ ID NO: 261
C L V F D Q Y G N Y K R R C

SEQ ID NO: 262
I V C C N M F G C H T C R N

SEQ ID NO: 263
Q V C C T S R G C R V C A P V

SEQ ID NO: 264
R V C C S M V G C R S C N L

SEQ ID NO: 265
R V C C T F A G C R V C H K

SEQ ID NO: 266
R V C C T S D G C R G C R Q

SEQ ID NO: 267
T V C C T V Q G C W P C S R

SEQ ID NO: 268
V C C H Q T F G C Y R C K Q

SEQ ID NO: 269
C V V C S A L G C R A C V P R

SEQ ID NO: 270
V W D C F V R G W E V A A V A V G E

SEQ ID NO: 271
L T C L I F K P G T H R H C P V

SEQ ID NO: 272
R Y C S P L I P G S A L G C P R

SEQ ID NO: 273
I R C R L D P P G S Y K T C V F

SEQ ID NO: 274
R G V I C N H A G C R I W Y G

SEQ ID NO: 275
T T Q S C T L R Y C W L L Q

SEQ ID NO: 276
W W I S C L R D L R C L E Y F

SEQ ID NO: 277
R H A C K T W Y R M C I V S

SEQ ID NO: 278
A V S C S R L T G R C H S L

SEQ ID NO: 279
W V A C N R V T G S C R P I

SEQ ID NO: 280
S H G V C C T Q S S C R S C R

SEQ ID NO: 281
W V A C N R L S G C C R P I

SEQ ID NO: 282
H T V C C Q D W G C R S C S G

SEQ ID NO: 283
M A C C T P R G C R P C

SEQ ID NO: 284
R S V C C S S Y G C R A C F G

SEQ ID NO: 285
C K L T C T S S T C S C V F

SEQ ID NO: 286
C M L K C T N A I C E C I F

-continued

SEQ ID NO: 287
C R V W C N Q A E C M C I F

SEQ ID NO: 288
S R C S F D V T K Q E C V F

SEQ ID NO: 289
L E C Q P Y R G P L Y Y C Q D

SEQ ID NO: 290
S I C C T P Q L C H S C D G

SEQ ID NO: 291
T T C C T S E G C H K C I T L

SEQ ID NO: 292
C V A C S S D G C S P I I C

SEQ ID NO: 293
A I C S E D E G G E L C C W H

SEQ ID NO: 294
H E I C C G P P G C H S C S V T

SEQ ID NO: 295
L S V C S C P P G Q L Y C M V E

SEQ ID NO: 296
S T W C C L H P G V G E C Q A V

SEQ ID NO: 297
V T Q C F D G P G S F R C C Y Q

SEQ ID NO: 298
R Q C N C L S P G E L V N C Q Q

SEQ ID NO: 299
M V S C T D L G C V V V G G G

SEQ ID NO: 300
V V H C L Q S G C Y S V G S G

SEQ ID NO: 301
T I K C G S S G W C W V E A G

SEQ ID NO: 302
M V S C T D L G C V V V G G G

SEQ ID NO: 303
H E I C C G P P G C H S C S V T

SEQ ID NO: 304
L S V C S C P P G Q L Y C M V E

SEQ ID NO: 305
S T W C C L H P G V G E C Q A V

SEQ ID NO: 306
V T Q C F D G P G S F R C C Y Q

SEQ ID NO: 307
R Q C N C L S P G E L V N C Q Q

Aspect 812. The IL-2Rα ligand of any one of aspects 804 to 811, wherein,
the amino acid sequence independently comprises from 1 to 4 glycines (G) (SEQ ID NO: 1041) on the N-terminus, on the C-terminus, or on both the N- and C-termini;
the amino acid sequence comprises a truncated amino acid sequence; or
the amino acid sequence comprises a truncated amino acid sequence, wherein the truncated amino acid sequence independently comprises from 1 to 4 glycines (G) (SEQ ID NO: 1041) on the N-terminus, on the C-terminus, or on both the N- and C-termini.

Aspect 813. The IL-2Rα ligand of any one of aspects 811 to 812, wherein from 1 to 5 of the amino acids is independently substituted with another amino acid.

Aspect 814. The IL-2Rα ligand of any one of aspects 1 to 6, wherein the IL-2Rα ligand comprises an amino acid sequence selected from any one of SEQ ID NO: 400 to SEQ ID NO: 423:

```
                                       SEQ ID NO: 400
W D D F I L G W E A G V A A V G E V

SEQ ID NO: 401
F L P W P V Y F S Q V L G G R R

SEQ ID NO: 402
Y V M C S A F G C K S I G G

SEQ ID NO: 403
H V I C S V N G G C R G G G

SEQ ID NO: 404
G G I R F C L R S E P T A C W I V G G

SEQ ID NO: 405
G G I R C R Y E K Q S G I C L F G G

SEQ ID NO: 423
G G G G C S L V W A D S W V C I F G G

SEQ ID NO: 406
G G G C S L M W Q D G W W V C I G G

SEQ ID NO: 407
G G E W E C R F L P G R R G C S L F G G

SEQ ID NO: 408
G G K G C T L Q N P G S G W V C L F G G

SEQ ID NO: 409
G G T C R L K R S G P N S W E C I G G

SEQ ID NO: 410
G G W C I G Q P L F R Q G S C K G G

SEQ ID NO: 411
F V L C G L Q G C R S G G

SEQ ID NO: 412
F V P W D E Y F L Q I L G G

SEQ ID NO: 413
G G G W V I C S A L G C P F G G

SEQ ID NO: 414
G G G R R F C L R S E P T A C W T V G G

SEQ ID NO: 415
G G G S R C S L V W A D S W V C I F G G

SEQ ID NO: 416
G G D W E C L F L P G R R G C T L F G G

SEQ ID NO: 417
F I P W D E Y F A Q L L G G

SEQ ID NO: 418
F V P W D V Y F S Q I L G G

SEQ ID NO: 419
F I P W D E Y F K Q V L G G

SEQ ID NO: 420
F V P W P E Y F L Q I M G G

SEQ ID NO: 421
F I P W E E Y F S Q L L G G

SEQ ID NO: 422
F I P W P E Y F S Q L L G G
```

Aspect 815. The IL-2Rα ligand of aspect 814, wherein the amino acid sequence comprises a truncated amino acid sequence.

Aspect 816. The IL-2Rα ligand of any one of aspects 814 to 815, wherein the amino acid sequence independently comprises from 1 to 4 glycines (G) (SEQ ID NO: 1041) on the N-terminus, on the C-terminus, or on both the N- and C-termini.

Aspect 817. The IL-2Rα ligand of any one of aspects 814 to 816, wherein from 1 to 5 of the amino acids is independently substituted with another amino acid.

Aspect 818. The IL-2Rα ligand of any one of aspects 1 to 6, wherein the IL-2Rα ligand comprises an amino acid sequence selected from any one of SEQ ID NO: 1 to SEQ ID NO: 307 and SEQ ID NO. 400 to SEQ ID NO: 423.

Aspect 819. The IL-2Rα ligand of any one of aspects 1 to 6, wherein the IL-2Rα ligand comprises an amino acid sequence having greater than 70%, greater than 75%, greater than 80%, greater than 85%, greater than 90%, or greater than 95% sequence similarity to any one of SEQ ID NO: 1 to SEQ ID NO: 307 and SEQ ID NO. 400 to SEQ ID NO: 423.

Aspect 820. The IL-2Rα ligand of any one of aspects 1 to 6, wherein the IL-2Rα ligand comprises a truncated amino acid sequence of any one of SEQ ID NO: 1 to SEQ ID NO: 307 and SEQ ID NO. 400 to SEQ ID NO: 423.

Aspect 821. The IL-2Rα ligand of any one of aspects 1 to 6, wherein the IL-2Rα ligand comprises an amino acid sequence having greater than 70%, greater than 75%, greater than 80%, greater than 85%, greater than 90%, or greater than 95% sequence similarity to a truncated amino acid sequence of any one of SEQ ID NO: 1 to SEQ ID NO: 307 and SEQ ID NO. 400 to SEQ ID NO: 423.

Aspect 822. A compound comprising an IL-2Rα ligand of any one of aspects 1 to 821.

Aspect 823. The compound of aspect 822, wherein the compound is selected from a peptide, a conjugate, a fusion protein, and a single chain tandem peptide.

Aspect 825. The compound of aspect 823, wherein the compound is a peptide.

Aspect 825. The compound of aspect 824, wherein the peptide has a molecular weight within a range from 500 Daltons to 15,000 Daltons.

Aspect 826. The compound of any one of aspects 825 to 826, wherein the peptide comprises from 5 amino acids to 4,000 amino acids.

Aspect 827. The compound of aspect 823, wherein the compound comprises a conjugate.

Aspect 828. The compound of aspect 827, wherein the conjugate comprises at least one IL-2Rα ligand.

Aspect 829. The compound of aspect 827, wherein the conjugate comprises: at least two IL-2Rα ligands; and at least one linker attached to each of the at least two IL-2Rα ligands.

Aspect 830. The compound of any one of aspects 823 to 829, wherein the conjugate comprises at least one IL-2Rβ ligand and/or at least one IL-2Rγc ligand.

Aspect 831. The compound of any one of aspects 823 to 829, wherein the conjugate comprises: at least two IL-2Rβ ligands; and at least one linker attached to each of the at least two IL-2Rβ ligands.

Aspect 832. The compound of aspect 823, wherein the conjugate comprises: at least two IL-2Rγc ligands; and at least one linker attached to each of the at least two IL-2Rγc ligands.

Aspect 833. The compound of aspect 823, wherein the conjugate comprises: at least one IL-2Rβ ligand; at least one IL-2Rγc ligand; and at least one linker attached to the at least one IL-2Rβ ligand and to the at least one IL-2Rγc ligand.

Aspect 834. The compound of any one of aspects 823 to 833, wherein the conjugate comprises at least one moiety, amino acid, or polypeptide configured to modify a property of the conjugate.

Aspect 835. The compound of aspect 834, wherein the property is selected from aqueous solubility, polarity, lipophilicity, pharmacokinetic profile, targeting, bioavailability, pH-dependent binding, bioactivity, pharmacodynamics, cellular activity, metabolism, therapeutic efficacy, and caging (reversible incapacitation).

Aspect 836. The compound of any one of aspects 834 to 835, wherein the at least one moiety is cleavable in vivo.

Aspect 837. The compound of any one of aspects 834 to 836, wherein the at least one moiety comprises an irreversibly cleavable promoiety.

Aspect 838. The compound of aspect 837, wherein the promoiety is configured to be releasable in a target-specific environment.

Aspect 839. The compound of aspect 838, wherein the target-specific environment comprises an enzyme, pH, or a combination thereof.

Aspect 840. The compound of any one of aspects 834 to 839, wherein the moiety comprises a small molecule, polymer, a peptide, or an antibody.

Aspect 841. The compound of any one of aspects 834 to 840, wherein the moiety comprises a pharmacokinetic moiety.

Aspect 842. The compound of aspect 841, wherein the pharmacokinetic moiety comprises a polyethylene glycol.

Aspect 843. The compound of any one of aspects 834 to 842, wherein the moiety comprises a tumor-targeting moiety.

Aspect 844. The compound of aspect 843, wherein the tumor-targeting moiety comprises a tumor-specific antibody, a tumor-specific antibody fragment, a tumor-specific protein, or a tumor-specific peptide.

Aspect 845. The compound of any one of aspects 834 to 844, wherein the moiety comprises an immune cell-targeting moiety.

Aspect 846. The compound of any one of aspects 822 to 845, wherein the compound comprises a linker covalently bound to the IL-2Rα ligand.

Aspect 847. The compound of aspect 846, wherein the linker is selected from a peptide having from 2 amino acids to 200 amino acids.

Aspect 848. The compound of any one of aspects 846 to 847, wherein the linker comprises a polyethylene glycol.

Aspect 849. The compound of any one of aspects 822 to 848, wherein the compound comprises a heteromer, wherein the heteromer comprises:
an IL-2Rα ligand;
an IL-2Rβ ligand;
an IL-2Rγc ligand; and
a linker;
wherein each of the IL-2Rα ligand, the IL-2Rβ ligand and the IL-2Rγc ligand comprise an amino-terminus (N-terminus), a carboxy terminus (C-terminus), and an amino acid side chain;
wherein the IL-2Rα ligand is bonded to the linker through the amino-terminus (N-terminus), the carboxy terminus (C-terminus), an amino acid side chain, or a combination of any of the foregoing;
wherein the IL-2Rβ ligand is bonded to the linker through the amino-terminus (N-terminus), the carboxy terminus (C-terminus), an amino acid side chain, or a combination of any of the foregoing; and
wherein the IL-2Rγc ligand is bonded to the linker through the amino-terminus (N-terminus), the carboxy terminus (C-terminus), an amino acid side chain, or a combination of any of the foregoing.

Aspect 850. The compound of any one of aspects 822 to 848, wherein the compound comprises a heteromer, wherein the heteromer comprises:
an IL-2Rα ligand;
an IL-2Rβ ligand;
an IL-2Rγc ligand; and
a linker;
wherein each of the IL-2Rα ligand, the IL-2Rβ ligand, and the IL-2Rγc ligand comprises an amino-terminus (N-terminus) and a carboxy terminus (C-terminus); and
wherein each of the IL-2Rα ligand, the IL-2Rβ ligand, and the IL-2Rγc ligand is covalently bound to the linker.

Aspect 851. The compound of aspect 850, wherein each of the IL-2Rα ligand, the IL-2Rβ ligand, and the IL-2Rγc ligand is covalently bound to the linker through the respective C-terminus and/or through the respective N-terminus.

Aspect 852. The compound of aspect 850, wherein,
the IL-2Rα ligand is covalently bound to the linker through an amino acid side chain;
the IL-2Rβ ligand is covalently bound to the linker through an amino acid side chain; and/or
the IL-2Rγc ligand is covalently bound to the linker through an amino acid side chain.

Aspect 853. The compound of aspect 850, wherein,
the IL-2Rα ligand is covalently bound to the linker through an amino acid side chain, through the C-terminus, or through the N-terminus;
the IL-2Rβ ligand is covalently bound to the linker through an amino acid side chain, through the C-terminus, or through the N-terminus; and
the IL-2Rγc ligand is covalently bound to the linker through an amino acid side chain, through the C-terminus, or through the N-terminus.

Aspect 854. The compound of any one of aspects 850 to 853, wherein the heteromer is configured to activate the IL-2 receptor.

Aspect 855. The compound of any one of aspects 850 to 853, wherein the linker is configured such that the heteromer activates the IL-2 receptor.

Aspect 856. The compound of any one of aspects 822 to 855, wherein the compound is an IL-2R agonist.

Aspect 857. The compound of any one of aspects 822 to 855, wherein the compound is an IL-2R antagonist.

Aspect 858. The compound of any one of aspects 822 to 855, wherein the compound comprises a conformation configured to activate human IL-2Rβγc signaling pathways.

Aspect 859. The compound of any one of aspects 822 to 858, wherein the compound comprises a single chain peptide.

Aspect 860. The compound of aspect 859, wherein the single chain peptide comprises at least one IL-2Rβ ligand.

Aspect 861. The compound of any one of aspects 859 to 860, wherein the single chain peptide comprises: at least two IL-2Rβ ligands; and at least one linker attached to the at least two IL-2Rβ ligands.

Aspect 862. The compound of any one of aspects 859 to 861, wherein the single chain peptide comprises a least one IL-2Rγc ligand.

Aspect 863. The compound of any one of aspects 859 to 862, wherein the single chain peptide comprises: at least two IL-2Rγc ligands; and at least one linker attached to the at least two IL-2Rγc ligands.

Aspect 864. The compound of any one of aspects 859 to 863, wherein the single chain tandem peptide comprises:
at least one IL-2Rα ligand;
at least one IL-2Rβ ligand;
at least one IL-2Rγc ligand; and
at least one linker attached to the at least one IL-2Rα ligand, to the at least one IL-2Rβ ligand, and to the at least one IL-2Rγc ligand.

Aspect 865. The compound of any one of aspects 822 to 864, wherein the compound is a fusion protein.

Aspect 866. The compound of aspect 865, wherein the fusion protein comprises:
at least one IL-2Rα ligand;
at least one IL-2Rβ ligand;
at least one IL-2Rγc ligand; and
a peptide linker domain, wherein the peptide linker domain is bound to the at least one IL-2Rα ligand, to the at least one IL-2Rβ ligand, and to the at least one IL-2Rγc ligand.

Aspect 867. The compound of aspect 865, wherein, each peptide linker domain has an amino-terminus (N-terminus) and a carboxy terminus (C-terminus); and the C-terminus of the IL-2Rα ligand is fused through a peptide bond to the N-terminus of the peptide linker domain, and the C-terminus of the peptide linker domain is fused to a protein fusion partner.

Aspect 868. The compound of aspect 867, wherein the protein fusion partner comprises an IgG molecule, an IgG Fab fragment, or an Fc fragment, Aspect 868. The compound of any one of aspects 867 to 868, wherein the protein fusion partner comprises IL-2, a variant of IL-2, a mutant of IL-2, or an IL-2R agonist.

Aspect 870. The compound of aspect 865, wherein, each peptide linker domain has an amino-terminus (N-terminus) and a carboxy terminus (C-terminus); and the N-terminus of the IL-2Rα ligand is fused through a peptide bond to the C-terminus of the peptide linker domain, and the N-terminus of the peptide linker domain is fused to a protein fusion partner.

Aspect 871. The compound of aspect 870 wherein the protein fusion partner comprises an IgG molecule, an IgG Fab fragment, or an Fc fragment, Aspect 872. The compound of any one of aspects 870 to 871, wherein the protein fusion partner comprises IL-2, a variant of IL-2, a mutant of IL-2, or an IL-2R agonist.

Aspect 873. A nucleic acid encoding the fusion protein of aspect 865.

Aspect 874. The compound of any one of aspects 822 to 872, wherein the compound comprises a label.

Aspect 875. The compound of aspect 874, wherein the label is selected from a radioisotope, a fluorophore, or a combination thereof.

Aspect 876. The compound of any one of aspects 822 to 875, wherein the compound comprises a cage to protect peripheral tissues for the toxicity of IL-2R activation.

Aspect 877. The compound of any one of aspects 822 to 876, wherein the compound comprises a promoiety.

Aspect 878. The compound of aspect 877, wherein the promoiety comprises a moiety configured to sustain a circulating reservoir of the compound.

Aspect 879. The compound of any one of aspects 822 to 878, wherein the compound comprises a moiety configured to target IL-2R-directed immuno-stimulation of the effector immune cells in the tumor.

Aspect 880. The compound of any one of aspects 822 to 879, wherein the compound comprises a cleavable moiety.

Aspect 881. The compound of aspect 880, wherein the cleavable moiety is cleavable by electromagnetic radiation, thermal energy, pH, or a combination of any of the foregoing.

Aspect 882. The compound of any one of aspects 822 to 881, wherein the compound comprises a moiety that is toxic to cells having high IL-2Rα expression.

Aspect 883. The compound of aspect 882, wherein the cells having high IL-2Rα expression are Treg cells.

Aspect 884. The compound of aspect 882, wherein the toxic moiety is a cleavable moiety.

Aspect 885. The compound of aspect 884, the cleavable moiety is cleavable by electromagnetic radiation, thermal energy, pH, or a combination of any of the foregoing.

Aspect 886. The compound of any one of aspects 882 to 885, wherein the toxic moiety is activated by electromagnetic radiation, thermal energy, pH, or a combination of any of the foregoing.

Aspect 887. The compound of any one of aspects 822 to 886, wherein the compound comprises an imaging agent, a diagnostic agent, a targeting agent, a therapeutic agent, or a combination of any of the foregoing.

Aspect 888. A pharmaceutical composition comprising;
the IL-2Rα ligand of any one of aspects 1 to 821;
a compound of any one of aspects 822 to 887; or
a combination of any of the foregoing.

Aspect 889. A method of treating cancer in a patient, comprising administering to a patient in need of such treatment, a therapeutically effective amount of the pharmaceutical composition of aspect 880.

Aspect 890. A method of treating cancer in a patient, comprising administering to a patient in need of such treatment, a therapeutically effective amount of;
the IL-2Rα ligand of any one of aspects 1 to 821;
the compound of any one of aspects 822 to 887; or
a combination of any of the foregoing.

Aspect 891. The method of any one of aspects 889 and 890, wherein the cancer comprises a solid tumor.

Aspect 892. A method of treating an autoimmune disease in a patient, comprising administering to a patient in need of such treatment, a therapeutically effective amount of the pharmaceutical composition of aspect 888.

Aspect 893. A method of treating an autoimmune disease in a patient, comprising administering to a patient in need of such treatment, a therapeutically effective amount of;
the IL-2Rα ligand of any one of aspects 1 to 821;
the compound of any one of aspects 822 to 887; or
a combination of any of the foregoing.

Aspect 894. A method of treating an autoimmune disease in a patient, comprising administering to a patient in need of such treatment, a therapeutically effective amount of the pharmaceutical composition of aspect 888.

Aspect 895. A method of treating an autoimmune disease in a patient, comprising administering to a patient in need of such treatment, a therapeutically effective amount of;
the IL-2Rα ligand of any one of aspects 1 to 821;
the compound of any one of aspects 822 to 8887; or
a combination of any of the foregoing.

Aspect 896. A method of screening compounds for IL-2α activity, comprising:
contacting a cell with,
the IL-2Rα ligand of any one of aspects 1 to 821;
the compound of any one of aspects 822 to 887; or
a combination of any of the foregoing.
wherein the cell expresses the IL-2α subunit; and
contacting the cell with a test compound; and
determining the activity of the test compound.

Aspect 897. A method of activating the human IL-2 receptor, comprising contacting a cell expressing the human IL-2 receptor in vivo with the IL-2Rα ligand of any one of aspects 1 to 821 or a compound comprising the IL-2Rα ligand of any one of aspects 1 to 821.

Aspect 898. A method of activating the human IL-2 receptor in a patient, comprising administering to a patient an effective amount of the IL-2Rα ligand of any one of aspects 1 to 821 or a compound comprising the IL-2Rα ligand of any one of aspects 1 to 821.

Aspect 899. A method of treating a disease in a patient, wherein the IL-2 receptor signaling pathway is associated with the etiology of the disease, comprising administering to a patient in need of such treatment a therapeutically effective amount of the IL-2Rα ligand of any one of aspects 1 to 821 or a compound comprising the IL-2Rα ligand of any one of aspects 1 to 821.

Aspect 900. A method of treating a disease in a patient, wherein activation of the IL-2 receptor is effective in treating the disease, comprising administering to a patient in need of such treatment a therapeutically effective amount of the IL-2Rα ligand of any one of aspects 1 to 821 or a compound comprising the IL-2Rα ligand of any one of aspects 1 to 821.

Aspect 901. A method of treating a disease in a patient, wherein inhibition of the IL-2 receptor is effective in treating the disease, comprising administering to a patient in need of such treatment a therapeutically effective amount the IL-2Rα ligand of any one of aspects 1 to 821 or of a compound comprising the IL-2Rα ligand of any one of aspects 1 to 821.

Aspect 902. A method of treating a disease in a patient, wherein cells expressing the IL-2Rα subunit (CD25) are associated with the etiology of the disease, comprising administering to a patient in need of such treatment a therapeutically effective amount of the IL-2Rα ligand of any one of aspects 1 to 821 or a compound comprising the IL-2Rα ligand of any one of aspects 1 to 821.

Aspect 903. A method of treating a disease in a patient, wherein binding to the IL-2Rα subunit (CD25) is effective in treating the disease, comprising administering to a patient in need of such treatment a therapeutically effective amount the IL-2Rα ligand of any one of aspects 1 to 821 or of a compound comprising the IL-2Rα ligand of any one of aspects 1 to 821.

Aspect 904. A method of treating a disease in a patient, wherein inhibiting binding of an IL-2R agonist to the IL-2Rα subunit (CD25) is effective in treating the disease, comprising administering to a patient in need of such treatment a therapeutically effective amount of the IL-2Rα ligand of any one of aspects 1 to 821 or a compound comprising the IL-2Rα ligand of any one of aspects 1 to 821.

Aspect 905. A method of treating a disease in a patient, wherein reducing the sensitivity of Treg cells to IL-2 is effective in treating the disease, comprising administering to a patient in need of such treatment a therapeutically effective amount of the IL-2Rα ligand of any one of aspects 1 to 821 or a compound comprising the IL-2Rα ligand of any one of aspects 1 to 821.

Aspect 906. A method of treating a disease in a patient, wherein inhibiting binding to the IL-2Rα subunit (CD25) is effective in treating the disease, comprising administering to a patient in need of such treatment a therapeutically effective amount of the IL-2Rα ligand of any one of aspects 1 to 821 or a compound comprising the IL-2Rα ligand of any one of aspects 1 to 821.

Aspect 907. A method of treating a disease in a patient, wherein the etiology of the disease is associated with activation of Treg cells, comprising administering to a patient in need of such treatment a therapeutically effective amount of the IL-2Rα ligand of any one of aspects 1 to 821 or a compound comprising the IL-2Rα ligand of any one of aspects 1 to 821.

Aspect 908. A method of treating a disease in a patient, wherein the etiology of the disease is associated with cells exhibiting a high IL-2Rα expression, comprising administering to a patient in need of such treatment a therapeutically effective amount of the IL-2Rα ligand of any one of aspects 1 to 821 or a compound comprising the IL-2Rα ligand of any one of aspects 1 to 821.

Aspect 909. A method of imaging cells expressing the IL-2Rα subunit comprising administering to a patient an effective amount of the IL-2Rα ligand of any one of aspects 1 to 821 or a compound comprising the IL-2Rα ligand of any one of aspects 1 to 821.

Aspect 910. A method of diagnosing a disease in a patient wherein the disease is associated with cells expressing the IL-2Rα subunit comprising administering to a patient an effective amount of the IL-2Rα ligand of any one of aspects 1 to 821 or a compound comprising the IL-2Rα ligand of any one of aspects 1 to 821.

Aspect 911. A method of targeting a compound to cells expressing the IL-2Rα subunit comprising administering to a patient an effective amount of the IL-2Rα ligand of any one of aspects 1 to 821 or a compound comprising the IL-2Rα ligand of any one of aspects 1 to 821.

Aspect 912. A method of delivering a cytotoxic compound to cells expressing the IL-2Rα subunit comprising administering to a patient an effective amount of the IL-2Rα ligand of any one of aspects 1 to 821 or a compound comprising a cytotoxic moiety and the IL-2Rα ligand of any one of aspects 1 to 821.

Aspect 913. The method of any one of aspects 897 to 912, wherein the compound comprises the compound of any one of aspects 822 to 887.

Finally, it should be noted that there are alternative ways of implementing the embodiments disclosed herein. Accordingly, the present embodiments are to be considered as illustrative and not restrictive, and the claims are not to be limited to the details given herein but may be modified within the scope and equivalents thereof.

What is claimed is:

1. An IL-2Rα ligand, wherein, the IL-2Rα ligand binds to the human IL-2Rα subunit with an $IC_{50}$ of less than 100 μM; and the IL-2Rα ligand comprises an amino acid sequence selected from any one of SEQ ID NOS: 4, 9, 24, 31, 44, 50, 67, 79, 100, 112, 135, 144, 154, 172, 180, 203, 210, 219, 234, 250, and 418:

```
                                     SEQ ID NO: 4
F L H W P V Y F C Q V M

SEQ ID NO: 9
F I P W D E Y F K Q V L

SEQ ID NO: 24
F V H C T L L G C W S G

SEQ ID NO: 31
W V I C S A V G C R P F

SEQ ID NO: 44
H V I C S V N G G C R G

SEQ ID NO: 50
E Q F C L V S D P M A C W S L

SEQ ID NO: 67
R R F C L R S E P A A C W F V

SEQ ID NO: 79
S K C V Y D Y N F G T C I F

SEQ ID NO: 100
S L N C K T R P G L R W C T W T

SEQ ID NO: 112
A W E C L F L P G H R G C S L F

SEQ ID NO: 135
R Q F C L V S P G Y E D C W F V

SEQ ID NO: 144
S A C Q L K W D E G W T C L F

SEQ ID NO: 154
R G C S L V W S G S W E C I F

SEQ ID NO: 172
G C T L S W N Q G W W H C V

SEQ ID NO: 180
A R C S L H H T G S R Y E C I F

SEQ ID NO: 203
T C R L K R S G P N S W E C I

SEQ ID NO: 210
V R C R L A R P G L T W E C L S

SEQ ID NO: 219
Q L C P W S D P G S W G P C P L

SEQ ID NO: 234
G C Q L V W Q D D S Y M C F Y

SEQ ID NO: 250
W C I G Q P L F R Q G S C K

SEQ ID NO: 418
F V P W D V Y F S Q I L G G.
```

2. The IL-2Rα ligand of claim 1, wherein the IL-2Rα ligand comprises the amino acid sequence of SEQ ID NO: 4.

3. The IL-2Rα ligand of claim 1, wherein the IL-2Rα ligand comprises the amino acid sequence of SEQ ID NO: 9.

4. The IL-2Rα ligand of claim 1, wherein the IL-2Rα ligand comprises the amino acid sequence of SEQ ID NO: 24.

5. The IL-2Rα ligand of claim 1, wherein the IL-2Rα ligand comprises the amino acid sequence of SEQ ID NO: 31.

6. The IL-2Rα ligand of claim 1, wherein the IL-2Rα ligand comprises the amino acid sequence of SEQ ID NO: 44.

7. The IL-2Rα ligand of claim 1, wherein the IL-2Rα ligand comprises the amino acid sequence of SEQ ID NO: 50.

8. The IL-2Rα ligand of claim 1, wherein the IL-2Rα ligand comprises the amino acid sequence of SEQ ID NO: 67.

9. The IL-2Rα ligand of claim 1, wherein the IL-2Rα ligand comprises the amino acid sequence of SEQ ID NO: 79.

10. The IL-2Rα ligand of claim 1, wherein the IL-2Rα ligand comprises the amino acid sequence of SEQ ID NO: 100.

11. The IL-2Rα ligand of claim 1, wherein the IL-2Rα ligand comprises the amino acid sequence of SEQ ID NO: 112.

12. The IL-2Rα ligand of claim 1, wherein the IL-2Rα ligand comprises the amino acid sequence of SEQ ID NO: 135.

13. The IL-2Rα ligand of claim 1, wherein the IL-2Rα ligand comprises the amino acid sequence of SEQ ID NO: 144.

14. The IL-2Rα ligand of claim 1, wherein the IL-2Rα ligand comprises the amino acid sequence of SEQ ID NO: 154.

15. The IL-2Rα ligand of claim 1, wherein the IL-2Rα ligand comprises the amino acid sequence of SEQ ID NO: 172.

16. The IL-2Rα ligand of claim 1, wherein the IL-2Rα ligand comprises the amino acid sequence of SEQ ID NO: 180.

17. The IL-2Rα ligand of claim 1, wherein the IL-2Rα ligand comprises the amino acid sequence of SEQ ID NO: 203.

18. The IL-2Rα ligand of claim 1, wherein the IL-2Rα ligand comprises the amino acid sequence of SEQ ID NO: 210.

19. The IL-2Rα ligand of claim 1, wherein the IL-2Rα ligand comprises the amino acid sequence of SEQ ID NO: 219.

20. The IL-2Rα ligand of claim 1, wherein the IL-2Rα ligand comprises the amino acid sequence of SEQ ID NO: 234.

21. The IL-2Rα ligand of claim 1, wherein the IL-2Rα ligand comprises the amino acid sequence of SEQ ID. NO: 250.

22. The IL-2Rα ligand of claim 1, wherein the IL-2Rα ligand comprises the amino acid sequence of SEQ ID. NO: 418.

23. A compound comprising at least one IL-2Rα ligand of claim 1.

24. The compound of claim 23, wherein the compound is selected from a peptide, a conjugate, and a fusion protein.

25. A pharmaceutical composition comprising the IL-2Rα ligand of claim 1.

26. A pharmaceutical composition comprising the compound of claim 23.

* * * * *

SEQUENCE LISTING

<160> NUMBER OF SEQ ID NOS: 1041

<210> SEQ ID NO 1
<211> LENGTH: 12
<212> TYPE: PRT
<213> ORGANISM: Artificial Sequence
<220> FEATURE:
<223> OTHER INFORMATION: Description of Artificial Sequence: Synthetic

```
        peptide
<220> FEATURE:
<221> NAME/KEY: MOD_RES
<222> LOCATION: (1)..(1)
<223> OTHER INFORMATION: Any amino acid comprising a large hydrophobic
      side chain or an aromatic side chain
<220> FEATURE:
<221> NAME/KEY: MOD_RES
<222> LOCATION: (2)..(2)
<223> OTHER INFORMATION: Any amino acid comprising a large hydrophobic
      side chain
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (4)..(4)
<223> OTHER INFORMATION: Any amino acid comprising a large hydrophobic
      side chain
<220> FEATURE:
<221> NAME/KEY: MOD_RES
<222> LOCATION: (5)..(5)
<223> OTHER INFORMATION: Any amino acid comprising a small hydrophobic
      side chain or a polar/neutral side chain
<220> FEATURE:
<221> NAME/KEY: MOD_RES
<222> LOCATION: (6)..(6)
<223> OTHER INFORMATION: Any amino acid comprising a large hydrophobic
      side chain
<220> FEATURE:
<221> NAME/KEY: MOD_RES
<222> LOCATION: (7)..(7)
<223> OTHER INFORMATION: Any amino acid comprising a large hydrophobic
      side chain
<220> FEATURE:
<221> NAME/KEY: MOD_RES
<222> LOCATION: (8)..(8)
<223> OTHER INFORMATION: Any amino acid comprising a large hydrophobic
      side chain
<220> FEATURE:
<221> NAME/KEY: MOD_RES
<222> LOCATION: (9)..(9)
<223> OTHER INFORMATION: Any amino acid comprising a small hydrophobic
      side chain
<220> FEATURE:
<221> NAME/KEY: MOD_RES
<222> LOCATION: (10)..(10)
<223> OTHER INFORMATION: Any amino acid comprising a polar/neutral side
      chain
<220> FEATURE:
<221> NAME/KEY: MOD_RES
<222> LOCATION: (11)..(11)
<223> OTHER INFORMATION: Any amino acid comprising a large hydrophobic
      side chain
<220> FEATURE:
<221> NAME/KEY: MOD_RES
<222> LOCATION: (12)..(12)
<223> OTHER INFORMATION: Any amino acid comprising a large hydrophobic
      side chain

<400> SEQUENCE: 1

Xaa Xaa Xaa Xaa Xaa Xaa Xaa Xaa Xaa Xaa Xaa Xaa
1               5                   10

<210> SEQ ID NO 2
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Leu Asp Leu Thr Tyr Asp Glu Leu Leu Ala Cys Thr
1               5                   10
```

<210> SEQ ID NO 3
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Trp Ala Tyr Asp Trp Ser Cys Phe Arg Arg Arg Leu
1               5                   10

<210> SEQ ID NO 4
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Phe Leu His Trp Pro Val Tyr Phe Cys Gln Val Met
1               5                   10

<210> SEQ ID NO 5
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Phe Leu Pro Trp Pro Val Tyr Phe Ser Gln Val Leu
1               5                   10

<210> SEQ ID NO 6
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Phe Val Glu Trp Gln Ala Tyr Phe Ser Gln Met Met
1               5                   10

<210> SEQ ID NO 7
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid comprising a large hydrophobic
      side chain
<220> FEATURE:
<221> NAME/KEY: MOD_RES
<222> LOCATION: (2)..(2)
<223> OTHER INFORMATION: Any amino acid comprising a large hydrophobic
      side chain
<220> FEATURE:
<221> NAME/KEY: MOD_RES
<222> LOCATION: (3)..(3)
<223> OTHER INFORMATION: Any amino acid comprising a small hydrophobic -continued

```
      side chain
<220> FEATURE:
<221> NAME/KEY: MOD_RES
<222> LOCATION: (4)..(4)
<223> OTHER INFORMATION: Any amino acid comprising a large hydrophobic
      side chain
<220> FEATURE:
<221> NAME/KEY: MOD_RES
<222> LOCATION: (5)..(5)
<223> OTHER INFORMATION: Any amino acid comprising an acidic side chain
<220> FEATURE:
<221> NAME/KEY: MOD_RES
<222> LOCATION: (6)..(6)
<223> OTHER INFORMATION: Any amino acid comprising an acidic side chain
<220> FEATURE:
<221> NAME/KEY: MOD_RES
<222> LOCATION: (7)..(7)
<223> OTHER INFORMATION: Any amino acid comprising a large hydrophobic
      side chain
<220> FEATURE:
<221> NAME/KEY: MOD_RES
<222> LOCATION: (8)..(8)
<223> OTHER INFORMATION: Any amino acid comprising a large hydrophobic
      side chain
<220> FEATURE:
<221> NAME/KEY: MOD_RES
<222> LOCATION: (9)..(9)
<223> OTHER INFORMATION: Any amino acid
<220> FEATURE:
<221> NAME/KEY: MOD_RES
<222> LOCATION: (10)..(10)
<223> OTHER INFORMATION: Any amino acid comprising a polar/neutral side
      chain
<220> FEATURE:
<221> NAME/KEY: MOD_RES
<222> LOCATION: (11)..(11)
<223> OTHER INFORMATION: Any amino acid comprising a large hydrophobic
      side chain
<220> FEATURE:
<221> NAME/KEY: MOD_RES
<222> LOCATION: (12)..(12)
<223> OTHER INFORMATION: Any amino acid comprising a large hydrophobic
      side chain

<400> SEQUENCE: 7

Xaa Xaa Xaa Xaa Xaa Xaa Xaa Xaa Xaa Xaa Xaa Xaa
1               5                   10

<210> SEQ ID NO 8
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Phe Ile Pro Trp Asp Glu Tyr Phe Ala Gln Leu Leu
1               5                   10

<210> SEQ ID NO 9
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Phe Ile Pro Trp Asp Glu Tyr Phe Lys Gln Val Leu
1               5                   10

<210> SEQ ID NO 10
```

```
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Phe Val Pro Trp Asp Val Tyr Phe Ser Gln Ile Leu
1               5                   10

<210> SEQ ID NO 11
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Phe Ile Pro Trp Asp Glu Tyr Phe Lys Gln Val Leu
1               5                   10

<210> SEQ ID NO 12
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Phe Val Pro Trp Pro Glu Tyr Phe Leu Gln Ile Met
1               5                   10

<210> SEQ ID NO 13
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Phe Ile Pro Trp Glu Glu Tyr Phe Ser Gln Leu Leu
1               5                   10

<210> SEQ ID NO 14
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Phe Ile Pro Trp Pro Glu Tyr Phe Ser Gln Leu Leu
1               5                   10

<210> SEQ ID NO 15
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15
```

Phe Val Pro Trp Asp Glu Tyr Phe Leu Gln Ile Leu
1               5                   10

<210> SEQ ID NO 16
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid comprising a small hydrophobic
      side chain
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (4)..(4)
<223> OTHER INFORMATION: Any amino acid comprising a small hydrophobic
      side chain

<400> SEQUENCE: 16

Xaa Xaa Xaa Xaa
1

<210> SEQ ID NO 17
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (3)..(3)
<223> OTHER INFORMATION: Any amino acid comprising a small hydrophobic
      side chain
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (5)..(5)
<223> OTHER INFORMATION: Any amino acid
<220> FEATURE:
<221> NAME/KEY: MOD_RES
<222> LOCATION: (6)..(6)
<223> OTHER INFORMATION: Any amino acid comprising a small hydrophobic
      side chain
<220> FEATURE:
<221> NAME/KEY: MOD_RES
<222> LOCATION: (8)..(8)
<223> OTHER INFORMATION: Any amino acid comprising a basic side chain or
      a polar/neutral side chain

<400> SEQUENCE: 17

Xaa Cys Xaa Xaa Xaa Xaa Cys Xaa
1               5

<210> SEQ ID NO 18
<211> LENGTH: 12

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid comprising a large hydrophobic
      side chain
<220> FEATURE:
<221> NAME/KEY: MOD_RES
<222> LOCATION: (2)..(2)
<223> OTHER INFORMATION: Any amino acid comprising a large hydrophobic
      side chain
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (5)..(5)
<223> OTHER INFORMATION: Any amino acid comprising a small hydrophobic
      side chain
<220> FEATURE:
<221> NAME/KEY: MOD_RES
<222> LOCATION: (6)..(6)
<223> OTHER INFORMATION: Any amino acid
<220> FEATURE:
<221> NAME/KEY: MOD_RES
<222> LOCATION: (7)..(7)
<223> OTHER INFORMATION: Any amino acid
<220> FEATURE:
<221> NAME/KEY: MOD_RES
<222> LOCATION: (8)..(8)
<223> OTHER INFORMATION: Any amino acid comprising a small hydrophobic
      side chain
<220> FEATURE:
<221> NAME/KEY: MOD_RES
<222> LOCATION: (10)..(10)
<223> OTHER INFORMATION: Any amino acid comprising a basic side chain or
      a polar/neutral side chain
<220> FEATURE:
<221> NAME/KEY: MOD_RES
<222> LOCATION: (11)..(11)
<223> OTHER INFORMATION: Any amino acid comprising a small hydrophobic
      side chain
<220> FEATURE:
<221> NAME/KEY: MOD_RES
<222> LOCATION: (12)..(12)
<223> OTHER INFORMATION: Any amino acid

<400> SEQUENCE: 18

Xaa Xaa Xaa Cys Xaa Xaa Xaa Xaa Cys Xaa Xaa Xaa
1               5                   10

<210> SEQ ID NO 19
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Phe Val Leu Cys Gly Leu Gln Gly Cys Arg Gly Ser
1               5                   10

<210> SEQ ID NO 20
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 20

Lys Val Ile Cys Gly Trp Asp Gly Cys Arg
1               5                   10

<210> SEQ ID NO 21
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Leu Val Phe Cys Gly Lys Asn Gly Cys His Ser Gly
1               5                   10

<210> SEQ ID NO 22
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Val Val Leu Cys Thr Pro Lys Gly Cys Arg Ser Ala
1               5                   10

<210> SEQ ID NO 23
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Tyr Val Met Cys Ser Ala Phe Gly Cys Lys Ser Ile
1               5                   10

<210> SEQ ID NO 24
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Phe Val His Cys Thr Leu Leu Gly Cys Trp Ser Gly
1               5                   10

<210> SEQ ID NO 25
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid comprising a small hydrophobic
      side chain
<220> FEATURE:
<221> NAME/KEY: MOD_RES
<222> LOCATION: (2)..(2)
<223> OTHER INFORMATION: Any amino acid comprising a small hydrophobic
```

```
      side chain
<220> FEATURE:
<221> NAME/KEY: MOD_RES
<222> LOCATION: (3)..(3)
<223> OTHER INFORMATION: Any amino acid comprising a large hydrophobic
      side chain
<220> FEATURE:
<221> NAME/KEY: MOD_RES
<222> LOCATION: (4)..(4)
<223> OTHER INFORMATION: Any amino acid comprising a small hydrophobic
      side chain

<400> SEQUENCE: 25

Xaa Xaa Xaa Xaa Cys
1               5

<210> SEQ ID NO 26
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid comprising a large hydrophobic
      side chain
<220> FEATURE:
<221> NAME/KEY: MOD_RES
<222> LOCATION: (3)..(3)
<223> OTHER INFORMATION: Any amino acid comprising a small hydrophobic
      side chain
<220> FEATURE:
<221> NAME/KEY: MOD_RES
<222> LOCATION: (4)..(4)
<223> OTHER INFORMATION: Any amino acid comprising a small hydrophobic
      side chain
<220> FEATURE:
<221> NAME/KEY: MOD_RES
<222> LOCATION: (5)..(5)
<223> OTHER INFORMATION: Any amino acid comprising a large hydrophobic
      side chain
<220> FEATURE:
<221> NAME/KEY: MOD_RES
<222> LOCATION: (6)..(6)
<223> OTHER INFORMATION: Any amino acid comprising a small hydrophobic
      side chain
<220> FEATURE:
<221> NAME/KEY: MOD_RES
<222> LOCATION: (8)..(8)
<223> OTHER INFORMATION: Any amino acid comprising a basic side chain

<400> SEQUENCE: 26

Xaa Cys Xaa Xaa Xaa Xaa Cys Xaa
1               5

<210> SEQ ID NO 27
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid comprising a large hydrophobic
      side chain
<220> FEATURE:
<221> NAME/KEY: MOD_RES
<222> LOCATION: (2)..(2)
<223> OTHER INFORMATION: Any amino acid comprising a large hydrophobic
      side chain
<220> FEATURE:
```

```
<221> NAME/KEY: MOD_RES
<222> LOCATION: (4)..(4)
<223> OTHER INFORMATION: Any amino acid comprising a small hydrophobic
      side chain
<220> FEATURE:
<221> NAME/KEY: MOD_RES
<222> LOCATION: (5)..(5)
<223> OTHER INFORMATION: Any amino acid comprising a small hydrophobic
      side chain
<220> FEATURE:
<221> NAME/KEY: MOD_RES
<222> LOCATION: (6)..(6)
<223> OTHER INFORMATION: Any amino acid comprising a large hydrophobic
      side chain
<220> FEATURE:
<221> NAME/KEY: MOD_RES
<222> LOCATION: (7)..(7)
<223> OTHER INFORMATION: Any amino acid comprising a small hydrophobic
      side chain
<220> FEATURE:
<221> NAME/KEY: MOD_RES
<222> LOCATION: (9)..(9)
<223> OTHER INFORMATION: Any amino acid comprising a basic side chain
<220> FEATURE:
<221> NAME/KEY: MOD_RES
<222> LOCATION: (10)..(10)
<223> OTHER INFORMATION: Any amino acid comprising a small hydrophobic
      side chain

<400> SEQUENCE: 27

Xaa Xaa Cys Xaa Xaa Xaa Xaa Cys Xaa Xaa
1               5                   10

<210> SEQ ID NO 28
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid comprising a large hydrophobic
      side chain
<220> FEATURE:
<221> NAME/KEY: MOD_RES
<222> LOCATION: (2)..(2)
<223> OTHER INFORMATION: Any amino acid comprising a large hydrophobic
      side chain
<220> FEATURE:
<221> NAME/KEY: MOD_RES
<222> LOCATION: (3)..(3)
<223> OTHER INFORMATION: Any amino acid comprising a large hydrophobic
      side chain
<220> FEATURE:
<221> NAME/KEY: MOD_RES
<222> LOCATION: (5)..(5)
<223> OTHER INFORMATION: Any amino acid comprising a small hydrophobic
      side chain
<220> FEATURE:
<221> NAME/KEY: MOD_RES
<222> LOCATION: (6)..(6)
<223> OTHER INFORMATION: Any amino acid comprising a small hydrophobic
      side chain
<220> FEATURE:
<221> NAME/KEY: MOD_RES
<222> LOCATION: (7)..(7)
<223> OTHER INFORMATION: Any amino acid comprising a large hydrophobic
      side chain
<220> FEATURE:
<221> NAME/KEY: MOD_RES
<222> LOCATION: (8)..(8)
<223> OTHER INFORMATION: Any amino acid comprising a small hydrophobic
      side chain
<220> FEATURE:
<221> NAME/KEY: MOD_RES
```

```
<222> LOCATION: (10)..(10)
<223> OTHER INFORMATION: Any amino acid comprising a basic side chain
<220> FEATURE:
<221> NAME/KEY: MOD_RES
<222> LOCATION: (11)..(11)
<223> OTHER INFORMATION: Any amino acid comprising a small hydrophobic
      side chain
<220> FEATURE:
<221> NAME/KEY: MOD_RES
<222> LOCATION: (12)..(12)
<223> OTHER INFORMATION: Any amino acid comprising a large hydrophobic
      side chain

<400> SEQUENCE: 28

Xaa Xaa Xaa Cys Xaa Xaa Xaa Xaa Cys Xaa Xaa Xaa
1               5                   10

<210> SEQ ID NO 29
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Trp Val Ile Cys Ser Ala Leu Gly Cys Arg Ser Leu
1               5                   10

<210> SEQ ID NO 30
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Trp Val Ile Cys Ser Ala Leu Gly Cys Arg Ser Met
1               5                   10

<210> SEQ ID NO 31
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Trp Val Ile Cys Ser Ala Val Gly Cys Arg Pro Phe
1               5                   10

<210> SEQ ID NO 32
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Trp Val Ile Cys Ser Ala Met Gly Cys Arg Ser Ile
1               5                   10

<210> SEQ ID NO 33
<211> LENGTH: 12
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 33

Trp Val Ile Cys Ser Ala Leu Gly Cys Arg Ser Ile
1               5                   10

<210> SEQ ID NO 34
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Trp Val Ile Cys Ser Ala Phe Gly Cys Arg Ser Met
1               5                   10

<210> SEQ ID NO 35
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Trp Val Ile Cys Ser Ala Leu Gly Cys Arg Pro Phe
1               5                   10

<210> SEQ ID NO 36
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Trp Val Ile Cys Ser Ala Leu Gly Cys Lys Ala Trp
1               5                   10

<210> SEQ ID NO 37
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid comprising a small hydrophobic
      side chain or an acidic side chain
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (5)..(5)
```

```
<223> OTHER INFORMATION: Any amino acid comprising a small hydrophobic
      side chain

<400> SEQUENCE: 37

Xaa Xaa Xaa Xaa Xaa
1               5

<210> SEQ ID NO 38
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid comprising a large hydrophobic
      side chain
<220> FEATURE:
<221> NAME/KEY: MOD_RES
<222> LOCATION: (3)..(3)
<223> OTHER INFORMATION: Any amino acid comprising a small hydrophobic
      side chain or an acidic side chain
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (5)..(5)
<223> OTHER INFORMATION: Any amino acid
<220> FEATURE:
<221> NAME/KEY: MOD_RES
<222> LOCATION: (6)..(6)
<223> OTHER INFORMATION: Any amino acid
<220> FEATURE:
<221> NAME/KEY: MOD_RES
<222> LOCATION: (7)..(7)
<223> OTHER INFORMATION: Any amino acid comprising a small hydrophobic
      side chain
<220> FEATURE:
<221> NAME/KEY: MOD_RES
<222> LOCATION: (9)..(9)
<223> OTHER INFORMATION: Any amino acid comprising a basic side chain

<400> SEQUENCE: 38

Xaa Cys Xaa Xaa Xaa Xaa Xaa Cys Xaa
1               5

<210> SEQ ID NO 39
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid comprising a large hydrophobic
      side chain
<220> FEATURE:
<221> NAME/KEY: MOD_RES
<222> LOCATION: (3)..(3)
<223> OTHER INFORMATION: Any amino acid comprising a small hydrophobic
      side chain or an acidic side chain
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (5)..(5)
<223> OTHER INFORMATION: Any amino acid
```

```
<220> FEATURE:
<221> NAME/KEY: MOD_RES
<222> LOCATION: (6)..(6)
<223> OTHER INFORMATION: Any amino acid
<220> FEATURE:
<221> NAME/KEY: MOD_RES
<222> LOCATION: (7)..(7)
<223> OTHER INFORMATION: Any amino acid comprising a small hydrophobic
      side chain
<220> FEATURE:
<221> NAME/KEY: MOD_RES
<222> LOCATION: (9)..(9)
<223> OTHER INFORMATION: Any amino acid comprising a basic side chain
<220> FEATURE:
<221> NAME/KEY: MOD_RES
<222> LOCATION: (10)..(10)
<223> OTHER INFORMATION: Any amino acid

<400> SEQUENCE: 39

Xaa Cys Xaa Xaa Xaa Xaa Xaa Cys Xaa Xaa
1               5                   10

<210> SEQ ID NO 40
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid comprising an aromatic side
      chain or a large hydrophobic side chain
<220> FEATURE:
<221> NAME/KEY: MOD_RES
<222> LOCATION: (2)..(2)
<223> OTHER INFORMATION: Any amino acid comprising a large hydrophobic
      side chain
<220> FEATURE:
<221> NAME/KEY: MOD_RES
<222> LOCATION: (3)..(3)
<223> OTHER INFORMATION: Any amino acid comprising a large hydrophobic
      side chain
<220> FEATURE:
<221> NAME/KEY: MOD_RES
<222> LOCATION: (5)..(5)
<223> OTHER INFORMATION: Any amino acid comprising a small hydrophobic
      side chain or an acidic side chain
<220> FEATURE:
<221> NAME/KEY: MOD_RES
<222> LOCATION: (6)..(6)
<223> OTHER INFORMATION: Any amino acid
<220> FEATURE:
<221> NAME/KEY: MOD_RES
<222> LOCATION: (7)..(7)
<223> OTHER INFORMATION: Any amino acid
<220> FEATURE:
<221> NAME/KEY: MOD_RES
<222> LOCATION: (8)..(8)
<223> OTHER INFORMATION: Any amino acid
<220> FEATURE:
<221> NAME/KEY: MOD_RES
<222> LOCATION: (9)..(9)
<223> OTHER INFORMATION: Any amino acid comprising a small hydrophobic
      side chain
<220> FEATURE:
<221> NAME/KEY: MOD_RES
<222> LOCATION: (11)..(11)
<223> OTHER INFORMATION: Any amino acid comprising a basic side chain
<220> FEATURE:
<221> NAME/KEY: MOD_RES
<222> LOCATION: (12)..(12)
<223> OTHER INFORMATION: Any amino acid

<400> SEQUENCE: 40
```

```
Xaa Xaa Xaa Cys Xaa Xaa Xaa Xaa Xaa Cys Xaa Xaa
1               5                   10

<210> SEQ ID NO 41
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Tyr Val Leu Cys Ser Asn Arg Asn Gly Cys Arg Pro
1               5                   10

<210> SEQ ID NO 42
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Tyr Val Thr Cys Arg Trp Gly Tyr Gly Cys Thr Arg
1               5                   10

<210> SEQ ID NO 43
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Trp Val Ala Cys Ser Trp Asp His Gly Cys Arg Ser
1               5                   10

<210> SEQ ID NO 44
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

His Val Ile Cys Ser Val Asn Gly Gly Cys Arg Gly
1               5                   10

<210> SEQ ID NO 45
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Any amino acid

<400> SEQUENCE: 45

Trp Val Xaa Cys Lys Pro Leu His Gly Cys Tyr Gly
1               5                   10

<210> SEQ ID NO 46
```

```
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid comprising a large hydrophobic
      side chain
<220> FEATURE:
<221> NAME/KEY: MOD_RES
<222> LOCATION: (2)..(2)
<223> OTHER INFORMATION: Any amino acid comprising a basic side chain
<220> FEATURE:
<221> NAME/KEY: MOD_RES
<222> LOCATION: (3)..(3)
<223> OTHER INFORMATION: Any amino acid comprising a small hydrophobic
      side chain or a polar neutral side chain
<220> FEATURE:
<221> NAME/KEY: MOD_RES
<222> LOCATION: (4)..(4)
<223> OTHER INFORMATION: Any amino acid comprising an acidic side chain
<220> FEATURE:
<221> NAME/KEY: MOD_RES
<222> LOCATION: (5)..(5)
<223> OTHER INFORMATION: Any amino acid comprising a small hydrophobic
      side chain
<220> FEATURE:
<221> NAME/KEY: MOD_RES
<222> LOCATION: (6)..(6)
<223> OTHER INFORMATION: Any amino acid
<220> FEATURE:
<221> NAME/KEY: MOD_RES
<222> LOCATION: (7)..(7)
<223> OTHER INFORMATION: Any amino acid comprising a small hydrophobic
      side chain

<400> SEQUENCE: 46

Xaa Xaa Xaa Xaa Xaa Xaa Xaa
1               5

<210> SEQ ID NO 47
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid comprising a large hydrophobic
      side chain or an
      aromatic side chain
<220> FEATURE:
<221> NAME/KEY: MOD_RES
<222> LOCATION: (3)..(3)
<223> OTHER INFORMATION: Any amino acid comprising a large hydrophobic
      side chain
<220> FEATURE:
<221> NAME/KEY: MOD_RES
<222> LOCATION: (4)..(4)
<223> OTHER INFORMATION: Any amino acid comprising a basic side chain
<220> FEATURE:
<221> NAME/KEY: MOD_RES
<222> LOCATION: (5)..(5)
<223> OTHER INFORMATION: Any amino acid comprising a small hydrophobic
      side chain or a polar neutral side chain
<220> FEATURE:
<221> NAME/KEY: MOD_RES
<222> LOCATION: (6)..(6)
<223> OTHER INFORMATION: Any amino acid comprising an acidic side chain
<220> FEATURE:
<221> NAME/KEY: MOD_RES
<222> LOCATION: (7)..(7)
```

```
<223> OTHER INFORMATION: Any amino acid comprising a small hydrophobic
      side chain
<220> FEATURE:
<221> NAME/KEY: MOD_RES
<222> LOCATION: (8)..(8)
<223> OTHER INFORMATION: Any amino acid
<220> FEATURE:
<221> NAME/KEY: MOD_RES
<222> LOCATION: (9)..(9)
<223> OTHER INFORMATION: Any amino acid comprising a small hydrophobic
      side chain
<220> FEATURE:
<221> NAME/KEY: MOD_RES
<222> LOCATION: (11)..(11)
<223> OTHER INFORMATION: Any amino acid comprising an aromatic side
      chain or a large hydrophobic side chain

<400> SEQUENCE: 47

Xaa Cys Xaa Xaa Xaa Xaa Xaa Xaa Xaa Cys Xaa
1               5                   10

<210> SEQ ID NO 48
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (2)..(2)
<223> OTHER INFORMATION: Any amino acid comprising a large hydrophobic
      side chain or an aromatic side chain
<220> FEATURE:
<221> NAME/KEY: MOD_RES
<222> LOCATION: (4)..(4)
<223> OTHER INFORMATION: Any amino acid comprising a large hydrophobic
      side chain
<220> FEATURE:
<221> NAME/KEY: MOD_RES
<222> LOCATION: (5)..(5)
<223> OTHER INFORMATION: Any amino acid comprising a basic side chain
<220> FEATURE:
<221> NAME/KEY: MOD_RES
<222> LOCATION: (6)..(6)
<223> OTHER INFORMATION: Any amino acid comprising a small hydrophobic
      side chain or a polar neutral side chain
<220> FEATURE:
<221> NAME/KEY: MOD_RES
<222> LOCATION: (7)..(7)
<223> OTHER INFORMATION: Any amino acid comprising an acidic side chain
<220> FEATURE:
<221> NAME/KEY: MOD_RES
<222> LOCATION: (8)..(8)
<223> OTHER INFORMATION: Any amino acid comprising a small hydrophobic
      side chain
<220> FEATURE:
<221> NAME/KEY: MOD_RES
<222> LOCATION: (9)..(9)
<223> OTHER INFORMATION: Any amino acid
<220> FEATURE:
<221> NAME/KEY: MOD_RES
<222> LOCATION: (10)..(10)
<223> OTHER INFORMATION: Any amino acid comprising a small hydrophobic
      side chain
<220> FEATURE:
<221> NAME/KEY: MOD_RES
<222> LOCATION: (12)..(12)
<223> OTHER INFORMATION: Any amino acid comprising an aromatic side
      chain or a large hydrophobic side chain
<220> FEATURE:
<221> NAME/KEY: MOD_RES
<222> LOCATION: (13)..(13)
```

```
<223> OTHER INFORMATION: Any amino acid comprising a small hydrophobic
      side chain or a polar neutral side chain

<400> SEQUENCE: 48

Xaa Xaa Cys Xaa Xaa Xaa Xaa Xaa Xaa Cys Xaa Xaa
1               5                   10

<210> SEQ ID NO 49
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (3)..(3)
<223> OTHER INFORMATION: Any amino acid comprising a large hydrophobic
      side chain or an aromatic side chain
<220> FEATURE:
<221> NAME/KEY: MOD_RES
<222> LOCATION: (5)..(5)
<223> OTHER INFORMATION: Any amino acid comprising a large hydrophobic
      side chain
<220> FEATURE:
<221> NAME/KEY: MOD_RES
<222> LOCATION: (6)..(6)
<223> OTHER INFORMATION: Any amino acid comprising a basic side chain
<220> FEATURE:
<221> NAME/KEY: MOD_RES
<222> LOCATION: (7)..(7)
<223> OTHER INFORMATION: Any amino acid comprising a small hydrophobic
      side chain or a polar neutral side chain
<220> FEATURE:
<221> NAME/KEY: MOD_RES
<222> LOCATION: (8)..(8)
<223> OTHER INFORMATION: Any amino acid comprising an acidic side chain
<220> FEATURE:
<221> NAME/KEY: MOD_RES
<222> LOCATION: (9)..(9)
<223> OTHER INFORMATION: Any amino acid comprising a small hydrophobic
      side chain
<220> FEATURE:
<221> NAME/KEY: MOD_RES
<222> LOCATION: (10)..(10)
<223> OTHER INFORMATION: Any amino acid
<220> FEATURE:
<221> NAME/KEY: MOD_RES
<222> LOCATION: (11)..(11)
<223> OTHER INFORMATION: Any amino acid comprising a small hydrophobic
      side chain
<220> FEATURE:
<221> NAME/KEY: MOD_RES
<222> LOCATION: (13)..(13)
<223> OTHER INFORMATION: Any amino acid comprising an aromatic side
      chain or a large hydrophobic side chain
<220> FEATURE:
<221> NAME/KEY: MOD_RES
<222> LOCATION: (14)..(14)
<223> OTHER INFORMATION: Any amino acid comprising a small hydrophobic
      side chain or a polar neutral side chain
<220> FEATURE:
<221> NAME/KEY: MOD_RES
<222> LOCATION: (15)..(15)
<223> OTHER INFORMATION: Any amino acid

<400> SEQUENCE: 49

Xaa Xaa Xaa Cys Xaa Xaa Xaa Xaa Xaa Xaa Xaa Cys Xaa Xaa Xaa
```

<210> SEQ ID NO 50
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Glu Gln Phe Cys Leu Val Ser Asp Pro Met Ala Cys Trp Ser Leu
1               5                   10                  15

<210> SEQ ID NO 51
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Lys Tyr Trp Cys Leu Arg Ser Glu Pro Asp Ala Cys Phe Ala Thr
1               5                   10                  15

<210> SEQ ID NO 52
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Arg Val Tyr Cys Leu Ala Ser Glu Pro Asn Ser Cys Trp Ser Thr
1               5                   10                  15

<210> SEQ ID NO 53
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Thr Lys Leu Cys Leu Lys Ser Glu Pro Gln Ala Cys Trp Ser Met
1               5                   10                  15

<210> SEQ ID NO 54
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Ile Arg Phe Cys Leu Arg Ser Glu Pro Thr Ala Cys Trp Ile Val
1               5                   10                  15

<210> SEQ ID NO 55
<211> LENGTH: 7
<212> TYPE: PRT
<213> ORGANISM: Artificial Sequence
<220> FEATURE:
<223> OTHER INFORMATION: Description of Artificial Sequence: Synthetic

```
        peptide
<220> FEATURE:
<221> NAME/KEY: MOD_RES
<222> LOCATION: (1)..(1)
<223> OTHER INFORMATION: Any amino acid comprising a large hydrophobic
      side chain
<220> FEATURE:
<221> NAME/KEY: MOD_RES
<222> LOCATION: (2)..(2)
<223> OTHER INFORMATION: Any amino acid comprising a basic side chain
<220> FEATURE:
<221> NAME/KEY: MOD_RES
<222> LOCATION: (3)..(3)
<223> OTHER INFORMATION: Any amino acid comprising a small hydrophobic
      side chain or a polar neutral side chain
<220> FEATURE:
<221> NAME/KEY: MOD_RES
<222> LOCATION: (4)..(4)
<223> OTHER INFORMATION: Any amino acid comprising a large hydrophobic
      side chain
<220> FEATURE:
<221> NAME/KEY: MOD_RES
<222> LOCATION: (5)..(5)
<223> OTHER INFORMATION: Any amino acid comprising a small hydrophobic
      side chain
<220> FEATURE:
<221> NAME/KEY: MOD_RES
<222> LOCATION: (6)..(6)
<223> OTHER INFORMATION: Any amino acid comprising a small hydrophobic
      side chain or a polar neutral side chain
<220> FEATURE:
<221> NAME/KEY: MOD_RES
<222> LOCATION: (7)..(7)
<223> OTHER INFORMATION: Any amino acid comprising a small hydrophobic
      side chain

<400> SEQUENCE: 55

Xaa Xaa Xaa Xaa Xaa Xaa Xaa
1               5

<210> SEQ ID NO 56
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid comprising a large hydrophobic
      side chain
<220> FEATURE:
<221> NAME/KEY: MOD_RES
<222> LOCATION: (3)..(3)
<223> OTHER INFORMATION: Any amino acid comprising a large hydrophobic
      side chain
<220> FEATURE:
<221> NAME/KEY: MOD_RES
<222> LOCATION: (4)..(4)
<223> OTHER INFORMATION: Any amino acid comprising a basic side chain
<220> FEATURE:
<221> NAME/KEY: MOD_RES
<222> LOCATION: (5)..(5)
<223> OTHER INFORMATION: Any amino acid comprising a small hydrophobic
      side chain or a polar neutral side chain
<220> FEATURE:
<221> NAME/KEY: MOD_RES
<222> LOCATION: (6)..(6)
<223> OTHER INFORMATION: Any amino acid comprising a large hydrophobic
      side chain
<220> FEATURE:
<221> NAME/KEY: MOD_RES
<222> LOCATION: (7)..(7)
<223> OTHER INFORMATION: Any amino acid comprising a small hydrophobic
      side chain
<220> FEATURE:
```

```
<221> NAME/KEY: MOD_RES
<222> LOCATION: (8)..(8)
<223> OTHER INFORMATION: Any amino acid comprising a small hydrophobic
      side chain or a polar neutral side chain
<220> FEATURE:
<221> NAME/KEY: MOD_RES
<222> LOCATION: (9)..(9)
<223> OTHER INFORMATION: Any amino acid comprising a small hydrophobic
      side chain
<220> FEATURE:
<221> NAME/KEY: MOD_RES
<222> LOCATION: (11)..(11)
<223> OTHER INFORMATION: Any amino acid comprising an aromatic side
      chain or a large hydrophobic side chain

<400> SEQUENCE: 56

Xaa Cys Xaa Xaa Xaa Xaa Xaa Xaa Xaa Cys Xaa
 1               5                  10

<210> SEQ ID NO 57
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any basic amino acid
<220> FEATURE:
<221> NAME/KEY: MOD_RES
<222> LOCATION: (2)..(2)
<223> OTHER INFORMATION: Any amino acid comprising a large hydrophobic
      side chain
<220> FEATURE:
<221> NAME/KEY: MOD_RES
<222> LOCATION: (4)..(4)
<223> OTHER INFORMATION: Any amino acid comprising a large hydrophobic
      side chain
<220> FEATURE:
<221> NAME/KEY: MOD_RES
<222> LOCATION: (5)..(5)
<223> OTHER INFORMATION: Any amino acid comprising a basic side chain
<220> FEATURE:
<221> NAME/KEY: MOD_RES
<222> LOCATION: (6)..(6)
<223> OTHER INFORMATION: Any amino acid comprising a small hydrophobic
      side chain or a polar neutral side chain
<220> FEATURE:
<221> NAME/KEY: MOD_RES
<222> LOCATION: (7)..(7)
<223> OTHER INFORMATION: Any amino acid comprising a large hydrophobic
      side chain
<220> FEATURE:
<221> NAME/KEY: MOD_RES
<222> LOCATION: (8)..(8)
<223> OTHER INFORMATION: Any amino acid comprising a small hydrophobic
      side chain
<220> FEATURE:
<221> NAME/KEY: MOD_RES
<222> LOCATION: (9)..(9)
<223> OTHER INFORMATION: Any amino acid comprising a small hydrophobic
      side chain or a polar neutral side chain
<220> FEATURE:
<221> NAME/KEY: MOD_RES
<222> LOCATION: (10)..(10)
<223> OTHER INFORMATION: Any amino acid comprising a small hydrophobic
      side chain
<220> FEATURE:
<221> NAME/KEY: MOD_RES
<222> LOCATION: (12)..(12)
<223> OTHER INFORMATION: Any amino acid comprising an aromatic side
      chain or a large hydrophobic side chain
<220> FEATURE:
<221> NAME/KEY: MOD_RES
<222> LOCATION: (13)..(13)
```

<223> OTHER INFORMATION: Any amino acid comprising a small hydrophobic
      side chain or a polar neutral side chain

<400> SEQUENCE: 57

Xaa Xaa Cys Xaa Xaa Xaa Xaa Xaa Xaa Xaa Cys Xaa Xaa
1               5                   10

<210> SEQ ID NO 58
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any basic amino acid
<220> FEATURE:
<221> NAME/KEY: MOD_RES
<222> LOCATION: (2)..(2)
<223> OTHER INFORMATION: Any basic amino acid
<220> FEATURE:
<221> NAME/KEY: MOD_RES
<222> LOCATION: (3)..(3)
<223> OTHER INFORMATION: Any amino acid comprising a large hydrophobic
      side chain
<220> FEATURE:
<221> NAME/KEY: MOD_RES
<222> LOCATION: (5)..(5)
<223> OTHER INFORMATION: Any amino acid comprising a large hydrophobic
      side chain
<220> FEATURE:
<221> NAME/KEY: MOD_RES
<222> LOCATION: (6)..(6)
<223> OTHER INFORMATION: Any amino acid comprising a basic side chain
<220> FEATURE:
<221> NAME/KEY: MOD_RES
<222> LOCATION: (7)..(7)
<223> OTHER INFORMATION: Any amino acid comprising a small hydrophobic
      side chain or a polar neutral side chain
<220> FEATURE:
<221> NAME/KEY: MOD_RES
<222> LOCATION: (8)..(8)
<223> OTHER INFORMATION: Any amino acid comprising a large hydrophobic
      side chain
<220> FEATURE:
<221> NAME/KEY: MOD_RES
<222> LOCATION: (9)..(9)
<223> OTHER INFORMATION: Any amino acid comprising a small hydrophobic
      side chain
<220> FEATURE:
<221> NAME/KEY: MOD_RES
<222> LOCATION: (10)..(10)
<223> OTHER INFORMATION: Any amino acid comprising a small hydrophobic
      side chain or a polar neutral side chain
<220> FEATURE:
<221> NAME/KEY: MOD_RES
<222> LOCATION: (11)..(11)
<223> OTHER INFORMATION: Any amino acid comprising a small hydrophobic
      side chain
<220> FEATURE:
<221> NAME/KEY: MOD_RES
<222> LOCATION: (13)..(13)
<223> OTHER INFORMATION: Any amino acid comprising an aromatic side
      chain or a large hydrophobic side chain
<220> FEATURE:
<221> NAME/KEY: MOD_RES
<222> LOCATION: (14)..(14)
<223> OTHER INFORMATION: Any amino acid comprising a small hydrophobic
      side chain or a polar neutral side chain
<220> FEATURE:
<221> NAME/KEY: MOD_RES
<222> LOCATION: (15)..(15)
<223> OTHER INFORMATION: Any amino acid comprising a large hydrophobic
      side chain

```
<400> SEQUENCE: 58

Xaa Xaa Xaa Cys Xaa Xaa Xaa Xaa Xaa Xaa Cys Xaa Xaa Xaa
1               5                   10                  15

<210> SEQ ID NO 59
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Arg Arg Phe Cys Leu Arg Ser Glu Pro Thr Ala Cys Trp Ile Val
1               5                   10                  15

<210> SEQ ID NO 60
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Lys Leu Phe Cys Leu Arg Ser Gly Asp Arg Ala Cys Trp Val Val
1               5                   10                  15

<210> SEQ ID NO 61
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Met Arg Phe Cys Leu Arg Ser Glu Pro Thr Ala Cys Trp Thr Val
1               5                   10                  15

<210> SEQ ID NO 62
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Arg Arg Phe Cys Leu Arg Ser Glu Pro Thr Ala Cys Trp Asp Val
1               5                   10                  15

<210> SEQ ID NO 63
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Arg Arg Phe Cys Leu Arg Ser Asp Pro Thr Ala Cys Trp Ile Val
1               5                   10                  15

<210> SEQ ID NO 64
<211> LENGTH: 15
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 64

Lys Arg Phe Cys Leu Arg Ser Glu Pro Thr Ala Cys Trp Thr Val
1               5                   10                  15

<210> SEQ ID NO 65
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Arg Arg Phe Cys Leu Arg Ser Glu Pro Met Ala Cys Trp Thr Val
1               5                   10                  15

<210> SEQ ID NO 66
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Arg Arg Phe Cys Leu Arg Ser Glu Pro Thr Ala Cys Trp Thr Val
1               5                   10                  15

<210> SEQ ID NO 67
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Arg Arg Phe Cys Leu Arg Ser Glu Pro Ala Ala Cys Trp Phe Val
1               5                   10                  15

<210> SEQ ID NO 68
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Arg Arg Phe Cys Leu Arg Ser Glu Pro Thr Ala Cys Trp Tyr Val
1               5                   10                  15

<210> SEQ ID NO 69
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid comprising a large hydrophobic
      side chain or a basic side chain
```

```
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (3)..(3)
<223> OTHER INFORMATION: Any amino acid comprising an acidic side chain
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (5)..(5)
<223> OTHER INFORMATION: Any amino acid
<220> FEATURE:
<221> NAME/KEY: MOD_RES
<222> LOCATION: (6)..(6)
<223> OTHER INFORMATION: Any amino acid
<220> FEATURE:
<221> NAME/KEY: MOD_RES
<222> LOCATION: (7)..(7)
<223> OTHER INFORMATION: Any amino acid comprising a small hydrophobic
      side chain
<220> FEATURE:
<221> NAME/KEY: MOD_RES
<222> LOCATION: (8)..(8)
<223> OTHER INFORMATION: Any amino acid

<400> SEQUENCE: 69

Xaa Xaa Xaa Xaa Xaa Xaa Xaa Xaa
1               5

<210> SEQ ID NO 70
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid comprising a basic side chain
<220> FEATURE:
<221> NAME/KEY: MOD_RES
<222> LOCATION: (3)..(3)
<223> OTHER INFORMATION: Any amino acid comprising a large hydrophobic
      side chain or a basic side chain
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (5)..(5)
<223> OTHER INFORMATION: Any amino acid comprising an acidic side chain
<220> FEATURE:
<221> NAME/KEY: MOD_RES
<222> LOCATION: (6)..(6)
<223> OTHER INFORMATION: Any amino acid
<220> FEATURE:
<221> NAME/KEY: MOD_RES
<222> LOCATION: (7)..(7)
<223> OTHER INFORMATION: Any amino acid
<220> FEATURE:
<221> NAME/KEY: MOD_RES
<222> LOCATION: (8)..(8)
<223> OTHER INFORMATION: Any amino acid
<220> FEATURE:
<221> NAME/KEY: MOD_RES
<222> LOCATION: (9)..(9)
<223> OTHER INFORMATION: Any amino acid comprising a small hydrophobic
      side chain
<220> FEATURE:
<221> NAME/KEY: MOD_RES
```

```
<222> LOCATION: (10)..(10)
<223> OTHER INFORMATION: Any amino acid
<220> FEATURE:
<221> NAME/KEY: MOD_RES
<222> LOCATION: (12)..(12)
<223> OTHER INFORMATION: Any amino acid comprising a large hydrophobic
      side chain

<400> SEQUENCE: 70

Xaa Cys Xaa Xaa Xaa Xaa Xaa Xaa Xaa Xaa Cys Xaa
1               5                   10

<210> SEQ ID NO 71
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (2)..(2)
<223> OTHER INFORMATION: Any amino acid comprising a basic side chain
<220> FEATURE:
<221> NAME/KEY: MOD_RES
<222> LOCATION: (4)..(4)
<223> OTHER INFORMATION: Any amino acid comprising a large hydrophobic
      side chain or a basic side chain
<220> FEATURE:
<221> NAME/KEY: MOD_RES
<222> LOCATION: (5)..(5)
<223> OTHER INFORMATION: Any amino acid
<220> FEATURE:
<221> NAME/KEY: MOD_RES
<222> LOCATION: (6)..(6)
<223> OTHER INFORMATION: Any amino acid comprising an acidic side chain
<220> FEATURE:
<221> NAME/KEY: MOD_RES
<222> LOCATION: (7)..(7)
<223> OTHER INFORMATION: Any amino acid
<220> FEATURE:
<221> NAME/KEY: MOD_RES
<222> LOCATION: (8)..(8)
<223> OTHER INFORMATION: Any amino acid
<220> FEATURE:
<221> NAME/KEY: MOD_RES
<222> LOCATION: (9)..(9)
<223> OTHER INFORMATION: Any amino acid
<220> FEATURE:
<221> NAME/KEY: MOD_RES
<222> LOCATION: (10)..(10)
<223> OTHER INFORMATION: Any amino acid comprising a small hydrophobic
      side chain
<220> FEATURE:
<221> NAME/KEY: MOD_RES
<222> LOCATION: (11)..(11)
<223> OTHER INFORMATION: Any amino acid
<220> FEATURE:
<221> NAME/KEY: MOD_RES
<222> LOCATION: (13)..(13)
<223> OTHER INFORMATION: Any amino acid comprising a large hydrophobic
      side chain
<220> FEATURE:
<221> NAME/KEY: MOD_RES
<222> LOCATION: (14)..(14)
<223> OTHER INFORMATION: Any amino acid comprising a large hydrophobic
      side chain

<400> SEQUENCE: 71

Xaa Xaa Cys Xaa Xaa Xaa Xaa Xaa Xaa Xaa Xaa Cys Xaa Xaa
1               5                   10
```

```
<210> SEQ ID NO 72
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Arg Ser Cys Asn Arg Tyr Gly Ile Trp Gly His Cys Asp Thr
1               5                   10

<210> SEQ ID NO 73
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Ile Lys Cys Arg Val Leu Glu Ala Gly Thr Pro Cys Val Phe
1               5                   10

<210> SEQ ID NO 74
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Ile Arg Cys Arg Tyr Glu Lys Gln Ser Gly Ile Cys Leu Phe
1               5                   10

<210> SEQ ID NO 75
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Leu Arg Cys Arg Leu Asp Thr Arg Asp Gly Thr Cys Arg Phe
1               5                   10

<210> SEQ ID NO 76
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Met Arg Cys Ile Leu Ser Pro Ser Arg Glu His Cys Leu Phe
1               5                   10

<210> SEQ ID NO 77
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 77

Asn His Cys Thr Met Asp Trp Arg Leu Gly Ala Cys Ile Phe
1               5                   10

<210> SEQ ID NO 78
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Ser Gly Cys Arg Leu Ser Leu Leu Asp Gly His Cys Tyr Phe
1               5                   10

<210> SEQ ID NO 79
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Ser Lys Cys Val Tyr Asp Tyr Asn Phe Gly Thr Cys Ile Phe
1               5                   10

<210> SEQ ID NO 80
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Ser Arg Cys Val Met Ser Leu Gln Leu Gly Ala Cys Ile Phe
1               5                   10

<210> SEQ ID NO 81
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Thr Arg Cys Thr Val Ile Gly Pro Pro Trp Ser Cys Arg Phe
1               5                   10

<210> SEQ ID NO 82
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Val Phe Cys Ile Gly Tyr Gly Ala Ala Gln Ser Cys His Ser
1               5                   10

<210> SEQ ID NO 83
<211> LENGTH: 14
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 83

Val Arg Cys Leu Tyr Asp Ser Ile Thr Arg Thr Cys Thr Phe
1               5                   10

<210> SEQ ID NO 84
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Val Ser Cys Lys Ile Asp Arg Arg Ser Gly Ser Cys Leu Phe
1               5                   10

<210> SEQ ID NO 85
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Val Ser Cys Arg Phe Arg Pro Asp Leu Gly Phe Cys Ile Phe
1               5                   10

<210> SEQ ID NO 86
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Asp Arg Cys Asp Thr Arg Thr Trp Gly Tyr Tyr Cys Trp Ile
1               5                   10

<210> SEQ ID NO 87
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid comprising a large hydrophobic
      side chain or a basic side chain
<220> FEATURE:
<221> NAME/KEY: MOD_RES
<222> LOCATION: (2)..(2)
<223> OTHER INFORMATION: Any amino acid comprising a large hydrophobic
      side chain
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (4)..(4)
<223> OTHER INFORMATION: Any amino acid comprising a small hydrophobic
      side chain
```

<220> FEATURE:
<221> NAME/KEY: MOD_RES
<222> LOCATION: (5)..(5)
<223> OTHER INFORMATION: Any amino acid comprising a small hydrophobic
       side chain
<220> FEATURE:
<221> NAME/KEY: MOD_RES
<222> LOCATION: (6)..(6)
<223> OTHER INFORMATION: Any amino acid comprising a large hydrophobic
       side chain or a
       basic side chain
<220> FEATURE:
<221> NAME/KEY: MOD_RES
<222> LOCATION: (7)..(7)
<223> OTHER INFORMATION: Any amino acid comprising a basic side chain or
       an acidic side chain
<220> FEATURE:
<221> NAME/KEY: MOD_RES
<222> LOCATION: (8)..(8)
<223> OTHER INFORMATION: Any amino acid comprising a small hydrophobic
       side chain or a polar neutral side chain

<400> SEQUENCE: 87

Xaa Xaa Xaa Xaa Xaa Xaa Xaa Xaa
1               5

<210> SEQ ID NO 88
<211> LENGTH: 12
<212> TYPE: PRT
<213> ORGANISM: Artificial Sequence
<220> FEATURE:
<223> OTHER INFORMATION: Description of Artificial Sequence: Synthetic
       peptide
<220> FEATURE:
<221> NAME/KEY: MOD_RES
<222> LOCATION: (1)..(1)
<223> OTHER INFORMATION: Any amino acid comprising a large hydrophobic
       side chain or an acidic side chain
<220> FEATURE:
<221> NAME/KEY: MOD_RES
<222> LOCATION: (3)..(3)
<223> OTHER INFORMATION: Any amino acid comprising a large hydrophobic
       side chain or a basic side chain
<220> FEATURE:
<221> NAME/KEY: MOD_RES
<222> LOCATION: (4)..(4)
<223> OTHER INFORMATION: Any amino acid comprising a large hydrophobic
       side chain
<220> FEATURE:
<221> NAME/KEY: MOD_RES
<222> LOCATION: (5)..(5)
<223> OTHER INFORMATION: Any amino acid
<220> FEATURE:
<221> NAME/KEY: MOD_RES
<222> LOCATION: (6)..(6)
<223> OTHER INFORMATION: Any amino acid comprising a small hydrophobic
       side chain
<220> FEATURE:
<221> NAME/KEY: MOD_RES
<222> LOCATION: (7)..(7)
<223> OTHER INFORMATION: Any amino acid comprising a small hydrophobic
       side chain
<220> FEATURE:
<221> NAME/KEY: MOD_RES
<222> LOCATION: (8)..(8)
<223> OTHER INFORMATION: Any amino acid comprising a large hydrophobic
       side chain or a basic side chain
<220> FEATURE:
<221> NAME/KEY: MOD_RES
<222> LOCATION: (9)..(9)
<223> OTHER INFORMATION: Any amino acid comprising a basic side chain or
       an acidic side chain
<220> FEATURE:
<221> NAME/KEY: MOD_RES
<222> LOCATION: (10)..(10)
<223> OTHER INFORMATION: Any amino acid comprising a small hydrophobic
       side chain or a polar neutral side chain

```
<220> FEATURE:
<221> NAME/KEY: MOD_RES
<222> LOCATION: (12)..(12)
<223> OTHER INFORMATION: Any amino acid

<400> SEQUENCE: 88

Xaa Cys Xaa Xaa Xaa Xaa Xaa Xaa Xaa Xaa Cys Xaa
1               5                   10

<210> SEQ ID NO 89
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid comprising a large hydrophobic
      side chain
<220> FEATURE:
<221> NAME/KEY: MOD_RES
<222> LOCATION: (2)..(2)
<223> OTHER INFORMATION: Any amino acid comprising a large hydrophobic
      side chain or an acidic side chain
<220> FEATURE:
<221> NAME/KEY: MOD_RES
<222> LOCATION: (4)..(4)
<223> OTHER INFORMATION: Any amino acid comprising a large hydrophobic
      side chain or a basic side chain
<220> FEATURE:
<221> NAME/KEY: MOD_RES
<222> LOCATION: (5)..(5)
<223> OTHER INFORMATION: Any amino acid comprising a large hydrophobic
      side chain
<220> FEATURE:
<221> NAME/KEY: MOD_RES
<222> LOCATION: (6)..(6)
<223> OTHER INFORMATION: Any amino acid
<220> FEATURE:
<221> NAME/KEY: MOD_RES
<222> LOCATION: (7)..(7)
<223> OTHER INFORMATION: Any amino acid comprising a small hydrophobic
      side chain
<220> FEATURE:
<221> NAME/KEY: MOD_RES
<222> LOCATION: (8)..(8)
<223> OTHER INFORMATION: Any amino acid comprising a small hydrophobic
      side chain
<220> FEATURE:
<221> NAME/KEY: MOD_RES
<222> LOCATION: (9)..(9)
<223> OTHER INFORMATION: Any amino acid comprising a large hydrophobic
      side chain or a basic side chain
<220> FEATURE:
<221> NAME/KEY: MOD_RES
<222> LOCATION: (10)..(10)
<223> OTHER INFORMATION: Any amino acid comprising a basic side chain or
      an acidic side chain
<220> FEATURE:
<221> NAME/KEY: MOD_RES
<222> LOCATION: (11)..(11)
<223> OTHER INFORMATION: Any amino acid comprising a small hydrophobic
      side chain or a polar neutral side chain
<220> FEATURE:
<221> NAME/KEY: MOD_RES
<222> LOCATION: (13)..(13)
<223> OTHER INFORMATION: Any amino acid
<220> FEATURE:
<221> NAME/KEY: MOD_RES
<222> LOCATION: (14)..(14)
<223> OTHER INFORMATION: Any amino acid

<400> SEQUENCE: 89

Xaa Xaa Cys Xaa Xaa Xaa Xaa Xaa Xaa Xaa Xaa Cys Xaa Xaa
```

```
                1               5                    10
```

<210> SEQ ID NO 90
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (2)..(2)
<223> OTHER INFORMATION: Any amino acid comprising a large hydrophobic
      side chain
<220> FEATURE:
<221> NAME/KEY: MOD_RES
<222> LOCATION: (3)..(3)
<223> OTHER INFORMATION: Any amino acid comprising a large hydrophobic
      side chain or an acidic side chain
<220> FEATURE:
<221> NAME/KEY: MOD_RES
<222> LOCATION: (5)..(5)
<223> OTHER INFORMATION: Any amino acid comprising a large hydrophobic
      side chain or a basic side chain
<220> FEATURE:
<221> NAME/KEY: MOD_RES
<222> LOCATION: (6)..(6)
<223> OTHER INFORMATION: Any amino acid comprising a large hydrophobic
      side chain
<220> FEATURE:
<221> NAME/KEY: MOD_RES
<222> LOCATION: (7)..(7)
<223> OTHER INFORMATION: Any amino acid
<220> FEATURE:
<221> NAME/KEY: MOD_RES
<222> LOCATION: (8)..(8)
<223> OTHER INFORMATION: Any amino acid comprising a small hydrophobic
      side chain
<220> FEATURE:
<221> NAME/KEY: MOD_RES
<222> LOCATION: (9)..(9)
<223> OTHER INFORMATION: Any amino acid comprising a small hydrophobic
      side chain
<220> FEATURE:
<221> NAME/KEY: MOD_RES
<222> LOCATION: (10)..(10)
<223> OTHER INFORMATION: Any amino acid comprising a large hydrophobic
      side chain or a basic side chain
<220> FEATURE:
<221> NAME/KEY: MOD_RES
<222> LOCATION: (11)..(11)
<223> OTHER INFORMATION: Any amino acid comprising a basic side chain or
      an acidic side chain
<220> FEATURE:
<221> NAME/KEY: MOD_RES
<222> LOCATION: (12)..(12)
<223> OTHER INFORMATION: Any amino acid comprising a small hydrophobic
      side chain or a polar neutral side chain
<220> FEATURE:
<221> NAME/KEY: MOD_RES
<222> LOCATION: (14)..(14)
<223> OTHER INFORMATION: Any amino acid
<220> FEATURE:
<221> NAME/KEY: MOD_RES
<222> LOCATION: (15)..(15)
<223> OTHER INFORMATION: Any amino acid
<220> FEATURE:
<221> NAME/KEY: MOD_RES
<222> LOCATION: (16)..(16)
<223> OTHER INFORMATION: Any amino acid

<400> SEQUENCE: 90

Xaa Xaa Xaa Cys Xaa Xaa Xaa Xaa Xaa Xaa Xaa Xaa Cys Xaa Xaa Xaa

```
                1               5                   10                  15

<210> SEQ ID NO 91
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Gly Ser Arg Cys Tyr Trp Asp Pro Gly Arg Glu Val Cys Ile Phe Lys
1               5                   10                  15

<210> SEQ ID NO 92
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Glu Trp Glu Cys Arg Phe Leu Pro Gly Arg Gly Cys Ser Leu Phe
1               5                   10                  15

<210> SEQ ID NO 93
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Phe Trp Glu Cys Val Tyr Ser Pro Gly Ser Arg Gly Cys Arg Met Val
1               5                   10                  15

<210> SEQ ID NO 94
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Gly Phe Arg Cys Thr Tyr Asp Pro Gly Thr His Ser Cys Trp Ser Ile
1               5                   10                  15

<210> SEQ ID NO 95
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Lys Trp Ile Cys Arg Leu Val Pro Gly Asn Gly Ala Cys His Ser Phe
1               5                   10                  15

<210> SEQ ID NO 96
<211> LENGTH: 16
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 96

Pro Trp Val Cys Glu His Tyr Pro Gly Arg Arg Gly Cys Val Leu Met
1               5                   10                  15

<210> SEQ ID NO 97
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Gln Trp Ser Cys Val Phe Ser Pro Gly Val Arg Gly Cys Lys Leu Val
1               5                   10                  15

<210> SEQ ID NO 98
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Arg Phe Ile Cys Arg Ile Gln Pro Gly Arg Glu Gly Cys Trp Ser Leu
1               5                   10                  15

<210> SEQ ID NO 99
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Arg Trp Glu Cys Ile Tyr Ile Pro Gly Arg Lys Gly Cys Thr Leu Gln
1               5                   10                  15

<210> SEQ ID NO 100
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Ser Leu Asn Cys Lys Thr Arg Pro Gly Leu Arg Trp Cys Thr Trp Thr
1               5                   10                  15

<210> SEQ ID NO 101
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Ser Trp Glu Cys Val Tyr Met Pro Gly His Gln Gly Cys Arg Leu Phe
1               5                   10                  15

<210> SEQ ID NO 102

```
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Val Arg Phe Cys Arg Ser Gly Pro Gly Trp Val Ser Cys Gly Thr Gln
1               5                   10                  15

<210> SEQ ID NO 103
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Val Arg Leu Cys Arg Val Gly Pro Gly Tyr Glu Ser Cys Pro Ala Asn
1               5                   10                  15

<210> SEQ ID NO 104
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Val Arg Met Cys Tyr Val Ala Pro Gly Tyr Val Ser Cys Pro Arg Met
1               5                   10                  15

<210> SEQ ID NO 105
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid comprising a large hydrophobic
      side chain
<220> FEATURE:
<221> NAME/KEY: MOD_RES
<222> LOCATION: (2)..(2)
<223> OTHER INFORMATION: Any amino acid comprising a large hydrophobic
      side chain
<220> FEATURE:
<221> NAME/KEY: MOD_RES
<222> LOCATION: (3)..(3)
<223> OTHER INFORMATION: Any amino acid comprising a large hydrophobic
      side chain
<220> FEATURE:
<221> NAME/KEY: MOD_RES
<222> LOCATION: (4)..(4)
<223> OTHER INFORMATION: Any amino acid comprising a small hydrophobic
      side chain
<220> FEATURE:
<221> NAME/KEY: MOD_RES
<222> LOCATION: (5)..(5)
<223> OTHER INFORMATION: Any amino acid comprising a small hydrophobic
      side chain
<220> FEATURE:
<221> NAME/KEY: MOD_RES
<222> LOCATION: (6)..(6)
<223> OTHER INFORMATION: Any amino acid comprising a basic side chain
<220> FEATURE:
<221> NAME/KEY: MOD_RES
```

```
<222> LOCATION: (7)..(7)
<223> OTHER INFORMATION: Any amino acid comprising a basic side chain
<220> FEATURE:
<221> NAME/KEY: MOD_RES
<222> LOCATION: (8)..(8)
<223> OTHER INFORMATION: Any amino acid comprising a small hydrophobic
      side chain

<400> SEQUENCE: 105

Xaa Xaa Xaa Xaa Xaa Xaa Xaa Xaa
1               5

<210> SEQ ID NO 106
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid comprising an acidic side chain
<220> FEATURE:
<221> NAME/KEY: MOD_RES
<222> LOCATION: (3)..(3)
<223> OTHER INFORMATION: Any amino acid comprising a large hydrophobic
      side chain
<220> FEATURE:
<221> NAME/KEY: MOD_RES
<222> LOCATION: (4)..(4)
<223> OTHER INFORMATION: Any amino acid comprising a large hydrophobic
      side chain
<220> FEATURE:
<221> NAME/KEY: MOD_RES
<222> LOCATION: (5)..(5)
<223> OTHER INFORMATION: Any amino acid comprising a large hydrophobic
      side chain
<220> FEATURE:
<221> NAME/KEY: MOD_RES
<222> LOCATION: (6)..(6)
<223> OTHER INFORMATION: Any amino acid comprising a small hydrophobic
      side chain
<220> FEATURE:
<221> NAME/KEY: MOD_RES
<222> LOCATION: (7)..(7)
<223> OTHER INFORMATION: Any amino acid comprising a small hydrophobic
      side chain
<220> FEATURE:
<221> NAME/KEY: MOD_RES
<222> LOCATION: (8)..(8)
<223> OTHER INFORMATION: Any amino acid comprising a basic side chain
<220> FEATURE:
<221> NAME/KEY: MOD_RES
<222> LOCATION: (9)..(9)
<223> OTHER INFORMATION: Any amino acid comprising a basic side chain
<220> FEATURE:
<221> NAME/KEY: MOD_RES
<222> LOCATION: (10)..(10)
<223> OTHER INFORMATION: Any amino acid comprising a small hydrophobic
      side chain
<220> FEATURE:
<221> NAME/KEY: MOD_RES
<222> LOCATION: (12)..(12)
<223> OTHER INFORMATION: Any amino acid comprising a small hydrophobic
      side chain or a polar neutral side chain

<400> SEQUENCE: 106

Xaa Cys Xaa Xaa Xaa Xaa Xaa Xaa Xaa Xaa Cys Xaa
1               5                   10

<210> SEQ ID NO 107
<211> LENGTH: 14
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid comprising a large hydrophobic
      side chain
<220> FEATURE:
<221> NAME/KEY: MOD_RES
<222> LOCATION: (2)..(2)
<223> OTHER INFORMATION: Any amino acid comprising an acidic side chain
<220> FEATURE:
<221> NAME/KEY: MOD_RES
<222> LOCATION: (4)..(4)
<223> OTHER INFORMATION: Any amino acid comprising a large hydrophobic
      side chain
<220> FEATURE:
<221> NAME/KEY: MOD_RES
<222> LOCATION: (5)..(5)
<223> OTHER INFORMATION: Any amino acid comprising a large hydrophobic
      side chain
<220> FEATURE:
<221> NAME/KEY: MOD_RES
<222> LOCATION: (6)..(6)
<223> OTHER INFORMATION: Any amino acid comprising a large hydrophobic
      side chain
<220> FEATURE:
<221> NAME/KEY: MOD_RES
<222> LOCATION: (7)..(7)
<223> OTHER INFORMATION: Any amino acid comprising a small hydrophobic
      side chain
<220> FEATURE:
<221> NAME/KEY: MOD_RES
<222> LOCATION: (8)..(8)
<223> OTHER INFORMATION: Any amino acid comprising a small hydrophobic
      side chain
<220> FEATURE:
<221> NAME/KEY: MOD_RES
<222> LOCATION: (9)..(9)
<223> OTHER INFORMATION: Any amino acid comprising a basic side chain
<220> FEATURE:
<221> NAME/KEY: MOD_RES
<222> LOCATION: (10)..(10)
<223> OTHER INFORMATION: Any amino acid comprising a basic side chain
<220> FEATURE:
<221> NAME/KEY: MOD_RES
<222> LOCATION: (11)..(11)
<223> OTHER INFORMATION: Any amino acid comprising a small hydrophobic
      side chain
<220> FEATURE:
<221> NAME/KEY: MOD_RES
<222> LOCATION: (13)..(13)
<223> OTHER INFORMATION: Any amino acid comprising a small hydrophobic
      side chain or a polar neutral side chain
<220> FEATURE:
<221> NAME/KEY: MOD_RES
<222> LOCATION: (14)..(14)
<223> OTHER INFORMATION: Any amino acid comprising a large hydrophobic
      side chain

<400> SEQUENCE: 107

Xaa Xaa Cys Xaa Xaa Xaa Xaa Xaa Xaa Xaa Xaa Cys Xaa Xaa
1               5                   10

<210> SEQ ID NO 108
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid comprising an acidic side chain
<220> FEATURE:
```

```
<221> NAME/KEY: MOD_RES
<222> LOCATION: (2)..(2)
<223> OTHER INFORMATION: Any amino acid comprising a large hydrophobic
      side chain
<220> FEATURE:
<221> NAME/KEY: MOD_RES
<222> LOCATION: (3)..(3)
<223> OTHER INFORMATION: Any amino acid comprising an acidic side chain
<220> FEATURE:
<221> NAME/KEY: MOD_RES
<222> LOCATION: (5)..(5)
<223> OTHER INFORMATION: Any amino acid comprising a large hydrophobic
      side chain
<220> FEATURE:
<221> NAME/KEY: MOD_RES
<222> LOCATION: (6)..(6)
<223> OTHER INFORMATION: Any amino acid comprising a large hydrophobic
      side chain
<220> FEATURE:
<221> NAME/KEY: MOD_RES
<222> LOCATION: (7)..(7)
<223> OTHER INFORMATION: Any amino acid comprising a large hydrophobic
      side chain
<220> FEATURE:
<221> NAME/KEY: MOD_RES
<222> LOCATION: (8)..(8)
<223> OTHER INFORMATION: Any amino acid comprising a small hydrophobic
      side chain
<220> FEATURE:
<221> NAME/KEY: MOD_RES
<222> LOCATION: (9)..(9)
<223> OTHER INFORMATION: Any amino acid comprising a small hydrophobic
      side chain
<220> FEATURE:
<221> NAME/KEY: MOD_RES
<222> LOCATION: (10)..(10)
<223> OTHER INFORMATION: Any amino acid comprising a basic side chain
<220> FEATURE:
<221> NAME/KEY: MOD_RES
<222> LOCATION: (11)..(11)
<223> OTHER INFORMATION: Any amino acid comprising a basic side chain
<220> FEATURE:
<221> NAME/KEY: MOD_RES
<222> LOCATION: (12)..(12)
<223> OTHER INFORMATION: Any amino acid comprising a small hydrophobic
      side chain
<220> FEATURE:
<221> NAME/KEY: MOD_RES
<222> LOCATION: (14)..(14)
<223> OTHER INFORMATION: Any amino acid comprising a small hydrophobic
      side chain or a polar neutral side chain
<220> FEATURE:
<221> NAME/KEY: MOD_RES
<222> LOCATION: (15)..(15)
<223> OTHER INFORMATION: Any amino acid comprising a large hydrophobic
      side chain
<220> FEATURE:
<221> NAME/KEY: MOD_RES
<222> LOCATION: (16)..(16)
<223> OTHER INFORMATION: Any amino acid comprising a large hydrophobic
      side chain

<400> SEQUENCE: 108

Xaa Xaa Xaa Cys Xaa Xaa Xaa Xaa Xaa Xaa Xaa Xaa Cys Xaa Xaa Xaa
1               5                   10                  15

<210> SEQ ID NO 109
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Asn Trp Glu Cys Ile Phe Ser Pro Gly Arg Arg Gly Cys Ser Leu Thr
```

<210> SEQ ID NO 110
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Asp Trp Glu Cys Leu Phe Leu Pro Gly Arg Arg Gly Cys Leu Leu Phe
1               5                   10                  15

<210> SEQ ID NO 111
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Glu Trp Glu Cys Leu Phe Met Pro Gly Arg Arg Gly Cys Leu Leu Met
1               5                   10                  15

<210> SEQ ID NO 112
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Ala Trp Glu Cys Leu Phe Leu Pro Gly His Arg Gly Cys Ser Leu Phe
1               5                   10                  15

<210> SEQ ID NO 113
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

Glu Trp Glu Cys Leu Phe Leu Pro Gly Arg Lys Gly Cys Thr Leu Phe
1               5                   10                  15

<210> SEQ ID NO 114
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114

Asp Trp Glu Cys Ile Phe Leu Pro Gly Arg Arg Gly Cys Thr Leu Phe
1               5                   10                  15

<210> SEQ ID NO 115
<211> LENGTH: 16
<212> TYPE: PRT
<213> ORGANISM: Artificial Sequence
<220> FEATURE:
<223> OTHER INFORMATION: Description of Artificial Sequence: Synthetic -continued

```
      peptide

<400> SEQUENCE: 115

Val Tyr Glu Cys Leu Phe Met Pro Gly Arg Lys Gly Cys Phe Gly Met
1               5                   10                  15

<210> SEQ ID NO 116
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

Glu Trp Glu Cys Trp Phe Leu Pro Gly Arg Arg Gly Cys Thr Leu Ile
1               5                   10                  15

<210> SEQ ID NO 117
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117

Asp Trp His Cys Leu Phe Leu Pro Gly His Arg Gly Cys Thr Leu Phe
1               5                   10                  15

<210> SEQ ID NO 118
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

Asp Trp Glu Cys Leu Phe Leu Pro Gly Arg Arg Gly Cys Thr Leu Phe
1               5                   10                  15

<210> SEQ ID NO 119
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 119

Tyr Trp Glu Cys Val Phe Met Pro Gly His Arg Gly Cys Ser Leu Ile
1               5                   10                  15

<210> SEQ ID NO 120
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

Thr Trp Asp Cys Leu Phe Leu Pro Gly Arg Arg Gly Cys Thr Leu Met
1               5                   10                  15

<210> SEQ ID NO 121
```

```
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 121

Asn Trp Glu Cys Ile Phe Ser Pro Gly Arg Arg Gly Cys Ser Leu Thr
1               5                   10                  15

<210> SEQ ID NO 122
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid comprising an acidic side chain
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (3)..(3)
<223> OTHER INFORMATION: Any amino acid comprising an acidic side chain
      or an aromatic side chain
<220> FEATURE:
<221> NAME/KEY: MOD_RES
<222> LOCATION: (4)..(4)
<223> OTHER INFORMATION: Any amino acid comprising a small hydrophobic
      side chain
<220> FEATURE:
<221> NAME/KEY: MOD_RES
<222> LOCATION: (5)..(5)
<223> OTHER INFORMATION: Any amino acid comprising a small hydrophobic
      side chain
<220> FEATURE:
<221> NAME/KEY: MOD_RES
<222> LOCATION: (6)..(6)
<223> OTHER INFORMATION: Any amino acid comprising an aromatic chain
<220> FEATURE:
<221> NAME/KEY: MOD_RES
<222> LOCATION: (7)..(7)
<223> OTHER INFORMATION: Any amino acid
<220> FEATURE:
<221> NAME/KEY: MOD_RES
<222> LOCATION: (8)..(8)
<223> OTHER INFORMATION: Any amino acid

<400> SEQUENCE: 122

Xaa Xaa Xaa Xaa Xaa Xaa Xaa Xaa
1               5

<210> SEQ ID NO 123
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (3)..(3)
<223> OTHER INFORMATION: Any amino acid comprising an acidic side chain
<220> FEATURE:
<221> NAME/KEY: MOD_RES
```

```
<222> LOCATION: (4)..(4)
<223> OTHER INFORMATION: Any amino acid
<220> FEATURE:
<221> NAME/KEY: MOD_RES
<222> LOCATION: (5)..(5)
<223> OTHER INFORMATION: Any amino acid comprising an acidic side chain
      or an aromatic side chain
<220> FEATURE:
<221> NAME/KEY: MOD_RES
<222> LOCATION: (6)..(6)
<223> OTHER INFORMATION: Any amino acid comprising a small hydrophobic
      side chain
<220> FEATURE:
<221> NAME/KEY: MOD_RES
<222> LOCATION: (7)..(7)
<223> OTHER INFORMATION: Any amino acid comprising a small hydrophobic
      side chain
<220> FEATURE:
<221> NAME/KEY: MOD_RES
<222> LOCATION: (8)..(8)
<223> OTHER INFORMATION: Any amino acid comprising an aromatic chain
<220> FEATURE:
<221> NAME/KEY: MOD_RES
<222> LOCATION: (9)..(9)
<223> OTHER INFORMATION: Any amino acid
<220> FEATURE:
<221> NAME/KEY: MOD_RES
<222> LOCATION: (10)..(10)
<223> OTHER INFORMATION: Any amino acid
<220> FEATURE:
<221> NAME/KEY: MOD_RES
<222> LOCATION: (12)..(12)
<223> OTHER INFORMATION: Any amino acid

<400> SEQUENCE: 123

Xaa Cys Xaa Xaa Xaa Xaa Xaa Xaa Xaa Xaa Cys Xaa
1               5                   10

<210> SEQ ID NO 124
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (4)..(4)
<223> OTHER INFORMATION: Any amino acid comprising an acidic side chain
<220> FEATURE:
<221> NAME/KEY: MOD_RES
<222> LOCATION: (5)..(5)
<223> OTHER INFORMATION: Any amino acid
<220> FEATURE:
<221> NAME/KEY: MOD_RES
<222> LOCATION: (6)..(6)
<223> OTHER INFORMATION: Any amino acid comprising an acidic side chain
      or an aromatic side chain
<220> FEATURE:
<221> NAME/KEY: MOD_RES
<222> LOCATION: (7)..(7)
<223> OTHER INFORMATION: Any amino acid comprising a small hydrophobic
      side chain
<220> FEATURE:
<221> NAME/KEY: MOD_RES
<222> LOCATION: (8)..(8)
<223> OTHER INFORMATION: Any amino acid comprising a small hydrophobic
      side chain
<220> FEATURE:
```

```
<221> NAME/KEY: MOD_RES
<222> LOCATION: (9)..(9)
<223> OTHER INFORMATION: Any amino acid comprising an aromatic chain
<220> FEATURE:
<221> NAME/KEY: MOD_RES
<222> LOCATION: (10)..(10)
<223> OTHER INFORMATION: Any amino acid
<220> FEATURE:
<221> NAME/KEY: MOD_RES
<222> LOCATION: (11)..(11)
<223> OTHER INFORMATION: Any amino acid
<220> FEATURE:
<221> NAME/KEY: MOD_RES
<222> LOCATION: (13)..(13)
<223> OTHER INFORMATION: Any amino acid
<220> FEATURE:
<221> NAME/KEY: MOD_RES
<222> LOCATION: (14)..(14)
<223> OTHER INFORMATION: Any amino acid comprising a large hydrophobic
      side chain

<400> SEQUENCE: 124

Xaa Xaa Cys Xaa Xaa Xaa Xaa Xaa Xaa Xaa Xaa Cys Xaa Xaa
1               5                   10

<210> SEQ ID NO 125
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (5)..(5)
<223> OTHER INFORMATION: Any amino acid comprising an acidic side chain
<220> FEATURE:
<221> NAME/KEY: MOD_RES
<222> LOCATION: (6)..(6)
<223> OTHER INFORMATION: Any amino acid
<220> FEATURE:
<221> NAME/KEY: MOD_RES
<222> LOCATION: (7)..(7)
<223> OTHER INFORMATION: Any amino acid comprising an acidic side chain
      or an aromatic side chain
<220> FEATURE:
<221> NAME/KEY: MOD_RES
<222> LOCATION: (8)..(8)
<223> OTHER INFORMATION: Any amino acid comprising a small hydrophobic
      side chain
<220> FEATURE:
<221> NAME/KEY: MOD_RES
<222> LOCATION: (9)..(9)
<223> OTHER INFORMATION: Any amino acid comprising a small hydrophobic
      side chain
<220> FEATURE:
<221> NAME/KEY: MOD_RES
<222> LOCATION: (10)..(10)
<223> OTHER INFORMATION: Any amino acid comprising an aromatic chain
<220> FEATURE:
<221> NAME/KEY: MOD_RES
<222> LOCATION: (11)..(11)
<223> OTHER INFORMATION: Any amino acid
<220> FEATURE:
<221> NAME/KEY: MOD_RES
```

```
<222> LOCATION: (12)..(12)
<223> OTHER INFORMATION: Any amino acid
<220> FEATURE:
<221> NAME/KEY: MOD_RES
<222> LOCATION: (14)..(14)
<223> OTHER INFORMATION: Any amino acid
<220> FEATURE:
<221> NAME/KEY: MOD_RES
<222> LOCATION: (15)..(15)
<223> OTHER INFORMATION: Any amino acid comprising a large hydrophobic
      side chain
<220> FEATURE:
<221> NAME/KEY: MOD_RES
<222> LOCATION: (16)..(16)
<223> OTHER INFORMATION: Any amino acid comprising a large hydrophobic
      side chain

<400> SEQUENCE: 125

Xaa Xaa Xaa Cys Xaa Xaa Xaa Xaa Xaa Xaa Xaa Cys Xaa Xaa Xaa
1               5                   10                  15

<210> SEQ ID NO 126
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 126

Ala Gly Trp Cys Lys Leu Asn Pro Gly Thr Gln Val Cys Ser Phe Tyr
1               5                   10                  15

<210> SEQ ID NO 127
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 127

Glu Thr Pro Cys Asp Leu His Pro Gly His Trp Ser Cys Ser Met Val
1               5                   10                  15

<210> SEQ ID NO 128
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 128

Phe Phe Leu Cys Asp Asp Phe Pro Gly Leu Pro Arg Cys Glu Trp Ile
1               5                   10                  15

<210> SEQ ID NO 129
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 129

Gly Leu Arg Cys Tyr Phe Asp Pro Gly Ser Gln Ile Cys Thr Phe Leu
1               5                   10                  15
```

-continued

```
<210> SEQ ID NO 130
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 130

Gly Gln Arg Cys Thr Tyr Asp Pro Gly Gln Asp Ala Cys Val Phe Ser
1               5                   10                  15

<210> SEQ ID NO 131
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

Gly Ser Arg Cys Tyr Trp Asp Pro Gly Arg Glu Val Cys Ile Phe Lys
1               5                   10                  15

<210> SEQ ID NO 132
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 132

Lys Leu Trp Cys Gln Asn Asn Pro Gly Asn Ser Ile Cys Asp Met Tyr
1               5                   10                  15

<210> SEQ ID NO 133
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 133

Lys Ser Trp Cys Phe Asp His Pro Gly Tyr Pro Ile Cys Gln Phe Tyr
1               5                   10                  15

<210> SEQ ID NO 134
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 134

Arg Leu Phe Cys Leu Met Asn Pro Gly Pro Pro Asp Cys Trp Ile Tyr
1               5                   10                  15

<210> SEQ ID NO 135
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 135
```

Arg Gln Phe Cys Leu Val Ser Pro Gly Tyr Glu Asp Cys Trp Phe Val
1               5                   10                  15

<210> SEQ ID NO 136
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 136

Thr Arg Met Cys Phe Asp Asp Pro Gly Trp His Ser Cys Pro Val Val
1               5                   10                  15

<210> SEQ ID NO 137
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 137

Thr Arg Trp Cys Ser Leu His Pro Gly Val Gly Glu Cys Val Thr Leu
1               5                   10                  15

<210> SEQ ID NO 138
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 138

Thr Thr Val Cys Asp Tyr His Pro Gly Ser Arg Tyr Cys Ile Asn Glu
1               5                   10                  15

<210> SEQ ID NO 139
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 139

Tyr Ala Ser Cys Thr Tyr Leu Pro Gly His Arg Gly Cys Thr Leu Val
1               5                   10                  15

<210> SEQ ID NO 140
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 140

Trp Leu Pro Cys Asp Asp Tyr Pro Gly His Gly Tyr Cys Tyr Ser Arg
1               5                   10                  15

<210> SEQ ID NO 141
<211> LENGTH: 9
<212> TYPE: PRT
<213> ORGANISM: Artificial Sequence

```
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (2)..(2)
<223> OTHER INFORMATION: Any amino acid comprising a large hydrophobic
      side chain
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (5)..(5)
<223> OTHER INFORMATION: Any amino acid
<220> FEATURE:
<221> NAME/KEY: MOD_RES
<222> LOCATION: (6)..(6)
<223> OTHER INFORMATION: Any amino acid comprising an acidic side chain,
      a small hydrophobic side chain, or a polar neutral side chain
<220> FEATURE:
<221> NAME/KEY: MOD_RES
<222> LOCATION: (7)..(7)
<223> OTHER INFORMATION: Any amino acid
<220> FEATURE:
<221> NAME/KEY: MOD_RES
<222> LOCATION: (8)..(8)
<223> OTHER INFORMATION: Any amino acid comprising a large hydrophobic
      side chain
<220> FEATURE:
<221> NAME/KEY: MOD_RES
<222> LOCATION: (9)..(9)
<223> OTHER INFORMATION: Any amino acid comprising a large hydrophobic
      side chain

<400> SEQUENCE: 141

Xaa Xaa Xaa Xaa Xaa Xaa Xaa Xaa Xaa
1               5

<210> SEQ ID NO 142
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (4)..(4)
<223> OTHER INFORMATION: Any amino acid comprising a large hydrophobic
      side chain
<220> FEATURE:
<221> NAME/KEY: MOD_RES
<222> LOCATION: (5)..(5)
<223> OTHER INFORMATION: Any amino acid
<220> FEATURE:
<221> NAME/KEY: MOD_RES
<222> LOCATION: (6)..(6)
<223> OTHER INFORMATION: Any amino acid
<220> FEATURE:
```

```
<221> NAME/KEY: MOD_RES
<222> LOCATION: (7)..(7)
<223> OTHER INFORMATION: Any amino acid
<220> FEATURE:
<221> NAME/KEY: MOD_RES
<222> LOCATION: (8)..(8)
<223> OTHER INFORMATION: Any amino acid comprising an acidic side chain,
      a small hydrophobic side chain, or a polar neutral side chain
<220> FEATURE:
<221> NAME/KEY: MOD_RES
<222> LOCATION: (9)..(9)
<223> OTHER INFORMATION: Any amino acid
<220> FEATURE:
<221> NAME/KEY: MOD_RES
<222> LOCATION: (10)..(10)
<223> OTHER INFORMATION: Any amino acid comprising a large hydrophobic
      side chain
<220> FEATURE:
<221> NAME/KEY: MOD_RES
<222> LOCATION: (11)..(11)
<223> OTHER INFORMATION: Any amino acid comprising a large hydrophobic
      side chain
<220> FEATURE:
<221> NAME/KEY: MOD_RES
<222> LOCATION: (13)..(13)
<223> OTHER INFORMATION: Any amino acid comprising a large hydrophobic
      side chain

<400> SEQUENCE: 142

Xaa Cys Xaa Xaa Xaa Xaa Xaa Xaa Xaa Xaa Xaa Cys Xaa
1               5                   10

<210> SEQ ID NO 143
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (5)..(5)
<223> OTHER INFORMATION: Any amino acid comprising a large hydrophobic
      side chain
<220> FEATURE:
<221> NAME/KEY: MOD_RES
<222> LOCATION: (6)..(6)
<223> OTHER INFORMATION: Any amino acid
<220> FEATURE:
<221> NAME/KEY: MOD_RES
<222> LOCATION: (7)..(7)
<223> OTHER INFORMATION: Any amino acid
<220> FEATURE:
<221> NAME/KEY: MOD_RES
<222> LOCATION: (8)..(8)
<223> OTHER INFORMATION: Any amino acid
<220> FEATURE:
<221> NAME/KEY: MOD_RES
<222> LOCATION: (9)..(9)
<223> OTHER INFORMATION: Any amino acid comprising an acidic side chain,
      a small hydrophobic side chain, or a polar neutral side chain
<220> FEATURE:
<221> NAME/KEY: MOD_RES
<222> LOCATION: (10)..(10)
<223> OTHER INFORMATION: Any amino acid
```

```
<220> FEATURE:
<221> NAME/KEY: MOD_RES
<222> LOCATION: (11)..(11)
<223> OTHER INFORMATION: Any amino acid comprising a large hydrophobic
      side chain
<220> FEATURE:
<221> NAME/KEY: MOD_RES
<222> LOCATION: (12)..(12)
<223> OTHER INFORMATION: Any amino acid comprising a large hydrophobic
      side chain
<220> FEATURE:
<221> NAME/KEY: MOD_RES
<222> LOCATION: (14)..(14)
<223> OTHER INFORMATION: Any amino acid comprising a large hydrophobic
      side chain
<220> FEATURE:
<221> NAME/KEY: MOD_RES
<222> LOCATION: (15)..(15)
<223> OTHER INFORMATION: Any amino acid comprising a large hydrophobic
      side chain
<220> FEATURE:
<221> NAME/KEY: MOD_RES
<222> LOCATION: (16)..(16)
<223> OTHER INFORMATION: Any amino acid

<400> SEQUENCE: 143

Xaa Xaa Cys Xaa Xaa Xaa Xaa Xaa Xaa Xaa Xaa Xaa Cys Xaa Xaa Xaa
1               5                   10                  15

<210> SEQ ID NO 144
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 144

Ser Ala Cys Gln Leu Lys Trp Asp Glu Gly Trp Thr Cys Leu Phe
1               5                   10                  15

<210> SEQ ID NO 145
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 145

Asn His Cys Thr Leu Ser Lys Thr Tyr Pro Trp Val Cys Val Phe
1               5                   10                  15

<210> SEQ ID NO 146
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 146

Gln Arg Cys Asn Arg Ser Leu Leu Asp Ala Leu Ile Cys Gln Ala
1               5                   10                  15

<210> SEQ ID NO 147
<211> LENGTH: 15
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 147

Arg Gly Cys Met Leu Arg Leu Gln Pro Glu Leu Ala Cys Val Phe
1               5                   10                  15

<210> SEQ ID NO 148
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 148

Gly Gly Cys Ser Leu Val Trp Ala Asp Ser Trp Val Cys Ile Phe
1               5                   10                  15

<210> SEQ ID NO 149
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid comprising a small hydrophobic
      side chain
<220> FEATURE:
<221> NAME/KEY: MOD_RES
<222> LOCATION: (2)..(2)
<223> OTHER INFORMATION: Any amino acid comprising a large hydrophobic
      side chain
<220> FEATURE:
<221> NAME/KEY: MOD_RES
<222> LOCATION: (3)..(3)
<223> OTHER INFORMATION: Any amino acid comprising a large hydrophobic
      side chain
<220> FEATURE:
<221> NAME/KEY: MOD_RES
<222> LOCATION: (4)..(4)
<223> OTHER INFORMATION: Any amino acid comprising a large hydrophobic
      side chain
<220> FEATURE:
<221> NAME/KEY: MOD_RES
<222> LOCATION: (5)..(5)
<223> OTHER INFORMATION: Any amino acid
<220> FEATURE:
<221> NAME/KEY: MOD_RES
<222> LOCATION: (6)..(6)
<223> OTHER INFORMATION: Any amino acid comprising an acidic side chain
<220> FEATURE:
<221> NAME/KEY: MOD_RES
<222> LOCATION: (7)..(7)
<223> OTHER INFORMATION: Any amino acid comprising a small hydrophobic
      side chain
<220> FEATURE:
<221> NAME/KEY: MOD_RES
<222> LOCATION: (8)..(8)
<223> OTHER INFORMATION: Any amino acid comprising a large hydrophobic
      side chain
<220> FEATURE:
<221> NAME/KEY: MOD_RES
<222> LOCATION: (9)..(9)
<223> OTHER INFORMATION: Any amino acid comprising a large hydrophobic
      side chain or an acidic side chain

<400> SEQUENCE: 149

Xaa Xaa Xaa Xaa Xaa Xaa Xaa Xaa Xaa
1               5

```
<210> SEQ ID NO 150
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid comprising a small hydrophobic
      side chain or a basic side chain
<220> FEATURE:
<221> NAME/KEY: MOD_RES
<222> LOCATION: (3)..(3)
<223> OTHER INFORMATION: Any amino acid comprising a small hydrophobic
      side chain
<220> FEATURE:
<221> NAME/KEY: MOD_RES
<222> LOCATION: (4)..(4)
<223> OTHER INFORMATION: Any amino acid comprising a large hydrophobic
      side chain
<220> FEATURE:
<221> NAME/KEY: MOD_RES
<222> LOCATION: (5)..(5)
<223> OTHER INFORMATION: Any amino acid comprising a large hydrophobic
      side chain
<220> FEATURE:
<221> NAME/KEY: MOD_RES
<222> LOCATION: (6)..(6)
<223> OTHER INFORMATION: Any amino acid comprising a large hydrophobic
      side chain
<220> FEATURE:
<221> NAME/KEY: MOD_RES
<222> LOCATION: (7)..(7)
<223> OTHER INFORMATION: Any amino acid
<220> FEATURE:
<221> NAME/KEY: MOD_RES
<222> LOCATION: (8)..(8)
<223> OTHER INFORMATION: Any amino acid comprising an acidic side chain
<220> FEATURE:
<221> NAME/KEY: MOD_RES
<222> LOCATION: (9)..(9)
<223> OTHER INFORMATION: Any amino acid comprising a small hydrophobic
      side chain
<220> FEATURE:
<221> NAME/KEY: MOD_RES
<222> LOCATION: (10)..(10)
<223> OTHER INFORMATION: Any amino acid comprising a large hydrophobic
      side chain
<220> FEATURE:
<221> NAME/KEY: MOD_RES
<222> LOCATION: (11)..(11)
<223> OTHER INFORMATION: Any amino acid comprising a large hydrophobic
      side chain or an acidic side chain
<220> FEATURE:
<221> NAME/KEY: MOD_RES
<222> LOCATION: (13)..(13)
<223> OTHER INFORMATION: Any amino acid comprising a large hydrophobic
      side chain

<400> SEQUENCE: 150

Xaa Cys Xaa Xaa Xaa Xaa Xaa Xaa Xaa Xaa Xaa Cys Xaa
1               5                   10

<210> SEQ ID NO 151
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid comprising a small hydrophobic
      side chain or a basic side chain
```

```
<220> FEATURE:
<221> NAME/KEY: MOD_RES
<222> LOCATION: (2)..(2)
<223> OTHER INFORMATION: Any amino acid comprising a small hydrophobic
      side chain or a basic side chain
<220> FEATURE:
<221> NAME/KEY: MOD_RES
<222> LOCATION: (4)..(4)
<223> OTHER INFORMATION: Any amino acid comprising a small hydrophobic
      side chain
<220> FEATURE:
<221> NAME/KEY: MOD_RES
<222> LOCATION: (5)..(5)
<223> OTHER INFORMATION: Any amino acid comprising a large hydrophobic
      side chain
<220> FEATURE:
<221> NAME/KEY: MOD_RES
<222> LOCATION: (6)..(6)
<223> OTHER INFORMATION: Any amino acid comprising a large hydrophobic
      side chain
<220> FEATURE:
<221> NAME/KEY: MOD_RES
<222> LOCATION: (7)..(7)
<223> OTHER INFORMATION: Any amino acid comprising a large hydrophobic
      side chain
<220> FEATURE:
<221> NAME/KEY: MOD_RES
<222> LOCATION: (8)..(8)
<223> OTHER INFORMATION: Any amino acid
<220> FEATURE:
<221> NAME/KEY: MOD_RES
<222> LOCATION: (9)..(9)
<223> OTHER INFORMATION: Any amino acid comprising an acidic side chain
<220> FEATURE:
<221> NAME/KEY: MOD_RES
<222> LOCATION: (10)..(10)
<223> OTHER INFORMATION: Any amino acid comprising a small hydrophobic
      side chain
<220> FEATURE:
<221> NAME/KEY: MOD_RES
<222> LOCATION: (11)..(11)
<223> OTHER INFORMATION: Any amino acid comprising a large hydrophobic
      side chain
<220> FEATURE:
<221> NAME/KEY: MOD_RES
<222> LOCATION: (12)..(12)
<223> OTHER INFORMATION: Any amino acid comprising a large hydrophobic
      side chain or an acidic side chain
<220> FEATURE:
<221> NAME/KEY: MOD_RES
<222> LOCATION: (14)..(14)
<223> OTHER INFORMATION: Any amino acid comprising a large hydrophobic
      side chain
<220> FEATURE:
<221> NAME/KEY: MOD_RES
<222> LOCATION: (15)..(15)
<223> OTHER INFORMATION: Any amino acid comprising a large hydrophobic
      side chain

<400> SEQUENCE: 151

Xaa Xaa Cys Xaa Xaa Xaa Xaa Xaa Xaa Xaa Xaa Xaa Cys Xaa Xaa
1               5                   10                  15

<210> SEQ ID NO 152
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 152

Ser Arg Cys Ser Leu Val Trp Thr Asp Thr Trp Val Cys Val Phe
1               5                   10                  15
```

```
<210> SEQ ID NO 153
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 153

Ser Arg Cys Thr Leu Val Phe Asp Asp Ser Trp Val Cys Val Phe
1               5                   10                  15

<210> SEQ ID NO 154
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 154

Arg Gly Cys Ser Leu Val Trp Ser Gly Ser Trp Glu Cys Ile Phe
1               5                   10                  15

<210> SEQ ID NO 155
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 155

Gln Ala Cys Gln Leu Val Trp Leu Asp Ser Trp Val Cys Ile Phe
1               5                   10                  15

<210> SEQ ID NO 156
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 156

Val Gly Cys Ser Leu Val Trp Thr Asp Arg Trp Glu Cys Ile Phe
1               5                   10                  15

<210> SEQ ID NO 157
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 157

Ser Gly Cys Ser Leu Gln Trp Ala Asp Gly Trp Val Cys Ile Phe
1               5                   10                  15

<210> SEQ ID NO 158
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 158
```

```
Ala Arg Cys Ser Leu Val Trp Asp Glu Ala Trp Val Cys Ile Phe
1               5                   10                  15

<210> SEQ ID NO 159
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 159

Arg Gly Cys Ser Leu Val Trp Ala Gly Ser Trp Glu Cys Ile Phe
1               5                   10                  15

<210> SEQ ID NO 160
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 160

Ser Arg Cys Ser Leu Val Trp Ala Glu Asn Trp Val Cys Ile Phe
1               5                   10                  15

<210> SEQ ID NO 161
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 161

Arg Arg Cys Thr Leu Val Phe Leu Asp Ser Trp Glu Cys Ile Phe
1               5                   10                  15

<210> SEQ ID NO 162
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 162

Arg Gly Cys Thr Leu Ala Trp Glu Asp Ser Trp Val Cys Ile Phe
1               5                   10                  15

<210> SEQ ID NO 163
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 163

Arg Gly Cys Ser Leu Arg Phe Ala Glu Ala Trp Glu Cys Ile Phe
1               5                   10                  15

<210> SEQ ID NO 164
<211> LENGTH: 15
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 164

Ala Ser Cys Ser Leu Val Trp Gln Asp Ser Trp Val Cys Ile Phe
1               5                   10                  15

<210> SEQ ID NO 165
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 165

Ser Arg Cys Ser Leu Val Trp Ala Asp Ser Trp Val Cys Ile Phe
1               5                   10                  15

<210> SEQ ID NO 166
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 166

Gly Arg Cys His Leu Val Trp Ser Asp Arg Trp Glu Cys Ile Phe
1               5                   10                  15

<210> SEQ ID NO 167
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid comprising a small hydrophobic
      side chain
<220> FEATURE:
<221> NAME/KEY: MOD_RES
<222> LOCATION: (2)..(2)
<223> OTHER INFORMATION: Any amino acid comprising a large hydrophobic
      side chain
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (4)..(4)
<223> OTHER INFORMATION: Any amino acid comprising a large hydrophobic
      side chain
<220> FEATURE:
<221> NAME/KEY: MOD_RES
<222> LOCATION: (5)..(5)
<223> OTHER INFORMATION: Any amino acid comprising an acidic side chain
      or a polar neutral side chain
<220> FEATURE:
<221> NAME/KEY: MOD_RES
<222> LOCATION: (6)..(6)
<223> OTHER INFORMATION: Any amino acid
<220> FEATURE:
<221> NAME/KEY: MOD_RES
<222> LOCATION: (7)..(7)
<223> OTHER INFORMATION: Any amino acid
<220> FEATURE:
<221> NAME/KEY: MOD_RES
```

<222> LOCATION: (8)..(8)
<223> OTHER INFORMATION: Any amino acid comprising a large hydrophobic
      side chain
<220> FEATURE:
<221> NAME/KEY: MOD_RES
<222> LOCATION: (9)..(9)
<223> OTHER INFORMATION: Any amino acid comprising a large hydrophobic
      side chain
<220> FEATURE:
<221> NAME/KEY: MOD_RES
<222> LOCATION: (10)..(10)
<223> OTHER INFORMATION: Any amino acid comprising a large hydrophobic
      side chain or an acidic side chain

<400> SEQUENCE: 167

Xaa Xaa Xaa Xaa Xaa Xaa Xaa Xaa Xaa Xaa
1               5                   10

<210> SEQ ID NO 168
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid comprising a small hydrophobic
      side chain
<220> FEATURE:
<221> NAME/KEY: MOD_RES
<222> LOCATION: (3)..(3)
<223> OTHER INFORMATION: Any amino acid comprising a small hydrophobic
      side chain
<220> FEATURE:
<221> NAME/KEY: MOD_RES
<222> LOCATION: (4)..(4)
<223> OTHER INFORMATION: Any amino acid comprising a large hydrophobic
      side chain
<220> FEATURE:
<221> NAME/KEY: MOD_RES
<222> LOCATION: (5)..(5)
<223> OTHER INFORMATION: Any amino acid
<220> FEATURE:
<221> NAME/KEY: MOD_RES
<222> LOCATION: (6)..(6)
<223> OTHER INFORMATION: Any amino acid comprising a large hydrophobic
      side chain
<220> FEATURE:
<221> NAME/KEY: MOD_RES
<222> LOCATION: (7)..(7)
<223> OTHER INFORMATION: Any amino acid comprising an acidic side chain
      or a polar neutral side chain
<220> FEATURE:
<221> NAME/KEY: MOD_RES
<222> LOCATION: (8)..(8)
<223> OTHER INFORMATION: Any amino acid
<220> FEATURE:
<221> NAME/KEY: MOD_RES
<222> LOCATION: (9)..(9)
<223> OTHER INFORMATION: Any amino acid
<220> FEATURE:
<221> NAME/KEY: MOD_RES
<222> LOCATION: (10)..(10)
<223> OTHER INFORMATION: Any amino acid comprising a large hydrophobic
      side chain
<220> FEATURE:
<221> NAME/KEY: MOD_RES
<222> LOCATION: (11)..(11)
<223> OTHER INFORMATION: Any amino acid comprising a large hydrophobic
      side chain
<220> FEATURE:
<221> NAME/KEY: MOD_RES
<222> LOCATION: (12)..(12)
<223> OTHER INFORMATION: Any amino acid comprising a large hydrophobic
      side chain or an acidic side chain

```
<220> FEATURE:
<221> NAME/KEY: MOD_RES
<222> LOCATION: (14)..(14)
<223> OTHER INFORMATION: Any amino acid comprising a large hydrophobic
      side chain

<400> SEQUENCE: 168

Xaa Cys Xaa Xaa Xaa Xaa Xaa Xaa Xaa Xaa Xaa Xaa Cys Xaa
1               5                   10

<210> SEQ ID NO 169
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 169

Gly Cys Thr Leu Lys Trp Glu Ser Pro Asn Trp Thr Cys Tyr
1               5                   10

<210> SEQ ID NO 170
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 170

Ser Cys Thr Val Arg Trp Asp Gly Asp Trp Trp Val Cys Glu
1               5                   10

<210> SEQ ID NO 171
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 171

Gly Cys Ser Leu Met Trp Gln Asp Gly Trp Trp Val Cys Ile
1               5                   10

<210> SEQ ID NO 172
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 172

Gly Cys Thr Leu Ser Trp Asn Gln Gly Trp Trp His Cys Val
1               5                   10

<210> SEQ ID NO 173
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 173

Gly Cys Met Leu Thr Arg Gly Lys Phe Trp Trp Glu Cys Ile
```

1               5                  10

<210> SEQ ID NO 174
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 174

Gly Cys Val Leu Gln Phe Ser Gly Val Trp Trp Glu Cys Val
1               5                   10

<210> SEQ ID NO 175
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid comprising a polar/neutral side
      chain or a basic side chain
<220> FEATURE:
<221> NAME/KEY: MOD_RES
<222> LOCATION: (2)..(2)
<223> OTHER INFORMATION: Any amino acid comprising a large hydrophobic
      side chain
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (4)..(4)
<223> OTHER INFORMATION: Any amino acid comprising a polar neutral side
      chain or a basic side chain
<220> FEATURE:
<221> NAME/KEY: MOD_RES
<222> LOCATION: (7)..(7)
<223> OTHER INFORMATION: Any amino acid
<220> FEATURE:
<221> NAME/KEY: MOD_RES
<222> LOCATION: (8)..(8)
<223> OTHER INFORMATION: Any amino acid
<220> FEATURE:
<221> NAME/KEY: MOD_RES
<222> LOCATION: (9)..(9)
<223> OTHER INFORMATION: Any amino acid comprising a large hydrophobic
      side chain
<220> FEATURE:
<221> NAME/KEY: MOD_RES
<222> LOCATION: (10)..(10)
<223> OTHER INFORMATION: Any amino acid comprising an acidic side chain
      or a polar/neutral side chain

<400> SEQUENCE: 175

Xaa Xaa Xaa Xaa Pro Gly Xaa Xaa Xaa Xaa
1               5                   10

<210> SEQ ID NO 176
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid

```
<220> FEATURE:
<221> NAME/KEY: MOD_RES
<222> LOCATION: (3)..(3)
<223> OTHER INFORMATION: Any amino acid comprising a polar/neutral side
      chain or a basic side chain
<220> FEATURE:
<221> NAME/KEY: MOD_RES
<222> LOCATION: (4)..(4)
<223> OTHER INFORMATION: Any amino acid comprising a large hydrophobic
      side chain
<220> FEATURE:
<221> NAME/KEY: MOD_RES
<222> LOCATION: (5)..(5)
<223> OTHER INFORMATION: Any amino acid
<220> FEATURE:
<221> NAME/KEY: MOD_RES
<222> LOCATION: (6)..(6)
<223> OTHER INFORMATION: Any amino acid comprising a polar neutral side
      chain or a basic side chain
<220> FEATURE:
<221> NAME/KEY: MOD_RES
<222> LOCATION: (9)..(9)
<223> OTHER INFORMATION: Any amino acid
<220> FEATURE:
<221> NAME/KEY: MOD_RES
<222> LOCATION: (10)..(10)
<223> OTHER INFORMATION: Any amino acid
<220> FEATURE:
<221> NAME/KEY: MOD_RES
<222> LOCATION: (11)..(11)
<223> OTHER INFORMATION: Any amino acid comprising a large hydrophobic
      side chain
<220> FEATURE:
<221> NAME/KEY: MOD_RES
<222> LOCATION: (12)..(12)
<223> OTHER INFORMATION: Any amino acid comprising an acidic side chain
      or a polar/neutral side chain
<220> FEATURE:
<221> NAME/KEY: MOD_RES
<222> LOCATION: (14)..(14)
<223> OTHER INFORMATION: Any amino acid comprising a large hydrophobic
      side chain

<400> SEQUENCE: 176

Xaa Cys Xaa Xaa Xaa Xaa Pro Gly Xaa Xaa Xaa Xaa Cys Xaa
1               5                   10

<210> SEQ ID NO 177
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (4)..(4)
<223> OTHER INFORMATION: Any amino acid comprising a polar/neutral side
      chain or a basic side chain
<220> FEATURE:
<221> NAME/KEY: MOD_RES
<222> LOCATION: (5)..(5)
<223> OTHER INFORMATION: Any amino acid comprising a large hydrophobic
      side chain
<220> FEATURE:
<221> NAME/KEY: MOD_RES
<222> LOCATION: (6)..(6)
<223> OTHER INFORMATION: Any amino acid
<220> FEATURE:
```

```
<221> NAME/KEY: MOD_RES
<222> LOCATION: (7)..(7)
<223> OTHER INFORMATION: Any amino acid comprising a polar neutral side
      chain or a basic side chain
<220> FEATURE:
<221> NAME/KEY: MOD_RES
<222> LOCATION: (10)..(10)
<223> OTHER INFORMATION: Any amino acid
<220> FEATURE:
<221> NAME/KEY: MOD_RES
<222> LOCATION: (11)..(11)
<223> OTHER INFORMATION: Any amino acid
<220> FEATURE:
<221> NAME/KEY: MOD_RES
<222> LOCATION: (12)..(12)
<223> OTHER INFORMATION: Any amino acid comprising a large hydrophobic
      side chain
<220> FEATURE:
<221> NAME/KEY: MOD_RES
<222> LOCATION: (13)..(13)
<223> OTHER INFORMATION: Any amino acid comprising an acidic side chain
      or a polar/neutral side chain
<220> FEATURE:
<221> NAME/KEY: MOD_RES
<222> LOCATION: (15)..(15)
<223> OTHER INFORMATION: Any amino acid comprising a large hydrophobic
      side chain
<220> FEATURE:
<221> NAME/KEY: MOD_RES
<222> LOCATION: (16)..(16)
<223> OTHER INFORMATION: Any amino acid comprising a large hydrophobic
      side chain

<400> SEQUENCE: 177

Xaa Xaa Cys Xaa Xaa Xaa Xaa Pro Gly Xaa Xaa Xaa Xaa Cys Xaa Xaa
1               5                   10                  15

<210> SEQ ID NO 178
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 178

Gln Arg Cys Gln Leu Ser Trp Ser Gly Gly Glu Leu Gly Cys Met Phe
1               5                   10                  15

<210> SEQ ID NO 179
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 179

Ala Gly Cys Met Leu Leu Lys Pro Gly Leu Tyr Trp Glu Cys Ile Phe
1               5                   10                  15

<210> SEQ ID NO 180
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 180

Ala Arg Cys Ser Leu His His Thr Gly Ser Arg Tyr Glu Cys Ile Phe
1               5                   10                  15
```

<210> SEQ ID NO 181
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 181

Ala Thr Cys Met Leu Arg Leu Leu Gly Asp Gly Trp Gly Cys Val Phe
1               5                   10                  15

<210> SEQ ID NO 182
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 182

Gly Pro Cys Arg Leu Ser Asn Pro Gly Thr Gly Trp Glu Cys Ile Phe
1               5                   10                  15

<210> SEQ ID NO 183
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 183

Lys Gly Cys Thr Leu Gln Asn Pro Gly Ser Gly Trp Val Cys Leu Phe
1               5                   10                  15

<210> SEQ ID NO 184
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 184

Leu Ala Cys Ile Leu Ser Lys Pro Gly Glu His Trp Glu Cys Leu Phe
1               5                   10                  15

<210> SEQ ID NO 185
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 185

Asn Gly Cys Thr Leu Ser Phe Ser Gly Met Ser Trp Thr Cys Val Tyr
1               5                   10                  15

<210> SEQ ID NO 186
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 186

Asn Ser Cys Ile Leu Ser Asn Pro Gly Leu Gly Trp Gln Cys Val Phe
1               5                   10                  15

<210> SEQ ID NO 187
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 187

Asn Thr Cys Lys Leu Phe Arg Ser Gly Asn Ile Trp Gln Cys Ile Phe
1               5                   10                  15

<210> SEQ ID NO 188
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 188

Pro Ser Cys Arg Leu Trp Asn Pro Gly Phe Gly Trp Glu Cys Ile Phe
1               5                   10                  15

<210> SEQ ID NO 189
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 189

Gln Ser Cys Thr Leu Gln Arg Leu Gly His Leu Tyr Gln Cys Trp Phe
1               5                   10                  15

<210> SEQ ID NO 190
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 190

Ser Ala Cys Thr Pro Asn Trp Thr Gly Arg Trp Trp Glu Cys Val Phe
1               5                   10                  15

<210> SEQ ID NO 191
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 191

Ser Lys Cys His Leu Ile Val Ser Gly Lys Phe His Glu Cys Val Phe
1               5                   10                  15

<210> SEQ ID NO 192
<211> LENGTH: 16
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 192

Ser Ser Cys Thr Leu Phe Asn Pro Gly Thr Gly Trp Thr Cys Val Phe
1               5                   10                  15

<210> SEQ ID NO 193
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 193

Ser Thr Cys Arg Met Gly Asn Pro Gly Gly Val Trp Gly Cys Tyr Phe
1               5                   10                  15

<210> SEQ ID NO 194
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 194

Thr His Cys Leu Val Gln Trp Pro Gly Pro Val Val Ala Cys Arg Ser
1               5                   10                  15

<210> SEQ ID NO 195
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 195

Thr Arg Cys Arg Leu Leu Lys Leu Gly Ser Leu Trp Glu Cys Phe Gly
1               5                   10                  15

<210> SEQ ID NO 196
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid comprising a basic side chain
<220> FEATURE:
<221> NAME/KEY: MOD_RES
<222> LOCATION: (2)..(2)
<223> OTHER INFORMATION: Any amino acid comprising a large hydrophobic
      side chain
<220> FEATURE:
<221> NAME/KEY: MOD_RES
<222> LOCATION: (3)..(3)
<223> OTHER INFORMATION: Any amino acid comprising a basic side chain or
      a polar/neutral side chain
<220> FEATURE:
<221> NAME/KEY: MOD_RES
<222> LOCATION: (4)..(4)
<223> OTHER INFORMATION: Any amino acid comprising a basic side chain or
```

```
      a polar/neutral side chain
<220> FEATURE:
<221> NAME/KEY: MOD_RES
<222> LOCATION: (5)..(5)
<223> OTHER INFORMATION: Any amino acid
<220> FEATURE:
<221> NAME/KEY: MOD_RES
<222> LOCATION: (6)..(6)
<223> OTHER INFORMATION: Any amino acid
<220> FEATURE:
<221> NAME/KEY: MOD_RES
<222> LOCATION: (7)..(7)
<223> OTHER INFORMATION: Any amino acid
<220> FEATURE:
<221> NAME/KEY: MOD_RES
<222> LOCATION: (8)..(8)
<223> OTHER INFORMATION: Any amino acid
<220> FEATURE:
<221> NAME/KEY: MOD_RES
<222> LOCATION: (9)..(9)
<223> OTHER INFORMATION: Any amino acid
<220> FEATURE:
<221> NAME/KEY: MOD_RES
<222> LOCATION: (10)..(10)
<223> OTHER INFORMATION: Any amino acid comprising an aromatic side
      chain or a large hydrophobic side chain
<220> FEATURE:
<221> NAME/KEY: MOD_RES
<222> LOCATION: (11)..(11)
<223> OTHER INFORMATION: Any amino acid comprising an acidic side chain

<400> SEQUENCE: 196

Xaa Xaa Xaa Xaa Xaa Xaa Xaa Xaa Xaa Xaa Xaa
1               5                   10

<210> SEQ ID NO 197
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (3)..(3)
<223> OTHER INFORMATION: Any amino acid comprising a basic side chain
<220> FEATURE:
<221> NAME/KEY: MOD_RES
<222> LOCATION: (4)..(4)
<223> OTHER INFORMATION: Any amino acid comprising a large hydrophobic
      side chain
<220> FEATURE:
<221> NAME/KEY: MOD_RES
<222> LOCATION: (5)..(5)
<223> OTHER INFORMATION: Any amino acid comprising a basic side chain or
      a polar/neutral side chain
<220> FEATURE:
<221> NAME/KEY: MOD_RES
<222> LOCATION: (6)..(6)
<223> OTHER INFORMATION: Any amino acid comprising a basic side chain or
      a polar/neutral side chain
<220> FEATURE:
<221> NAME/KEY: MOD_RES
<222> LOCATION: (7)..(7)
<223> OTHER INFORMATION: Any amino acid
<220> FEATURE:
<221> NAME/KEY: MOD_RES
<222> LOCATION: (8)..(8)
<223> OTHER INFORMATION: Any amino acid
<220> FEATURE:
<221> NAME/KEY: MOD_RES
<222> LOCATION: (9)..(9)
<223> OTHER INFORMATION: Any amino acid
```

```
<220> FEATURE:
<221> NAME/KEY: MOD_RES
<222> LOCATION: (10)..(10)
<223> OTHER INFORMATION: Any amino acid
<220> FEATURE:
<221> NAME/KEY: MOD_RES
<222> LOCATION: (11)..(11)
<223> OTHER INFORMATION: Any amino acid
<220> FEATURE:
<221> NAME/KEY: MOD_RES
<222> LOCATION: (12)..(12)
<223> OTHER INFORMATION: Any amino acid comprising an aromatic side
      chain or a large hydrophobic side chain
<220> FEATURE:
<221> NAME/KEY: MOD_RES
<222> LOCATION: (13)..(13)
<223> OTHER INFORMATION: Any amino acid comprising an acidic side chain
<220> FEATURE:
<221> NAME/KEY: MOD_RES
<222> LOCATION: (15)..(15)
<223> OTHER INFORMATION: Any amino acid comprising a large hydrophobic
      side chain

<400> SEQUENCE: 197

Xaa Cys Xaa Xaa Xaa Xaa Xaa Xaa Xaa Xaa Xaa Xaa Xaa Cys Xaa
1               5                   10                  15

<210> SEQ ID NO 198
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 198

Ala Cys Trp Arg Ser Trp Arg Tyr Pro Thr Arg Thr Phe Cys Ser
1               5                   10                  15

<210> SEQ ID NO 199
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 199

Lys Cys Arg Leu Arg Gln Met Ser Arg Gly Gly Trp Glu Cys Leu
1               5                   10                  15

<210> SEQ ID NO 200
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 200

Asn Cys Arg Val Arg His Leu Pro Tyr Pro Phe Trp Ser Cys Leu
1               5                   10                  15

<210> SEQ ID NO 201
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 201

Arg Cys Arg Leu Gln Lys Ala Gly Gly Asn Thr Trp Glu Cys Ile
1               5                   10                  15

<210> SEQ ID NO 202
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 202

Arg Cys Thr Leu Arg Phe Asp Ala Gln Thr Gly Trp Glu Cys Asn
1               5                   10                  15

<210> SEQ ID NO 203
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 203

Thr Cys Arg Leu Lys Arg Ser Gly Pro Asn Ser Trp Glu Cys Ile
1               5                   10                  15

<210> SEQ ID NO 204
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 204

Thr Cys Thr Val His Arg Ile Gly Leu Ala Glu Trp Glu Cys Val
1               5                   10                  15

<210> SEQ ID NO 205
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid comprising a basic side chain
<220> FEATURE:
<221> NAME/KEY: MOD_RES
<222> LOCATION: (2)..(2)
<223> OTHER INFORMATION: Any amino acid comprising a basic side chain or
      an aromatic side chain or a large hydrophobic side chain
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (7)..(7)
<223> OTHER INFORMATION: Any amino acid
<220> FEATURE:
<221> NAME/KEY: MOD_RES
<222> LOCATION: (8)..(8)
```

```
<223> OTHER INFORMATION: Any amino acid
<220> FEATURE:
<221> NAME/KEY: MOD_RES
<222> LOCATION: (9)..(9)
<223> OTHER INFORMATION: Any amino acid
<220> FEATURE:
<221> NAME/KEY: MOD_RES
<222> LOCATION: (10)..(10)
<223> OTHER INFORMATION: Any amino acid

<400> SEQUENCE: 205

Xaa Xaa Xaa Xaa Pro Gly Xaa Xaa Xaa Xaa
1               5                   10

<210> SEQ ID NO 206
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid comprising a basic side chain
<220> FEATURE:
<221> NAME/KEY: MOD_RES
<222> LOCATION: (3)..(3)
<223> OTHER INFORMATION: Any amino acid comprising a basic side chain
<220> FEATURE:
<221> NAME/KEY: MOD_RES
<222> LOCATION: (4)..(4)
<223> OTHER INFORMATION: Any amino acid comprising a basic side chain or
      an aromatic side chain or a large hydrophobic side chain
<220> FEATURE:
<221> NAME/KEY: MOD_RES
<222> LOCATION: (5)..(5)
<223> OTHER INFORMATION: Any amino acid
<220> FEATURE:
<221> NAME/KEY: MOD_RES
<222> LOCATION: (6)..(6)
<223> OTHER INFORMATION: Any amino acid
<220> FEATURE:
<221> NAME/KEY: MOD_RES
<222> LOCATION: (9)..(9)
<223> OTHER INFORMATION: Any amino acid
<220> FEATURE:
<221> NAME/KEY: MOD_RES
<222> LOCATION: (10)..(10)
<223> OTHER INFORMATION: Any amino acid
<220> FEATURE:
<221> NAME/KEY: MOD_RES
<222> LOCATION: (11)..(11)
<223> OTHER INFORMATION: Any amino acid
<220> FEATURE:
<221> NAME/KEY: MOD_RES
<222> LOCATION: (12)..(12)
<223> OTHER INFORMATION: Any amino acid
<220> FEATURE:
<221> NAME/KEY: MOD_RES
<222> LOCATION: (14)..(14)
<223> OTHER INFORMATION: Any amino acid comprising a large hydrophobic
      side chain

<400> SEQUENCE: 206

Xaa Cys Xaa Xaa Xaa Xaa Pro Gly Xaa Xaa Xaa Xaa Cys Xaa
1               5                   10

<210> SEQ ID NO 207
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (1)..(1)
<223> OTHER INFORMATION: Any amino acid comprising a large hydrophobic
      side chain
<220> FEATURE:
<221> NAME/KEY: MOD_RES
<222> LOCATION: (2)..(2)
<223> OTHER INFORMATION: Any amino acid comprising a basic side chain
<220> FEATURE:
<221> NAME/KEY: MOD_RES
<222> LOCATION: (4)..(4)
<223> OTHER INFORMATION: Any amino acid comprising a basic side chain
<220> FEATURE:
<221> NAME/KEY: MOD_RES
<222> LOCATION: (5)..(5)
<223> OTHER INFORMATION: Any amino acid comprising a basic side chain or
      an aromatic side chain or a large hydrophobic side chain
<220> FEATURE:
<221> NAME/KEY: MOD_RES
<222> LOCATION: (6)..(6)
<223> OTHER INFORMATION: Any amino acid
<220> FEATURE:
<221> NAME/KEY: MOD_RES
<222> LOCATION: (7)..(7)
<223> OTHER INFORMATION: Any amino acid
<220> FEATURE:
<221> NAME/KEY: MOD_RES
<222> LOCATION: (10)..(10)
<223> OTHER INFORMATION: Any amino acid
<220> FEATURE:
<221> NAME/KEY: MOD_RES
<222> LOCATION: (11)..(11)
<223> OTHER INFORMATION: Any amino acid
<220> FEATURE:
<221> NAME/KEY: MOD_RES
<222> LOCATION: (12)..(12)
<223> OTHER INFORMATION: Any amino acid
<220> FEATURE:
<221> NAME/KEY: MOD_RES
<222> LOCATION: (13)..(13)
<223> OTHER INFORMATION: Any amino acid
<220> FEATURE:
<221> NAME/KEY: MOD_RES
<222> LOCATION: (15)..(15)
<223> OTHER INFORMATION: Any amino acid comprising a large hydrophobic
      side chain
<220> FEATURE:
<221> NAME/KEY: MOD_RES
<222> LOCATION: (16)..(16)
<223> OTHER INFORMATION: Any amino acid comprising a small hydrophobic
      side chain

<400> SEQUENCE: 207

Xaa Xaa Cys Xaa Xaa Xaa Xaa Pro Gly Xaa Xaa Xaa Xaa Cys Xaa Xaa
1               5                   10                  15

<210> SEQ ID NO 208
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 208

Val Lys Cys Lys Leu Val Asn Pro Gly Ser Gly Trp Ala Cys His Phe
1               5                   10                  15

<210> SEQ ID NO 209
<211> LENGTH: 16
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 209

Val Arg Cys Phe Met Ser Glu Pro Gly Arg Val Ser Tyr Cys Thr Ala
1               5                   10                  15

<210> SEQ ID NO 210
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 210

Val Arg Cys Arg Leu Ala Arg Pro Gly Leu Thr Trp Glu Cys Leu Ser
1               5                   10                  15

<210> SEQ ID NO 211
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 211

Val Arg Cys Arg Val Leu Tyr Pro Gly Gln Met Ala Val Cys Val Ser
1               5                   10                  15

<210> SEQ ID NO 212
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 212

Val Thr Cys Tyr Arg Ala Val Pro Gly Val Glu Ala Tyr Cys Phe Ser
1               5                   10                  15

<210> SEQ ID NO 213
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 213

Val Tyr Cys Arg Arg Glu Lys Pro Gly Gly Glu Met His Cys Arg Ser
1               5                   10                  15

<210> SEQ ID NO 214
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid comprising an aromatic side
      chain or a large hydrophobic side chain
<220> FEATURE:
<221> NAME/KEY: MOD_RES
<222> LOCATION: (2)..(2)

```
<223> OTHER INFORMATION: Any amino acid comprising a large hydrophobic
      side chain
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (7)..(7)
<223> OTHER INFORMATION: Any amino acid
<220> FEATURE:
<221> NAME/KEY: MOD_RES
<222> LOCATION: (8)..(8)
<223> OTHER INFORMATION: Any amino acid
<220> FEATURE:
<221> NAME/KEY: MOD_RES
<222> LOCATION: (9)..(9)
<223> OTHER INFORMATION: Any amino acid
<220> FEATURE:
<221> NAME/KEY: MOD_RES
<222> LOCATION: (10)..(10)
<223> OTHER INFORMATION: Any amino acid comprising an aromatic side
      chain or a large hydrophobic side chain

<400> SEQUENCE: 214

Xaa Xaa Xaa Xaa Pro Gly Xaa Xaa Xaa Xaa
1               5                   10

<210> SEQ ID NO 215
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (3)..(3)
<223> OTHER INFORMATION: Any amino acid comprising an aromatic side
      chain or a large hydrophobic side chain
<220> FEATURE:
<221> NAME/KEY: MOD_RES
<222> LOCATION: (4)..(4)
<223> OTHER INFORMATION: Any amino acid comprising a large hydrophobic
      side chain
<220> FEATURE:
<221> NAME/KEY: MOD_RES
<222> LOCATION: (5)..(5)
<223> OTHER INFORMATION: Any amino acid
<220> FEATURE:
<221> NAME/KEY: MOD_RES
<222> LOCATION: (6)..(6)
<223> OTHER INFORMATION: Any amino acid
<220> FEATURE:
<221> NAME/KEY: MOD_RES
<222> LOCATION: (9)..(9)
<223> OTHER INFORMATION: Any amino acid
<220> FEATURE:
<221> NAME/KEY: MOD_RES
<222> LOCATION: (10)..(10)
<223> OTHER INFORMATION: Any amino acid
<220> FEATURE:
<221> NAME/KEY: MOD_RES
<222> LOCATION: (11)..(11)
<223> OTHER INFORMATION: Any amino acid
<220> FEATURE:
<221> NAME/KEY: MOD_RES
<222> LOCATION: (12)..(12)
<223> OTHER INFORMATION: Any amino acid comprising an aromatic side
```

```
      chain or a large hydrophobic side chain
<220> FEATURE:
<221> NAME/KEY: MOD_RES
<222> LOCATION: (14)..(14)
<223> OTHER INFORMATION: Any amino acid

<400> SEQUENCE: 215

Xaa Cys Xaa Xaa Xaa Xaa Pro Gly Xaa Xaa Xaa Xaa Cys Xaa
1               5                   10

<210> SEQ ID NO 216
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (4)..(4)
<223> OTHER INFORMATION: Any amino acid comprising an aromatic side
      chain or a large hydrophobic side chain
<220> FEATURE:
<221> NAME/KEY: MOD_RES
<222> LOCATION: (5)..(5)
<223> OTHER INFORMATION: Any amino acid comprising a large hydrophobic
      side chain
<220> FEATURE:
<221> NAME/KEY: MOD_RES
<222> LOCATION: (6)..(6)
<223> OTHER INFORMATION: Any amino acid
<220> FEATURE:
<221> NAME/KEY: MOD_RES
<222> LOCATION: (7)..(7)
<223> OTHER INFORMATION: Any amino acid
<220> FEATURE:
<221> NAME/KEY: MOD_RES
<222> LOCATION: (10)..(10)
<223> OTHER INFORMATION: Any amino acid
<220> FEATURE:
<221> NAME/KEY: MOD_RES
<222> LOCATION: (11)..(11)
<223> OTHER INFORMATION: Any amino acid
<220> FEATURE:
<221> NAME/KEY: MOD_RES
<222> LOCATION: (12)..(12)
<223> OTHER INFORMATION: Any amino acid
<220> FEATURE:
<221> NAME/KEY: MOD_RES
<222> LOCATION: (13)..(13)
<223> OTHER INFORMATION: Any amino acid comprising an aromatic side
      chain or a large hydrophobic side chain
<220> FEATURE:
<221> NAME/KEY: MOD_RES
<222> LOCATION: (15)..(15)
<223> OTHER INFORMATION: Any amino acid
<220> FEATURE:
<221> NAME/KEY: MOD_RES
<222> LOCATION: (16)..(16)
<223> OTHER INFORMATION: Any amino acid comprising a large hydrophobic
      side chain

<400> SEQUENCE: 216

Xaa Xaa Cys Xaa Xaa Xaa Xaa Pro Gly Xaa Xaa Xaa Cys Xaa Xaa
1               5                   10                  15

<210> SEQ ID NO 217
```

```
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 217

Ala Thr Cys His Leu Leu Ala Pro Gly Val Asp Asn Thr Cys Ile Phe
1               5                   10                  15

<210> SEQ ID NO 218
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 218

His Gly Cys Thr Leu Thr Lys Pro Gly Ala Glu Trp Val Cys Ser Phe
1               5                   10                  15

<210> SEQ ID NO 219
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 219

Gln Leu Cys Pro Trp Ser Asp Pro Gly Ser Trp Gly Pro Cys Pro Leu
1               5                   10                  15

<210> SEQ ID NO 220
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 220

Arg Asp Cys Ala Gly Met Glu Pro Gly Thr Ser Val Phe Cys Asp Asn
1               5                   10                  15

<210> SEQ ID NO 221
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 221

Arg Asp Cys Phe Ile Leu Glu Pro Gly Thr Ser Val Tyr Cys Asp Leu
1               5                   10                  15

<210> SEQ ID NO 222
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 222
```

```
Thr Asp Cys Gln Glu Thr Trp Pro Gly Asp Arg Pro Trp Cys His Ile
1               5                   10                  15
```

```
<210> SEQ ID NO 223
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 223

Val Lys Cys Phe Met Ser Thr Pro Gly Gln Ile Ala Tyr Cys Thr Thr
1               5                   10                  15
```

```
<210> SEQ ID NO 224
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 224

Val Lys Cys Tyr Arg Asn Ser Pro Gly Val Glu Ala Tyr Cys Val Gly
1               5                   10                  15
```

```
<210> SEQ ID NO 225
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid comprising an acidic side chain
      or a polar/neutral side chain
<220> FEATURE:
<221> NAME/KEY: MOD_RES
<222> LOCATION: (2)..(2)
<223> OTHER INFORMATION: Any amino acid comprising an acidic side chain
      or a polar/neutral side chain
<220> FEATURE:
<221> NAME/KEY: MOD_RES
<222> LOCATION: (3)..(3)
<223> OTHER INFORMATION: Any amino acid comprising a large hydrophobic
      side chain
<220> FEATURE:
<221> NAME/KEY: MOD_RES
<222> LOCATION: (4)..(4)
<223> OTHER INFORMATION: Any amino acid comprising a polar/neutral side
      chain
<220> FEATURE:
<221> NAME/KEY: MOD_RES
<222> LOCATION: (5)..(5)
<223> OTHER INFORMATION: Any amino acid
<220> FEATURE:
<221> NAME/KEY: MOD_RES
<222> LOCATION: (6)..(6)
<223> OTHER INFORMATION: Any amino acid
<220> FEATURE:
<221> NAME/KEY: MOD_RES
<222> LOCATION: (7)..(7)
<223> OTHER INFORMATION: Any amino acid comprising a large hydrophobic
      side chain
<220> FEATURE:
<221> NAME/KEY: MOD_RES
<222> LOCATION: (8)..(8)
<223> OTHER INFORMATION: Any amino acid
<220> FEATURE:
<221> NAME/KEY: MOD_RES
<222> LOCATION: (9)..(9)
```

```
<223> OTHER INFORMATION: Any amino acid
<220> FEATURE:
<221> NAME/KEY: MOD_RES
<222> LOCATION: (10)..(10)
<223> OTHER INFORMATION: Any amino acid

<400> SEQUENCE: 225

Xaa Xaa Xaa Xaa Xaa Xaa Xaa Xaa Xaa Xaa
1               5                   10

<210> SEQ ID NO 226
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (3)..(3)
<223> OTHER INFORMATION: Any amino acid comprising an acidic side chain
      or a polar/neutral side chain
<220> FEATURE:
<221> NAME/KEY: MOD_RES
<222> LOCATION: (4)..(4)
<223> OTHER INFORMATION: Any amino acid comprising an acidic side chain
      or a polar/neutral side chain
<220> FEATURE:
<221> NAME/KEY: MOD_RES
<222> LOCATION: (5)..(5)
<223> OTHER INFORMATION: Any amino acid comprising a large hydrophobic
      side chain
<220> FEATURE:
<221> NAME/KEY: MOD_RES
<222> LOCATION: (6)..(6)
<223> OTHER INFORMATION: Any amino acid comprising a polar/neutral side
      chain
<220> FEATURE:
<221> NAME/KEY: MOD_RES
<222> LOCATION: (7)..(7)
<223> OTHER INFORMATION: Any amino acid
<220> FEATURE:
<221> NAME/KEY: MOD_RES
<222> LOCATION: (8)..(8)
<223> OTHER INFORMATION: Any amino acid
<220> FEATURE:
<221> NAME/KEY: MOD_RES
<222> LOCATION: (9)..(9)
<223> OTHER INFORMATION: Any amino acid comprising a large hydrophobic
      side chain
<220> FEATURE:
<221> NAME/KEY: MOD_RES
<222> LOCATION: (10)..(10)
<223> OTHER INFORMATION: Any amino acid
<220> FEATURE:
<221> NAME/KEY: MOD_RES
<222> LOCATION: (11)..(11)
<223> OTHER INFORMATION: Any amino acid
<220> FEATURE:
<221> NAME/KEY: MOD_RES
<222> LOCATION: (12)..(12)
<223> OTHER INFORMATION: Any amino acid
<220> FEATURE:
<221> NAME/KEY: MOD_RES
<222> LOCATION: (14)..(14)
<223> OTHER INFORMATION: Any amino acid

<400> SEQUENCE: 226

Xaa Cys Xaa Xaa Xaa Xaa Xaa Xaa Xaa Xaa Xaa Xaa Cys Xaa
1               5                   10
```

```
<210> SEQ ID NO 227
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 227

Asp Cys Leu Asp Leu Arg Gly Thr Val Gly Met Val Cys Gln
1               5                   10

<210> SEQ ID NO 228
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 228

Pro Cys Gln Arg Leu Ala Glu Tyr Tyr Ser Gln Gln Cys Leu
1               5                   10

<210> SEQ ID NO 229
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 229

Ser Cys Met Asp Leu Lys Gly Ser Val Gly Trp Val Cys Asp
1               5                   10

<210> SEQ ID NO 230
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 230

Thr Cys Glu Ser Leu Ala Lys Met Tyr Glu Val Glu Cys Asn
1               5                   10

<210> SEQ ID NO 231
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 231

Thr Cys Glu Ser Leu Ala Arg Met Tyr Asn Glu Asn Cys Ile
1               5                   10

<210> SEQ ID NO 232
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 232
```

```
Trp Cys Trp Glu Pro His Asp Gln Tyr Tyr Val Arg Cys Pro
1               5                   10

<210> SEQ ID NO 233
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 233

Tyr Cys His Asp Phe Lys Gly Thr Val Gly Thr Leu Cys Ile
1               5                   10

<210> SEQ ID NO 234
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 234

Gly Cys Gln Leu Val Trp Gln Asp Asp Ser Tyr Met Cys Phe Tyr
1               5                   10                  15

<210> SEQ ID NO 235
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: F, I, L, M, V, W, or Y
<220> FEATURE:
<221> NAME/KEY: MOD_RES
<222> LOCATION: (6)..(6)
<223> OTHER INFORMATION: F, I, L, M, V, W, or Y
<220> FEATURE:
<221> NAME/KEY: MOD_RES
<222> LOCATION: (8)..(8)
<223> OTHER INFORMATION: H, N, Q, F, I, L, M, V, W, or Y

<400> SEQUENCE: 235

Xaa Gly Gln Pro Leu Xaa Arg Xaa Gly Ser
1               5                   10

<210> SEQ ID NO 236
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: F, I, L, M, V, W, or Y
<220> FEATURE:
<221> NAME/KEY: MOD_RES
<222> LOCATION: (8)..(8)
<223> OTHER INFORMATION: F, I, L, M, V, W, or Y
<220> FEATURE:
<221> NAME/KEY: MOD_RES
<222> LOCATION: (10)..(10)
<223> OTHER INFORMATION: H, N, Q, F, I, L, M, V, W, or Y
```

```
<400> SEQUENCE: 236

Trp Cys Xaa Gly Gln Pro Leu Xaa Arg Xaa Gly Ser Cys Lys
1               5                   10

<210> SEQ ID NO 237
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 237

Trp Cys Ile Gly Gln Pro Leu Phe Arg Gln Gly Ser Cys Lys
1               5                   10

<210> SEQ ID NO 238
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 238

Trp Cys Val Gly Gln Pro Leu Tyr Arg Leu Gly Ser Cys Lys
1               5                   10

<210> SEQ ID NO 239
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 239

Trp Asp Gln Phe Gln Leu Gly Trp Glu Ala Gly Val Ala Ala
1               5                   10

<210> SEQ ID NO 240
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 240

Phe Leu Pro Trp Pro Val Tyr Phe Ser Gln Val Leu Gly Gly Gly
1               5                   10                  15

<210> SEQ ID NO 241
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 241

Tyr Val Met Cys Ser Ala Phe Gly Cys Lys Ser Ile
1               5                   10

<210> SEQ ID NO 242
<211> LENGTH: 12
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 242

His Val Ile Cys Ser Val Asn Gly Gly Cys Arg Gly
1               5                  10

<210> SEQ ID NO 243
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 243

Ile Arg Phe Cys Leu Arg Ser Glu Pro Thr Ala Cys Trp Ile Val
1               5                   10                  15

<210> SEQ ID NO 244
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 244

Ile Arg Cys Arg Tyr Glu Lys Gln Ser Gly Ile Cys Leu Phe
1               5                   10

<210> SEQ ID NO 245
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 245

Gly Gly Cys Ser Leu Val Trp Ala Asp Ser Trp Val Cys Ile Phe
1               5                   10                  15

<210> SEQ ID NO 246
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 246

Gly Cys Ser Leu Met Trp Gln Asp Gly Trp Trp Val Cys Ile
1               5                   10

<210> SEQ ID NO 247
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 247

Glu Trp Glu Cys Arg Phe Leu Pro Gly Arg Arg Gly Cys Ser Leu Phe
1               5                   10                  15
```

<210> SEQ ID NO 248
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 248

Lys Gly Cys Thr Leu Gln Asn Pro Gly Ser Gly Trp Val Cys Leu Phe
1               5                   10                  15

<210> SEQ ID NO 249
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 249

Thr Cys Arg Leu Lys Arg Ser Gly Pro Asn Ser Trp Glu Cys Ile
1               5                   10                  15

<210> SEQ ID NO 250
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 250

Trp Cys Ile Gly Gln Pro Leu Phe Arg Gln Gly Ser Cys Lys
1               5                   10

<210> SEQ ID NO 251
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 251

Ala Val Ser Cys Asn Ser Trp Arg Cys Ile Pro Trp
1               5                   10

<210> SEQ ID NO 252
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 252

Ala Val Cys Cys Asp Gly Asn Ser Cys Arg Arg Cys
1               5                   10

<210> SEQ ID NO 253
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 253

Phe Val His Cys Ser Leu Met Gly Cys Trp Cys Gly
1               5                   10

<210> SEQ ID NO 254
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 254

Arg Cys Leu Asp Leu Gly Gly Ser Val Gly Leu Val Cys Phe
1               5                   10

<210> SEQ ID NO 255
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 255

Val Cys Phe Asn Phe Arg Gly Thr Val Gly Arg His Cys Trp
1               5                   10

<210> SEQ ID NO 256
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 256

Val Arg Cys Arg Gln Asn Glu Pro Gly Gly Ala Tyr Trp Cys Ser Ser
1               5                   10                  15

<210> SEQ ID NO 257
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 257

Cys Val Leu Arg Glu Gly Ala Glu Gly Trp Glu Cys Val Trp Arg
1               5                   10                  15

<210> SEQ ID NO 258
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 258

Cys Arg Met Met Gln Gly Thr Tyr Gly Trp Thr Cys Leu Phe
1               5                   10

<210> SEQ ID NO 259
<211> LENGTH: 14

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 259

Cys Ile Leu Asn Asp Thr Ile Gln Gly Trp Val Cys Ile Tyr
1               5                   10

<210> SEQ ID NO 260
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 260

Cys Thr Leu Tyr Arg Ser Ala Pro Gly Val Trp Leu Cys Ile Phe
1               5                   10                  15

<210> SEQ ID NO 261
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 261

Cys Leu Val Phe Asp Gln Tyr Gly Asn Tyr Lys Arg Arg Cys
1               5                   10

<210> SEQ ID NO 262
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 262

Ile Val Cys Cys Asn Met Phe Gly Cys His Thr Cys Arg Asn
1               5                   10

<210> SEQ ID NO 263
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 263

Gln Val Cys Cys Thr Ser Arg Gly Cys Arg Val Cys Ala Pro Val
1               5                   10                  15

<210> SEQ ID NO 264
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 264

Arg Val Cys Cys Ser Met Val Gly Cys Arg Ser Cys Asn Leu
```

```
<210> SEQ ID NO 265
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 265

Arg Val Cys Cys Thr Phe Ala Gly Cys Arg Val Cys His Lys
1               5                   10

<210> SEQ ID NO 266
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 266

Arg Val Cys Cys Thr Ser Asp Gly Cys Arg Gly Cys Arg Gln
1               5                   10

<210> SEQ ID NO 267
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 267

Thr Val Cys Cys Thr Val Gln Gly Cys Trp Pro Cys Ser Arg
1               5                   10

<210> SEQ ID NO 268
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 268

Val Cys Cys His Gln Thr Phe Gly Cys Tyr Arg Cys Lys Gln
1               5                   10

<210> SEQ ID NO 269
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 269

Cys Val Val Cys Ser Ala Leu Gly Cys Arg Ala Cys Val Pro Arg
1               5                   10                  15

<210> SEQ ID NO 270
<211> LENGTH: 18
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 270

Val Trp Asp Cys Phe Val Arg Gly Trp Glu Ala Gly Val Ala Ala Val
1               5                   10                  15

Gly Glu

<210> SEQ ID NO 271
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 271

Leu Thr Cys Leu Ile Phe Lys Pro Gly Thr Arg His Cys Pro Val
1               5                   10                  15

<210> SEQ ID NO 272
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 272

Arg Tyr Cys Ser Pro Leu Ile Pro Gly Ser Ala Leu Gly Cys Pro Arg
1               5                   10                  15

<210> SEQ ID NO 273
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 273

Ile Arg Cys Arg Leu Asp Pro Pro Gly Ser Tyr Lys Thr Cys Val Phe
1               5                   10                  15

<210> SEQ ID NO 274
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 274

Arg Gly Val Ile Cys Asn His Ala Gly Cys Arg Ile Trp Tyr Gly
1               5                   10                  15

<210> SEQ ID NO 275
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 275

Thr Thr Gln Ser Cys Thr Leu Arg Tyr Cys Trp Leu Leu Gln
1               5                   10

```
<210> SEQ ID NO 276
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 276

Trp Trp Ile Ser Cys Leu Arg Asp Leu Arg Cys Leu Glu Tyr Phe
1               5                   10                  15

<210> SEQ ID NO 277
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 277

Arg His Ala Cys Lys Thr Trp Tyr Arg Met Cys Ile Val Ser
1               5                   10

<210> SEQ ID NO 278
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 278

Ala Val Ser Cys Ser Arg Leu Thr Gly Arg Cys His Ser Leu
1               5                   10

<210> SEQ ID NO 279
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 279

Trp Val Ala Cys Asn Arg Val Thr Gly Ser Cys Arg Pro Ile
1               5                   10

<210> SEQ ID NO 280
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 280

Ser His Gly Val Cys Cys Thr Gln Ser Ser Cys Arg Ser Cys Arg
1               5                   10                  15

<210> SEQ ID NO 281
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 281

Trp Val Ala Cys Asn Arg Leu Ser Gly Cys Cys Arg Pro Ile
1               5                   10

<210> SEQ ID NO 282
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 282

His Thr Val Cys Cys Gln Asp Trp Gly Cys Arg Ser Cys Ser Gly
1               5                   10                  15

<210> SEQ ID NO 283
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 283

Met Ala Cys Cys Thr Pro Arg Gly Cys Arg Pro Cys
1               5                   10

<210> SEQ ID NO 284
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 284

Arg Ser Val Cys Cys Ser Ser Tyr Gly Cys Arg Ala Cys Phe Gly
1               5                   10                  15

<210> SEQ ID NO 285
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 285

Cys Lys Leu Thr Cys Thr Ser Ser Thr Cys Ser Cys Val Phe
1               5                   10

<210> SEQ ID NO 286
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 286

Cys Met Leu Lys Cys Thr Asn Ala Ile Cys Glu Cys Ile Phe
1               5                   10

<210> SEQ ID NO 287
<211> LENGTH: 14
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 287

Cys Arg Val Trp Cys Asn Gln Ala Glu Cys Met Cys Ile Phe
1               5                   10

<210> SEQ ID NO 288
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 288

Ser Arg Cys Ser Phe Asp Val Thr Lys Gln Glu Cys Val Phe
1               5                   10

<210> SEQ ID NO 289
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 289

Leu Glu Cys Gln Pro Tyr Arg Gly Pro Leu Tyr Tyr Cys Gln Asp
1               5                   10                  15

<210> SEQ ID NO 290
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 290

Ser Ile Cys Cys Thr Pro Gln Leu Cys His Ser Cys Asp Gly
1               5                   10

<210> SEQ ID NO 291
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 291

Thr Thr Cys Cys Thr Ser Glu Gly Cys His Lys Cys Ile Thr Leu
1               5                   10                  15

<210> SEQ ID NO 292
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 292

Cys Val Ala Cys Ser Ser Asp Gly Cys Ser Pro Ile Ile Cys
1               5                   10
```

<210> SEQ ID NO 293
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 293

Ala Ile Cys Ser Glu Asp Glu Gly Gly Glu Leu Cys Cys Trp His
1               5                   10                  15

<210> SEQ ID NO 294
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 294

His Glu Ile Cys Cys Gly Pro Pro Gly Cys His Ser Cys Ser Val Thr
1               5                   10                  15

<210> SEQ ID NO 295
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 295

Leu Ser Val Cys Ser Cys Pro Pro Gly Gln Leu Tyr Cys Met Val Glu
1               5                   10                  15

<210> SEQ ID NO 296
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 296

Ser Thr Trp Cys Cys Leu His Pro Gly Val Gly Glu Cys Gln Ala Val
1               5                   10                  15

<210> SEQ ID NO 297
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 297

Val Thr Gln Cys Phe Asp Gly Pro Gly Ser Phe Arg Cys Cys Tyr Gln
1               5                   10                  15

<210> SEQ ID NO 298
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 298

Arg Gln Cys Asn Cys Leu Ser Pro Gly Glu Leu Val Asn Cys Gln Gln
1               5                   10                  15

<210> SEQ ID NO 299
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 299

Met Val Ser Cys Thr Asp Leu Gly Cys Val Val Gly Gly Gly
1               5                   10                  15

<210> SEQ ID NO 300
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 300

Val Val His Cys Leu Gln Ser Gly Cys Tyr Ser Val Gly Ser Gly
1               5                   10                  15

<210> SEQ ID NO 301
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 301

Thr Ile Lys Cys Gly Ser Ser Gly Trp Cys Trp Val Glu Ala Gly
1               5                   10                  15

<210> SEQ ID NO 302
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 302

Met Val Ser Cys Thr Asp Leu Gly Cys Val Val Gly Gly Gly
1               5                   10                  15

<210> SEQ ID NO 303
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 303

His Glu Ile Cys Cys Gly Pro Pro Gly Cys His Ser Cys Ser Val Thr
1               5                   10                  15

<210> SEQ ID NO 304
<211> LENGTH: 16
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 304

Leu Ser Val Cys Ser Cys Pro Pro Gly Gln Leu Tyr Cys Met Val Glu
1               5                   10                  15

<210> SEQ ID NO 305
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 305

Ser Thr Trp Cys Cys Leu His Pro Gly Val Gly Glu Cys Gln Ala Val
1               5                   10                  15

<210> SEQ ID NO 306
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 306

Val Thr Gln Cys Phe Asp Gly Pro Gly Ser Phe Arg Cys Cys Tyr Gln
1               5                   10                  15

<210> SEQ ID NO 307
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 307

Arg Gln Cys Asn Cys Leu Ser Pro Gly Glu Leu Val Asn Cys Gln Gln
1               5                   10                  15

<210> SEQ ID NO 308
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 308

Phe Val Arg Cys Ser Ala Asn Gly Cys Val
1               5                   10

<210> SEQ ID NO 309
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 309

Ser Val Arg Cys Ser Ala Ser Gly Cys Val
```

```
1               5                   10
```

<210> SEQ ID NO 310
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 310

```
Tyr Val Ala Cys Ser Val Ser Gly Cys Val
1               5                   10
```

<210> SEQ ID NO 311
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 311

```
Tyr Val Ile Cys Gly Ala Ser Gly Cys Val
1               5                   10
```

<210> SEQ ID NO 312
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 312

```
Tyr Val Arg Cys Thr Ala Ile Gly Cys Val
1               5                   10
```

<210> SEQ ID NO 313
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 313

```
Phe Val Arg Cys Ser Ala Thr Gly Cys Val
1               5                   10
```

<210> SEQ ID NO 314
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 314

```
Tyr Val Ile Cys Ser Ala Ser Gly Cys Val
1               5                   10
```

<210> SEQ ID NO 315
<211> LENGTH: 10
<212> TYPE: PRT
<213> ORGANISM: Artificial Sequence
<220> FEATURE:
<223> OTHER INFORMATION: Description of Artificial Sequence: Synthetic

```
                                peptide

<400> SEQUENCE: 315

Trp Val Arg Cys Ser Ala Ser Gly Cys Val
1               5                   10

<210> SEQ ID NO 316
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 316

Phe Val Arg Cys Ser Ala Ser Gly Cys Val
1               5                   10

<210> SEQ ID NO 317
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 317

Phe Val Arg Cys Thr Ala Ser Gly Cys Val
1               5                   10

<210> SEQ ID NO 318
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 318

Phe Val Arg Cys Thr Ser Asp Gly Cys Val
1               5                   10

<210> SEQ ID NO 319
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 319

Tyr Val Arg Cys Thr Ala Ser Gly Cys Val
1               5                   10

<210> SEQ ID NO 320
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 320

Phe Arg Arg Cys Ser Ala Ser Gly Cys Val
1               5                   10

<210> SEQ ID NO 321
```

```
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 321

Leu Arg Arg Cys Ser Ala Asn Gly Cys Val
1               5                   10

<210> SEQ ID NO 322
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 322

Leu Arg Arg Cys Ser Ala Asn Gly Cys Val
1               5                   10

<210> SEQ ID NO 323
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 323

Phe Val Arg Cys Ser Leu Ile Gly Cys Val
1               5                   10

<210> SEQ ID NO 324
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 324

Phe Val Arg Cys Asn Ala Ser Gly Cys Val
1               5                   10

<210> SEQ ID NO 325
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 325

Phe Val Arg Cys Thr Arg Glu Gly Cys Val
1               5                   10

<210> SEQ ID NO 326
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 326
```

Phe Val Arg Cys Thr Ser Asp Gly Cys Val
1               5                   10

<210> SEQ ID NO 327
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 327

Tyr Val Ile Cys Ser Ala Ser Gly Cys Val
1               5                   10

<210> SEQ ID NO 328
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 328

Phe Val Arg Cys Thr Glu Trp Gly Cys Val
1               5                   10

<210> SEQ ID NO 329
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 329

Phe Val Arg Cys Thr Ala Ser Gly Cys Ile
1               5                   10

<210> SEQ ID NO 330
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 330

Tyr Val Arg Cys Ser Glu Ser Gly Cys Val Gly Ser Ser Trp Asn Ala
1               5                   10                  15

<210> SEQ ID NO 331
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 331

Phe Val Arg Cys Ser Glu Ser Gly Cys Val Gly Ser Ser Trp Ser Ala
1               5                   10                  15

<210> SEQ ID NO 332
<211> LENGTH: 16
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 332

Tyr Val Arg Cys Ser Ala Ser Gly Cys Val Gly Ser Ser Trp Phe Leu
1               5                   10                  15

<210> SEQ ID NO 333
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 333

Tyr Val Arg Cys Ser Asp Ser Gly Cys Val Gly Ser Thr Trp Gly Trp
1               5                   10                  15

<210> SEQ ID NO 334
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 334

Tyr Val Arg Cys Ser Glu Ser Gly Cys Val Gly Ser Thr Trp Val Phe
1               5                   10                  15

<210> SEQ ID NO 335
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 335

Tyr Val Arg Cys Ser Glu Ser Gly Cys Val Gly Ser Thr Trp Val Phe
1               5                   10                  15

<210> SEQ ID NO 336
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 336

Tyr Val Leu Cys Ala Leu Ser Gly Cys Val Gly Ser Ser Trp Ser Ser
1               5                   10                  15

<210> SEQ ID NO 337
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 337

Tyr Val Arg Cys Gly Glu Ser Gly Cys Val Gly Ser Thr Trp Ser Thr
1               5                   10                  15

```
<210> SEQ ID NO 338
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 338

Tyr Val Arg Cys Ser Ala Thr Gly Cys Val Gly Ser Thr Trp Thr Phe
1               5                   10                  15

<210> SEQ ID NO 339
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 339

Tyr Val Arg Cys Gly Glu Thr Gly Cys Val Gly Ser Thr Trp Ser Phe
1               5                   10                  15

<210> SEQ ID NO 340
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 340

Tyr Val Arg Cys Gly Val Ser Gly Cys Val Gly Ser Ser Trp Val Leu
1               5                   10                  15

<210> SEQ ID NO 341
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 341

Tyr Val Arg Cys Gly Glu Ser Gly Cys Val Gly Ser Thr Trp Ser Thr
1               5                   10                  15

<210> SEQ ID NO 342
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 342

Phe Val Arg Cys Ser Glu Ser Gly Cys Val Gly Ser Ser Trp Ser Thr
1               5                   10                  15

<210> SEQ ID NO 343
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 343
```

Tyr Val Arg Cys Ser Glu Ser Gly Cys Val Gly Ser Ser Trp Trp Ala
1               5                   10                  15

<210> SEQ ID NO 344
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 344

Tyr Val Arg Cys Ser Val Thr Gly Cys Val Gly Ser Ser Trp Ser Ile
1               5                   10                  15

<210> SEQ ID NO 345
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 345

Tyr Val Arg Cys Ser Val Thr Gly Cys Val Gly Ser Ser Trp Ser Ile
1               5                   10                  15

<210> SEQ ID NO 346
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 346

Tyr Val Arg Cys Ser Glu Ser Gly Cys Val Gly Ser Ser Trp Ser Val
1               5                   10                  15

<210> SEQ ID NO 347
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 347

Phe Val Arg Cys Ser Ala Asp Gly Cys Val Gly Ser Ser Trp Leu Gln
1               5                   10                  15

<210> SEQ ID NO 348
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 348

Tyr Val Arg Cys Ser Ala Asp Gly Cys Val Gly Ser Ser Trp Ile Thr
1               5                   10                  15

<210> SEQ ID NO 349
<211> LENGTH: 16
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 349

Tyr Val Arg Cys Asn Pro Ser Gly Cys Val Gly Ser Ser Trp Ser Ile
1               5                   10                  15

<210> SEQ ID NO 350
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 350

Tyr Val Arg Cys Ser Val Thr Gly Cys Val Gly Ser Ser Trp Ser Ile
1               5                   10                  15

<210> SEQ ID NO 351
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 351

Tyr Val Arg Cys Ser Glu Ser Gly Cys Val Gly Ser Ser Trp Ser Val
1               5                   10                  15

<210> SEQ ID NO 352
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 352

Phe Val Arg Cys Ser Ala Asn Gly Cys Val Gly Ser Thr Trp Gln Ala
1               5                   10                  15

<210> SEQ ID NO 353
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 353

Tyr Val Arg Cys Thr Glu Ser Gly Cys Val Gly Ser Thr Trp Thr Tyr
1               5                   10                  15

<210> SEQ ID NO 354
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 354

Tyr Val Arg Cys Ser Val Thr Gly Cys Val Gly Ser Thr Trp Ser Val
1               5                   10                  15
```

<210> SEQ ID NO 355
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 355

Tyr Val Arg Cys Ser Glu Ile Gly Cys Val Gly Ser Thr Trp Ser Leu
1               5                   10                  15

<210> SEQ ID NO 356
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 356

Thr Val Arg Cys Ser Ala Thr Gly Cys Val Gly Ser Ser Trp Val Gly
1               5                   10                  15

<210> SEQ ID NO 357
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 357

Tyr Val Arg Cys Ser Ala Thr Gly Cys Val Gly Ser Ser Trp Val Gly
1               5                   10                  15

<210> SEQ ID NO 358
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 358

Phe Val Arg Cys Ser Ala Ser Gly Cys Val Gly Ser Ser Trp Val Gly
1               5                   10                  15

<210> SEQ ID NO 359
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 359

Tyr Val Arg Cys Ser Ala Asp Gly Cys Val Gly Ser Thr Trp Asn Leu
1               5                   10                  15

<210> SEQ ID NO 360
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 360

Tyr Val Arg Ser Ser Gln Ser Gly Cys Val Gly Ser Gly Trp Val Leu
1               5                   10                  15

<210> SEQ ID NO 361
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 361

Tyr Val Ala Cys Ser Glu Ser Gly Cys Val Gly Ser Ser Trp Ser Val
1               5                   10                  15

<210> SEQ ID NO 362
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 362

Phe Val Ala Cys Gly Glu Leu Gly Cys Val Gly Ser Ser Trp Ser Ile
1               5                   10                  15

<210> SEQ ID NO 363
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 363

Tyr Val Ala Cys Ser Glu Ser Gly Cys Val Gly Ser Ser Trp Leu Ala
1               5                   10                  15

<210> SEQ ID NO 364
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 364

Tyr Cys Arg Cys Thr Glu Ser Gly Cys Val Gly Ser Thr Trp Thr Tyr
1               5                   10                  15

<210> SEQ ID NO 365
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 365

Phe Val Arg Cys Thr Ala Ile Gly Cys Val Gly Ser Ser Trp Ser Val
1               5                   10                  15

<210> SEQ ID NO 366
<211> LENGTH: 16
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 366

Tyr Val Arg Cys Ser Ala Asp Gly Cys Val Gly Ser Ser Trp Ser Ala
1               5                   10                  15

<210> SEQ ID NO 367
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 367

Tyr Val Arg Cys Ser Ala Ser Gly Cys Val Gly Ser Ser Trp Asn Tyr
1               5                   10                  15

<210> SEQ ID NO 368
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 368

Tyr Val Leu Cys Ser Ala Ser Gly Cys Val Gly Ser Leu Trp Thr His
1               5                   10                  15

<210> SEQ ID NO 369
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 369

Tyr Val Arg Cys Thr Asp Ser Gly Cys Val Gly Ser Ser Trp His Leu
1               5                   10                  15

<210> SEQ ID NO 370
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 370

Tyr Val Ala Cys Ser Glu Ser Gly Cys Val Gly Ser Thr Trp Ile Thr
1               5                   10                  15

<210> SEQ ID NO 371
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 371

Tyr Val Ala Cys Ser Glu Ser Gly Cys Val Gly Ser Thr Trp Thr Phe
1               5                   10                  15
```

<210> SEQ ID NO 372
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 372

Tyr Val Arg Cys Gly Ala Ala Gly Cys Val Val Ser Ser Trp Val Tyr
1               5                   10                  15

<210> SEQ ID NO 373
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 373

Phe Val Arg Cys Gly Ala Ser Gly Cys Val Gly Ser Thr Trp Gly Ser
1               5                   10                  15

<210> SEQ ID NO 374
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 374

Tyr Val Ala Cys Ser Glu Ile Gly Cys Val Gly Ser Thr Trp Ser Leu
1               5                   10                  15

<210> SEQ ID NO 375
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 375

Tyr Val Ala Cys Ser Glu Ser Gly Cys Val Gly Ser Ser Trp Thr Trp
1               5                   10                  15

<210> SEQ ID NO 376
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 376

Tyr Val Ala Cys Ser Val Ser Gly Cys Val Gly Ser Ser Trp Ser Val
1               5                   10                  15

<210> SEQ ID NO 377
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide -continued

```
<400> SEQUENCE: 377

Tyr Val Arg Cys Ser Glu Ser Gly Cys Val Gly Ser Thr Trp Thr Thr
1               5                   10                  15

<210> SEQ ID NO 378
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 378

Tyr Val Arg Cys Ser Glu Ser Gly Cys Val Ser Ser Phe Trp Ser Ala
1               5                   10                  15

Pro Trp Lys Ala
            20

<210> SEQ ID NO 379
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 379

Tyr Val Arg Cys Ser Glu Asn Gly Cys Val Gly His Ser Trp Thr Gln
1               5                   10                  15

Gly Leu Arg Thr
            20

<210> SEQ ID NO 380
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 380

Tyr Val Arg Cys Ser Glu Ser Gly Cys Val Ser Gln Arg Pro His Val
1               5                   10                  15

Leu Glu Val Trp
            20

<210> SEQ ID NO 381
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 381

Tyr Val Leu Cys Ser Glu Arg Gly Cys Val Gly Gln Asn Trp Ala Val
1               5                   10                  15

Gly Lys Leu Pro
            20

<210> SEQ ID NO 382
<211> LENGTH: 20
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 382

Tyr Val Arg Cys Ser Glu Ile Gly Cys Val Gly Ser His Trp Ser Ser
1               5                   10                  15

Tyr Gly Lys His
            20

<210> SEQ ID NO 383
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 383

Tyr Val Arg Cys Ser Glu Asn Gly Cys Val Gly Ser Ser Trp Gly Arg
1               5                   10                  15

Val Thr Leu Asp
            20

<210> SEQ ID NO 384
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 384

Tyr Val Arg Cys Ser Glu Ser Gly Cys Val Gly Cys Glu Leu Val Trp
1               5                   10                  15

Tyr Phe Ile Thr
            20

<210> SEQ ID NO 385
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 385

Tyr Val Arg Cys Ser Glu Ser Gly Cys Val Gly Ser Ser Trp Gly Ala
1               5                   10                  15

Val Ala Ser Ile
            20

<210> SEQ ID NO 386
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 386

Tyr Val Arg Cys Ser Glu Ser Gly Cys Val Gly Ser Ser Trp Gly Ala
1               5                   10                  15

Val Ala Ser Ile
            20
```

```
<210> SEQ ID NO 387
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 387

Tyr Val Arg Cys Ser Glu Ser Gly Cys Val Gly Ser Ser Trp Ser Val
1               5                   10                  15

Ser Pro Arg Gly
            20

<210> SEQ ID NO 388
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 388

Tyr Val Arg Cys Gly Glu Ser Gly Cys Val Ser Ser Ser Trp Ser Thr
1               5                   10                  15

Met Gly Asn Ser
            20

<210> SEQ ID NO 389
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 389

Tyr Val Arg Cys Ser Glu Asn Gly Cys Val Gly Ser Ser Trp Glu His
1               5                   10                  15

Ser Ala Ile Ile
            20

<210> SEQ ID NO 390
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 390

Tyr Val Arg Cys Ser Glu Gly Gly Cys Val Gly Ser Thr Trp Thr Ala
1               5                   10                  15

Ser Tyr Pro Asn
            20

<210> SEQ ID NO 391
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 391
```

-continued

Tyr Val Arg Cys Ser Glu Ser Gly Cys Val Gly Ser Thr Trp Asn Gly
1               5                   10                  15

Val Leu Ser Arg
            20

<210> SEQ ID NO 392
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 392

Tyr Val Arg Cys Ser Glu Ser Gly Cys Val Gly Ser Thr Trp Asn Gly
1               5                   10                  15

Val Leu Ser Arg
            20

<210> SEQ ID NO 393
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 393

Thr Val Arg Cys Ser Gln Ser Gly Cys Val Gly Cys Gln Leu Val Trp
1               5                   10                  15

Tyr Phe Thr Thr
            20

<210> SEQ ID NO 394
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 394

Tyr Val Asn Cys Ser Gln Ser Gly Cys Val Gly Ser Thr Trp Asn Gly
1               5                   10                  15

Val Phe Ser Asn
            20

<210> SEQ ID NO 395
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 395

Tyr Val Ala Cys Ser Glu Ser Gly Cys Val Ser Val Asp Ser Ser Ala
1               5                   10                  15

Gly Ala Leu Phe
            20

<210> SEQ ID NO 396
<211> LENGTH: 20
<212> TYPE: PRT

<213> ORGANISM: Artificial Sequence
<220> FEATURE:
<223> OTHER INFORMATION: Description of Artificial Sequence: Synthetic
      peptide

<400> SEQUENCE: 396

Tyr Val Arg Cys Asn Glu Thr Gly Cys Val Gly Ser Ser Trp Ile Ala
1               5                   10                  15

Ala Gly Pro Phe
            20

<210> SEQ ID NO 397
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 397

Tyr Val Arg Cys Ser Glu Ser Gly Cys Val Gly Ser Thr Trp Leu Phe
1               5                   10                  15

Asn Pro Trp Gly
            20

<210> SEQ ID NO 398
<400> SEQUENCE: 398

000

<210> SEQ ID NO 399
<400> SEQUENCE: 399

000

<210> SEQ ID NO 400
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 400

Trp Asp Asp Phe Ile Leu Gly Trp Glu Ala Gly Val Ala Ala Val Gly
1               5                   10                  15

Glu Val

<210> SEQ ID NO 401
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 401

Phe Leu Pro Trp Pro Val Tyr Phe Ser Gln Val Leu Gly Gly Arg Arg
1               5                   10                  15

<210> SEQ ID NO 402
<211> LENGTH: 14
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 402

Tyr Val Met Cys Ser Ala Phe Gly Cys Lys Ser Ile Gly Gly
1               5                   10

<210> SEQ ID NO 403
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 403

His Val Ile Cys Ser Val Asn Gly Gly Cys Arg Gly Gly Gly
1               5                   10

<210> SEQ ID NO 404
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 404

Gly Gly Ile Arg Phe Cys Leu Arg Ser Glu Pro Thr Ala Cys Trp Ile
1               5                   10                  15

Val Gly Gly

<210> SEQ ID NO 405
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 405

Gly Gly Ile Arg Cys Arg Tyr Glu Lys Gln Ser Gly Ile Cys Leu Phe
1               5                   10                  15

Gly Gly

<210> SEQ ID NO 406
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 406

Gly Gly Gly Cys Ser Leu Met Trp Gln Asp Gly Trp Trp Val Cys Ile
1               5                   10                  15

Gly Gly

<210> SEQ ID NO 407
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 407

Gly Gly Glu Trp Glu Cys Arg Phe Leu Pro Gly Arg Arg Gly Cys Ser
1               5                   10                  15

Leu Phe Gly Gly
            20

<210> SEQ ID NO 408
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 408

Gly Gly Lys Gly Cys Thr Leu Gln Asn Pro Gly Ser Gly Trp Val Cys
1               5                   10                  15

Leu Phe Gly Gly
            20

<210> SEQ ID NO 409
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 409

Gly Gly Thr Cys Arg Leu Lys Arg Ser Gly Pro Asn Ser Trp Glu Cys
1               5                   10                  15

Ile Gly Gly

<210> SEQ ID NO 410
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 410

Gly Gly Trp Cys Ile Gly Gln Pro Leu Phe Arg Gln Gly Ser Cys Lys
1               5                   10                  15

Gly Gly

<210> SEQ ID NO 411
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 411

Phe Val Leu Cys Gly Leu Gln Gly Cys Arg Ser Gly Gly
1               5                   10

<210> SEQ ID NO 412
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 412

Phe Val Pro Trp Asp Glu Tyr Phe Leu Gln Ile Leu Gly Gly
1               5                   10

<210> SEQ ID NO 413
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 413

Gly Gly Gly Trp Val Ile Cys Ser Ala Leu Gly Cys Pro Phe Gly Gly
1               5                   10                  15

<210> SEQ ID NO 414
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 414

Gly Gly Gly Arg Arg Phe Cys Leu Arg Ser Glu Pro Thr Ala Cys Trp
1               5                   10                  15

Thr Val Gly Gly
            20

<210> SEQ ID NO 415
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 415

Gly Gly Gly Ser Arg Cys Ser Leu Val Trp Ala Asp Ser Trp Val Cys
1               5                   10                  15

Ile Phe Gly Gly
            20

<210> SEQ ID NO 416
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 416

Gly Gly Asp Trp Glu Cys Leu Phe Leu Pro Gly Arg Arg Gly Cys Thr
1               5                   10                  15

Leu Phe Gly Gly
            20

<210> SEQ ID NO 417
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 417

Phe Ile Pro Trp Asp Glu Tyr Phe Ala Gln Leu Leu Gly Gly
1               5                   10

<210> SEQ ID NO 418
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 418

Phe Val Pro Trp Asp Val Tyr Phe Ser Gln Ile Leu Gly Gly
1               5                   10

<210> SEQ ID NO 419
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 419

Phe Ile Pro Trp Asp Glu Tyr Phe Lys Gln Val Leu Gly Gly
1               5                   10

<210> SEQ ID NO 420
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 420

Phe Val Pro Trp Pro Glu Tyr Phe Leu Gln Ile Met Gly Gly
1               5                   10

<210> SEQ ID NO 421
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 421

Phe Ile Pro Trp Glu Glu Tyr Phe Ser Gln Leu Leu Gly Gly
1               5                   10

<210> SEQ ID NO 422
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 422

Phe Ile Pro Trp Pro Glu Tyr Phe Ser Gln Leu Leu Gly Gly
1               5                   10

<210> SEQ ID NO 423

<211> LENGTH: 19
<212> TYPE: PRT
<213> ORGANISM: Artificial Sequence
<220> FEATURE:
<223> OTHER INFORMATION: Description of Artificial Sequence: Synthetic peptide

<400> SEQUENCE: 423

Gly Gly Gly Gly Cys Ser Leu Val Trp Ala Asp Ser Trp Val Cys Ile
1               5                   10                  15
Phe Gly Gly

<210> SEQ ID NO 424

<400> SEQUENCE: 424

000

<210> SEQ ID NO 425

<400> SEQUENCE: 425

000

<210> SEQ ID NO 426

<400> SEQUENCE: 426

000

<210> SEQ ID NO 427

<400> SEQUENCE: 427

000

<210> SEQ ID NO 428

<400> SEQUENCE: 428

000

<210> SEQ ID NO 429

<400> SEQUENCE: 429

000

<210> SEQ ID NO 430

<400> SEQUENCE: 430

000

<210> SEQ ID NO 431

<400> SEQUENCE: 431

000

<210> SEQ ID NO 432

<400> SEQUENCE: 432

000

<210> SEQ ID NO 433

<400> SEQUENCE: 433

000

<210> SEQ ID NO 434

<400> SEQUENCE: 434

000

<210> SEQ ID NO 435

<400> SEQUENCE: 435

000

<210> SEQ ID NO 436

<400> SEQUENCE: 436

000

<210> SEQ ID NO 437

<400> SEQUENCE: 437

000

<210> SEQ ID NO 438

<400> SEQUENCE: 438

000

<210> SEQ ID NO 439

<400> SEQUENCE: 439

000

<210> SEQ ID NO 440

<400> SEQUENCE: 440

000

<210> SEQ ID NO 441

<400> SEQUENCE: 441

000

<210> SEQ ID NO 442

<400> SEQUENCE: 442

000

<210> SEQ ID NO 443

<400> SEQUENCE: 443

000

<210> SEQ ID NO 444

<400> SEQUENCE: 444

000

<210> SEQ ID NO 445

<400> SEQUENCE: 445

000

<210> SEQ ID NO 446

<400> SEQUENCE: 446

000

<210> SEQ ID NO 447

<400> SEQUENCE: 447

000

<210> SEQ ID NO 448

<400> SEQUENCE: 448

000

<210> SEQ ID NO 449

<400> SEQUENCE: 449

000

<210> SEQ ID NO 450

<400> SEQUENCE: 450

000

<210> SEQ ID NO 451

<400> SEQUENCE: 451

000

<210> SEQ ID NO 452

<400> SEQUENCE: 452

000

<210> SEQ ID NO 453

<400> SEQUENCE: 453

000

<210> SEQ ID NO 454

<400> SEQUENCE: 454

000

<210> SEQ ID NO 455

<400> SEQUENCE: 455

000

<210> SEQ ID NO 456

<400> SEQUENCE: 456

000

<210> SEQ ID NO 457

<400> SEQUENCE: 457

000

<210> SEQ ID NO 458

<400> SEQUENCE: 458

000

<210> SEQ ID NO 459

<400> SEQUENCE: 459

000

<210> SEQ ID NO 460

<400> SEQUENCE: 460

000

<210> SEQ ID NO 461

<400> SEQUENCE: 461

000

<210> SEQ ID NO 462

<400> SEQUENCE: 462

000

<210> SEQ ID NO 463

<400> SEQUENCE: 463

000

<210> SEQ ID NO 464

<400> SEQUENCE: 464

000

<210> SEQ ID NO 465

<400> SEQUENCE: 465

000

<210> SEQ ID NO 466

<400> SEQUENCE: 466

000

<210> SEQ ID NO 467

<400> SEQUENCE: 467

000

<210> SEQ ID NO 468

<400> SEQUENCE: 468

000

<210> SEQ ID NO 469

<400> SEQUENCE: 469

000

<210> SEQ ID NO 470

<400> SEQUENCE: 470

000

<210> SEQ ID NO 471

<400> SEQUENCE: 471

000

<210> SEQ ID NO 472

<400> SEQUENCE: 472

000

<210> SEQ ID NO 473

<400> SEQUENCE: 473

000

<210> SEQ ID NO 474

<400> SEQUENCE: 474

000

<210> SEQ ID NO 475

<400> SEQUENCE: 475

000

<210> SEQ ID NO 476

<400> SEQUENCE: 476

000

<210> SEQ ID NO 477

<400> SEQUENCE: 477

000

<210> SEQ ID NO 478

<400> SEQUENCE: 478

000

<210> SEQ ID NO 479

<400> SEQUENCE: 479

000

<210> SEQ ID NO 480

<400> SEQUENCE: 480

000

<210> SEQ ID NO 481

<400> SEQUENCE: 481

000

<210> SEQ ID NO 482

<400> SEQUENCE: 482

000

<210> SEQ ID NO 483

<400> SEQUENCE: 483

000

<210> SEQ ID NO 484

<400> SEQUENCE: 484

000

<210> SEQ ID NO 485

<400> SEQUENCE: 485

000

<210> SEQ ID NO 486

<400> SEQUENCE: 486

000

<210> SEQ ID NO 487

<400> SEQUENCE: 487

000

<210> SEQ ID NO 488

<400> SEQUENCE: 488

000

<210> SEQ ID NO 489

<400> SEQUENCE: 489

000

<210> SEQ ID NO 490

<400> SEQUENCE: 490

000

<210> SEQ ID NO 491

<400> SEQUENCE: 491

000

<210> SEQ ID NO 492

<400> SEQUENCE: 492

000

<210> SEQ ID NO 493

<400> SEQUENCE: 493

000

<210> SEQ ID NO 494

<400> SEQUENCE: 494

000

<210> SEQ ID NO 495

<400> SEQUENCE: 495

000

<210> SEQ ID NO 496

<400> SEQUENCE: 496

000

<210> SEQ ID NO 497

<400> SEQUENCE: 497

000

<210> SEQ ID NO 498

<400> SEQUENCE: 498

000

<210> SEQ ID NO 499

<400> SEQUENCE: 499

000

<210> SEQ ID NO 500

<400> SEQUENCE: 500

000

-continued

<210> SEQ ID NO 501

<400> SEQUENCE: 501

000

<210> SEQ ID NO 502

<400> SEQUENCE: 502

000

<210> SEQ ID NO 503

<400> SEQUENCE: 503

000

<210> SEQ ID NO 504

<400> SEQUENCE: 504

000

<210> SEQ ID NO 505

<400> SEQUENCE: 505

000

<210> SEQ ID NO 506

<400> SEQUENCE: 506

000

<210> SEQ ID NO 507

<400> SEQUENCE: 507

000

<210> SEQ ID NO 508

<400> SEQUENCE: 508

000

<210> SEQ ID NO 509

<400> SEQUENCE: 509

000

<210> SEQ ID NO 510

<400> SEQUENCE: 510

000

<210> SEQ ID NO 511

<400> SEQUENCE: 511

000

<210> SEQ ID NO 512

-continued

<400> SEQUENCE: 512

000

<210> SEQ ID NO 513

<400> SEQUENCE: 513

000

<210> SEQ ID NO 514

<400> SEQUENCE: 514

000

<210> SEQ ID NO 515

<400> SEQUENCE: 515

000

<210> SEQ ID NO 516

<400> SEQUENCE: 516

000

<210> SEQ ID NO 517

<400> SEQUENCE: 517

000

<210> SEQ ID NO 518

<400> SEQUENCE: 518

000

<210> SEQ ID NO 519

<400> SEQUENCE: 519

000

<210> SEQ ID NO 520

<400> SEQUENCE: 520

000

<210> SEQ ID NO 521

<400> SEQUENCE: 521

000

<210> SEQ ID NO 522

<400> SEQUENCE: 522

000

<210> SEQ ID NO 523

<400> SEQUENCE: 523

000

<210> SEQ ID NO 524
<400> SEQUENCE: 524
000

<210> SEQ ID NO 525
<400> SEQUENCE: 525
000

<210> SEQ ID NO 526
<400> SEQUENCE: 526
000

<210> SEQ ID NO 527
<400> SEQUENCE: 527
000

<210> SEQ ID NO 528
<400> SEQUENCE: 528
000

<210> SEQ ID NO 529
<400> SEQUENCE: 529
000

<210> SEQ ID NO 530
<400> SEQUENCE: 530
000

<210> SEQ ID NO 531
<400> SEQUENCE: 531
000

<210> SEQ ID NO 532
<400> SEQUENCE: 532
000

<210> SEQ ID NO 533
<400> SEQUENCE: 533
000

<210> SEQ ID NO 534
<400> SEQUENCE: 534
000

-continued

<210> SEQ ID NO 535

<400> SEQUENCE: 535

000

<210> SEQ ID NO 536

<400> SEQUENCE: 536

000

<210> SEQ ID NO 537

<400> SEQUENCE: 537

000

<210> SEQ ID NO 538

<400> SEQUENCE: 538

000

<210> SEQ ID NO 539

<400> SEQUENCE: 539

000

<210> SEQ ID NO 540

<400> SEQUENCE: 540

000

<210> SEQ ID NO 541

<400> SEQUENCE: 541

000

<210> SEQ ID NO 542

<400> SEQUENCE: 542

000

<210> SEQ ID NO 543

<400> SEQUENCE: 543

000

<210> SEQ ID NO 544

<400> SEQUENCE: 544

000

<210> SEQ ID NO 545

<400> SEQUENCE: 545

000

```
<210> SEQ ID NO 546
<400> SEQUENCE: 546
000

<210> SEQ ID NO 547
<400> SEQUENCE: 547
000

<210> SEQ ID NO 548
<400> SEQUENCE: 548
000

<210> SEQ ID NO 549
<400> SEQUENCE: 549
000

<210> SEQ ID NO 550
<400> SEQUENCE: 550
000

<210> SEQ ID NO 551
<400> SEQUENCE: 551
000

<210> SEQ ID NO 552
<400> SEQUENCE: 552
000

<210> SEQ ID NO 553
<400> SEQUENCE: 553
000

<210> SEQ ID NO 554
<400> SEQUENCE: 554
000

<210> SEQ ID NO 555
<400> SEQUENCE: 555
000

<210> SEQ ID NO 556
<400> SEQUENCE: 556
000

<210> SEQ ID NO 557
```

<400> SEQUENCE: 557

000

<210> SEQ ID NO 558

<400> SEQUENCE: 558

000

<210> SEQ ID NO 559

<400> SEQUENCE: 559

000

<210> SEQ ID NO 560

<400> SEQUENCE: 560

000

<210> SEQ ID NO 561

<400> SEQUENCE: 561

000

<210> SEQ ID NO 562

<400> SEQUENCE: 562

000

<210> SEQ ID NO 563

<400> SEQUENCE: 563

000

<210> SEQ ID NO 564

<400> SEQUENCE: 564

000

<210> SEQ ID NO 565

<400> SEQUENCE: 565

000

<210> SEQ ID NO 566

<400> SEQUENCE: 566

000

<210> SEQ ID NO 567

<400> SEQUENCE: 567

000

<210> SEQ ID NO 568

<400> SEQUENCE: 568

000

<210> SEQ ID NO 569

<400> SEQUENCE: 569

000

<210> SEQ ID NO 570

<400> SEQUENCE: 570

000

<210> SEQ ID NO 571

<400> SEQUENCE: 571

000

<210> SEQ ID NO 572

<400> SEQUENCE: 572

000

<210> SEQ ID NO 573

<400> SEQUENCE: 573

000

<210> SEQ ID NO 574

<400> SEQUENCE: 574

000

<210> SEQ ID NO 575

<400> SEQUENCE: 575

000

<210> SEQ ID NO 576

<400> SEQUENCE: 576

000

<210> SEQ ID NO 577

<400> SEQUENCE: 577

000

<210> SEQ ID NO 578

<400> SEQUENCE: 578

000

<210> SEQ ID NO 579

<400> SEQUENCE: 579

000

```
<210> SEQ ID NO 580
<400> SEQUENCE: 580
000

<210> SEQ ID NO 581
<400> SEQUENCE: 581
000

<210> SEQ ID NO 582
<400> SEQUENCE: 582
000

<210> SEQ ID NO 583
<400> SEQUENCE: 583
000

<210> SEQ ID NO 584
<400> SEQUENCE: 584
000

<210> SEQ ID NO 585
<400> SEQUENCE: 585
000

<210> SEQ ID NO 586
<400> SEQUENCE: 586
000

<210> SEQ ID NO 587
<400> SEQUENCE: 587
000

<210> SEQ ID NO 588
<400> SEQUENCE: 588
000

<210> SEQ ID NO 589
<400> SEQUENCE: 589
000

<210> SEQ ID NO 590
<400> SEQUENCE: 590
000

<210> SEQ ID NO 591
```

```
<400> SEQUENCE: 591

000

<210> SEQ ID NO 592

<400> SEQUENCE: 592

000

<210> SEQ ID NO 593

<400> SEQUENCE: 593

000

<210> SEQ ID NO 594

<400> SEQUENCE: 594

000

<210> SEQ ID NO 595

<400> SEQUENCE: 595

000

<210> SEQ ID NO 596

<400> SEQUENCE: 596

000

<210> SEQ ID NO 597

<400> SEQUENCE: 597

000

<210> SEQ ID NO 598

<400> SEQUENCE: 598

000

<210> SEQ ID NO 599

<400> SEQUENCE: 599

000

<210> SEQ ID NO 600

<400> SEQUENCE: 600

000

<210> SEQ ID NO 601

<400> SEQUENCE: 601

000

<210> SEQ ID NO 602

<400> SEQUENCE: 602
```

000

<210> SEQ ID NO 603

<400> SEQUENCE: 603

000

<210> SEQ ID NO 604

<400> SEQUENCE: 604

000

<210> SEQ ID NO 605

<400> SEQUENCE: 605

000

<210> SEQ ID NO 606

<400> SEQUENCE: 606

000

<210> SEQ ID NO 607

<400> SEQUENCE: 607

000

<210> SEQ ID NO 608

<400> SEQUENCE: 608

000

<210> SEQ ID NO 609

<400> SEQUENCE: 609

000

<210> SEQ ID NO 610

<400> SEQUENCE: 610

000

<210> SEQ ID NO 611

<400> SEQUENCE: 611

000

<210> SEQ ID NO 612

<400> SEQUENCE: 612

000

<210> SEQ ID NO 613

<400> SEQUENCE: 613

000

<210> SEQ ID NO 614

<400> SEQUENCE: 614

000

<210> SEQ ID NO 615

<400> SEQUENCE: 615

000

<210> SEQ ID NO 616

<400> SEQUENCE: 616

000

<210> SEQ ID NO 617

<400> SEQUENCE: 617

000

<210> SEQ ID NO 618

<400> SEQUENCE: 618

000

<210> SEQ ID NO 619

<400> SEQUENCE: 619

000

<210> SEQ ID NO 620

<400> SEQUENCE: 620

000

<210> SEQ ID NO 621

<400> SEQUENCE: 621

000

<210> SEQ ID NO 622

<400> SEQUENCE: 622

000

<210> SEQ ID NO 623

<400> SEQUENCE: 623

000

<210> SEQ ID NO 624

<400> SEQUENCE: 624

000

<210> SEQ ID NO 625

<400> SEQUENCE: 625

000

<210> SEQ ID NO 626

<400> SEQUENCE: 626

000

<210> SEQ ID NO 627

<400> SEQUENCE: 627

000

<210> SEQ ID NO 628

<400> SEQUENCE: 628

000

<210> SEQ ID NO 629

<400> SEQUENCE: 629

000

<210> SEQ ID NO 630

<400> SEQUENCE: 630

000

<210> SEQ ID NO 631

<400> SEQUENCE: 631

000

<210> SEQ ID NO 632

<400> SEQUENCE: 632

000

<210> SEQ ID NO 633

<400> SEQUENCE: 633

000

<210> SEQ ID NO 634

<400> SEQUENCE: 634

000

<210> SEQ ID NO 635

<400> SEQUENCE: 635

000

<210> SEQ ID NO 636

```
<400> SEQUENCE: 636

000

<210> SEQ ID NO 637

<400> SEQUENCE: 637

000

<210> SEQ ID NO 638

<400> SEQUENCE: 638

000

<210> SEQ ID NO 639

<400> SEQUENCE: 639

000

<210> SEQ ID NO 640

<400> SEQUENCE: 640

000

<210> SEQ ID NO 641

<400> SEQUENCE: 641

000

<210> SEQ ID NO 642

<400> SEQUENCE: 642

000

<210> SEQ ID NO 643

<400> SEQUENCE: 643

000

<210> SEQ ID NO 644

<400> SEQUENCE: 644

000

<210> SEQ ID NO 645

<400> SEQUENCE: 645

000

<210> SEQ ID NO 646

<400> SEQUENCE: 646

000

<210> SEQ ID NO 647

<400> SEQUENCE: 647
```

000

<210> SEQ ID NO 648

<400> SEQUENCE: 648

000

<210> SEQ ID NO 649

<400> SEQUENCE: 649

000

<210> SEQ ID NO 650

<400> SEQUENCE: 650

000

<210> SEQ ID NO 651

<400> SEQUENCE: 651

000

<210> SEQ ID NO 652

<400> SEQUENCE: 652

000

<210> SEQ ID NO 653

<400> SEQUENCE: 653

000

<210> SEQ ID NO 654

<400> SEQUENCE: 654

000

<210> SEQ ID NO 655

<400> SEQUENCE: 655

000

<210> SEQ ID NO 656

<400> SEQUENCE: 656

000

<210> SEQ ID NO 657

<400> SEQUENCE: 657

000

<210> SEQ ID NO 658

<400> SEQUENCE: 658

000

-continued

<210> SEQ ID NO 659
<400> SEQUENCE: 659
000

<210> SEQ ID NO 660
<400> SEQUENCE: 660
000

<210> SEQ ID NO 661
<400> SEQUENCE: 661
000

<210> SEQ ID NO 662
<400> SEQUENCE: 662
000

<210> SEQ ID NO 663
<400> SEQUENCE: 663
000

<210> SEQ ID NO 664
<400> SEQUENCE: 664
000

<210> SEQ ID NO 665
<400> SEQUENCE: 665
000

<210> SEQ ID NO 666
<400> SEQUENCE: 666
000

<210> SEQ ID NO 667
<400> SEQUENCE: 667
000

<210> SEQ ID NO 668
<400> SEQUENCE: 668
000

<210> SEQ ID NO 669
<400> SEQUENCE: 669
000

<210> SEQ ID NO 670

<400> SEQUENCE: 670

000

<210> SEQ ID NO 671

<400> SEQUENCE: 671

000

<210> SEQ ID NO 672

<400> SEQUENCE: 672

000

<210> SEQ ID NO 673

<400> SEQUENCE: 673

000

<210> SEQ ID NO 674

<400> SEQUENCE: 674

000

<210> SEQ ID NO 675

<400> SEQUENCE: 675

000

<210> SEQ ID NO 676

<400> SEQUENCE: 676

000

<210> SEQ ID NO 677

<400> SEQUENCE: 677

000

<210> SEQ ID NO 678

<400> SEQUENCE: 678

000

<210> SEQ ID NO 679

<400> SEQUENCE: 679

000

<210> SEQ ID NO 680

<400> SEQUENCE: 680

000

<210> SEQ ID NO 681

<400> SEQUENCE: 681

000

<210> SEQ ID NO 682

<400> SEQUENCE: 682

000

<210> SEQ ID NO 683

<400> SEQUENCE: 683

000

<210> SEQ ID NO 684

<400> SEQUENCE: 684

000

<210> SEQ ID NO 685

<400> SEQUENCE: 685

000

<210> SEQ ID NO 686

<400> SEQUENCE: 686

000

<210> SEQ ID NO 687

<400> SEQUENCE: 687

000

<210> SEQ ID NO 688

<400> SEQUENCE: 688

000

<210> SEQ ID NO 689

<400> SEQUENCE: 689

000

<210> SEQ ID NO 690

<400> SEQUENCE: 690

000

<210> SEQ ID NO 691

<400> SEQUENCE: 691

000

<210> SEQ ID NO 692

<400> SEQUENCE: 692

000

-continued

<210> SEQ ID NO 693

<400> SEQUENCE: 693

000

<210> SEQ ID NO 694

<400> SEQUENCE: 694

000

<210> SEQ ID NO 695

<400> SEQUENCE: 695

000

<210> SEQ ID NO 696

<400> SEQUENCE: 696

000

<210> SEQ ID NO 697

<400> SEQUENCE: 697

000

<210> SEQ ID NO 698

<400> SEQUENCE: 698

000

<210> SEQ ID NO 699

<400> SEQUENCE: 699

000

<210> SEQ ID NO 700

<400> SEQUENCE: 700

000

<210> SEQ ID NO 701

<400> SEQUENCE: 701

000

<210> SEQ ID NO 702

<400> SEQUENCE: 702

000

<210> SEQ ID NO 703

<400> SEQUENCE: 703

000

<210> SEQ ID NO 704

<400> SEQUENCE: 704

000

<210> SEQ ID NO 705

<400> SEQUENCE: 705

000

<210> SEQ ID NO 706

<400> SEQUENCE: 706

000

<210> SEQ ID NO 707

<400> SEQUENCE: 707

000

<210> SEQ ID NO 708

<400> SEQUENCE: 708

000

<210> SEQ ID NO 709

<400> SEQUENCE: 709

000

<210> SEQ ID NO 710

<400> SEQUENCE: 710

000

<210> SEQ ID NO 711

<400> SEQUENCE: 711

000

<210> SEQ ID NO 712

<400> SEQUENCE: 712

000

<210> SEQ ID NO 713

<400> SEQUENCE: 713

000

<210> SEQ ID NO 714

<400> SEQUENCE: 714

000

<210> SEQ ID NO 715

<400> SEQUENCE: 715

000

<210> SEQ ID NO 716

<400> SEQUENCE: 716

000

<210> SEQ ID NO 717

<400> SEQUENCE: 717

000

<210> SEQ ID NO 718

<400> SEQUENCE: 718

000

<210> SEQ ID NO 719

<400> SEQUENCE: 719

000

<210> SEQ ID NO 720

<400> SEQUENCE: 720

000

<210> SEQ ID NO 721

<400> SEQUENCE: 721

000

<210> SEQ ID NO 722

<400> SEQUENCE: 722

000

<210> SEQ ID NO 723

<400> SEQUENCE: 723

000

<210> SEQ ID NO 724

<400> SEQUENCE: 724

000

<210> SEQ ID NO 725

<400> SEQUENCE: 725

000

<210> SEQ ID NO 726

<400> SEQUENCE: 726

000

<210> SEQ ID NO 727

<400> SEQUENCE: 727

000

<210> SEQ ID NO 728

<400> SEQUENCE: 728

000

<210> SEQ ID NO 729

<400> SEQUENCE: 729

000

<210> SEQ ID NO 730

<400> SEQUENCE: 730

000

<210> SEQ ID NO 731

<400> SEQUENCE: 731

000

<210> SEQ ID NO 732

<400> SEQUENCE: 732

000

<210> SEQ ID NO 733

<400> SEQUENCE: 733

000

<210> SEQ ID NO 734

<400> SEQUENCE: 734

000

<210> SEQ ID NO 735

<400> SEQUENCE: 735

000

<210> SEQ ID NO 736

<400> SEQUENCE: 736

000

<210> SEQ ID NO 737

<400> SEQUENCE: 737

000

<210> SEQ ID NO 738

<400> SEQUENCE: 738

000

<210> SEQ ID NO 739

<400> SEQUENCE: 739

000

<210> SEQ ID NO 740

<400> SEQUENCE: 740

000

<210> SEQ ID NO 741

<400> SEQUENCE: 741

000

<210> SEQ ID NO 742

<400> SEQUENCE: 742

000

<210> SEQ ID NO 743

<400> SEQUENCE: 743

000

<210> SEQ ID NO 744

<400> SEQUENCE: 744

000

<210> SEQ ID NO 745

<400> SEQUENCE: 745

000

<210> SEQ ID NO 746

<400> SEQUENCE: 746

000

<210> SEQ ID NO 747

<400> SEQUENCE: 747

000

<210> SEQ ID NO 748

<400> SEQUENCE: 748

000

<210> SEQ ID NO 749

<400> SEQUENCE: 749

000

<210> SEQ ID NO 750

<400> SEQUENCE: 750

000

<210> SEQ ID NO 751

<400> SEQUENCE: 751

000

<210> SEQ ID NO 752

<400> SEQUENCE: 752

000

<210> SEQ ID NO 753

<400> SEQUENCE: 753

000

<210> SEQ ID NO 754

<400> SEQUENCE: 754

000

<210> SEQ ID NO 755

<400> SEQUENCE: 755

000

<210> SEQ ID NO 756

<400> SEQUENCE: 756

000

<210> SEQ ID NO 757

<400> SEQUENCE: 757

000

<210> SEQ ID NO 758

<400> SEQUENCE: 758

000

<210> SEQ ID NO 759

<400> SEQUENCE: 759

000

<210> SEQ ID NO 760

<400> SEQUENCE: 760

000

<210> SEQ ID NO 761
<400> SEQUENCE: 761
000

<210> SEQ ID NO 762
<400> SEQUENCE: 762
000

<210> SEQ ID NO 763
<400> SEQUENCE: 763
000

<210> SEQ ID NO 764
<400> SEQUENCE: 764
000

<210> SEQ ID NO 765
<400> SEQUENCE: 765
000

<210> SEQ ID NO 766
<400> SEQUENCE: 766
000

<210> SEQ ID NO 767
<400> SEQUENCE: 767
000

<210> SEQ ID NO 768
<400> SEQUENCE: 768
000

<210> SEQ ID NO 769
<400> SEQUENCE: 769
000

<210> SEQ ID NO 770
<400> SEQUENCE: 770
000

<210> SEQ ID NO 771
<400> SEQUENCE: 771
000

<210> SEQ ID NO 772

<400> SEQUENCE: 772

000

<210> SEQ ID NO 773

<400> SEQUENCE: 773

000

<210> SEQ ID NO 774

<400> SEQUENCE: 774

000

<210> SEQ ID NO 775

<400> SEQUENCE: 775

000

<210> SEQ ID NO 776

<400> SEQUENCE: 776

000

<210> SEQ ID NO 777

<400> SEQUENCE: 777

000

<210> SEQ ID NO 778

<400> SEQUENCE: 778

000

<210> SEQ ID NO 779

<400> SEQUENCE: 779

000

<210> SEQ ID NO 780

<400> SEQUENCE: 780

000

<210> SEQ ID NO 781

<400> SEQUENCE: 781

000

<210> SEQ ID NO 782

<400> SEQUENCE: 782

000

```
<210> SEQ ID NO 783
<400> SEQUENCE: 783
000

<210> SEQ ID NO 784
<400> SEQUENCE: 784
000

<210> SEQ ID NO 785
<400> SEQUENCE: 785
000

<210> SEQ ID NO 786
<400> SEQUENCE: 786
000

<210> SEQ ID NO 787
<400> SEQUENCE: 787
000

<210> SEQ ID NO 788
<400> SEQUENCE: 788
000

<210> SEQ ID NO 789
<400> SEQUENCE: 789
000

<210> SEQ ID NO 790
<400> SEQUENCE: 790
000

<210> SEQ ID NO 791
<400> SEQUENCE: 791
000

<210> SEQ ID NO 792
<400> SEQUENCE: 792
000

<210> SEQ ID NO 793
<400> SEQUENCE: 793
000

<210> SEQ ID NO 794
```

<400> SEQUENCE: 794

000

<210> SEQ ID NO 795

<400> SEQUENCE: 795

000

<210> SEQ ID NO 796

<400> SEQUENCE: 796

000

<210> SEQ ID NO 797

<400> SEQUENCE: 797

000

<210> SEQ ID NO 798

<400> SEQUENCE: 798

000

<210> SEQ ID NO 799

<400> SEQUENCE: 799

000

<210> SEQ ID NO 800

<400> SEQUENCE: 800

000

<210> SEQ ID NO 801

<400> SEQUENCE: 801

000

<210> SEQ ID NO 802

<400> SEQUENCE: 802

000

<210> SEQ ID NO 803

<400> SEQUENCE: 803

000

<210> SEQ ID NO 804

<400> SEQUENCE: 804

000

<210> SEQ ID NO 805

<400> SEQUENCE: 805

000

<210> SEQ ID NO 806
<400> SEQUENCE: 806
000

<210> SEQ ID NO 807
<400> SEQUENCE: 807
000

<210> SEQ ID NO 808
<400> SEQUENCE: 808
000

<210> SEQ ID NO 809
<400> SEQUENCE: 809
000

<210> SEQ ID NO 810
<400> SEQUENCE: 810
000

<210> SEQ ID NO 811
<400> SEQUENCE: 811
000

<210> SEQ ID NO 812
<400> SEQUENCE: 812
000

<210> SEQ ID NO 813
<400> SEQUENCE: 813
000

<210> SEQ ID NO 814
<400> SEQUENCE: 814
000

<210> SEQ ID NO 815
<400> SEQUENCE: 815
000

<210> SEQ ID NO 816
<400> SEQUENCE: 816
000

<210> SEQ ID NO 817

<400> SEQUENCE: 817

000

<210> SEQ ID NO 818

<400> SEQUENCE: 818

000

<210> SEQ ID NO 819

<400> SEQUENCE: 819

000

<210> SEQ ID NO 820

<400> SEQUENCE: 820

000

<210> SEQ ID NO 821

<400> SEQUENCE: 821

000

<210> SEQ ID NO 822

<400> SEQUENCE: 822

000

<210> SEQ ID NO 823

<400> SEQUENCE: 823

000

<210> SEQ ID NO 824

<400> SEQUENCE: 824

000

<210> SEQ ID NO 825

<400> SEQUENCE: 825

000

<210> SEQ ID NO 826

<400> SEQUENCE: 826

000

<210> SEQ ID NO 827

<400> SEQUENCE: 827

000

<210> SEQ ID NO 828

<400> SEQUENCE: 828

000

<210> SEQ ID NO 829

<400> SEQUENCE: 829

000

<210> SEQ ID NO 830

<400> SEQUENCE: 830

000

<210> SEQ ID NO 831

<400> SEQUENCE: 831

000

<210> SEQ ID NO 832

<400> SEQUENCE: 832

000

<210> SEQ ID NO 833

<400> SEQUENCE: 833

000

<210> SEQ ID NO 834

<400> SEQUENCE: 834

000

<210> SEQ ID NO 835

<400> SEQUENCE: 835

000

<210> SEQ ID NO 836

<400> SEQUENCE: 836

000

<210> SEQ ID NO 837

<400> SEQUENCE: 837

000

<210> SEQ ID NO 838

<400> SEQUENCE: 838

000

<210> SEQ ID NO 839

<400> SEQUENCE: 839

000

<210> SEQ ID NO 840

<400> SEQUENCE: 840

000

<210> SEQ ID NO 841

<400> SEQUENCE: 841

000

<210> SEQ ID NO 842

<400> SEQUENCE: 842

000

<210> SEQ ID NO 843

<400> SEQUENCE: 843

000

<210> SEQ ID NO 844

<400> SEQUENCE: 844

000

<210> SEQ ID NO 845

<400> SEQUENCE: 845

000

<210> SEQ ID NO 846

<400> SEQUENCE: 846

000

<210> SEQ ID NO 847

<400> SEQUENCE: 847

000

<210> SEQ ID NO 848

<400> SEQUENCE: 848

000

<210> SEQ ID NO 849

<400> SEQUENCE: 849

000

<210> SEQ ID NO 850

<400> SEQUENCE: 850

000

<210> SEQ ID NO 851

<400> SEQUENCE: 851

000

<210> SEQ ID NO 852

<400> SEQUENCE: 852

000

<210> SEQ ID NO 853

<400> SEQUENCE: 853

000

<210> SEQ ID NO 854

<400> SEQUENCE: 854

000

<210> SEQ ID NO 855

<400> SEQUENCE: 855

000

<210> SEQ ID NO 856

<400> SEQUENCE: 856

000

<210> SEQ ID NO 857

<400> SEQUENCE: 857

000

<210> SEQ ID NO 858

<400> SEQUENCE: 858

000

<210> SEQ ID NO 859

<400> SEQUENCE: 859

000

<210> SEQ ID NO 860

<400> SEQUENCE: 860

000

<210> SEQ ID NO 861

<400> SEQUENCE: 861

000

<210> SEQ ID NO 862

<400> SEQUENCE: 862

000

<210> SEQ ID NO 863

<400> SEQUENCE: 863

000

<210> SEQ ID NO 864

<400> SEQUENCE: 864

000

<210> SEQ ID NO 865

<400> SEQUENCE: 865

000

<210> SEQ ID NO 866

<400> SEQUENCE: 866

000

<210> SEQ ID NO 867

<400> SEQUENCE: 867

000

<210> SEQ ID NO 868

<400> SEQUENCE: 868

000

<210> SEQ ID NO 869

<400> SEQUENCE: 869

000

<210> SEQ ID NO 870

<400> SEQUENCE: 870

000

<210> SEQ ID NO 871

<400> SEQUENCE: 871

000

<210> SEQ ID NO 872

<400> SEQUENCE: 872

000

<210> SEQ ID NO 873

<400> SEQUENCE: 873

000

<210> SEQ ID NO 874

<400> SEQUENCE: 874

000

<210> SEQ ID NO 875

<400> SEQUENCE: 875

000

<210> SEQ ID NO 876

<400> SEQUENCE: 876

000

<210> SEQ ID NO 877

<400> SEQUENCE: 877

000

<210> SEQ ID NO 878

<400> SEQUENCE: 878

000

<210> SEQ ID NO 879

<400> SEQUENCE: 879

000

<210> SEQ ID NO 880

<400> SEQUENCE: 880

000

<210> SEQ ID NO 881

<400> SEQUENCE: 881

000

<210> SEQ ID NO 882

<400> SEQUENCE: 882

000

<210> SEQ ID NO 883

<400> SEQUENCE: 883

000

<210> SEQ ID NO 884

<400> SEQUENCE: 884

000

<210> SEQ ID NO 885

<400> SEQUENCE: 885

000

<210> SEQ ID NO 886

<400> SEQUENCE: 886

000

<210> SEQ ID NO 887

<400> SEQUENCE: 887

000

<210> SEQ ID NO 888

<400> SEQUENCE: 888

000

<210> SEQ ID NO 889

<400> SEQUENCE: 889

000

<210> SEQ ID NO 890

<400> SEQUENCE: 890

000

<210> SEQ ID NO 891

<400> SEQUENCE: 891

000

<210> SEQ ID NO 892

<400> SEQUENCE: 892

000

<210> SEQ ID NO 893

<400> SEQUENCE: 893

000

<210> SEQ ID NO 894

<400> SEQUENCE: 894

000

<210> SEQ ID NO 895

<400> SEQUENCE: 895

000

```
<210> SEQ ID NO 896
<400> SEQUENCE: 896
000

<210> SEQ ID NO 897
<400> SEQUENCE: 897
000

<210> SEQ ID NO 898
<400> SEQUENCE: 898
000

<210> SEQ ID NO 899
<400> SEQUENCE: 899
000

<210> SEQ ID NO 900
<400> SEQUENCE: 900
000

<210> SEQ ID NO 901
<400> SEQUENCE: 901
000

<210> SEQ ID NO 902
<400> SEQUENCE: 902
000

<210> SEQ ID NO 903
<400> SEQUENCE: 903
000

<210> SEQ ID NO 904
<400> SEQUENCE: 904
000

<210> SEQ ID NO 905
<400> SEQUENCE: 905
000

<210> SEQ ID NO 906
<400> SEQUENCE: 906
000

<210> SEQ ID NO 907
```

-continued

```
<400> SEQUENCE: 907
000

<210> SEQ ID NO 908
<400> SEQUENCE: 908
000

<210> SEQ ID NO 909
<400> SEQUENCE: 909
000

<210> SEQ ID NO 910
<400> SEQUENCE: 910
000

<210> SEQ ID NO 911
<400> SEQUENCE: 911
000

<210> SEQ ID NO 912
<400> SEQUENCE: 912
000

<210> SEQ ID NO 913
<400> SEQUENCE: 913
000

<210> SEQ ID NO 914
<400> SEQUENCE: 914
000

<210> SEQ ID NO 915
<400> SEQUENCE: 915
000

<210> SEQ ID NO 916
<400> SEQUENCE: 916
000

<210> SEQ ID NO 917
<400> SEQUENCE: 917
000

<210> SEQ ID NO 918
<400> SEQUENCE: 918
```

000

<210> SEQ ID NO 919

<400> SEQUENCE: 919

000

<210> SEQ ID NO 920

<400> SEQUENCE: 920

000

<210> SEQ ID NO 921

<400> SEQUENCE: 921

000

<210> SEQ ID NO 922

<400> SEQUENCE: 922

000

<210> SEQ ID NO 923

<400> SEQUENCE: 923

000

<210> SEQ ID NO 924

<400> SEQUENCE: 924

000

<210> SEQ ID NO 925

<400> SEQUENCE: 925

000

<210> SEQ ID NO 926

<400> SEQUENCE: 926

000

<210> SEQ ID NO 927

<400> SEQUENCE: 927

000

<210> SEQ ID NO 928

<400> SEQUENCE: 928

000

<210> SEQ ID NO 929

<400> SEQUENCE: 929

000

<210> SEQ ID NO 930

<400> SEQUENCE: 930

000

<210> SEQ ID NO 931

<400> SEQUENCE: 931

000

<210> SEQ ID NO 932

<400> SEQUENCE: 932

000

<210> SEQ ID NO 933

<400> SEQUENCE: 933

000

<210> SEQ ID NO 934

<400> SEQUENCE: 934

000

<210> SEQ ID NO 935

<400> SEQUENCE: 935

000

<210> SEQ ID NO 936

<400> SEQUENCE: 936

000

<210> SEQ ID NO 937

<400> SEQUENCE: 937

000

<210> SEQ ID NO 938

<400> SEQUENCE: 938

000

<210> SEQ ID NO 939

<400> SEQUENCE: 939

000

<210> SEQ ID NO 940

<400> SEQUENCE: 940

000

-continued

<210> SEQ ID NO 941

<400> SEQUENCE: 941

000

<210> SEQ ID NO 942

<400> SEQUENCE: 942

000

<210> SEQ ID NO 943

<400> SEQUENCE: 943

000

<210> SEQ ID NO 944

<400> SEQUENCE: 944

000

<210> SEQ ID NO 945

<400> SEQUENCE: 945

000

<210> SEQ ID NO 946

<400> SEQUENCE: 946

000

<210> SEQ ID NO 947

<400> SEQUENCE: 947

000

<210> SEQ ID NO 948

<400> SEQUENCE: 948

000

<210> SEQ ID NO 949

<400> SEQUENCE: 949

000

<210> SEQ ID NO 950

<400> SEQUENCE: 950

000

<210> SEQ ID NO 951

<400> SEQUENCE: 951

000

<210> SEQ ID NO 952

```
<400> SEQUENCE: 952

000

<210> SEQ ID NO 953

<400> SEQUENCE: 953

000

<210> SEQ ID NO 954

<400> SEQUENCE: 954

000

<210> SEQ ID NO 955

<400> SEQUENCE: 955

000

<210> SEQ ID NO 956

<400> SEQUENCE: 956

000

<210> SEQ ID NO 957

<400> SEQUENCE: 957

000

<210> SEQ ID NO 958

<400> SEQUENCE: 958

000

<210> SEQ ID NO 959

<400> SEQUENCE: 959

000

<210> SEQ ID NO 960

<400> SEQUENCE: 960

000

<210> SEQ ID NO 961

<400> SEQUENCE: 961

000

<210> SEQ ID NO 962

<400> SEQUENCE: 962

000

<210> SEQ ID NO 963

<400> SEQUENCE: 963
```

000

<210> SEQ ID NO 964
<400> SEQUENCE: 964
000

<210> SEQ ID NO 965
<400> SEQUENCE: 965
000

<210> SEQ ID NO 966
<400> SEQUENCE: 966
000

<210> SEQ ID NO 967
<400> SEQUENCE: 967
000

<210> SEQ ID NO 968
<400> SEQUENCE: 968
000

<210> SEQ ID NO 969
<400> SEQUENCE: 969
000

<210> SEQ ID NO 970
<400> SEQUENCE: 970
000

<210> SEQ ID NO 971
<400> SEQUENCE: 971
000

<210> SEQ ID NO 972
<400> SEQUENCE: 972
000

<210> SEQ ID NO 973
<400> SEQUENCE: 973
000

<210> SEQ ID NO 974
<400> SEQUENCE: 974
000

<210> SEQ ID NO 975

<400> SEQUENCE: 975

000

<210> SEQ ID NO 976

<400> SEQUENCE: 976

000

<210> SEQ ID NO 977

<400> SEQUENCE: 977

000

<210> SEQ ID NO 978

<400> SEQUENCE: 978

000

<210> SEQ ID NO 979

<400> SEQUENCE: 979

000

<210> SEQ ID NO 980

<400> SEQUENCE: 980

000

<210> SEQ ID NO 981

<400> SEQUENCE: 981

000

<210> SEQ ID NO 982

<400> SEQUENCE: 982

000

<210> SEQ ID NO 983

<400> SEQUENCE: 983

000

<210> SEQ ID NO 984

<400> SEQUENCE: 984

000

<210> SEQ ID NO 985

<400> SEQUENCE: 985

000

<210> SEQ ID NO 986

<400> SEQUENCE: 986

000

<210> SEQ ID NO 987

<400> SEQUENCE: 987

000

<210> SEQ ID NO 988

<400> SEQUENCE: 988

000

<210> SEQ ID NO 989

<400> SEQUENCE: 989

000

<210> SEQ ID NO 990

<400> SEQUENCE: 990

000

<210> SEQ ID NO 991

<400> SEQUENCE: 991

000

<210> SEQ ID NO 992

<400> SEQUENCE: 992

000

<210> SEQ ID NO 993

<400> SEQUENCE: 993

000

<210> SEQ ID NO 994

<400> SEQUENCE: 994

000

<210> SEQ ID NO 995

<400> SEQUENCE: 995

000

<210> SEQ ID NO 996

<400> SEQUENCE: 996

000

<210> SEQ ID NO 997

<400> SEQUENCE: 997

000

<210> SEQ ID NO 998

<400> SEQUENCE: 998

000

<210> SEQ ID NO 999

<400> SEQUENCE: 999

000

<210> SEQ ID NO 1000
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1000

Met Gly Phe Tyr Pro Cys Trp Thr Ala Gln Leu Gly Glu Leu Cys Asp
1               5                   10                  15

Leu Ser Val Asp
            20

<210> SEQ ID NO 1001
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1001

Gly Phe Tyr Pro Cys Trp Thr Ala Gln Leu Gly Glu Leu Cys Asp Leu
1               5                   10                  15

Ser Val Asp

<210> SEQ ID NO 1002
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1002

Phe Tyr Pro Cys Trp Thr Ala Gln Leu Gly Glu Leu Cys Asp Leu Ser
1               5                   10                  15

Val Asp

<210> SEQ ID NO 1003
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1003

Tyr Pro Cys Trp Thr Ala Gln Leu Gly Glu Leu Cys Asp Leu Ser Val
1               5                   10                  15

Asp

<210> SEQ ID NO 1004
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1004

Met Gly Phe Tyr Pro Cys Trp Thr Ala Gln Leu Gly Glu Leu Cys Asp
1               5                   10                  15

Leu Ser Val

<210> SEQ ID NO 1005
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1005

Met Gly Phe Tyr Pro Cys Trp Thr Ala Gln Leu Gly Glu Leu Cys Asp
1               5                   10                  15

Leu Ser

<210> SEQ ID NO 1006
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1006

Met Gly Phe Tyr Pro Cys Trp Thr Ala Gln Leu Gly Glu Leu Cys Asp
1               5                   10                  15

Leu

<210> SEQ ID NO 1007
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1007

Gly Phe Tyr Pro Cys Trp Thr Ala Gln Leu Gly Glu Leu Cys Asp Leu
1               5                   10                  15

Ser Val

<210> SEQ ID NO 1008
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1008

Phe Tyr Pro Cys Trp Thr Ala Gln Leu Gly Glu Leu Cys Asp Leu

-continued

```
1               5                   10                  15

<210> SEQ ID NO 1009

<400> SEQUENCE: 1009

000

<210> SEQ ID NO 1010
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1010

Lys Tyr Cys Gly Phe Ala Gln Leu Gly Glu Leu Cys Val Leu
1               5                   10

<210> SEQ ID NO 1011
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1011

Gly Lys Tyr Cys Gly Phe Ala Gln Leu Gly Glu Leu Cys Val Leu
1               5                   10                  15

<210> SEQ ID NO 1012
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1012

Gly Gly Lys Tyr Cys Gly Phe Ala Gln Leu Gly Glu Leu Cys Val Leu
1               5                   10                  15

<210> SEQ ID NO 1013
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1013

Gly Gly Gly Lys Tyr Cys Gly Phe Ala Gln Leu Gly Glu Leu Cys Val
1               5                   10                  15

Leu

<210> SEQ ID NO 1014
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1014

Lys Tyr Cys Gly Phe Ala Gln Leu Gly Glu Leu Cys Val Leu Gly
```

<210> SEQ ID NO 1015
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1015

Lys Tyr Cys Gly Phe Ala Gln Leu Gly Glu Leu Cys Val Leu Gly Gly
1               5                   10                  15

<210> SEQ ID NO 1016
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1016

Lys Tyr Cys Gly Phe Ala Gln Leu Gly Glu Leu Cys Val Leu Gly Gly
1               5                   10                  15

Gly

<210> SEQ ID NO 1017
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1017

Gly Lys Tyr Cys Gly Phe Ala Gln Leu Gly Glu Leu Cys Val Leu Gly
1               5                   10                  15

<210> SEQ ID NO 1018
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1018

Gly Gly Lys Tyr Cys Gly Phe Ala Gln Leu Gly Glu Leu Cys Val Leu
1               5                   10                  15

Gly

<210> SEQ ID NO 1019

<400> SEQUENCE: 1019

000

<210> SEQ ID NO 1020
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1020

-continued

Tyr Trp Cys Trp Met Ala Gln Val Gly Glu Leu Cys Asp Leu
1               5                   10

<210> SEQ ID NO 1021
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1021

Tyr His Cys Trp Met Ala Gln Val Gly Glu Leu Cys Asp Leu
1               5                   10

<210> SEQ ID NO 1022
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1022

Tyr His Cys Trp Met Gly Gln Val Gly Glu Leu Cys Asp Leu
1               5                   10

<210> SEQ ID NO 1023
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1023

Tyr His Cys Trp Met Gly Gln Met Gly Glu Leu Cys Asp Leu
1               5                   10

<210> SEQ ID NO 1024
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1024

Tyr His Cys Trp Met Gly Gln Met Gly Glu Leu Cys Glu Leu
1               5                   10

<210> SEQ ID NO 1025
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1025

Tyr His Cys Trp Met Gly Gln Met Gly Glu Leu Cys Glu Met
1               5                   10

<210> SEQ ID NO 1026

<400> SEQUENCE: 1026

```
000

<210> SEQ ID NO 1027
<400> SEQUENCE: 1027

000

<210> SEQ ID NO 1028
<400> SEQUENCE: 1028

000

<210> SEQ ID NO 1029
<400> SEQUENCE: 1029

000

<210> SEQ ID NO 1030
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1030

Tyr Pro Cys Trp Leu Ala Arg Val Gly Glu Leu Cys Asp Leu Asp Ser
1               5                   10                  15

Gly Asp Val His
            20

<210> SEQ ID NO 1031
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1031

Ala Pro Cys Trp Leu Ala Arg Val Gly Glu Leu Cys Asp Leu Asp Ser
1               5                   10                  15

Gly Asp Val His
            20

<210> SEQ ID NO 1032
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1032

Ala Pro Cys Ala Leu Ala Arg Val Gly Glu Leu Cys Asp Leu Asp Ser
1               5                   10                  15

Gly Asp Val His
            20

<210> SEQ ID NO 1033
<211> LENGTH: 20
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 1033

Ala Pro Cys Ala Leu Ala Ala Val Gly Glu Leu Cys Asp Leu Asp Ser
1               5                   10                  15

Gly Asp Val His
            20

<210> SEQ ID NO 1034
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1034

Ala Pro Cys Ala Leu Ala Ala Val Gly Ala Leu Cys Asp Leu Asp Ser
1               5                   10                  15

Gly Asp Val His
            20

<210> SEQ ID NO 1035
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1035

Ala Pro Cys Ala Leu Ala Ala Val Gly Ala Leu Cys Asp Leu Ala Ser
1               5                   10                  15

Gly Asp Val His
            20

<210> SEQ ID NO 1036
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1036

Ala Pro Cys Ala Leu Ala Ala Val Gly Ala Leu Cys Asp Leu Ala Ala
1               5                   10                  15

Gly Asp Val His
            20

<210> SEQ ID NO 1037
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 1037

Arg Asp Gln Tyr Tyr Pro Cys Trp Met Ala Gln Leu Gly Glu Leu Cys
1               5                  10                 15

Asp Leu Asp Glu Val Phe
            20

<210> SEQ ID NO 1038
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1038

Arg Asp Gln Tyr Tyr Pro Cys Tyr Met Ala Gln Leu Gly Glu Leu Cys
1               5                  10                 15

Asp Leu Glu Glu Val Phe
            20

<210> SEQ ID NO 1039
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1039

Gly Gly Gly Ser
1

<210> SEQ ID NO 1040
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1040

Gly Gly Gly Gly Ser
1               5

<210> SEQ ID NO 1041
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(4)
<223> OTHER INFORMATION: This sequence may encompass 1-4 residues

<400> SEQUENCE: 1041

Gly Gly Gly Gly
1
```